United States Patent
Yonemura et al.

(10) Patent No.: US 10,266,552 B2
(45) Date of Patent: Apr. 23, 2019

(54) CONDENSED HETEROCYCLIC COMPOUND HAVING CYCLOALKYLPYRIDYL GROUP OR SALT THEREOF, AGRICULTURAL AND HORTICULTURAL INSECTICIDE COMPRISING THE COMPOUND, AND METHOD FOR USING THE INSECTICIDE

(71) Applicant: Nihon Nohyaku Co., Ltd., Tokyo (JP)

(72) Inventors: Ikki Yonemura, Osaka (JP); Akiyuki Suwa, Osaka (JP); Soichiro Matsuo, Osaka (JP); Takanori Aoki, Osaka (JP)

(73) Assignee: Nihon Nohyaku Co., Ltd., Tokyo (JP)

( * ) Notice: Subject to any disclaimer, the term of this patent is extended or adjusted under 35 U.S.C. 154(b) by 0 days.

(21) Appl. No.: 15/545,078

(22) PCT Filed: Jan. 29, 2016

(86) PCT No.: PCT/JP2016/052841
§ 371 (c)(1),
(2) Date: Jul. 20, 2017

(87) PCT Pub. No.: WO2016/121997
PCT Pub. Date: Aug. 4, 2016

(65) Prior Publication Data
US 2018/0002347 A1 Jan. 4, 2018

(30) Foreign Application Priority Data

Jan. 29, 2015 (JP) .................................. 2015-015041
Dec. 28, 2015 (JP) .................................. 2015-256132

(51) Int. Cl.
| | |
|---|---|
| C07D 513/04 | (2006.01) |
| A01N 43/52 | (2006.01) |
| C07D 471/04 | (2006.01) |
| C07D 413/04 | (2006.01) |
| A01N 43/90 | (2006.01) |
| A01N 43/78 | (2006.01) |
| A01N 43/76 | (2006.01) |
| A01N 43/54 | (2006.01) |
| C07D 401/04 | (2006.01) |
| C07D 417/04 | (2006.01) |
| C07D 498/04 | (2006.01) |

(52) U.S. Cl.
CPC .......... *C07D 513/04* (2013.01); *A01N 43/52* (2013.01); *A01N 43/54* (2013.01); *A01N 43/76* (2013.01); *A01N 43/78* (2013.01); *A01N 43/90* (2013.01); *C07D 401/04* (2013.01); *C07D 413/04* (2013.01); *C07D 417/04* (2013.01); *C07D 471/04* (2013.01); *C07D 498/04* (2013.01)

(58) Field of Classification Search
CPC .. C07D 513/04; C07D 471/04; C07D 417/04; C07D 413/04; C07D 498/04; C07D 401/04; A01N 43/52; A01N 43/90; A01N 43/78; A01N 43/76; A01N 43/54
See application file for complete search history.

(56) References Cited

U.S. PATENT DOCUMENTS

| | | | |
|---|---|---|---|
| 9,936,703 B2* | 4/2018 | Yonemura | .............. A01N 43/90 |
| 2011/0039843 A1 | 2/2011 | Iwakoshi et al. | |
| 2012/0015975 A1 | 1/2012 | Takahashi et al. | |
| 2012/0108586 A1 | 5/2012 | Iwakoshi et al. | |
| 2012/0178779 A1 | 7/2012 | Takahashi et al. | |
| 2012/0196891 A1 | 8/2012 | Iwakoshi | |
| 2012/0245167 A1 | 9/2012 | Iwakoshi et al. | |
| 2013/0190271 A1 | 7/2013 | Iwakoshi et al. | |
| 2013/0252981 A1 | 9/2013 | Takahashi et al. | |
| 2014/0018373 A1 | 1/2014 | Takyo et al. | |

(Continued)

FOREIGN PATENT DOCUMENTS

| | | |
|---|---|---|
| JP | 2009-280574 | 12/2009 |
| JP | 2010-275301 | 12/2010 |

(Continued)

OTHER PUBLICATIONS

International Search Report for PCT/JP2016/052841 dated Mar. 22, 2016.

(Continued)

*Primary Examiner* — John Pak
*Assistant Examiner* — Andriae M Holt
(74) *Attorney, Agent, or Firm* — Knobbe, Martens, Olson & Bear, LLP

(57) ABSTRACT

An object of the present invention is to provide and develop novel agricultural and horticultural insecticides in view of the still immense damage caused by insect pests etc. and the emergence of insect pests resistant to existing insecticides in crop production in the fields of agriculture, horticulture and the like.

Provided are a condensed heterocyclic compound represented by the general formula (1):

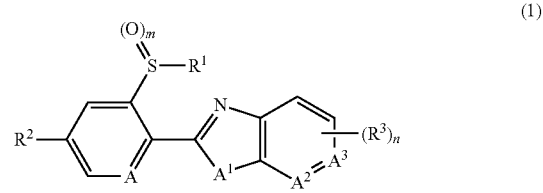

(1)

{wherein $R^1$ represents an ethyl group, $R^2$ represents a cycloalkyl group, $R^3$ represents a haloalkyl group, A, $A^2$ and $A^3$ each represent a nitrogen atom or a CH group, $A^1$ represents N-Me, m represents 0 or 2, and n represents 1} or a salt thereof; an agricultural and horticultural insecticide comprising the compound or a salt thereof as an active ingredient; and a method for using the insecticide.

9 Claims, No Drawings

(56) References Cited

U.S. PATENT DOCUMENTS

| | | |
|---|---|---|
| 2014/0194290 A1 | 7/2014 | Takahashi et al. |
| 2014/0364444 A1 | 12/2014 | Takyo et al. |
| 2015/0197532 A1 | 7/2015 | Takahashi et al. |
| 2015/0246911 A1 | 9/2015 | Takahashi et al. |
| 2015/0366208 A1 | 12/2015 | Shimizu et al. |
| 2016/0009715 A1 | 1/2016 | Takahashi et al. |
| 2016/0021886 A1 | 1/2016 | Yonemura et al. |
| 2016/0159743 A1 | 6/2016 | Takahashi et al. |
| 2016/0255837 A1 | 9/2016 | Edmunds et al. |
| 2016/0366884 A1 | 12/2016 | Yonemura et al. |

FOREIGN PATENT DOCUMENTS

| | | |
|---|---|---|
| JP | 2011-79774 | 4/2011 |
| JP | 2012-131780 | 7/2012 |
| WO | WO 2012/086848 A1 | 6/2012 |
| WO | WO 2013/018928 A1 | 2/2013 |
| WO | WO 2013/191188 A1 | 12/2013 |
| WO | WO 2014/119679 A1 | 8/2014 |
| WO | WO 2014/142292 A1 | 9/2014 |
| WO | WO 2015/000705 A1 | 1/2015 |
| WO | WO 2015/000715 A1 | 1/2015 |
| WO | WO 2015/072463 A1 | 5/2015 |
| WO | WO 2016/020286 A1 | 2/2016 |
| WO | WO 2016/023954 A2 | 2/2016 |
| WO | WO 2016/026848 A1 | 2/2016 |
| WO | WO 2016/096584 A1 | 6/2016 |

OTHER PUBLICATIONS

International Preliminary Report on Patentability for PCT/JP2016/052841 dated Aug. 1, 2017.

\* cited by examiner

CONDENSED HETEROCYCLIC COMPOUND HAVING CYCLOALKYLPYRIDYL GROUP OR SALT THEREOF, AGRICULTURAL AND HORTICULTURAL INSECTICIDE COMPRISING THE COMPOUND, AND METHOD FOR USING THE INSECTICIDE

CROSS REFERENCE TO RELATED APPLICATIONS

This application is a U.S. National Phase Application of PCT International Application Number PCT/JP2016/052841, filed on Jan. 29, 2016, designating the United States of America and published in Japanese, which is an International Application of and claims the benefit of priority to Japanese Patent Application No. 2015-015041, filed on Jan. 29, 2015, and Japanese Patent Application No. 2015-256132, filed on Dec. 28, 2015. The disclosures of the above-referenced applications are hereby expressly incorporated by reference in their entireties.

TECHNICAL FIELD

The present invention relates to an agricultural and horticultural insecticide comprising a condensed heterocyclic compound having a cycloalkylpyridyl group or a salt thereof as an active ingredient; and the method for using the insecticide.

BACKGROUND ART

Various compounds have been examined for their potential as an agricultural and horticultural insecticide, and among them, certain kinds of condensed heterocyclic compounds have been reported to be useful as an insecticide (for example, see Patent Literature 1 to 7). None of these references discloses any compound having a condensed heterocyclic ring bound to a cycloalkylpyridyl group.

CITATION LIST

Patent Literature

Patent Literature 1: JP-A 2009-280574
Patent Literature 2: JP-A 2010-275301
Patent Literature 3: JP-A 2011-79774
Patent Literature 4: JP-A 2012-131780
Patent Literature 5: WO 2012/086848
Patent Literature 6: WO 2014/142292
Patent Literature 7: WO 2015/715

SUMMARY OF INVENTION

Technical Problem

In crop production in the fields of agriculture, horticulture and the like, the damage caused by insect pests etc. is still immense, and insect pests resistant to existing insecticides have emerged. Under such circumstances, the development of novel agricultural and horticultural insecticides is desired.

Solution to Problem

The present inventors conducted extensive research to solve the above-described problems. As a result, the present inventors found that a condensed heterocyclic compound having a cycloalkylpyridyl group, etc. represented by the general formula (1) or a salt thereof has an excellent control effect on agricultural and horticultural insect pests, and reached the completion of the present invention.

That is, the present invention relates to the following.

[1] A condensed heterocyclic compound represented by the general formula (1):

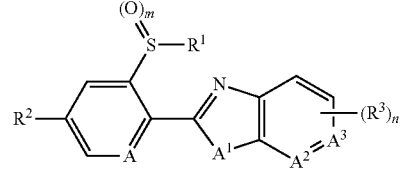

{wherein $R^1$ represents
(a1) a $(C_1\text{-}C_6)$ alkyl group;
(a2) a $(C_3\text{-}C_6)$ cycloalkyl group;
(a3) a $(C_2\text{-}C_6)$ alkenyl group; or
(a4) a $(C_2\text{-}C_6)$ alkynyl group,
$R^2$ represents
(b1) a $(C_3\text{-}C_6)$ cycloalkyl group;
(b2) a $(C_3\text{-}C_6)$ cycloalkyl $(C_1\text{-}C_6)$ alkyl group;
(b3) a halo $(C_3\text{-}C_6)$ cycloalkyl $(C_1\text{-}C_6)$ alkyl group;
(b4) a $(C_1\text{-}C_6)$ alkylthio group; or
(b5) a $(C_3\text{-}C_6)$ cycloalkyl group having, on the ring, 1 or 2 of the same or different substituting groups selected from
(a) a halogen atom,
(b) a cyano group,
(c) a cyano $(C_1\text{-}C_6)$ alkyl group,
(d) a formyl group;
(e) a hydroxy $(C_1\text{-}C_6)$ alkyl group,
(f) a halo $(C_1\text{-}C_6)$ alkyl group,
(g) a $(C_1\text{-}C_6)$ alkoxy $(C_1\text{-}C_6)$ alkyl group,
(h) a halo $(C_1\text{-}C_6)$ alkoxy $(C_1\text{-}C_6)$ alkyl group,
(i) a $(C_3\text{-}C_6)$ cycloalkyl $(C_1\text{-}C_6)$ alkoxy $(C_1\text{-}C_6)$ alkyl group,
(j) a $(C_1\text{-}C_6)$ alkylthio $(C_1\text{-}C_6)$ alkyl group,
(k) a $(C_1\text{-}C_6)$ alkylsulfinyl $(C_1\text{-}C_6)$ alkyl group,
(l) a $(C_1\text{-}C_6)$ alkylsulfonyl $(C_1\text{-}C_6)$ alkyl group,
(m) a $(C_1\text{-}C_6)$ alkylcarbonyl group,
(n) a carboxyl group,
(o) a $(C_1\text{-}C_6)$ alkoxycarbonyl group,
(p) a halo $(C_1\text{-}C_6)$ alkoxycarbonyl group,
(q) a $(C_3\text{-}C_6)$ cycloalkyl $(C_1\text{-}C_6)$ alkoxycarbonyl group,
(r) a $(C_1\text{-}C_6)$ alkylcarbonyloxy $(C_1\text{-}C_6)$ alkyl group,
(s) a $(C_3\text{-}C_6)$ cycloalkylcarbonyloxy $(C_1\text{-}C_6)$ alkyl group,
(t) a $(C_1\text{-}C_6)$ alkoxycarbonyloxy $(C_1\text{-}C_6)$ alkyl group,
(u) a $R^5(R^6)N$ group (wherein $R^5$ and $R^6$ may be the same or different, and each represent a hydrogen atom, a $(C_1\text{-}C_6)$ alkyl group, a $(C_3\text{-}C_6)$ cycloalkyl group, a $(C_3\text{-}C_6)$ cycloalkyl $(C_1\text{-}C_6)$ alkyl group, a halo $(C_1\text{-}C_6)$ alkyl group, a $(C_1\text{-}C_6)$ alkylcarbonyl group, a $(C_1\text{-}C_6)$ alkoxycarbonyl group, or a di-$(C_1\text{-}C_6)$ alkylaminocarbonyl group (wherein the alkyl groups of the di-$(C_1\text{-}C_6)$ alkylamino moiety may be the same or different)),
(v) a $R^5(R^6)N(C_1\text{-}C_6)$ alkyl group (wherein $R^5$ and $R^6$ are as defined above),
(w) a $R^5(R^6)N$ carbonyl group (wherein $R^5$ and $R^6$ are as defined above),
(x) a $R^5(R^6)N$ carbonyloxy $(C_1\text{-}C_6)$ alkyl group (wherein $R^5$ and $R^6$ are as defined above), and
(y) a $C(R^5)=NOR^6$ group (wherein $R^5$ and $R^6$ are as defined above), R³ represents
(c1) a halogen atom;
(c2) a cyano group;
(c3) a nitro group;
(c4) a ($C_1$-$C_6$) alkyl group;
(c5) a ($C_1$-$C_6$) alkoxy group;
(c6) a ($C_2$-$C_6$) alkenyloxy group;
(c7) a ($C_2$-$C_6$) alkynyloxy group;
(c8) a halo ($C_1$-$C_6$) alkyl group;
(c9) a halo ($C_1$-$C_6$) alkoxy group;
(c10) a halo ($C_2$-$C_6$) alkenyloxy group;
(c11) a halo ($C_2$-$C_6$) alkynyloxy group;
(c12) a ($C_1$-$C_6$) alkylthio group;
(c13) a ($C_1$-$C_6$) alkylsulfinyl group;
(c14) a ($C_1$-$C_6$) alkylsulfonyl group;
(c15) a halo ($C_1$-$C_6$) alkylthio group;
(c16) a halo ($C_1$-$C_6$) alkylsulfinyl group; or
(c17) a halo ($C_1$-$C_6$) alkylsulfonyl group,
  A, A² and A³ each represent CH or a nitrogen atom,
  A¹ represents O, S or N—R⁴ (wherein R⁴ represents
(d1) a ($C_1$-$C_6$) alkyl group;
(d2) a ($C_3$-$C_6$) cycloalkyl group;
(d3) a ($C_2$-$C_6$) alkenyl group; or
(d4) a ($C_2$-$C_6$) alkynyl group);
with the exception of the case where A¹ is N—R⁴ and both A² and A³ are a nitrogen atom,
  m represents 0, 1 or 2, and
  n represents 1 or 2}, or
a salt thereof.

[2] The condensed heterocyclic compound according to the above [1],
wherein R¹ is (a1) a ($C_1$-$C_6$) alkyl group,
  R² is
(b1) a ($C_3$-$C_6$) cycloalkyl group;
(b4) a ($C_1$-$C_6$) alkylthio group; or
(b5) a ($C_3$-$C_6$) cycloalkyl group having, on the ring, 1 or 2 of the same or different substituting groups selected from
(b) a cyano group,
(c) a cyano ($C_1$-$C_6$) alkyl group,
(d) a formyl group,
(e) a hydroxy ($C_1$-$C_6$) alkyl group,
(f) a halo ($C_1$-$C_6$) alkyl group,
(g) a ($C_1$-$C_6$) alkoxy ($C_1$-$C_6$) alkyl group,
(h) a halo ($C_1$-$C_6$) alkoxy ($C_1$-$C_6$) alkyl group,
(i) a ($C_3$-$C_6$) cycloalkyl ($C_1$-$C_6$) alkoxy ($C_1$-$C_6$) alkyl group,
(j) a ($C_1$-$C_6$) alkylthio ($C_1$-$C_6$) alkyl group,
(k) a ($C_1$-$C_6$) alkylsulfinyl ($C_1$-$C_6$) alkyl group,
(l) a ($C_1$-$C_6$) alkylsulfonyl ($C_1$-$C_6$) alkyl group,
(m) a ($C_1$-$C_6$) alkylcarbonyl group,
(n) a carboxyl group,
(o) a ($C_1$-$C_6$) alkoxycarbonyl group,
(p) a halo ($C_1$-$C_6$) alkoxycarbonyl group,
(q) a ($C_3$-$C_6$) cycloalkyl ($C_1$-$C_6$) alkoxycarbonyl group,
(r) a ($C_1$-$C_6$) alkylcarbonyloxy ($C_1$-$C_6$) alkyl group,
(s) a ($C_3$-$C_6$) cycloalkylcarbonyloxy ($C_1$-$C_6$) alkyl group,
(t) a ($C_1$-$C_6$) alkoxycarbonyloxy ($C_1$-$C_6$) alkyl group,
(u) a $R^5(R^6)N$ group (wherein R⁵ and R⁶ may be the same or different, and each represent a hydrogen atom, a ($C_1$-$C_6$) alkyl group, a ($C_3$-$C_6$) cycloalkyl group, a ($C_3$-$C_6$) cycloalkyl ($C_1$-$C_6$) alkyl group, a halo ($C_1$-$C_6$) alkyl group, a ($C_1$-$C_6$) alkylcarbonyl group, a ($C_1$-$C_6$) alkoxycarbonyl group, or a di-($C_1$-$C_6$) alkylaminocarbonyl group (wherein the alkyl groups of the di-($C_1$-$C_6$) alkylamino moiety may be the same or different)),
(v) a $R^5(R^6)N(C_1$-$C_6)$ alkyl group (wherein R⁵ and R⁶ are as defined above),
(w) a $R^5(R^6)N$ carbonyl group (wherein R⁵ and R⁶ are as defined above),
(x) a $R^5(R^6)N$ carbonyloxy ($C_1$-$C_6$) alkyl group (wherein R⁵ and R⁶ are as defined above), and
(y) a $C(R^5)=NOR^6$ group (wherein R⁵ and R⁶ are as defined above),
  R³ is
(c8) a halo ($C_1$-$C_6$) alkyl group;
(c9) a halo ($C_1$-$C_6$) alkoxy group;
(c12) a ($C_1$-$C_6$) alkylthio group; or
(c15) a halo ($C_1$-$C_6$) alkylthio group,
  A, A² and A³ each are CH or a nitrogen atom,
  A¹ is O, S or N—R⁴ (wherein R⁴ represents (d1) a ($C_1$-$C_6$) alkyl group),
with the exception of the case where A¹ is N—R⁴ and both A² and A³ are a nitrogen atom,
  m is 0, 1 or 2, and
  n is 1, or
a salt thereof.

[3] The condensed heterocyclic compound according to the above [1],
wherein R¹ is (a1) a ($C_1$-$C_6$) alkyl group,
  R² is
(b1) a ($C_3$-$C_6$) cycloalkyl group; or
(b5) a ($C_3$-$C_6$) cycloalkyl group having, on the ring, 1 or 2 of the same or different substituting groups selected from
(b) a cyano group,
(n) a carboxyl group,
(o) a ($C_1$-$C_6$) alkoxycarbonyl group,
(t) a ($C_1$-$C_6$) alkoxycarbonyloxy ($C_1$-$C_6$) alkyl group, and
(w) a $R^5(R^6)N$ carbonyl group (wherein R⁵ and R⁶ are as defined above),
  R³ is (c8) a halo ($C_1$-$C_6$) alkyl group,
  A, A² and A³ are a nitrogen atom,
  A¹ is N—R⁴ (wherein R⁴ represents (d1) a ($C_1$-$C_6$) alkyl group, with the exception of the case where both A² and A³ are a nitrogen atom),
  m is 0 or 2, and
  n is 1, or
a salt thereof.

[4] A condensed heterocyclic compound represented by the formula:

(1)

{wherein R¹ represents (a1) a ($C_1$-$C_6$) alkyl group; (a2) a ($C_3$-$C_6$) cycloalkyl group; (a3) a ($C_2$-$C_6$) alkenyl group; or (a4) a ($C_2$-$C_6$) alkynyl group,
  R² represents (b1) a ($C_3$-$C_6$) cycloalkyl group; (b2) a ($C_3$-$C_6$) cycloalkyl ($C_1$-$C_6$) alkyl group; (b3) a halo ($C_3$-$C_6$) cycloalkyl ($C_1$-$C_6$) alkyl group; or (b4) a ($C_1$-$C_6$) alkylthio group,
  R³ represents (c1) a halogen atom; (c2) a cyano group; (c3) a nitro group; (c4) a ($C_1$-$C_6$) alkyl group; (c5) a ($C_1$-$C_6$) alkoxy group; (c6) a ($C_2$-$C_6$) alkenyloxy group; (c7) a ($C_2$-$C_6$) alkynyloxy group; (c8) a halo ($C_1$-$C_6$) alkyl group; (c9) a halo ($C_1$-$C_6$) alkoxy group; (c10) a halo ($C_2$-$C_6$) alkenyloxy group; (c11) a halo ($C_2$-$C_6$) alkynyloxy group; (c12) a ($C_1$-$C_6$) alkylthio group; (c13) a ($C_1$-$C_6$) alkylsulfinyl group; (c14) a $(C_1-C_6)$ alkylsulfonyl group; (c15) a halo $(C_1-C_6)$ alkylthio group; (c16) a halo $(C_1-C_6)$ alkylsulfinyl group; or (c17) a halo $(C_1-C_6)$ alkylsulfonyl group, A, $A^2$ and $A^3$ each represent CH or a nitrogen atom, $A^1$ represents O, S or N—$R^4$ (wherein $R^4$ represents (d1) a $(C_1-C_6)$ alkyl group; (d2) a $(C_3-C_6)$ cycloalkyl group; (d3) a $(C_2-C_6)$ alkenyl group; or (d4) a $(C_2-C_6)$ alkynyl group), with the exception of the case where $A^1$ is N—$R^4$ and both $A^2$ and $A^3$ are a nitrogen atom, m represents 0, 1 or 2, and n represents 1 or 2}.

[5] The condensed heterocyclic compound according to the above [4], wherein $R^1$ represents (a1) a $(C_1-C_6)$ alkyl group, $R^2$ represents (b1) a $(C_3-C_6)$ cycloalkyl group; or (b4) a $(C_1-C_6)$ alkylthio group, $R^3$ represents (c8) a halo $(C_1-C_6)$ alkyl group; (c9) a halo $(C_1-C_6)$ alkoxy group; (c12) a $(C_1-C_6)$ alkylthio group; or (c15) a halo $(C_1-C_6)$ alkylthio group, A, $A^2$ and $A^3$ each represent CH or a nitrogen atom, $A^1$ represents N—$R^4$ (wherein $R^4$ represents (d1) a $(C_1-C_6)$ alkyl group), m represents 0 or 2, and n represents 1.

[6] The condensed heterocyclic compound according to the above [4], wherein $R^1$ represents (a1) a $(C_1-C_6)$ alkyl group, $R^2$ represents (b1) a $(C_3-C_6)$ cycloalkyl group, $R^3$ represents (c8) a halo $(C_1-C_6)$ alkyl group, A, $A^2$ and $A^3$ each represent CH or a nitrogen atom, $A^1$ represents O, S or N—$R^4$ (wherein $R^4$ represents (d1) a $(C_1-C_6)$ alkyl group), m represents 0 or 2, and n represents 1.

[7] An agricultural and horticultural insecticide comprising the condensed heterocyclic compound or a salt thereof according to any one of the above [1] to [6] as an active ingredient.

[8] A method for using an agricultural and horticultural insecticide, comprising treating plants or soil with an effective amount of the condensed heterocyclic compound or a salt thereof according to any one of the above [1] to [6].

[9] An ectoparasite control agent comprising an effective amount of the condensed heterocyclic compound or a salt thereof according to any one of the above [1] to [6] as an active ingredient.

Advantageous Effects of Invention

The condensed heterocyclic compound having a cycloalkylpyridyl group of the present invention or a salt thereof is not only highly effective as an agricultural and horticultural insecticide, but also is effective against pests which live on the exterior of or in the interior of pets such as dogs and cats and domestic animals such as cattle and sheep.

DESCRIPTION OF EMBODIMENTS

In the definition of the general formula (1) representing the condensed heterocyclic compound of the present invention or a salt thereof, "halo" refers to a "halogen atom" and represents a fluorine atom, a chlorine atom, a bromine atom or an iodine atom.

The "$(C_1-C_6)$ alkyl group" refers to a straight chain or branched chain alkyl group of 1 to 6 carbon atoms, for example, a methyl group, an ethyl group, a n-propyl group, an isopropyl group, a n-butyl group, an isobutyl group, a sec-butyl group, a tert-butyl group, a n-pentyl group, an isopentyl group, a tert-pentyl group, a neopentyl group, a 2,3-dimethylpropyl group, a 1-ethylpropyl group, a 1-methylbutyl group, a 2-methylbutyl group, a n-hexyl group, an isohexyl group, a 2-hexyl group, a 3-hexyl group, a 2-methylpentyl group, a 3-methylpentyl group, a 1,1,2-trimethylpropyl group, a 3,3-dimethylbutyl group or the like.

The "$(C_3-C_6)$ cycloalkyl group" refers to a cyclic alkyl group of 3 to 6 carbon atoms, for example, a cyclopropyl group, a cyclobutyl group, a cyclopentyl group, a cyclohexyl group or the like. The "$(C_1-C_6)$ alkoxy group" refers to a straight chain or branched chain alkoxy group of 1 to 6 carbon atoms, for example, a methoxy group, an ethoxy group, a n-propoxy group, an isopropoxy group, a n-butoxy group, a sec-butoxy group, a tert-butoxy group, a n-pentyloxy group, an isopentyloxy group, a tert-pentyloxy group, a neopentyloxy group, a 2,3-dimethylpropyloxy group, a 1-ethylpropyloxy group, a 1-methylbutyloxy group, a n-hexyloxy group, an isohexyloxy group, a 1,1,2-trimethylpropyloxy group or the like. The "$(C_2-C_6)$ alkenyloxy group" refers to a straight chain or branched chain alkenyloxy group of 2 to 6 carbon atoms, for example, a propenyloxy group, a butenyloxy group, a pentenyloxy group, a hexenyloxy group or the like. The "$(C_2-C_6)$ alkynyloxy group" refers to a straight chain or branched chain alkynyloxy group of 2 to 6 carbon atoms, for example, a propynyloxy group, a butynyloxy group, a pentynyloxy group, a hexynyloxy group or the like.

The "$(C_1-C_6)$ alkylthio group" refers to a straight chain or branched chain alkylthio group of 1 to 6 carbon atoms, for example, a methylthio group, an ethylthio group, a n-propylthio group, an isopropylthio group, a n-butylthio group, a sec-butylthio group, a tert-butylthio group, a n-pentylthio group, an isopentylthio group, a tert-pentylthio group, a neopentylthio group, a 2,3-dimethylpropylthio group, a 1-ethylpropylthio group, a 1-methylbutylthio group, a n-hexylthio group, an isohexylthio group, a 1,1,2-trimethylpropylthio group or the like. The "$(C_1-C_6)$ alkylsulfinyl group" refers to a straight chain or branched chain alkylsulfinyl group of 1 to 6 carbon atoms, for example, a methylsulfinyl group, an ethylsulfinyl group, a n-propylsulfinyl group, an isopropylsulfinyl group, a n-butylsulfinyl group, a sec-butylsulfinyl group, a tert-butylsulfinyl group, a n-pentylsulfinyl group, an isopentylsulfinyl group, a tert-pentylsulfinyl group, a neopentylsulfinyl group, a 2,3-dimethylpropylsulfinyl group, a 1-ethylpropylsulfinyl group, a 1-methylbutylsulfinyl group, a n-hexylsulfinyl group, an isohexylsulfinyl group, a 1,1,2-trimethylpropylsulfinyl group or the like. The "$(C_1-C_6)$ alkylsulfonyl group" refers to a straight chain or branched chain alkylsulfonyl group of 1 to 6 carbon atoms, for example, a methylsulfonyl group, an ethylsulfonyl group, a n-propylsulfonyl group, an isopropylsulfonyl group, a n-butylsulfonyl group, a sec-butylsulfonyl group, a tert-butylsulfonyl group, a n-pentylsulfonyl group, an isopentylsulfonyl group, a tert-pentylsulfonyl group, a neopentylsulfonyl group, a 2,3-dimethylpropylsulfonyl group, a 1-ethylpropylsulfonyl group, a 1-methylbutylsulfonyl group, a n-hexylsulfonyl group, an isohexylsulfonyl group, a 1,1,2-trimethylpropylsulfonyl group or the like.

The above-mentioned "$(C_1-C_6)$ alkyl group,"
"$(C_2-C_6)$ alkenyl group,"
"$(C_2-C_6)$ alkynyl group,"
"$(C_3-C_6)$ cycloalkyl group,"
"$(C_3-C_6)$ cycloalkyloxy group,"
"$(C_1-C_6)$ alkoxy group,"

"$(C_2-C_6)$ alkenyloxy group,"
"$(C_2-C_6)$ alkynyloxy group,"
"$(C_1-C_6)$ alkylthio group,"
"$(C_1-C_6)$ alkylsulfinyl group,"
"$(C_1-C_6)$ alkylsulfonyl group,"
"$(C_2-C_6)$ alkenylthio group,"
"$(C_2-C_6)$ alkynylthio group,"
"$(C_2-C_6)$ alkenylsulfinyl group,"
"$(C_2-C_6)$ alkynylsulfinyl group,"
"$(C_2-C_6)$ alkenylsulfonyl group,"
"$(C_2-C_6)$ alkynylsulfonyl group,"
"$(C_3-C_6)$ cycloalkyl group,"
"$(C_1-C_6)$ alkoxy group,"
"$(C_2-C_6)$ alkenyloxy group,"
"$(C_2-C_6)$ alkynyloxy group,"
"$(C_3-C_6)$ cycloalkylthio group,"
"$(C_3-C_6)$ cycloalkylsulfinyl group" or
"$(C_3-C_6)$ cycloalkylsulfonyl group"
may be substituted by one or more halogen atoms at a substitutable position(s), and in the case where the above-listed group is substituted by two or more halogen atoms, the halogen atoms may be the same or different.

The above-mentioned groups substituted by one or more halogen atoms are each expressed as
a "halo $(C_1-C_6)$ alkyl group,"
a "halo $(C_2-C_6)$ alkenyl group,"
a "halo $(C_2-C_6)$ alkynyl group,"
a "halo $(C_3-C_6)$ cycloalkyl group,"
a "halo $(C_3-C_6)$ cycloalkyloxy group,"
a "halo $(C_1-C_6)$ alkoxy group,"
a "halo $(C_2-C_6)$ alkenyloxy group,"
a "halo $(C_2-C_6)$ alkynyloxy group,"
a "halo $(C_1-C_6)$ alkylthio group,"
a "halo $(C_1-C_6)$ alkylsulfinyl group,"
a "halo $(C_1-C_6)$ alkylsulfonyl group,"
a "halo $(C_2-C_6)$ alkenylthio group,"
a "halo $(C_2-C_6)$ alkynylthio group,"
a "halo $(C_2-C_6)$ alkenylsulfinyl group,"
a "halo $(C_2-C_6)$ alkynylsulfinyl group,"
a "halo $(C_2-C_6)$ alkenylsulfonyl group,"
a "halo $(C_2-C_6)$ alkynylsulfonyl group,"
a "halo $(C_3-C_6)$ cycloalkyl group,"
a "halo $(C_1-C_6)$ alkoxy group,"
a "halo $(C_2-C_6)$ alkenyloxy group,"
a "halo $(C_2-C_6)$ alkynyloxy group,"
a "halo $(C_3-C_6)$ cycloalkylthio group,"
a "halo $(C_3-C_6)$ cycloalkylsulfinyl group" and
a "halo $(C_3-C_6)$ cycloalkylsulfonyl group".

The expressions "$(C_1-C_6)$," "$(C_2-C_6)$," "$(C_3-C_6)$," etc. each refer to the range of the number of carbon atoms in the substituting groups. The same definition holds true for the groups coupled to the above-mentioned substituting groups, and for example, the "$(C_1-C_6)$ alkoxy $(C_1-C_6)$ alkyl group" means that a straight chain or branched chain alkoxy group of 1 to 6 carbon atoms is bound to a straight chain or branched chain alkyl group of 1 to 6 carbon atoms.

Examples of the salt of the condensed heterocyclic compound represented by the general formula (1) of the present invention include inorganic acid salts, such as hydrochlorides, sulfates, nitrates and phosphates; organic acid salts, such as acetates, fumarates, maleates, oxalates, methanesulfonates, benzenesulfonates and p-toluenesulfonates; and salts with an inorganic or organic base such as a sodium ion, a potassium ion, a calcium ion and a trimethylammonium ion.

The condensed heterocyclic compound represented by the general formula (1) of the present invention and a salt thereof can have one or more chiral centers in the structural formula, and can exist as two or more kinds of optical isomers or diastereomers. All the optical isomers and mixtures of the isomers at any ratio are also included in the present invention. Further, the compound represented by the general formula (1) of the present invention and a salt thereof can exist as two kinds of geometric isomers due to a carbon-carbon double bond in the structural formula. All the geometric isomers and mixtures of the isomers at any ratio are also included in the present invention.

In one embodiment of the present invention, preferred are a condensed heterocyclic compound represented by the general formula (1) wherein $R^1$ is (a1) a $(C_1-C_6)$ alkyl group, $R^2$ is (b1) a $(C_3-C_6)$ cycloalkyl group or (b5) a $(C_3-C_6)$ cycloalkyl group having, on the ring, 1 or 2 of the same or different substituting groups selected from (b) a cyano group, (n) a carboxyl group, (o) a $(C_1-C_6)$ alkoxycarbonyl group, (t) a $(C_1-C_6)$ alkoxycarbonyloxy $(C_1-C_6)$ alkyl group, and (w) a $R^5(R^6)N$ carbonyl group (wherein $R^5$ and $R^6$ are as defined above), $R^3$ is (c8) a halo $(C_1-C_6)$ alkyl group, A, $A^2$ and $A^3$ are a nitrogen atom, $A^1$ is N—$R^4$ (wherein $R^4$ represents (d1) a $(C_1-C_6)$ alkyl group, with the exception of the case where both $A^2$ and $A^3$ are a nitrogen atom), m is 0 or 2, and n is 1, or a salt thereof.

The condensed heterocyclic compound of the present invention or a salt thereof can be produced according to, for example, the production method described below, but the present invention is not limited thereto.

Production Method 1

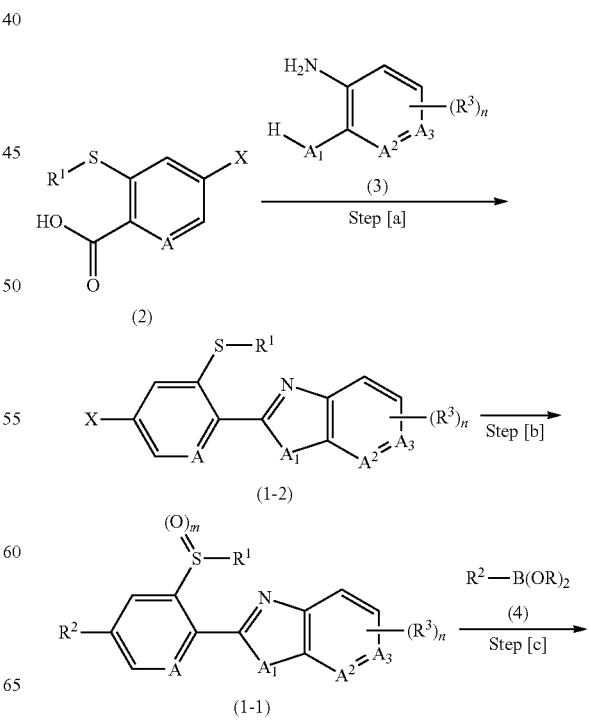

-continued

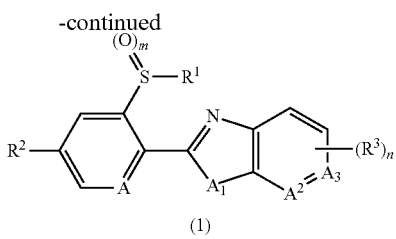

{In the formulae, $R^1$, $R^2$, $R^3$, m, n, A, $A^1$, $A^2$ and $A^3$ are as defined above, X represents a halogen atom and R represents a hydrogen atom, a ($C_1$-$C_3$) alkyl group, or the like.}

Production Method in Step [a]

The condensed heterocyclic compound represented by the general formula (1-2) can be produced by allowing the carboxylic acid represented by the general formula (2) to react with the heterocyclic compound represented by the general formula (3) in the presence of a condensing agent, a base and an inert solvent, and then allowing the resulting intermediate, with or without isolation thereof, to react under acidic conditions.

Examples of the condensing agent used in this reaction include diethyl phosphorocyanidate (DEPC), carbonyldiimidazole (CDI), 1,3-dicyclohexylcarbodiimide (DCC), chlorocarbonic esters and 2-chloro-1-methylpyridinium iodide. The amount of the condensing agent used is appropriately selected from the range of a 1- to 1.5-fold molar amount relative to that of the compound represented by the general formula (2).

Examples of the base used include inorganic bases such as sodium hydroxide, potassium hydroxide, sodium carbonate, potassium carbonate, sodium hydrogen carbonate and potassium hydrogen carbonate; acetates such as sodium acetate and potassium acetate; alkali metal alkoxides such as potassium t-butoxide, sodium methoxide and sodium ethoxide; tertiary amines such as triethylamine, diisopropylethylamine and 1,8-diazabicyclo[5.4.0]undec-7-ene; and nitrogen-containing aromatic compounds such as pyridine and dimethylaminopyridine. The amount of the base used is usually in the range of a 1- to 10-fold molar amount relative to that of the compound represented by the general formula (2).

The inert solvent used in this reaction may be any solvent unless it markedly inhibits the progress of the reaction, and the examples include aromatic hydrocarbons such as benzene, toluene and xylene; halogenated hydrocarbons such as methylene chloride, chloroform and carbon tetrachloride; halogenated aromatic hydrocarbons such as chlorobenzene and dichlorobenzene; straight-chain or cyclic ethers such as diethyl ether, methyl tert-butyl ether, dioxane and tetrahydrofuran; esters such as ethyl acetate; amides such as dimethylformamide and dimethylacetamide; ketones such as acetone and methyl ethyl ketone; and polar solvents such as dimethyl sulfoxide and 1,3-dimethyl-2-imidazolidinone. These inert solvents may be used alone or as a mixture of two or more kinds.

Since this reaction is an equimolar reaction of the reactants, they are basically used in equimolar amounts, but it is possible that any of the reactants is used in an excessive amount. The reaction temperature is in the range of room temperature to the boiling point of the inert solvent used. The reaction time varies with the reaction scale and the reaction temperature, but is basically in the range of a few minutes to 48 hours.

After the reaction is completed, the compound of interest can be produced by allowing the intermediate, with or without isolation thereof from the reaction system, to react in the presence of an acid and an inert solvent.

Examples of the acid used in this reaction include inorganic acids such as hydrochloric acid, sulfuric acid and nitric acid; organic acids such as formic acid, acetic acid, propionic acid, trifluoroacetic acid and benzoic acid; sulfonic acids such as methanesulfonic acid and trifluoromethanesulfonic acid; phosphoric acid; etc. The amount of the acid used is appropriately selected from the range of a 0.01- to 10-fold molar amount relative to that of the condensed heterocyclic compound represented by the general formula (2-2).

The inert solvent used in this reaction may be any solvent unless it markedly inhibits the progress of the reaction, and the examples include aromatic hydrocarbons such as benzene, toluene and xylene; halogenated hydrocarbons such as methylene chloride, chloroform and carbon tetrachloride; halogenated aromatic hydrocarbons such as chlorobenzene and dichlorobenzene; straight-chain or cyclic ethers such as diethyl ether, methyl tert-butyl ether, dioxane and tetrahydrofuran; esters such as ethyl acetate; amides such as dimethylformamide and dimethylacetamide; ketones such as acetone and methyl ethyl ketone; and polar solvents such as dimethyl sulfoxide and 1,3-dimethyl-2-imidazolidinone. These inert solvents may be used alone or as a mixture of two or more kinds.

After the reaction is completed, the compound of interest is isolated from the post-reaction mixture by a usual method. As needed, the compound of interest can be purified by recrystallization, column chromatography, etc.

Production Method in Step [b]

The condensed heterocyclic compound represented by the general formula (1-1) can be produced by allowing the condensed heterocyclic compound represented by the general formula (1-2) to react with an oxidizing agent in an inert solvent.

Examples of the oxidizing agent used in this reaction include peroxides such as a hydrogen peroxide solution, perbenzoic acid and m-chloroperoxybenzoic acid. The amount of the oxidizing agent used is appropriately selected from the range of a 0.8- to 5-fold molar amount relative to that of the condensed heterocyclic compound represented by the general formula (1-2).

The inert solvent that can be used in this reaction may be any solvent unless it markedly inhibits the reaction, and the examples include straight-chain or cyclic ethers such as diethyl ether, tetrahydrofuran and dioxane; aromatic hydrocarbons such as benzene, toluene and xylene; halogenated hydrocarbons such as methylene chloride, chloroform and carbon tetrachloride; halogenated aromatic hydrocarbons such as chlorobenzene and dichlorobenzene; nitriles such as acetonitrile; esters such as ethyl acetate; organic acids such as formic acid and acetic acid; and polar solvents such as N,N-dimethylformamide, N,N-dimethylacetamide, 1,3-dimethyl-2-imidazolidinone and water. These inert solvents may be used alone or as a mixture of two or more kinds.

The reaction temperature in this reaction is appropriately selected from the range of −10° C. to the reflux temperature of the inert solvent used. The reaction time varies with the reaction scale, the reaction temperature and the like and is not the same in every case, but is basically selected as appropriate from the range of a few minutes to 48 hours.

After the reaction is completed, the compound of interest is isolated from the post-reaction mixture by a usual method. As needed, the compound of interest can be purified by recrystallization, column chromatography, etc.

Production Method in Step [c]

The condensed heterocyclic compound represented by the general formula (1) can be produced by a cross coupling reaction of the condensed heterocyclic compound represented by the general formula (1-1) with the boric acid compound represented by the general formula (4) or an equivalent compound (e.g., a cyclopropylcyclic-triolborate sodium salt) in the presence of a metal catalyst, a base and an inert solvent according to the method described in Journal of Synthetic Organic Chemistry, Japan, Vol. 69 No. 7 2011; Chem. Rev. 2011, 4475; or WO 2013/018928.

Examples of the catalyst that can be used in this reaction include commercially available palladium compounds such as zero- and di-valent palladium metals and salts (including complexes) thereof, and such palladium compounds may be supported on activated carbon. Preferable examples of the palladium compounds include palladium(0)-carbon, palladium(II) acetate, palladium(II) chloride, bis(triphenylphosphine)palladium(II) chloride, and tetrakis(triphenylphosphine)palladium(0).

This reaction can also be performed with the addition of a ligand. Examples of the ligand include phosphine ligands such as triphenylphosphine (PPh$_3$), methyldiphenylphosphine (Ph$_2$PCH$_3$), trifurylphosphine (P(2-furyl)$_3$), tri(o-tolyl)phosphine (P(o-tol)$_3$), tri(cyclohexyl)phosphine (PCy$_3$), dicyclohexylphenylphosphine (PhPCy$_2$), tri(t-butyl)phosphine (P$^t$Bu$_3$), 2,2'-bis(diphenylphosphino)-1,1'-binaphthyl (BINAP), diphenylphosphinoferrocene (DPPF), 1,1'-bis(di-t-butylphosphino)ferrocene (D$^t$BPF), N,N-dimethyl-1-[2-(diphenylphosphino)ferrocenyl]ethylamine, 1-[2-(diphenylphosphino)ferrocenyl]ethyl methyl ether, and Xantphos; and phosphine-mimic ligands such as imidazol-2-ylidene carbene (see Angewandte Chemie International Edition in English, vol. 36, 2163 (1997)).

Examples of the base that can be used in this reaction include inorganic bases such as sodium hydroxide, potassium hydroxide, sodium carbonate, potassium carbonate, cesium carbonate, sodium hydrogen carbonate and potassium hydrogen carbonate; alkali metal hydrides such as sodium hydride and potassium hydride; and alkoxides such as sodium methoxide, sodium ethoxide and potassium tert-butoxide. The amount of the base used is usually in the range of an about 1- to 5-fold molar amount relative to that of the compound represented by the general formula (4).

The inert solvent that can be used in this reaction may be any solvent unless it markedly inhibits the reaction, and the examples include alcohols such as methanol, ethanol, propanol, butanol and 2-propanol; straight-chain or cyclic ethers such as diethyl ether, tetrahydrofuran and dioxane; aromatic hydrocarbons such as benzene, toluene and xylene; halogenated hydrocarbons such as methylene chloride, chloroform and carbon tetrachloride; halogenated aromatic hydrocarbons such as chlorobenzene and dichlorobenzene; nitriles such as acetonitrile; esters such as ethyl acetate; and polar solvents such as N,N-dimethylformamide, N,N-dimethylacetamide, dimethyl sulfoxide and 1,3-dimethyl-2-imidazolidinone. These inert solvents may be used alone or as a mixture of two or more kinds.

The reaction temperature in this reaction is usually in the range of about 0° C. to the boiling point of the solvent used. The reaction time varies with the reaction scale, the reaction temperature and the like, but is basically selected as appropriate from the range of a few minutes to 48 hours. The compound represented by the general formula (4) or an equivalent compound is usually used in an about 1- to 5-fold molar amount relative to that of the condensed heterocyclic compound represented by the general formula (1-1). This reaction can be conducted under the atmosphere of an inert gas such as nitrogen gas and argon gas. After the reaction is completed, the compound of interest is isolated from the post-reaction mixture by a usual method. As needed, the compound of interest can be purified by recrystallization, column chromatography, etc.

Production Method 2

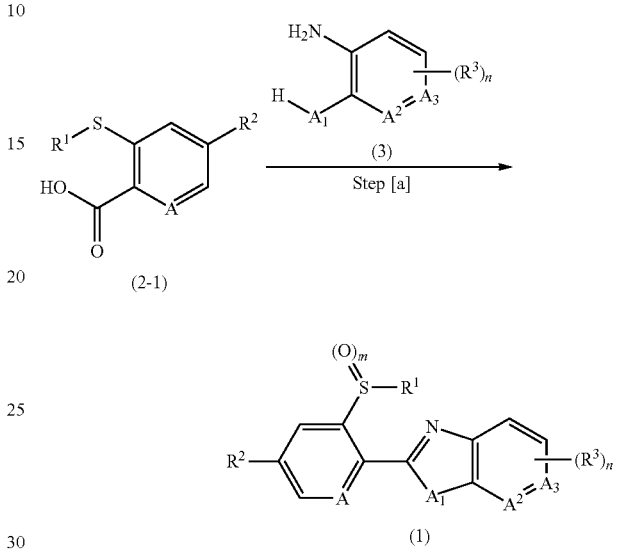

{In the formulae, R$^1$, R$^2$, R$^3$, m, n, A, A$^1$, A$^2$ and A$^3$ are as defined above.}

The condensed heterocyclic compound represented by the general formula (1) can be produced by allowing the carboxylic acid represented by the general formula (2-1) to react with the condensed heterocyclic compound represented by the general formula (3) according to the method described in Step [a] and/or Step [b].

Production Method 3

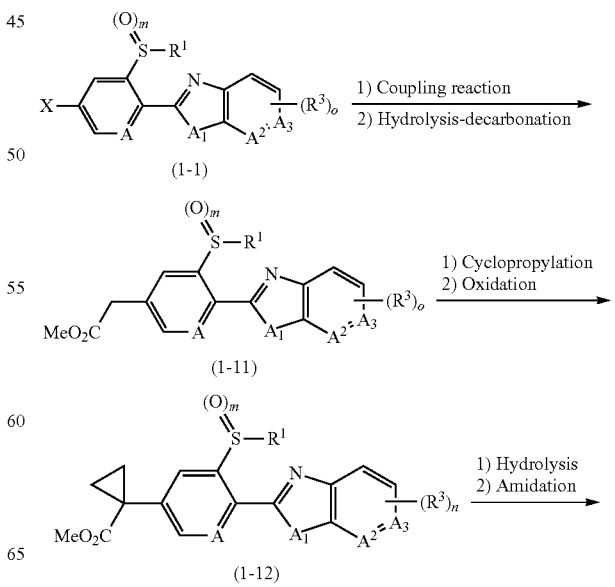

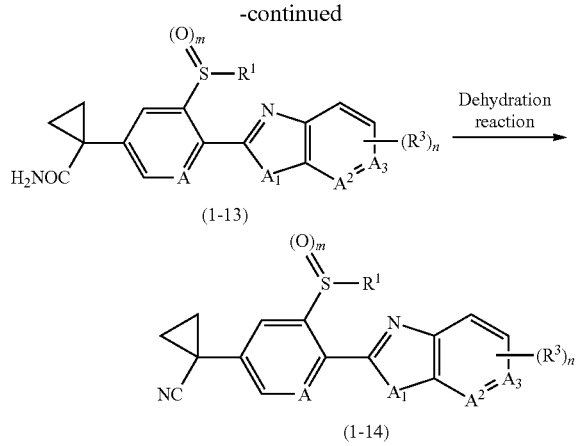

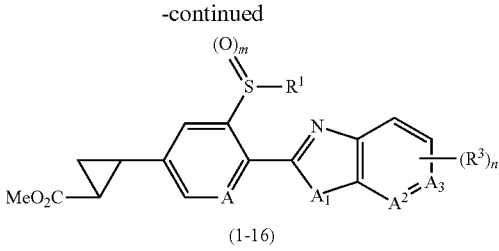

{In the formulae, $R^1$, $R^2$, $R^3$, m, n, A, $A^1$, $A^2$ and $A^3$ are as defined above, and X represents a leaving group such as a halogen atom.}

The condensed heterocyclic compound represented by the general formula (1-15) can be produced from the condensed heterocyclic compound represented by the general formula (1-1) according to the method described in Modern Arylation Methods, 221-269, Wiley-VCH.

The condensed heterocyclic compound represented by the general formula (1-16) can be produced from the condensed heterocyclic compound represented by the general formula (1-15) according to the method described in WO 2011/115065.

The condensed heterocyclic compounds represented by the general formulae (1-12) and (1-16) have a methoxycarbonyl group, and this functional group can be converted into a carboxylic acid and then subjected to Curtius rearrangement to give an amino compound. Alternatively, the methoxycarbonyl group can be reduced with aluminum hydride etc. to give an alcohol compound.

Production Method of Intermediate (2)

{In the formulae, $R^1$, $R^2$, $R^3$, m, n, A, $A^1$, $A^2$ and $A^3$ are as defined above.}

The condensed heterocyclic compound represented by the general formula (1-11) can be produced by allowing a coupling reaction of the condensed heterocyclic compound represented by the general formula (1-1) with a malonic acid ester to proceed in the presence of a metal catalyst and a base in an inert solvent according to the method described in Organic Letters, Vol. 9(17), 3469-3472, 2007, or Angewandte Chemie International Edition, Vol. 54(47), 13975-13979, 2015, and subjecting the product to hydrolysis under acidic conditions followed by decarbonation.

The condensed heterocyclic compound represented by the general formula (1-12) can be produced from the condensed heterocyclic compound represented by the general formula (1-11) according to the method described in WO 2014/113485, or Journal of Medicinal Chemistry, 57(7), 2963-2988; 2014.

The condensed heterocyclic compound represented by the general formula (1-13) can be produced by hydrolyzing the condensed heterocyclic compound represented by the general formula (1-12) by a usual method, allowing the product to react with a chlorinating agent such as thionyl chloride and oxalyl dichloride to give a carboxylic chloride, and allowing the carboxylic chloride to react with ammonia.

The condensed heterocyclic compound represented by the general formula (1-14) can be produced by allowing the condensed heterocyclic compound represented by the general formula (1-13) to react with a chlorinating agent such as phosphorus oxychloride by a usual method.

Production Method 4

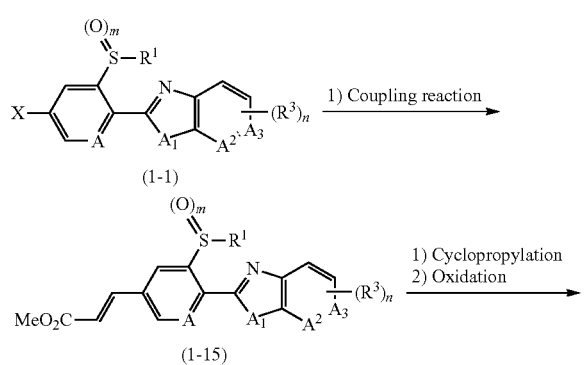

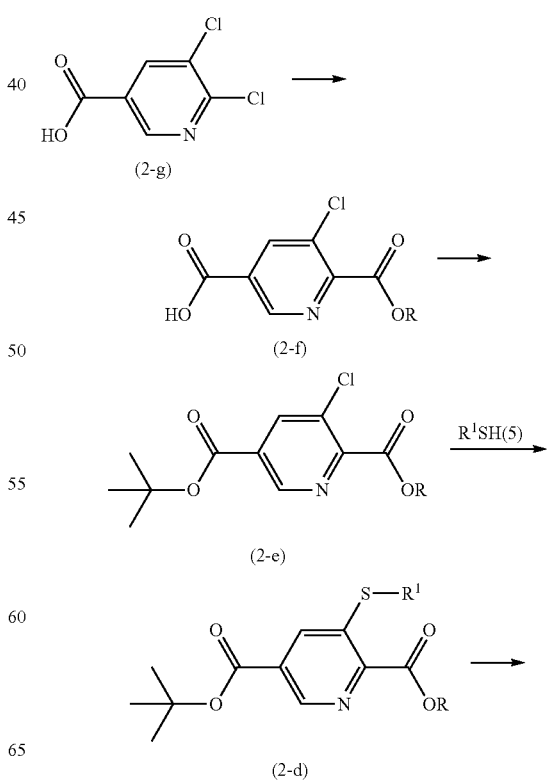

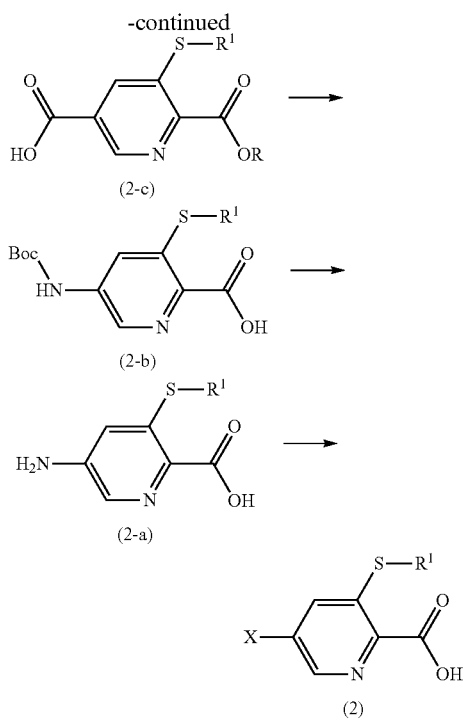

(In the formulae, $R^1$ is as defined above, Boc represents a tert-butoxycarbonyl group, R represents a ($C_1$-$C_3$) alkyl group, and X represents a halogen atom.)

The intermediate represented by the general formula (2) used to produce the compound of the present invention can be produced by the following method.

The commercially available dichloropyridinecarboxylic acid (2-g) can be subjected to introduction of an ester group by Heck reaction or the method described in JP-A 2005-272338 to synthesize the pyridinecarboxylic acid (2-f).

In order to synthesize the pyridinecarboxylic acid ester (2-e), the pyridinecarboxylic acid (2-f) having the introduced ester group can be first chlorinated with a chlorinating agent in an inert solvent to be converted into a pyridinecarboxylic chloride.

Examples of the solvent used in this reaction include ethers such as THF, ethylene glycol dimethyl ether, tert-butyl methyl ether and 1,4-dioxane; aromatic hydrocarbons such as toluene and xylene; halogenated hydrocarbons such as dichloromethane and chloroform; and mixtures thereof. Examples of the chlorinating agent used in this reaction include thionyl chloride and oxalyl dichloride. The chlorinating agent may be usually used in a 1- to 10-fold molar amount relative to a 1 molar amount of the pyridinecarboxylic acid (2-f) having the introduced ester group. The reaction temperature is usually in the range of 0 to 100° C. The reaction time is usually in the range of 0.1 to 24 hours. After completion of the reaction, the solvent and excess of the chlorinating agent is evaporated to give the pyridinecarboxylic chloride.

The pyridinecarboxylic chloride can then be allowed to react with tert-butyl alcohol in the presence of a base and an inert solvent to give the pyridine tert-butyl ester compound represented by the general formula (2-e). Examples of the solvent used in this reaction include ethers such as THF, ethylene glycol dimethyl ether, tert-butyl methyl ether and 1,4-dioxane; aromatic hydrocarbons such as toluene and xylene; halogenated hydrocarbons such as dichloromethane and chloroform; and mixtures thereof. Examples of the base used in the reaction include inorganic bases such as sodium hydroxide, potassium hydroxide, sodium carbonate, potassium carbonate, sodium hydrogen carbonate and potassium hydrogen carbonate; acetates such as sodium acetate and potassium acetate; alkali metal alkoxides such as potassium t-butoxide, sodium methoxide and sodium ethoxide; tertiary amines such as triethylamine, diisopropylethylamine and 1,8-diazabicyclo[5.4.0]undec-7-ene; and nitrogen-containing aromatic compounds such as pyridine and dimethyl aminopyridine. The amount of the base used may be usually in the range of a 1- to 10-fold molar amount relative to that of the pyridinecarboxylic chloride.

The pyridinecarboxylic acid ester (2-d) can be produced by allowing the pyridine tert-butyl ester compound represented by the general formula (2-e) to react with the compound represented by the general formula (5) in the presence of an inert solvent.

Examples of the base used in this reaction include inorganic bases such as sodium hydroxide, potassium hydroxide, sodium carbonate, potassium carbonate, sodium hydrogen carbonate and potassium hydrogen carbonate; acetates such as sodium acetate and potassium acetate; alkali metal alkoxides such as potassium t-butoxide, sodium methoxide and sodium ethoxide; tertiary amines such as triethylamine, diisopropylethylamine and 1,8-diazabicyclo[5.4.0]undec-7-ene; and nitrogen-containing aromatic compounds such as pyridine and dimethyl aminopyridine. The amount of the base used is usually in the range of a 1- to 10-fold molar amount relative to that of the tert-butyl ester compound represented by the general formula (2-e). In cases where an alkali salt of the compound represented by the general formula (5) is used, the base need not to be used.

The inert solvent used in this reaction may be any solvent unless it markedly inhibits the progress of the reaction, and the examples include aromatic hydrocarbons such as benzene, toluene and xylene; halogenated hydrocarbons such as methylene chloride, chloroform and carbon tetrachloride; halogenated aromatic hydrocarbons such as chlorobenzene and dichlorobenzene; straight-chain or cyclic ethers such as diethyl ether, methyl tert-butyl ether, dioxane and tetrahydrofuran; esters such as ethyl acetate; amides such as dimethylformamide and dimethylacetamide; ketones such as acetone and methyl ethyl ketone; and polar solvents such as dimethyl sulfoxide and 1,3-dimethyl-2-imidazolidinone. These inert solvents may be used alone or as a mixture of two or more kinds.

Since this reaction is an equimolar reaction of the reactants, the compound represented by the general formula (5) and the pyridine tert-butyl ester compound represented by the general formula (2-e) are basically used in equimolar amounts, but it is possible that any of the reactants is used in an excessive amount. The reaction temperature is in the range of −10° C. to the boiling point of the inert solvent used. The reaction time varies with the reaction scale and the reaction temperature, but is basically in the range of a few minutes to 48 hours. After the reaction is completed, the compound of interest is isolated from the post-reaction mixture by a usual method. As needed, the compound of interest can be purified by recrystallization, column chromatography, etc.

The pyridinecarboxylic acid (2-c) can be produced by allowing the reaction of the pyridine tert-butyl ester compound represented by the general formula (2-d) to proceed in the presence of an acid and/or an inert solvent.

Examples of the acid used in this reaction include inorganic acids such as hydrochloric acid, sulfuric acid and nitric acid; organic acids such as formic acid, acetic acid, propionic acid, trifluoroacetic acid and benzoic acid; sulfonic acids such as methanesulfonic acid and trifluoromethanesulfonic acid; etc. The amount of the acid used is appropriately selected from the range of a 1- to 10-fold molar amount relative to that of the tert-butyl ester compound represented by the general formula (2-d). In some cases, the acid can be used as a solvent.

The inert solvent used in this reaction may be any solvent unless it markedly inhibits the progress of the reaction, and the examples include aromatic hydrocarbons such as benzene, toluene and xylene; halogenated hydrocarbons such as methylene chloride, chloroform and carbon tetrachloride; halogenated aromatic hydrocarbons such as chlorobenzene and dichlorobenzene; straight-chain or cyclic ethers such as diethyl ether, methyl tert-butyl ether, dioxane and tetrahydrofuran; esters such as ethyl acetate; amides such as dimethylformamide and dimethylacetamide; ketones such as acetone and methyl ethyl ketone; and polar solvents such as dimethyl sulfoxide and 1,3-dimethyl-2-imidazolidinone. These inert solvents may be used alone or as a mixture of two or more kinds. In cases where the acid is used as a solvent, the inert solvent need not to be used.

The reaction temperature is in the range of room temperature to the boiling point of the inert solvent used. The reaction time varies with the reaction scale and the reaction temperature, but is basically in the range of a few minutes to 48 hours.

After the reaction is completed, the compound of interest is isolated from the post-reaction mixture by a usual method. As needed, the compound of interest can be purified by recrystallization, column chromatography, etc.

The pyridinecarboxylic acid (2-b) can be produced by allowing the pyridinecarboxylic acid represented by the general formula (2-c) to react with DPPA (diphenylphosphoryl azide) in the presence of tert-butyl alcohol according to the method described in J. A. Chem. Soc. 1972, 94, 6203-6205.

The aminopyridinecarboxylic acid (2-a) can be produced by allowing the reaction of the pyridinecarboxylic acid compound represented by the general formula (2-b) to proceed in the presence of an acid and an inert solvent.

Examples of the acid used in this reaction include inorganic acids such as hydrochloric acid, sulfuric acid and nitric acid; organic acids such as formic acid, acetic acid, propionic acid, trifluoroacetic acid and benzoic acid; sulfonic acids such as methanesulfonic acid and trifluoromethanesulfonic acid; etc. The amount of the acid used is appropriately selected from the range of a 1- to 10-fold molar amount relative to that of the tert-butyl ester compound represented by the general formula (2-d). In some cases, the acid can be used as a solvent.

The inert solvent used in this reaction may be any solvent unless it markedly inhibits the progress of the reaction, and the examples include aromatic hydrocarbons such as benzene, toluene and xylene; halogenated hydrocarbons such as methylene chloride, chloroform and carbon tetrachloride; halogenated aromatic hydrocarbons such as chlorobenzene and dichlorobenzene; straight-chain or cyclic ethers such as diethyl ether, methyl tert-butyl ether, dioxane and tetrahydrofuran; esters such as ethyl acetate; amides such as dimethylformamide and dimethylacetamide; ketones such as acetone and methyl ethyl ketone; and polar solvents such as dimethyl sulfoxide and 1,3-dimethyl-2-imidazolidinone. These inert solvents may be used alone or as a mixture of two or more kinds.

The reaction temperature is in the range of −10° C. to the boiling point of the inert solvent used. The reaction time varies with the reaction scale and the reaction temperature, but is basically in the range of a few minutes to 48 hours.

After the reaction is completed, the compound of interest is isolated from the post-reaction mixture by a usual method. As needed, the compound of interest can be purified by recrystallization, column chromatography, etc.

The halopyridinecarboxylic acid (2) can be produced from the aminopyridinecarboxylic acid compound represented by the general formula (2-a) by the so-called Sandmeyer reaction or according to the method described in Chem. Rev. 1988, 88, 765.

Production Method of Intermediate (2-1)

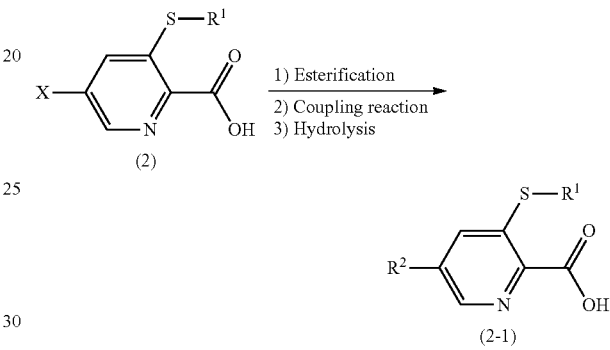

The halopyridinecarboxylic acid ester compound (2-1) can be produced by converting the pyridinecarboxylic acid compound represented by the general formula (2) into an ester compound by a usual method, allowing a coupling reaction to proceed according to the method described in Step [c] above, and subjecting the product to hydrolysis by a usual method.

Production Method of Intermediate (3)

The intermediate compound represented by the general formula (3) for the production is a known compound and can be produced by the method described in WO 2012/086848 or WO 2014/142135.

Next, specific examples of the compound of the present invention are shown below. In the following tables, Me stands for a methyl group, Et stands for an ethyl group, i-Pr stands for an isopropyl group, c-Pr stands for a cyclopropyl group, t-Bu stands for a tert-butyl group, c-Bu stands for a cyclobutyl group and c-Pent stands for a cyclopentyl group. Ac stands for an acetyl group. The physical property refers to a melting point (° C.) or NMR.

The data are separately listed in the table below.

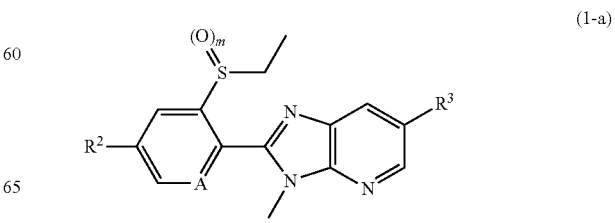

TABLE 1

| Compound No. | $R^2$ | $R^3$ | A | m | Physical Property |
|---|---|---|---|---|---|
| 1-1 | c-Pr | $SCF_3$ | CH | 0 | |
| 1-2 | c-Pr | $SCF_3$ | CH | 1 | |
| 1-3 | c-Pr | $SCF_3$ | CH | 2 | |
| 1-4 | c-Pr | $CF_3$ | CH | 0 | |
| 1-5 | c-Pr | $CF_3$ | CH | 1 | |
| 1-6 | c-Pr | $CF_3$ | CH | 2 | |
| 1-7 | c-Pr | $CF_2CF_3$ | CH | 0 | |
| 1-8 | c-Pr | $CF_2CF_3$ | CH | 1 | |
| 1-9 | c-Pr | $CF_2CF_3$ | CH | 2 | |
| 1-10 | c-Pr | $SCF_3$ | N | 0 | |
| 1-11 | c-Pr | $SCF_3$ | N | 1 | |
| 1-12 | c-Pr | $SCF_3$ | N | 2 | |
| 1-13 | c-Pr | $CF_3$ | N | 0 | |
| 1-14 | c-Pr | $CF_3$ | N | 1 | |
| 1-15 | c-Pr | $CF_3$ | N | 2 | NMR |
| 1-16 | c-Pr | $CF_2CF_3$ | N | 0 | NMR |
| 1-17 | c-Pr | $CF_2CF_3$ | N | 1 | |
| 1-18 | c-Pr | $CF_2CF_3$ | N | 2 | NMR |
| 1-19 | SMe | $SCF_3$ | CH | 0 | |
| 1-20 | SMe | $SCF_3$ | CH | 1 | |
| 1-21 | SMe | $SCF_3$ | CH | 2 | |
| 1-22 | SMe | $CF_3$ | CH | 0 | |
| 1-23 | SMe | $CF_3$ | CH | 1 | |
| 1-24 | SMe | $CF_3$ | CH | 2 | |
| 1-25 | SMe | $CF_2CF_3$ | CH | 0 | |
| 1-26 | SMe | $CF_2CF_3$ | CH | 1 | |
| 1-27 | SMe | $CF_2CF_3$ | CH | 2 | |
| 1-28 | SMe | $SCF_3$ | N | 0 | |
| 1-29 | SMe | $SCF_3$ | N | 1 | |
| 1-30 | SMe | $SCF_3$ | N | 2 | |
| 1-31 | SMe | $CF_3$ | N | 0 | |
| 1-32 | SMe | $CF_3$ | N | 1 | |
| 1-33 | SMe | $CF_3$ | N | 2 | |
| 1-34 | SMe | $CF_2CF_3$ | N | 0 | |
| 1-35 | SMe | $CF_2CF_3$ | N | 1 | |
| 1-36 | SMe | $CF_2CF_3$ | N | 2 | |
| 1-37 | c-Bu | $SCF_3$ | N | 0 | |
| 1-38 | c-Bu | $SCF_3$ | N | 1 | |
| 1-39 | c-Bu | $SCF_3$ | N | 2 | |
| 1-40 | c-Bu | $CF_3$ | N | 0 | |
| 1-41 | c-Bu | $CF_3$ | N | 1 | |
| 1-42 | c-Bu | $CF_3$ | N | 2 | |
| 1-43 | c-Pen | $SCF_3$ | N | 0 | |
| 1-44 | c-Pen | $SCF_3$ | N | 1 | |
| 1-45 | c-Pen | $SCF_3$ | N | 2 | |
| 1-46 | c-Pen | $CF_3$ | N | 0 | |
| 1-47 | c-Pen | $CF_3$ | N | 1 | |
| 1-48 | c-Pen | $CF_3$ | N | 2 | |

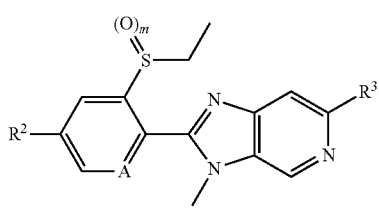

(1-b)

TABLE 2

| Compound No. | $R^2$ | $R^3$ | A | m | Physical Property |
|---|---|---|---|---|---|
| 2-1 | c-Pr | $SCF_3$ | CH | 0 | |
| 2-2 | c-Pr | $SCF_3$ | CH | 1 | |
| 2-3 | c-Pr | $SCF_3$ | CH | 2 | |
| 2-4 | c-Pr | $CF_3$ | CH | 0 | |
| 2-5 | c-Pr | $CF_3$ | CH | 1 | |
| 2-6 | c-Pr | $CF_3$ | CH | 2 | |
| 2-7 | c-Pr | $CF_2CF_3$ | CH | 0 | |
| 2-8 | c-Pr | $CF_2CF_3$ | CH | 1 | |
| 2-9 | c-Pr | $CF_2CF_3$ | CH | 2 | |
| 2-10 | c-Pr | $SCF_3$ | N | 0 | |
| 2-11 | c-Pr | $SCF_3$ | N | 1 | |
| 2-12 | c-Pr | $SCF_3$ | N | 2 | |
| 2-13 | c-Pr | $CF_3$ | N | 0 | |
| 2-14 | c-Pr | $CF_3$ | N | 1 | |
| 2-15 | c-Pr | $CF_3$ | N | 2 | 169-173 |
| 2-16 | c-Pr | $CF_2CF_3$ | N | 0 | |
| 2-17 | c-Pr | $CF_2CF_3$ | N | 1 | |
| 2-18 | c-Pr | $CF_2CF_3$ | N | 2 | |
| 2-19 | SMe | $SCF_3$ | CH | 0 | |
| 2-20 | SMe | $SCF_3$ | CH | 1 | |
| 2-21 | SMe | $SCF_3$ | CH | 2 | |
| 2-22 | SMe | $CF_3$ | CH | 0 | |
| 2-23 | SMe | $CF_3$ | CH | 1 | |
| 2-24 | SMe | $CF_3$ | CH | 2 | |
| 2-25 | SMe | $CF_2CF_3$ | CH | 0 | |
| 2-26 | SMe | $CF_2CF_3$ | CH | 1 | |
| 2-27 | SMe | $CF_2CF_3$ | CH | 2 | |
| 2-28 | SMe | $SCF_3$ | N | 0 | |
| 2-29 | SMe | $SCF_3$ | N | 1 | |
| 2-30 | SMe | $SCF_3$ | N | 2 | |
| 2-31 | SMe | $CF_3$ | N | 0 | |
| 2-32 | SMe | $CF_3$ | N | 1 | |
| 2-33 | SMe | $CF_3$ | N | 2 | |
| 2-34 | SMe | $CF_2CF_3$ | N | 0 | |
| 2-35 | SMe | $CF_2CF_3$ | N | 1 | |
| 2-36 | SMe | $CF_2CF_3$ | N | 2 | |
| 2-37 | c-Bu | $SCF_3$ | N | 0 | |
| 2-38 | c-Bu | $SCF_3$ | N | 1 | |
| 2-39 | c-Bu | $SCF_3$ | N | 2 | |
| 2-40 | c-Bu | $CF_3$ | N | 0 | |
| 2-41 | c-Bu | $CF_3$ | N | 1 | |
| 2-42 | c-Bu | $CF_3$ | N | 2 | |
| 2-43 | c-Pen | $SCF_3$ | N | 0 | |
| 2-44 | c-Pen | $SCF_3$ | N | 1 | |
| 2-45 | c-Pen | $SCF_3$ | N | 2 | |
| 2-46 | c-Pen | $CF_3$ | N | 0 | |
| 2-47 | c-Pen | $CF_3$ | N | 1 | |
| 2-48 | c-Pen | $CF_3$ | N | 2 | |

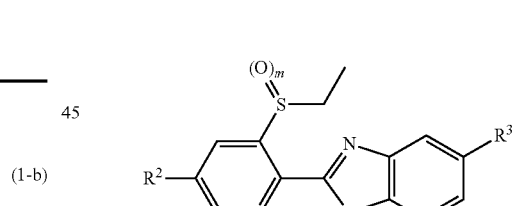

(1-c)

TABLE 3

| Compound No. | $R^2$ | $R^3$ | A | m | Physical Property |
|---|---|---|---|---|---|
| 3-1 | c-Pr | $SCF_3$ | CH | 0 | |
| 3-2 | c-Pr | $SCF_3$ | CH | 1 | |
| 3-3 | c-Pr | $SCF_3$ | CH | 2 | |
| 3-4 | c-Pr | $CF_3$ | CH | 0 | |
| 3-5 | c-Pr | $CF_3$ | CH | 1 | |
| 3-6 | c-Pr | $CF_3$ | CH | 2 | |
| 3-7 | c-Pr | $CF_2CF_3$ | CH | 0 | |
| 3-8 | c-Pr | $CF_2CF_3$ | CH | 1 | |
| 3-9 | c-Pr | $CF_2CF_3$ | CH | 2 | |
| 3-10 | c-Pr | $SCF_3$ | N | 0 | |
| 3-11 | c-Pr | $SCF_3$ | N | 1 | |
| 3-12 | c-Pr | $SCF_3$ | N | 2 | |
| 3-13 | c-Pr | $CF_3$ | N | 0 | NMR |

TABLE 3-continued

| Compound No. | R² | R³ | A | m | Physical Property |
|---|---|---|---|---|---|
| 3-14 | c-Pr | CF₃ | N | 1 | |
| 3-15 | c-Pr | CF₃ | N | 2 | 140-141 |
| 3-16 | c-Pr | CF₂CF₃ | N | 0 | |
| 3-17 | c-Pr | CF₂CF₃ | N | 1 | |
| 3-18 | c-Pr | CF₂CF₃ | N | 2 | |
| 3-19 | SMe | SCF₃ | CH | 0 | |
| 3-20 | SMe | SCF₃ | CH | 1 | |
| 3-21 | SMe | SCF₃ | CH | 2 | |
| 3-22 | SMe | CF₃ | CH | 0 | |
| 3-23 | SMe | CF₃ | CH | 1 | |
| 3-24 | SMe | CF₃ | CH | 2 | |
| 3-25 | SMe | CF₂CF₃ | CH | 0 | |
| 3-26 | SMe | CF₂CF₃ | CH | 1 | |
| 3-27 | SMe | CF₂CF₃ | CH | 2 | |
| 3-28 | SMe | SCF₃ | N | 0 | |
| 3-29 | SMe | SCF₃ | N | 1 | |
| 3-30 | SMe | SCF₃ | N | 2 | |
| 3-31 | SMe | CF₃ | N | 0 | |
| 3-32 | SMe | CF₃ | N | 1 | |
| 3-33 | SMe | CF₃ | N | 2 | |
| 3-34 | SMe | CF₂CF₃ | N | 0 | |
| 3-35 | SMe | CF₂CF₃ | N | 1 | |
| 3-36 | SMe | CF₂CF₃ | N | 2 | |
| 3-37 | c-Bu | SCF₃ | N | 0 | |
| 3-38 | c-Bu | SCF₃ | N | 1 | |
| 3-39 | c-Bu | SCF₃ | N | 2 | |
| 3-40 | c-Bu | CF₃ | N | 0 | |
| 3-41 | c-Bu | CF₃ | N | 1 | |
| 3-42 | c-Bu | CF₃ | N | 2 | |
| 3-43 | c-Pen | SCF₃ | N | 0 | |
| 3-44 | c-Pen | SCF₃ | N | 1 | |
| 3-45 | c-Pen | SCF₃ | N | 2 | |
| 3-46 | c-Pen | CF₃ | N | 0 | |
| 3-47 | c-Pen | CF₃ | N | 1 | |
| 3-48 | c-Pen | CF₃ | N | 2 | |

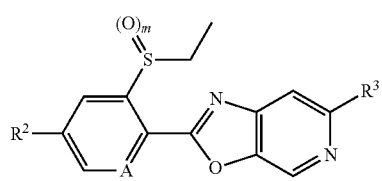

(1-d)

TABLE 4

| Compound No. | R² | R³ | A | m | Physical Property |
|---|---|---|---|---|---|
| 4-1 | c-Pr | SCF₃ | CH | 0 | |
| 4-2 | c-Pr | SCF₃ | CH | 1 | |
| 4-3 | c-Pr | SCF₃ | CH | 2 | |
| 4-4 | c-Pr | CF₃ | CH | 0 | |
| 4-5 | c-Pr | CF₃ | CH | 1 | |
| 4-6 | c-Pr | CF₃ | CH | 2 | |
| 4-7 | c-Pr | CF₂CF₃ | CH | 0 | |
| 4-8 | c-Pr | CF₂CF₃ | CH | 1 | |
| 4-9 | c-Pr | CF₂CF₃ | CH | 2 | |
| 4-10 | c-Pr | SCF₃ | N | 0 | |
| 4-11 | c-Pr | SCF₃ | N | 1 | |
| 4-12 | c-Pr | SCF₃ | N | 2 | |
| 4-13 | c-Pr | CF₃ | N | 0 | |
| 4-14 | c-Pr | CF₃ | N | 1 | |
| 4-15 | c-Pr | CF₃ | N | 2 | |
| 4-16 | c-Pr | CF₂CF₃ | N | 0 | |
| 4-17 | c-Pr | CF₂CF₃ | N | 1 | |
| 4-18 | c-Pr | CF₂CF₃ | N | 2 | |
| 4-19 | SMe | SCF₃ | CH | 0 | |
| 4-20 | SMe | SCF₃ | CH | 1 | |

TABLE 4-continued

| Compound No. | R² | R³ | A | m | Physical Property |
|---|---|---|---|---|---|
| 4-21 | SMe | SCF₃ | CH | 2 | |
| 4-22 | SMe | CF₃ | CH | 0 | |
| 4-23 | SMe | CF₃ | CH | 1 | |
| 4-24 | SMe | CF₃ | CH | 2 | |
| 4-25 | SMe | CF₂CF₃ | CH | 0 | |
| 4-26 | SMe | CF₂CF₃ | CH | 1 | |
| 4-27 | SMe | CF₂CF₃ | CH | 2 | |
| 4-28 | SMe | SCF₃ | N | 0 | |
| 4-29 | SMe | SCF₃ | N | 1 | |
| 4-30 | SMe | SCF₃ | N | 2 | |
| 4-31 | SMe | CF₃ | N | 0 | |
| 4-32 | SMe | CF₃ | N | 1 | |
| 4-33 | SMe | CF₃ | N | 2 | |
| 4-34 | SMe | CF₂CF₃ | N | 0 | |
| 4-35 | SMe | CF₂CF₃ | N | 1 | |
| 4-36 | SMe | CF₂CF₃ | N | 2 | |
| 4-37 | c-Bu | SCF₃ | N | 0 | |
| 4-38 | c-Bu | SCF₃ | N | 1 | |
| 4-39 | c-Bu | SCF₃ | N | 2 | |
| 4-40 | c-Bu | CF₃ | N | 0 | |
| 4-41 | c-Bu | CF₃ | N | 1 | |
| 4-42 | c-Bu | CF₃ | N | 2 | |
| 4-43 | c-Pen | SCF₃ | N | 0 | |
| 4-44 | c-Pen | SCF₃ | N | 1 | |
| 4-45 | c-Pen | SCF₃ | N | 2 | |
| 4-46 | c-Pen | CF₃ | N | 0 | |
| 4-47 | c-Pen | CF₃ | N | 1 | |
| 4-48 | c-Pen | CF₃ | N | 2 | |

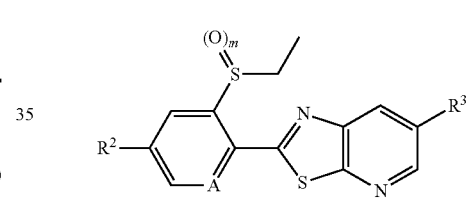

(1-e)

TABLE 5

| Compound No. | R² | R³ | A | m | Physical Property |
|---|---|---|---|---|---|
| 5-1 | c-Pr | SCF₃ | CH | 0 | |
| 5-2 | c-Pr | SCF₃ | CH | 1 | |
| 5-3 | c-Pr | SCF₃ | CH | 2 | |
| 5-4 | c-Pr | CF₃ | CH | 0 | |
| 5-5 | c-Pr | CF₃ | CH | 1 | |
| 5-6 | c-Pr | CF₃ | CH | 2 | |
| 5-7 | c-Pr | CF₂CF₃ | CH | 0 | |
| 5-8 | c-Pr | CF₂CF₃ | CH | 1 | |
| 5-9 | c-Pr | CF₂CF₃ | CH | 2 | |
| 5-10 | c-Pr | SCF₃ | N | 0 | |
| 5-11 | c-Pr | SCF₃ | N | 1 | |
| 5-12 | c-Pr | SCF₃ | N | 2 | |
| 5-13 | c-Pr | CF₃ | N | 0 | 177-178 |
| 5-14 | c-Pr | CF₃ | N | 1 | |
| 5-15 | c-Pr | CF₃ | N | 2 | 140-141 |
| 5-16 | c-Pr | CF₂CF₃ | N | 0 | |
| 5-17 | c-Pr | CF₂CF₃ | N | 1 | |
| 5-18 | c-Pr | CF₂CF₃ | N | 2 | |
| 5-19 | SMe | SCF₃ | CH | 0 | |
| 5-20 | SMe | SCF₃ | CH | 1 | |
| 5-21 | SMe | SCF₃ | CH | 2 | |
| 5-22 | SMe | CF₃ | CH | 0 | |
| 5-23 | SMe | CF₃ | CH | 1 | |
| 5-24 | SMe | CF₃ | CH | 2 | |
| 5-25 | SMe | CF₂CF₃ | CH | 0 | |
| 5-26 | SMe | CF₂CF₃ | CH | 1 | |
| 5-27 | SMe | CF₂CF₃ | CH | 2 | |

TABLE 5-continued

| Compound No. | R² | R³ | A | m | Physical Property |
|---|---|---|---|---|---|
| 5-28 | SMe | SCF₃ | N | 0 | |
| 5-29 | SMe | SCF₃ | N | 1 | |
| 5-30 | SMe | SCF₃ | N | 2 | |
| 5-31 | SMe | CF₃ | N | 0 | |
| 5-32 | SMe | CF₃ | N | 1 | |
| 5-33 | SMe | CF₃ | N | 2 | |
| 5-34 | SMe | CF₂CF₃ | N | 0 | |
| 5-35 | SMe | CF₂CF₃ | N | 1 | |
| 5-36 | SMe | CF₂CF₃ | N | 2 | |
| 5-37 | c-Bu | SCF₃ | N | 0 | |
| 5-38 | c-Bu | SCF₃ | N | 1 | |
| 5-39 | c-Bu | SCF₃ | N | 2 | |
| 5-40 | c-Bu | CF₃ | N | 0 | |
| 5-41 | c-Bu | CF₃ | N | 1 | |
| 5-42 | c-Bu | CF₃ | N | 2 | |
| 5-43 | c-Pen | SCF₃ | N | 0 | |
| 5-44 | c-Pen | SCF₃ | N | 1 | |
| 5-45 | c-Pen | SCF₃ | N | 2 | |
| 5-46 | c-Pen | CF₃ | N | 0 | |
| 5-47 | c-Pen | CF₃ | N | 1 | |
| 5-48 | c-Pen | CF₃ | N | 2 | |

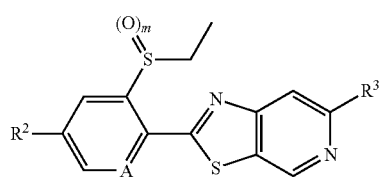

(1-f)

TABLE 6

| Compound No. | R² | R³ | A | m | Physical Property |
|---|---|---|---|---|---|
| 6-1 | c-Pr | SCF₃ | CH | 0 | |
| 6-2 | c-Pr | SCF₃ | CH | 1 | |
| 6-3 | c-Pr | SCF₃ | CH | 2 | |
| 6-4 | c-Pr | CF₃ | CH | 0 | |
| 6-5 | c-Pr | CF₃ | CH | 1 | |
| 6-6 | c-Pr | CF₃ | CH | 2 | |
| 6-7 | c-Pr | CF₂CF₃ | CH | 0 | |
| 6-8 | c-Pr | CF₂CF₃ | CH | 1 | |
| 6-9 | c-Pr | CF₂CF₃ | CH | 2 | |
| 6-10 | c-Pr | SCF₃ | N | 0 | |
| 6-11 | c-Pr | SCF₃ | N | 1 | |
| 6-12 | c-Pr | SCF₃ | N | 2 | |
| 6-13 | c-Pr | CF₃ | N | 0 | |
| 6-14 | c-Pr | CF₃ | N | 1 | |
| 6-15 | c-Pr | CF₃ | N | 2 | |
| 6-16 | c-Pr | CF₂CF₃ | N | 0 | |
| 6-17 | c-Pr | CF₂CF₃ | N | 1 | |
| 6-18 | c-Pr | CF₂CF₃ | N | 2 | |
| 6-19 | SMe | SCF₃ | CH | 0 | |
| 6-20 | SMe | SCF₃ | CH | 1 | |
| 6-21 | SMe | SCF₃ | CH | 2 | |
| 6-22 | SMe | CF₃ | CH | 0 | |
| 6-23 | SMe | CF₃ | CH | 1 | |
| 6-24 | SMe | CF₃ | CH | 2 | |
| 6-25 | SMe | CF₂CF₃ | CH | 0 | |
| 6-26 | SMe | CF₂CF₃ | CH | 1 | |
| 6-27 | SMe | CF₂CF₃ | CH | 2 | |
| 6-28 | SMe | SCF₃ | N | 0 | |
| 6-29 | SMe | SCF₃ | N | 1 | |
| 6-30 | SMe | SCF₃ | N | 2 | |
| 6-31 | SMe | CF₃ | N | 0 | |
| 6-32 | SMe | CF₃ | N | 1 | |
| 6-33 | SMe | CF₃ | N | 2 | |
| 6-34 | SMe | CF₂CF₃ | N | 0 | |

TABLE 6-continued

| Compound No. | R² | R³ | A | m | Physical Property |
|---|---|---|---|---|---|
| 6-35 | SMe | CF₂CF₃ | N | 1 | |
| 6-36 | SMe | CF₂CF₃ | N | 2 | |
| 6-37 | c-Bu | SCF₃ | N | 0 | |
| 6-38 | c-Bu | SCF₃ | N | 1 | |
| 6-39 | c-Bu | SCF₃ | N | 2 | |
| 6-40 | c-Bu | CF₃ | N | 0 | |
| 6-41 | c-Bu | CF₃ | N | 1 | |
| 6-42 | c-Bu | CF₃ | N | 2 | |
| 6-43 | c-Pen | SCF₃ | N | 0 | |
| 6-44 | c-Pen | SCF₃ | N | 1 | |
| 6-45 | c-Pen | SCF₃ | N | 2 | |
| 6-46 | c-Pen | CF₃ | N | 0 | |
| 6-47 | c-Pen | CF₃ | N | 1 | |
| 6-48 | c-Pen | CF₃ | N | 2 | |

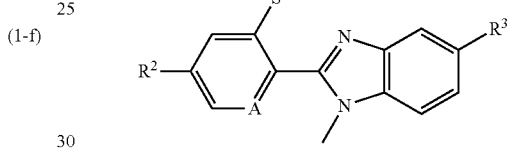

(1-g)

TABLE 7

| Compound No. | R² | R³ | A | m | Physical Property |
|---|---|---|---|---|---|
| 7-1 | c-Pr | SCF₃ | CH | 0 | |
| 7-2 | c-Pr | SCF₃ | CH | 1 | |
| 7-3 | c-Pr | SCF₃ | CH | 2 | |
| 7-4 | c-Pr | CF₃ | CH | 0 | |
| 7-5 | c-Pr | CF₃ | CH | 1 | |
| 7-6 | c-Pr | CF₃ | CH | 2 | |
| 7-7 | c-Pr | CF₂CF₃ | CH | 0 | |
| 7-8 | c-Pr | CF₂CF₃ | CH | 1 | |
| 7-9 | c-Pr | CF₂CF₃ | CH | 2 | |
| 7-10 | c-Pr | SCF₃ | N | 0 | |
| 7-11 | c-Pr | SCF₃ | N | 1 | |
| 7-12 | c-Pr | SCF₃ | N | 2 | |
| 7-13 | c-Pr | CF₃ | N | 0 | NMR |
| 7-14 | c-Pr | CF₃ | N | 1 | 192-193 |
| 7-15 | c-Pr | CF₃ | N | 2 | 88-90 |
| 7-16 | c-Pr | CF₂CF₃ | N | 0 | |
| 7-17 | c-Pr | CF₂CF₃ | N | 1 | |
| 7-18 | c-Pr | CF₂CF₃ | N | 2 | |
| 7-19 | SMe | SCF₃ | CH | 0 | |
| 7-20 | SMe | SCF₃ | CH | 1 | |
| 7-21 | SMe | SCF₃ | CH | 2 | |
| 7-22 | SMe | CF₃ | CH | 0 | |
| 7-23 | SMe | CF₃ | CH | 1 | |
| 7-24 | SMe | CF₃ | CH | 2 | |
| 7-25 | SMe | CF₂CF₃ | CH | 0 | |
| 7-26 | SMe | CF₂CF₃ | CH | 1 | |
| 7-27 | SMe | CF₂CF₃ | CH | 2 | |
| 7-28 | SMe | SCF₃ | N | 0 | |
| 7-29 | SMe | SCF₃ | N | 1 | |
| 7-30 | SMe | SCF₃ | N | 2 | |
| 7-31 | SMe | CF₃ | N | 0 | |
| 7-32 | SMe | CF₃ | N | 1 | |
| 7-33 | SMe | CF₃ | N | 2 | |
| 7-34 | SMe | CF₂CF₃ | N | 0 | |
| 7-35 | SMe | CF₂CF₃ | N | 1 | |
| 7-36 | SMe | CF₂CF₃ | N | 2 | |

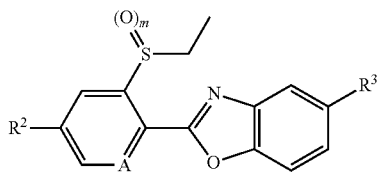

(1-h)

TABLE 8

| Compound No. | R² | R³ | A | m | Physical Property |
|---|---|---|---|---|---|
| 8-1 | c-Pr | SCF₃ | CH | 0 | |
| 8-2 | c-Pr | SCF₃ | CH | 1 | |
| 8-3 | c-Pr | SCF₃ | CH | 2 | |
| 8-4 | c-Pr | CF₃ | CH | 0 | |
| 8-5 | c-Pr | CF₃ | CH | 1 | |
| 8-6 | c-Pr | CF₃ | CH | 2 | |
| 8-7 | c-Pr | CF₂CF₃ | CH | 0 | |
| 8-8 | c-Pr | CF₂CF₃ | CH | 1 | |
| 8-9 | c-Pr | CF₂CF₃ | CH | 2 | |
| 8-10 | c-Pr | SCF₃ | N | 0 | 128.6-133.6 |
| 8-11 | c-Pr | SCF₃ | N | 1 | |
| 8-12 | c-Pr | SCF₃ | N | 2 | 118.4-121.4 |
| 8-13 | c-Pr | CF₃ | N | 0 | |
| 8-14 | c-Pr | CF₃ | N | 1 | |
| 8-15 | c-Pr | CF₃ | N | 2 | NMR |
| 8-16 | c-Pr | CF₂CF₃ | N | 0 | 135.7-137.0 |
| 8-17 | c-Pr | CF₂CF₃ | N | 1 | |
| 8-18 | c-Pr | CF₂CF₃ | N | 2 | 131.4-132.6 |
| 8-19 | SMe | SCF₃ | CH | 0 | |
| 8-20 | SMe | SCF₃ | CH | 1 | |
| 8-21 | SMe | SCF₃ | CH | 2 | |
| 8-22 | SMe | CF₃ | CH | 0 | |
| 8-23 | SMe | CF₃ | CH | 1 | |
| 8-24 | SMe | CF₃ | CH | 2 | |
| 8-25 | SMe | CF₂CF₃ | CH | 0 | |
| 8-26 | SMe | CF₂CF₃ | CH | 1 | |
| 8-27 | SMe | CF₂CF₃ | CH | 2 | |
| 8-28 | SMe | SCF₃ | N | 0 | |
| 8-29 | SMe | SCF₃ | N | 1 | |
| 8-30 | SMe | SCF₃ | N | 2 | |
| 8-31 | SMe | CF₃ | N | 0 | |
| 8-32 | SMe | CF₃ | N | 1 | |
| 8-33 | SMe | CF₃ | N | 2 | |
| 8-34 | SMe | CF₂CF₃ | N | 0 | |
| 8-35 | SMe | CF₂CF₃ | N | 1 | |
| 8-36 | SMe | CF₂CF₃ | N | 2 | |
| 8-37 | c-Bu | SCF₃ | N | 0 | |
| 8-38 | c-Bu | SCF₃ | N | 1 | |
| 8-39 | c-Bu | SCF₃ | N | 2 | |
| 8-40 | c-Bu | CF₃ | N | 0 | |
| 8-41 | c-Bu | CF₃ | N | 1 | |
| 8-42 | c-Bu | CF₃ | N | 2 | |
| 8-43 | c-Pen | SCF₃ | N | 0 | |
| 8-44 | c-Pen | SCF₃ | N | 1 | |
| 8-45 | c-Pen | SCF₃ | N | 2 | |
| 8-46 | c-Pen | CF₃ | N | 0 | |
| 8-47 | c-Pen | CF₃ | N | 1 | |
| 8-48 | c-Pen | CF₃ | N | 2 | |

(1-i)

TABLE 9

| Compound No. | R² | R³ | A | m | Physical Property |
|---|---|---|---|---|---|
| 9-1 | c-Pr | SCF₃ | CH | 0 | |
| 9-2 | c-Pr | SCF₃ | CH | 1 | |
| 9-3 | c-Pr | SCF₃ | CH | 2 | |
| 9-4 | c-Pr | CF₃ | CH | 0 | |
| 9-5 | c-Pr | CF₃ | CH | 1 | |
| 9-6 | c-Pr | CF₃ | CH | 2 | |
| 9-7 | c-Pr | CF₂CF₃ | CH | 0 | |
| 9-8 | c-Pr | CF₂CF₃ | CH | 1 | |
| 9-9 | c-Pr | CF₂CF₃ | CH | 2 | |
| 9-10 | c-Pr | SCF₃ | N | 0 | 148-149 |
| 9-11 | c-Pr | SCF₃ | N | 1 | |
| 9-12 | c-Pr | SCF₃ | N | 2 | 198-199 |
| 9-13 | c-Pr | CF₃ | N | 0 | |
| 9-14 | c-Pr | CF₃ | N | 1 | |
| 9-15 | c-Pr | CF₃ | N | 2 | |
| 9-16 | c-Pr | CF₂CF₃ | N | 0 | |
| 9-17 | c-Pr | CF₂CF₃ | N | 1 | |
| 9-18 | c-Pr | CF₂CF₃ | N | 2 | |
| 9-19 | SMe | SCF₃ | CH | 0 | |
| 9-20 | SMe | SCF₃ | CH | 1 | |
| 9-21 | SMe | SCF₃ | CH | 2 | |
| 9-22 | SMe | CF₃ | CH | 0 | |
| 9-23 | SMe | CF₃ | CH | 1 | |
| 9-24 | SMe | CF₃ | CH | 2 | |
| 9-25 | SMe | CF₂CF₃ | CH | 0 | |
| 9-26 | SMe | CF₂CF₃ | CH | 1 | |
| 9-27 | SMe | CF₂CF₃ | CH | 2 | |
| 9-28 | SMe | SCF₃ | N | 0 | |
| 9-29 | SMe | SCF₃ | N | 1 | |
| 9-30 | SMe | SCF₃ | N | 2 | |
| 9-31 | SMe | CF₃ | N | 0 | |

TABLE 9-continued

| | | | | |
|---|---|---|---|---|
| 9-32 | SMe | $CF_3$ | N | 1 |
| 9-33 | SMe | $CF_3$ | N | 2 |
| 9-34 | SMe | $CF_2CF_3$ | N | 0 |
| 9-35 | SMe | $CF_2CF_3$ | N | 1 |
| 9-36 | SMe | $CF_2CF_3$ | N | 2 |

| Compound No. | $^1$H-NMR Data |
|---|---|
| 1-15 | 8.74(d, 2H), 8.28(d, 1H), 8.07(d,1H), 3.85(s, 3H), 3.79(dd, 2H), 2.17-2.09(m, 1H), 1.34(t, 3H), 1.31-1.24(m, 2H), 0.98-0.94(m, 2H) |
| 1-16 | 8.65(d, 1H), 8.35(d, 1H), 8.28(d,1H), 7.40(d, 1H), 4.02(s, 3H), 2.95(dd, 2H), 2.02-1.97(m, 1H), 1.31(t, 3H), 1.18-1.13(m, 2H), 0.92-0.85(m, 2H) |
| 1-18 | 8.74(d, 1H), 8.69(d, 1H), 8.26(d,1H), 8.07(d, 1H), 3.85(s, 3H), 3.80(dd, 2H), 2.17-2.09(m, 1H), 1.35(t, 3H), 1.31-1.25(m, 2H), 0.99-0.94(m, 2H) |
| 3-13 | 8.71-8.72 (d,1H), 8.42-8.43(d,1H), 8.34-8.35 (d,1H), 7.37-7.38 (d,1H), 3.04-3.06(q,2H), 1.98-2.05 (m,1H), 1.44-1.47 (t,3H), 1.18-1.21 (m.2H), 0.88-0.90 (m,2H) |
| 7-13 | 8.26-8.27 (d,1H), 8.16 (s,1H), 7.59-7.60 (dd,1H), 7.48-7.50 (d,1H), 7.37-7.38 (d,1H), 3.90 (s,3H), 2.89-2.94 (q,2H), 1.95-.2.02 (m,1H), 1.29-1.33 (d,3H), 1.11-1.17 (m,2H), 0.82-0.86 (m,2H) |
| 8-15 | 8.76(d, 1H), 8.12 (m, 2H), 7.78-7.73 (m, 2H), 4.01 (q, 2H), 2.16-2.09 (m, 1H), 1.42 (t, 3H), 1.31-1.25 (m, 2H), 0.99-0.96 (m, 2H) |
| 11-1 | 8.87 (brs, 1H), 8.76 (brs, 1H), 8.47 (brs, 1H), 8.35 (brs, 1H), 3.83-3.71 (brm, 5H), 1.77 (brs, 2H), 1.27-1.11 (brm, 5H), |

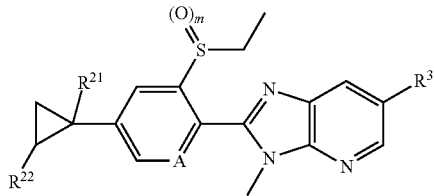

(1-a-1)

| Compound No. | $R^{21}$ | $R^{22}$ | $R^3$ | m | Physical Property |
|---|---|---|---|---|---|
| 11-1 | $CO_2H$ | H | $CF_3$ | 2 | NMR |
| 11-2 | $CO_2Me$ | H | $CF_3$ | 2 | 166-167 |
| 11-3 | $CO_2$i-Pr | H | $CF_3$ | 2 | 131-133 |
| 11-4 | $CO_2CH_2CF_3$ | H | $CF_3$ | 2 | |
| 11-5 | $CO_2CH_2$c-Pr | H | $CF_3$ | 2 | |
| 11-6 | $CONH_2$ | H | $CF_3$ | 2 | 215-218 |
| 11-7 | CONHMe | H | $CF_3$ | 2 | |
| 11-8 | CONHi-Pr | H | $CF_3$ | 2 | |
| 11-9 | CONHc-Pr | H | $CF_3$ | 2 | |
| 11-10 | $CONHCH_2CF_3$ | H | $CF_3$ | 2 | 192-194 |
| 11-11 | $CONHCH_2$c-Pr | H | $CF_3$ | 2 | |
| 11-12 | $CONMe_2$ | H | $CF_3$ | 2 | |
| 11-13 | CN | H | $CF_3$ | 2 | 176-177 |
| 11-14 | CHO | H | $CF_3$ | 2 | 80-82 |
| 11-15 | C(=O)Me | H | $CF_3$ | 2 | |
| 11-16 | $CH_2OH$ | H | $CF_3$ | 2 | 92-94 |
| 11-17 | $CH_2OMe$ | H | $CF_3$ | 2 | |
| 11-18 | $CH_2O$i-Pr | H | $CF_3$ | 2 | |
| 11-19 | $CH_2OCH_2CF_3$ | H | $CF_3$ | 2 | |
| 11-20 | $CH_2OCH_2$c-Pr | H | $CF_3$ | 2 | |
| 11-21 | $CH_2OC(=O)Me$ | H | $CF_3$ | 2 | |
| 11-22 | $CH_2OC(=O)$i-Pr | H | $CF_3$ | 2 | |
| 11-23 | $CH_2OC(=O)$c-Pr | H | $CF_3$ | 2 | |
| 11-24 | $CH_2OC(=O)OMe$ | H | $CF_3$ | 2 | |
| 11-25 | $CH_2OC(=O)NHMe$ | H | $CF_3$ | 2 | |
| 11-26 | $CH_2OC(=O)NMe_2$ | H | $CF_3$ | 2 | |
| 11-27 | $CH_2CN$ | H | $CF_3$ | 2 | 82-83 |
| 11-28 | $CH_2NH_2$ | H | $CF_3$ | 2 | |
| 11-29 | $CH_2NHMe$ | H | $CF_3$ | 2 | |
| 11-30 | $CH_2NH$i-Pr | H | $CF_3$ | 2 | |
| 11-31 | $CH_2NH$c-Pr | H | $CF_3$ | 2 | |
| 11-32 | $CH_2NHCH_2CF_3$ | H | $CF_3$ | 2 | |
| 11-33 | $CH_2NHCH_2$c-Pr | H | $CF_3$ | 2 | |

-continued

| Compound No. | R²¹ | R²² | R³ | m | Physical Property |
|---|---|---|---|---|---|
| 11-34 | CH₂NMe₂ | H | CF₃ | 2 | |
| 11-35 | CH₂NHAc | H | CF₃ | 2 | |
| 11-36 | CH₂N(Ac)Me | H | CF₃ | 2 | |
| 11-37 | CH₂N(Ac)i-Pr | H | CF₃ | 2 | |
| 11-38 | CH₂N(Ac)c-Pr | H | CF₃ | 2 | |
| 11-39 | CH₂N(Ac)CH₂CF₃ | H | CF₃ | 2 | |
| 11-40 | CH₂N(Ac)CH₂c-Pr | H | CF₃ | 2 | |
| 11-41 | CH₂NHCOOMe | H | CF₃ | 2 | |
| 11-42 | CH₂NHCOOt-Bu | H | CF₃ | 2 | |
| 11-43 | CH₂N(Me)CO₂Me | H | CF₃ | 2 | |
| 11-44 | CH₂N(Me)COOt-Bu | H | CF₃ | 2 | |
| 11-45 | CH₂NHCONHMe | H | CF₃ | 2 | |
| 11-46 | CH₂N(Me)CONHMe | H | CF₃ | 2 | |
| 11-47 | CH₂SMe | H | CF₃ | 2 | |
| 11-48 | CH₂SOMe | H | CF₃ | 2 | |
| 11-49 | CH₂SO₂Me | H | CF₃ | 2 | |
| 11-50 | CH=NOH | H | CF₃ | 2 | 194-195 |
| 11-51 | CH=NOMe | H | CF₃ | 2 | |
| 11-52 | CH=NOi-Pr | H | CF₃ | 2 | |
| 11-53 | CH=NOCH₂CF₃ | H | CF₃ | 2 | 82-83 |
| 11-54 | CH=NOCH₂c-Pr | H | CF₃ | 2 | |
| 11-55 | C(Me)=NOH | H | CF₃ | 2 | |
| 11-56 | C(Me)=NOMe | H | CF₃ | 2 | |
| 11-57 | C(Me)=NOi-Pr | H | CF₃ | 2 | |
| 11-58 | C(Me)=NOCH₂CF₃ | H | CF₃ | 2 | |
| 11-59 | C(Me)=NOCH₂c-Pr | H | CF₃ | 2 | |
| 11-60 | NH₂ | H | CF₃ | 2 | 83-86 |
| 11-61 | NHMe | H | CF₃ | 2 | |
| 11-62 | NHi-Pr | H | CF₃ | 2 | |
| 11-63 | NHCH₂CF₃ | H | CF₃ | 2 | |
| 11-64 | NHCH₂c-Pr | H | CF₃ | 2 | |
| 11-65 | NMe₂ | H | CF₃ | 2 | |
| 11-66 | N(Me)CH₂CF₃ | H | CF₃ | 2 | |
| 11-67 | N(Me)CH₂c-Pr | H | CF₃ | 2 | |
| 11-68 | NHAc | H | CF₃ | 2 | 240-241 |
| 11-69 | N(Ac)Me | H | CF₃ | 2 | |
| 11-70 | N(Ac)i-Pr | H | CF₃ | 2 | |
| 11-71 | N(Ac)CH₂CF₃ | H | CF₃ | 2 | |
| 11-72 | N(Ac)CH₂c-Pr | H | CF₃ | 2 | |
| 11-73 | NHCOOMe | H | CF₃ | 2 | 101-102 |
| 11-74 | N(COOMe)Me | H | CF₃ | 2 | |
| 11-75 | N(COOMe)i-Pr | H | CF₃ | 2 | |
| 11-76 | N(COOMe)CH₂CF₃ | H | CF₃ | 2 | |
| 11-77 | N(COOMe)CH₂c-Pr | H | CF₃ | 2 | |
| 11-78 | NHCONMe₂ | H | CF₃ | 2 | |
| 11-79 | N(CONMe₂)Me | H | CF₃ | 2 | |
| 11-80 | CH₂Cl | H | CF₃ | 2 | 158-159 |
| 11-81 | H | CO₂H | CF₃ | 2 | 190-192 |
| 11-82 | H | CO₂Me | CF₃ | 2 | 164-165 |
| 11-83 | H | CO₂i-Pr | CF₃ | 2 | |
| 11-84 | H | CO₂CH₂CF₃ | CF₃ | 2 | |
| 11-85 | H | CO₂CH₂c-Pr | CF₃ | 2 | |
| 11-86 | H | CONH₂ | CF₃ | 2 | 160-164 |
| 11-87 | H | CONHMe | CF₃ | 2 | |
| 11-88 | H | CONHi-Pr | CF₃ | 2 | |
| 11-89 | H | CONHc-Pr | CF₃ | 2 | |
| 11-90 | H | CONHCH₂CF₃ | CF₃ | 2 | |
| 11-91 | H | CONHCH₂c-Pr | CF₃ | 2 | |
| 11-92 | H | CONMe₂ | CF₃ | 2 | |
| 11-93 | H | CN | CF₃ | 2 | 70-72 |
| 11-94 | H | CHO | CF₃ | 2 | 50-52 |
| 11-95 | H | C(=O)Me | CF₃ | 2 | |
| 11-96 | H | CH₂OH | CF₃ | 2 | 77-80 |
| 11-97 | H | CH₂OMe | CF₃ | 2 | |
| 11-98 | H | CH₂Oi-Pr | CF₃ | 2 | |
| 11-99 | H | CH₂OCH₂CF₃ | CF₃ | 2 | |
| 11-100 | H | CH₂OCH₂c-Pr | CF₃ | 2 | |
| 11-101 | H | CH₂OC(=O)Me | CF₃ | 2 | |
| 11-102 | H | CH₂OC(=O)i-Pr | CF₃ | 2 | |
| 11-103 | H | CH₂OC(=O)c-Pr | CF₃ | 2 | |
| 11-104 | H | CH₂OC(=O)OMe | CF₃ | 2 | |
| 11-105 | H | CH₂OC(=O)NHMe | CF₃ | 2 | |
| 11-106 | H | CH₂OC(=O)NMe₂ | CF₃ | 2 | |
| 11-107 | H | CH₂CN | CF₃ | 2 | |
| 11-108 | H | CH₂NH₂ | CF₃ | 2 | |
| 11-109 | H | CH₂NHMe | CF₃ | 2 | |

-continued

| Compound No. | $R^{21}$ | $R^{22}$ | $R^3$ | m | Physical Property |
|---|---|---|---|---|---|
| 11-110 | H | $CH_2NHi$-Pr | $CF_3$ | 2 | |
| 11-111 | H | $CH_2NHc$-Pr | $CF_3$ | 2 | |
| 11-112 | H | $CH_2NHCH_2CF_3$ | $CF_3$ | 2 | |
| 11-113 | H | $CH_2NHCH_2c$-Pr | $CF_3$ | 2 | |
| 11-114 | H | $CH_2NMe_2$ | $CF_3$ | 2 | |
| 11-115 | H | $CH_2NHAc$ | $CF_3$ | 2 | |
| 11-116 | H | $CH_2N(Ac)Me$ | $CF_3$ | 2 | |
| 11-117 | H | $CH_2N(Ac)i$-Pr | $CF_3$ | 2 | |
| 11-118 | H | $CH_2N(Ac)c$-Pr | $CF_3$ | 2 | |
| 11-119 | H | $CH_2N(Ac)CH_2CF_3$ | $CF_3$ | 2 | |
| 11-120 | H | $CH_2N(Ac)CH_2c$-Pr | $CF_3$ | 2 | |
| 11-121 | H | $CH_2NHCOOMe$ | $CF_3$ | 2 | |
| 11-122 | H | $CH_2NHCOOt$-Bu | $CF_3$ | 2 | |
| 11-123 | H | $CH_2N(Me)CO_2Me$ | $CF_3$ | 2 | |
| 11-124 | H | $CH_2N(Me)COOt$-Bu | $CF_3$ | 2 | |
| 11-125 | H | $CH_2NHCONHMe$ | $CF_3$ | 2 | |
| 11-126 | H | $CH_2N(Me)CONHMe$ | $CF_3$ | 2 | |
| 11-127 | H | $CH_2SMe$ | $CF_3$ | 2 | |
| 11-128 | H | $CH_2SOMe$ | $CF_3$ | 2 | |
| 11-129 | H | $CH_2SO_2Me$ | $CF_3$ | 2 | |
| 11-130 | H | CH=NOH | $CF_3$ | 2 | |
| 11-131 | H | CH=NOMe | $CF_3$ | 2 | 50-51 |
| 11-132 | H | CH=NOi-Pr | $CF_3$ | 2 | |
| 11-133 | H | CH=NOCH$_2$CF$_3$ | $CF_3$ | 2 | |
| 11-134 | H | CH=NOCH$_2$c-Pr | $CF_3$ | 2 | |
| 11-135 | H | C(Me)=NOH | $CF_3$ | 2 | |
| 11-136 | H | C(Me)=NOMe | $CF_3$ | 2 | |
| 11-137 | H | C(Me)=NOi-Pr | $CF_3$ | 2 | |
| 11-138 | H | C(Me)=NOCH$_2$CF$_3$ | $CF_3$ | 2 | |
| 11-139 | H | C(Me)=NOCH$_2$c-Pr | $CF_3$ | 2 | |
| 11-140 | H | $NH_2$ | $CF_3$ | 2 | 54-55 |
| 11-141 | H | NHMe | $CF_3$ | 2 | 68-70 |
| 11-142 | H | NHi-Pr | $CF_3$ | 2 | |
| 11-143 | H | $NHCH_2CF_3$ | $CF_3$ | 2 | |
| 11-144 | H | $NHCH_2c$-Pr | $CF_3$ | 2 | |
| 11-145 | H | $NMe_2$ | $CF_3$ | 2 | |
| 11-146 | H | $N(Me)CH_2CF_3$ | $CF_3$ | 2 | |
| 11-147 | H | $N(Me)CH_2c$-Pr | $CF_3$ | 2 | |
| 11-148 | H | NHAc | $CF_3$ | 2 | 72-74 |
| 11-149 | H | N(Ac)Me | $CF_3$ | 2 | |
| 11-150 | H | N(Ac)i-Pr | $CF_3$ | 2 | |
| 11-151 | H | $N(Ac)CH_2CF_3$ | $CF_3$ | 2 | |
| 11-152 | H | $N(Ac)CH_2c$-Pr | $CF_3$ | 2 | |
| 11-153 | H | NHCOOMe | $CF_3$ | 2 | |
| 11-154 | H | N(COOMe)Me | $CF_3$ | 2 | |
| 11-155 | H | N(COOMe)i-Pr | $CF_3$ | 2 | |
| 11-156 | H | $N(COOMe)CH_2CF_3$ | $CF_3$ | 2 | |
| 11-157 | H | $N(COOMe)CH_2c$-Pr | $CF_3$ | 2 | |
| 11-158 | H | $NHCONMe_2$ | $CF_3$ | 2 | |
| 11-159 | H | $N(CONMe_2)Me$ | $CF_3$ | 2 | |
| 11-160 | H | $CH_2Cl$ | $CF_3$ | 2 | |
| 11-161 | $CO_2H$ | H | $SCF_3$ | 2 | |
| 11-162 | $CO_2Me$ | H | $SCF_3$ | 2 | |
| 11-163 | $CO_2i$-Pr | H | $SCF_3$ | 2 | |
| 11-164 | $CO_2CH_2CF_3$ | H | $SCF_3$ | 2 | |
| 11-165 | $CO_2CH_2c$-Pr | H | $SCF_3$ | 2 | |
| 11-166 | $CONH_2$ | H | $SCF_3$ | 2 | |
| 11-167 | CONHMe | H | $SCF_3$ | 2 | |
| 11-168 | CONHi-Pr | H | $SCF_3$ | 2 | |
| 11-169 | CONHc-Pr | H | $SCF_3$ | 2 | |
| 11-170 | $CONHCH_2CF_3$ | H | $SCF_3$ | 2 | |
| 11-171 | $CONHCH_2c$-Pr | H | $SCF_3$ | 2 | |
| 11-172 | $CONMe_2$ | H | $SCF_3$ | 2 | |
| 11-173 | CN | H | $SCF_3$ | 2 | |
| 11-174 | CHO | H | $SCF_3$ | 2 | |
| 11-175 | C(=O)Me | H | $SCF_3$ | 2 | |
| 11-176 | $CH_2OH$ | H | $SCF_3$ | 2 | |
| 11-177 | $CH_2OMe$ | H | $SCF_3$ | 2 | |
| 11-178 | $CH_2Oi$-Pr | H | $SCF_3$ | 2 | |
| 11-179 | $CH_2OCH_2CF_3$ | H | $SCF_3$ | 2 | |
| 11-180 | $CH_2OCH_2c$-Pr | H | $SCF_3$ | 2 | |
| 11-181 | $CH_2OC(=O)Me$ | H | $SCF_3$ | 2 | |
| 11-182 | $CH_2OC(=O)i$-Pr | H | $SCF_3$ | 2 | |
| 11-183 | $CH_2OC(=O)c$-Pr | H | $SCF_3$ | 2 | |
| 11-184 | $CH_2OC(=O)OMe$ | H | $SCF_3$ | 2 | |
| 11-185 | $CH_2OC(=O)NHMe$ | H | $SCF_3$ | 2 | |

-continued

| Compound No. | R²¹ | R²² | R³ | m | Physical Property |
|---|---|---|---|---|---|
| 11-186 | CH₂OC(=O)NMe₂ | H | SCF₃ | 2 | |
| 11-187 | CH₂CN | H | SCF₃ | 2 | |
| 11-188 | CH₂NH₂ | H | SCF₃ | 2 | |
| 11-189 | CH₂NHMe | H | SCF₃ | 2 | |
| 11-190 | CH₂NHi-Pr | H | SCF₃ | 2 | |
| 11-191 | CH₂NHc-Pr | H | SCF₃ | 2 | |
| 11-192 | CH₂NHCH₂CF₃ | H | SCF₃ | 2 | |
| 11-193 | CH₂NHCH₂c-Pr | H | SCF₃ | 2 | |
| 11-194 | CH₂NMe₂ | H | SCF₃ | 2 | |
| 11-195 | CH₂NHAc | H | SCF₃ | 2 | |
| 11-196 | CH₂N(Ac)Me | H | SCF₃ | 2 | |
| 11-197 | CH₂N(Ac)i-Pr | H | SCF₃ | 2 | |
| 11-198 | CH₂N(Ac)c-Pr | H | SCF₃ | 2 | |
| 11-199 | CH₂N(Ac)CH₂CF₃ | H | SCF₃ | 2 | |
| 11-200 | CH₂N(Ac)CH₂c-Pr | H | SCF₃ | 2 | |
| 11-201 | CH₂NHCOOMe | H | SCF₃ | 2 | |
| 11-202 | CH₂NHCOOt-Bu | H | SCF₃ | 2 | |
| 11-203 | CH₂N(Me)CO₂Me | H | SCF₃ | 2 | |
| 11-204 | CH₂N(Me)COOt-Bu | H | SCF₃ | 2 | |
| 11-205 | CH₂NHCONHMe | H | SCF₃ | 2 | |
| 11-206 | CH₂N(Me)CONHMe | H | SCF₃ | 2 | |
| 11-207 | CH₂SMe | H | SCF₃ | 2 | |
| 11-208 | CH₂SOMe | H | SCF₃ | 2 | |
| 11-209 | CH₂SO₂MeMe | H | SCF₃ | 2 | |
| 11-210 | CH=NOH | H | SCF₃ | 2 | |
| 11-211 | CH=NOMe | H | SCF₃ | 2 | |
| 11-212 | CH=NOi-Pr | H | SCF₃ | 2 | |
| 11-213 | CH=NOCH₂CF₃ | H | SCF₃ | 2 | |
| 11-214 | CH=NOCH₂c-Pr | H | SCF₃ | 2 | |
| 11-215 | C(Me)=NOH | H | SCF₃ | 2 | |
| 11-216 | C(Me)=NOMe | H | SCF₃ | 2 | |
| 11-217 | C(Me)=NOi-Pr | H | SCF₃ | 2 | |
| 11-218 | C(Me)=NOCH₂CF₃ | H | SCF₃ | 2 | |
| 11-219 | C(Me)=NOCH₂c-Pr | H | SCF₃ | 2 | |
| 11-220 | NH₂ | H | SCF₃ | 2 | |
| 11-221 | NHMe | H | SCF₃ | 2 | |
| 11-222 | NHi-Pr | H | SCF₃ | 2 | |
| 11-223 | NHCH₂CF₃ | H | SCF₃ | 2 | |
| 11-224 | NHCH₂c-Pr | H | SCF₃ | 2 | |
| 11-225 | NMe₂ | H | SCF₃ | 2 | |
| 11-226 | N(Me)CH₂CF₃ | H | SCF₃ | 2 | |
| 11-227 | N(Me)CH₂c-Pr | H | SCF₃ | 2 | |
| 11-228 | NHAc | H | SCF₃ | 2 | |
| 11-229 | N(Ac)Me | H | SCF₃ | 2 | |
| 11-230 | N(Ac)i-Pr | H | SCF₃ | 2 | |
| 11-231 | N(Ac)CH₂CF₃ | H | SCF₃ | 2 | |
| 11-232 | N(Ac)CH₂c-Pr | H | SCF₃ | 2 | |
| 11-233 | NHCOOMe | H | SCF₃ | 2 | |
| 11-234 | N(COOMe)Me | H | SCF₃ | 2 | |
| 11-235 | N(COOMe)i-Pr | H | SCF₃ | 2 | |
| 11-236 | N(COOMe)CH₂CF₃ | H | SCF₃ | 2 | |
| 11-237 | N(COOMe)CH₂c-Pr | H | SCF₃ | 2 | |
| 11-238 | NHCONMe₂ | H | SCF₃ | 2 | |
| 11-239 | N(CONMe₂)Me | H | SCF₃ | 2 | |
| 11-240 | CH₂Cl | H | SCF₃ | 2 | |
| 11-241 | H | CO₂H | SCF₃ | 2 | |
| 11-242 | H | CO₂Me | SCF₃ | 2 | |
| 11-243 | H | CO₂i-Pr | SCF₃ | 2 | |
| 11-244 | H | CO₂CH₂CF₃ | SCF₃ | 2 | |
| 11-245 | H | CO₂CH₂c-Pr | SCF₃ | 2 | |
| 11-246 | H | CONH₂ | SCF₃ | 2 | |
| 11-247 | H | CONHMe | SCF₃ | 2 | |
| 11-248 | H | CONHi-Pr | SCF₃ | 2 | |
| 11-249 | H | CONHc-Pr | SCF₃ | 2 | |
| 11-250 | H | CONHCH₂CF₃ | SCF₃ | 2 | |
| 11-251 | H | CONHCH₂c-Pr | SCF₃ | 2 | |
| 11-252 | H | CONMe₂ | SCF₃ | 2 | |
| 11-253 | H | CN | SCF₃ | 2 | |
| 11-254 | H | CHO | SCF₃ | 2 | |
| 11-255 | H | C(=O)Me | SCF₃ | 2 | |
| 11-256 | H | CH₂OH | SCF₃ | 2 | |
| 11-257 | H | CH₂OMe | SCF₃ | 2 | |
| 11-258 | H | CH₂Oi-Pr | SCF₃ | 2 | |
| 11-259 | H | CH₂OCH₂CF₃ | SCF₃ | 2 | |

-continued

| Compound No. | R²¹ | R²² | R³ | m | Physical Property |
|---|---|---|---|---|---|
| 11-260 | H | CH₂OCH₂c-Pr | SCF₃ | 2 | |
| 11-261 | H | CH₂OC(=O)Me | SCF₃ | 2 | |
| 11-262 | H | CH₂OC(=O)i-Pr | SCF₃ | 2 | |
| 11-263 | H | CH₂OC(=O)c-Pr | SCF₃ | 2 | |
| 11-264 | H | CH₂OC(=O)OMe | SCF₃ | 2 | |
| 11-265 | H | CH₂OC(=O)NHMe | SCF₃ | 2 | |
| 11-266 | H | CH₂OC(=O)NMe₂ | SCF₃ | 2 | |
| 11-267 | H | CH₂CN | SCF₃ | 2 | |
| 11-268 | H | CH₂NH₂ | SCF₃ | 2 | |
| 11-269 | H | CH₂NHMe | SCF₃ | 2 | |
| 11-270 | H | CH₂NHi-Pr | SCF₃ | 2 | |
| 11-271 | H | CH₂NHc-Pr | SCF₃ | 2 | |
| 11-272 | H | CH₂NHCH₂CF₃ | SCF₃ | 2 | |
| 11-273 | H | CH₂NHCH₂c-Pr | SCF₃ | 2 | |
| 11-274 | H | CH₂NMe₂ | SCF₃ | 2 | |
| 11-275 | H | CH₂NHAc | SCF₃ | 2 | |
| 11-276 | H | CH₂N(Ac)Me | SCF₃ | 2 | |
| 11-277 | H | CH₂N(Ac)i-Pr | SCF₃ | 2 | |
| 11-278 | H | CH₂N(Ac)c-Pr | SCF₃ | 2 | |
| 11-279 | H | CH₂N(Ac)CH₂CF₃ | SCF₃ | 2 | |
| 11-280 | H | CH₂N(Ac)CH₂c-Pr | SCF₃ | 2 | |
| 11-281 | H | CH₂NHCOOMe | SCF₃ | 2 | |
| 11-282 | H | CH₂NHCOOt-Bu | SCF₃ | 2 | |
| 11-283 | H | CH₂N(Me)CO₂Me | SCF₃ | 2 | |
| 11-284 | H | CH₂N(Me)COOt-Bu | SCF₃ | 2 | |
| 11-285 | H | CH₂NHCONHMe | SCF₃ | 2 | |
| 11-286 | H | CH₂N(Me)CONHMe | SCF₃ | 2 | |
| 11-287 | H | CH₂SMe | SCF₃ | 2 | |
| 11-288 | H | CH₂SOMe | SCF₃ | 2 | |
| 11-289 | H | CH₂SO₂MeMe | SCF₃ | 2 | |
| 11-290 | H | CH=NOH | SCF₃ | 2 | |
| 11-291 | H | CH=NOMe | SCF₃ | 2 | |
| 11-292 | H | CH=NOi-Pr | SCF₃ | 2 | |
| 11-293 | H | CH=NOCH₂CF₃ | SCF₃ | 2 | |
| 11-294 | H | CH=NOCH₂c-Pr | SCF₃ | 2 | |
| 11-295 | H | C(Me)=NOH | SCF₃ | 2 | |
| 11-296 | H | C(Me)=NOMe | SCF₃ | 2 | |
| 11-297 | H | C(Me)=NOi-Pr | SCF₃ | 2 | |
| 11-298 | H | C(Me)=NOCH₂CF₃ | SCF₃ | 2 | |
| 11-299 | H | C(Me)=NOCH₂c-Pr | SCF₃ | 2 | |
| 11-300 | H | NH₂ | SCF₃ | 2 | |
| 11-301 | H | NHMe | SCF₃ | 2 | |
| 11-302 | H | NHi-Pr | SCF₃ | 2 | |
| 11-303 | H | NHCH₂CF₃ | SCF₃ | 2 | |
| 11-304 | H | NHCH₂c-Pr | SCF₃ | 2 | |
| 11-305 | H | NMe₂ | SCF₃ | 2 | |
| 11-306 | H | N(Me)CH₂CF₃ | SCF₃ | 2 | |
| 11-307 | H | N(Me)CH₂c-Pr | SCF₃ | 2 | |
| 11-308 | H | NHAc | SCF₃ | 2 | |
| 11-309 | H | N(Ac)Me | SCF₃ | 2 | |
| 11-310 | H | N(Ac)i-Pr | SCF₃ | 2 | |
| 11-311 | H | N(Ac)CH₂CF₃ | SCF₃ | 2 | |
| 11-312 | H | N(Ac)CH₂c-Pr | SCF₃ | 2 | |
| 11-313 | H | NHCOOMe | SCF₃ | 2 | |
| 11-314 | H | N(COOMe)Me | SCF₃ | 2 | |
| 11-315 | H | N(COOMe)i-Pr | SCF₃ | 2 | |
| 11-316 | H | N(COOMe)CH₂CF₃ | SCF₃ | 2 | |
| 11-317 | H | N(COOMe)CH₂c-Pr | SCF₃ | 2 | |
| 11-318 | H | NHCONMe₂ | SCF₃ | 2 | |
| 11-319 | H | N(CONMe₂)Me | SCF₃ | 2 | |
| 11-320 | H | CH₂Cl | SCF₃ | 2 | |

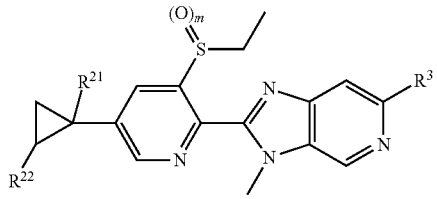

(1-b-1)

| Compound No. | $R^{21}$ | $R^{22}$ | $R^3$ | m | Physical Property |
|---|---|---|---|---|---|
| 12-1 | $CO_2H$ | H | $CF_3$ | 2 | 217-221 |
| 12-2 | $CO_2Me$ | H | $CF_3$ | 2 | 172-174 |
| 12-3 | $CO_2i$-Pr | H | $CF_3$ | 2 | |
| 12-4 | $CO_2CH_2CF_3$ | H | $CF_3$ | 2 | |
| 12-5 | $CO_2CH_2c$-Pr | H | $CF_3$ | 2 | |
| 12-6 | $CONH_2$ | H | $CF_3$ | 2 | 207-211 |
| 12-7 | CONHMe | H | $CF_3$ | 2 | |
| 12-8 | CONHi-Pr | H | $CF_3$ | 2 | |
| 12-9 | CONHc-Pr | H | $CF_3$ | 2 | |
| 12-10 | $CONHCH_2CF_3$ | H | $CF_3$ | 2 | |
| 12-11 | $CONHCH_2c$-Pr | H | $CF_3$ | 2 | |
| 12-12 | $CONMe_2$ | H | $CF_3$ | 2 | |
| 12-13 | CN | H | $CF_3$ | 2 | 196-200 |
| 12-14 | CHO | H | $CF_3$ | 2 | |
| 12-15 | C(=O)Me | H | $CF_3$ | 2 | |
| 12-16 | $CH_2OH$ | H | $CF_3$ | 2 | |
| 12-17 | $CH_2OMe$ | H | $CF_3$ | 2 | |
| 12-18 | $CH_2Oi$-Pr | H | $CF_3$ | 2 | |
| 12-19 | $CH_2OCH_2CF_3$ | H | $CF_3$ | 2 | |
| 12-20 | $CH_2OCH_2c$-Pr | H | $CF_3$ | 2 | |
| 12-21 | $CH_2OC(=O)Me$ | H | $CF_3$ | 2 | |
| 12-22 | $CH_2OC(=O)i$-Pr | H | $CF_3$ | 2 | |
| 12-23 | $CH_2OC(=O)c$-Pr | H | $CF_3$ | 2 | |
| 12-24 | $CH_2OC(=O)OMe$ | H | $CF_3$ | 2 | |
| 12-25 | $CH_2OC(=O)NHMe$ | H | $CF_3$ | 2 | |
| 12-26 | $CH_2OC(=O)NMe_2$ | H | $CF_3$ | 2 | |
| 12-27 | $CH_2CN$ | H | $CF_3$ | 2 | |
| 12-28 | $CH_2NH_2$ | H | $CF_3$ | 2 | |
| 12-29 | $CH_2NHMe$ | H | $CF_3$ | 2 | |
| 12-30 | $CH_2NHi$-Pr | H | $CF_3$ | 2 | |
| 12-31 | $CH_2NHc$-Pr | H | $CF_3$ | 2 | |
| 12-32 | $CH_2NHCH_2CF_3$ | H | $CF_3$ | 2 | |
| 12-33 | $CH_2NHCH_2c$-Pr | H | $CF_3$ | 2 | |
| 12-34 | $CH_2NMe_2$ | H | $CF_3$ | 2 | |
| 12-35 | $CH_2NHAc$ | H | $CF_3$ | 2 | |
| 12-36 | $CH_2N(Ac)Me$ | H | $CF_3$ | 2 | |
| 12-37 | $CH_2N(Ac)i$-Pr | H | $CF_3$ | 2 | |
| 12-38 | $CH_2N(Ac)c$-Pr | H | $CF_3$ | 2 | |
| 12-39 | $CH_2N(Ac)CH_2CF_3$ | H | $CF_3$ | 2 | |
| 12-40 | $CH_2N(Ac)CH_2c$-Pr | H | $CF_3$ | 2 | |
| 12-41 | $CH_2NHCOOMe$ | H | $CF_3$ | 2 | |
| 12-42 | $CH_2NHCOOt$-Bu | H | $CF_3$ | 2 | |
| 12-43 | $CH_2N(Me)CO_2Me$ | H | $CF_3$ | 2 | |
| 12-44 | $CH_2N(Me)COOt$-Bu | H | $CF_3$ | 2 | |
| 12-45 | $CH_2NHCONHMe$ | H | $CF_3$ | 2 | |
| 12-46 | $CH_2N(Me)CONHMe$ | H | $CF_3$ | 2 | |
| 12-47 | $CH_2SMe$ | H | $CF_3$ | 2 | |
| 12-48 | $CH_2SOMe$ | H | $CF_3$ | 2 | |
| 12-49 | $CH_2SO_2MeMe$ | H | $CF_3$ | 2 | |
| 12-50 | CH=NOH | H | $CF_3$ | 2 | |
| 12-51 | CH=NOMe | H | $CF_3$ | 2 | |
| 12-52 | CH=NOi-Pr | H | $CF_3$ | 2 | |
| 12-53 | $CH=NOCH_2CF_3$ | H | $CF_3$ | 2 | |
| 12-54 | $CH=NOCH_2c$-Pr | H | $CF_3$ | 2 | |
| 12-55 | C(Me)=NOH | H | $CF_3$ | 2 | |
| 12-56 | C(Me)=NOMe | H | $CF_3$ | 2 | |
| 12-57 | C(Me)=NOi-Pr | H | $CF_3$ | 2 | |
| 12-58 | $C(Me)=NOCH_2CF_3$ | H | $CF_3$ | 2 | |
| 12-59 | $C(Me)=NOCH_2c$-Pr | H | $CF_3$ | 2 | |
| 12-60 | $NH_2$ | H | $CF_3$ | 2 | |
| 12-61 | NHMe | H | $CF_3$ | 2 | |
| 12-62 | NHi-Pr | H | $CF_3$ | 2 | |
| 12-63 | $NHCH_2CF_3$ | H | $CF_3$ | 2 | |
| 12-64 | $NHCH_2c$-Pr | H | $CF_3$ | 2 | |
| 12-65 | $NMe_2$ | H | $CF_3$ | 2 | |
| 12-66 | $N(Me)CH_2CF_3$ | H | $CF_3$ | 2 | |
| 12-67 | $N(Me)CH_2c$-Pr | H | $CF_3$ | 2 | |
| 12-68 | NHAc | H | $CF_3$ | 2 | |
| 12-69 | N(Ac)Me | H | $CF_3$ | 2 | |
| 12-70 | N(Ac)i-Pr | H | $CF_3$ | 2 | |
| 12-71 | $N(Ac)CH_2CF_3$ | H | $CF_3$ | 2 | |
| 12-72 | $N(Ac)CH_2c$-Pr | H | $CF_3$ | 2 | |
| 12-73 | NHCOOMe | H | $CF_3$ | 2 | |
| 12-74 | N(COOMe)Me | H | $CF_3$ | 2 | |
| 12-75 | N(COOMe)i-Pr | H | $CF_3$ | 2 | |
| 12-76 | $N(COOMe)CH_2CF_3$ | H | $CF_3$ | 2 | |
| 12-77 | $N(COOMe)CH_2c$-Pr | H | $CF_3$ | 2 | |
| 12-78 | $NHCONMe_2$ | H | $CF_3$ | 2 | |

-continued

| Compound No. | $R^{21}$ | $R^{22}$ | $R^3$ | m | Physical Property |
|---|---|---|---|---|---|
| 12-79 | N(CONMe$_2$)Me | H | CF$_3$ | 2 | |
| 12-80 | CH$_2$Cl | H | CF$_3$ | 2 | |
| 12-81 | H | CO$_2$H | CF$_3$ | 2 | |
| 12-82 | H | CO$_2$Me | CF$_3$ | 2 | |
| 12-83 | H | CO$_2$i-Pr | CF$_3$ | 2 | |
| 12-84 | H | CO$_2$CH$_2$CF$_3$ | CF$_3$ | 2 | |
| 12-85 | H | CO$_2$CH$_2$c-Pr | CF$_3$ | 2 | |
| 12-86 | H | CONH$_2$ | CF$_3$ | 2 | |
| 12-87 | H | CONHMe | CF$_3$ | 2 | |
| 12-88 | H | CONHi-Pr | CF$_3$ | 2 | |
| 12-89 | H | CONHc-Pr | CF$_3$ | 2 | |
| 12-90 | H | CONHCH$_2$CF$_3$ | CF$_3$ | 2 | |
| 12-91 | H | CONHCH$_2$c-Pr | CF$_3$ | 2 | |
| 12-92 | H | CONMe$_2$ | CF$_3$ | 2 | |
| 12-93 | H | CN | CF$_3$ | 2 | |
| 12-94 | H | CHO | CF$_3$ | 2 | |
| 12-95 | H | C(=O)Me | CF$_3$ | 2 | |
| 12-96 | H | CH$_2$OH | CF$_3$ | 2 | |
| 12-97 | H | CH$_2$OMe | CF$_3$ | 2 | |
| 12-98 | H | CH$_2$Oi-Pr | CF$_3$ | 2 | |
| 12-99 | H | CH$_2$OCH$_2$CF$_3$ | CF$_3$ | 2 | |
| 12-100 | H | CH$_2$OCH$_2$c-Pr | CF$_3$ | 2 | |
| 12-101 | H | CH$_2$OC(=O)Me | CF$_3$ | 2 | |
| 12-102 | H | CH$_2$OC(=O)i-Pr | CF$_3$ | 2 | |
| 12-103 | H | CH$_2$OC(=O)c-Pr | CF$_3$ | 2 | |
| 12-104 | H | CH$_2$OC(=O)OMe | CF$_3$ | 2 | |
| 12-105 | H | CH$_2$OC(=O)NHMe | CF$_3$ | 2 | |
| 12-106 | H | CH$_2$OC(=O)NMe$_2$ | CF$_3$ | 2 | |
| 12-107 | H | CH$_2$CN | CF$_3$ | 2 | |
| 12-108 | H | CH$_2$NH$_2$ | CF$_3$ | 2 | |
| 12-109 | H | CH$_2$NHMe | CF$_3$ | 2 | |
| 12-110 | H | CH$_2$NHi-Pr | CF$_3$ | 2 | |
| 12-111 | H | CH$_2$NHc-Pr | CF$_3$ | 2 | |
| 12-112 | H | CH$_2$NHCH$_2$CF$_3$ | CF$_3$ | 2 | |
| 12-113 | H | CH$_2$NHCH$_2$c-Pr | CF$_3$ | 2 | |
| 12-114 | H | CH$_2$NMe$_2$ | CF$_3$ | 2 | |
| 12-115 | H | CH$_2$NHAc | CF$_3$ | 2 | |
| 12-116 | H | CH$_2$N(Ac)Me | CF$_3$ | 2 | |
| 12-117 | H | CH$_2$N(Ac)i-Pr | CF$_3$ | 2 | |
| 12-118 | H | CH$_2$N(Ac)c-Pr | CF$_3$ | 2 | |
| 12-119 | H | CH$_2$N(Ac)CH$_2$CF$_3$ | CF$_3$ | 2 | |
| 12-120 | H | CH$_2$N(Ac)CH$_2$c-Pr | CF$_3$ | 2 | |
| 12-121 | H | CH$_2$NHCOOMe | CF$_3$ | 2 | |
| 12-122 | H | CH$_2$NHCOOt-Bu | CF$_3$ | 2 | |
| 12-123 | H | CH$_2$N(Me)CO$_2$Me | CF$_3$ | 2 | |
| 12-124 | H | CH$_2$N(Me)COOt-Bu | CF$_3$ | 2 | |
| 12-125 | H | CH$_2$NHCONHMe | CF$_3$ | 2 | |
| 12-126 | H | CH$_2$N(Me)CONHMe | CF$_3$ | 2 | |
| 12-127 | H | CH$_2$SMe | CF$_3$ | 2 | |
| 12-128 | H | CH$_2$SOMe | CF$_3$ | 2 | |
| 12-129 | H | CH$_2$SO$_2$MeMe | CF$_3$ | 2 | |
| 12-130 | H | CH=NOH | CF$_3$ | 2 | |
| 12-131 | H | CH=NOMe | CF$_3$ | 2 | |
| 12-132 | H | CH=NOi-Pr | CF$_3$ | 2 | |
| 12-133 | H | CH=NOCH$_2$CF$_3$ | CF$_3$ | 2 | |
| 12-134 | H | CH=NOCH$_2$c-Pr | CF$_3$ | 2 | |
| 12-135 | H | C(Me)=NOH | CF$_3$ | 2 | |
| 12-136 | H | C(Me)=NOMe | CF$_3$ | 2 | |
| 12-137 | H | C(Me)=NOi-Pr | CF$_3$ | 2 | |
| 12-138 | H | C(Me)=NOCH$_2$CF$_3$ | CF$_3$ | 2 | |
| 12-139 | H | C(Me)=NOCH$_2$c-Pr | CF$_3$ | 2 | |
| 12-140 | H | NH$_2$ | CF$_3$ | 2 | |
| 12-141 | H | NHMe | CF$_3$ | 2 | |
| 12-142 | H | NHi-Pr | CF$_3$ | 2 | |
| 12-143 | H | NHCH$_2$CF$_3$ | CF$_3$ | 2 | |
| 12-144 | H | NHCH$_2$c-Pr | CF$_3$ | 2 | |
| 12-145 | H | NMe$_2$ | CF$_3$ | 2 | |
| 12-146 | H | N(Me)CH$_2$CF$_3$ | CF$_3$ | 2 | |
| 12-147 | H | N(Me)CH$_2$c-Pr | CF$_3$ | 2 | |
| 12-148 | H | NHAc | CF$_3$ | 2 | |
| 12-149 | H | N(Ac)Me | CF$_3$ | 2 | |
| 12-150 | H | N(Ac)i-Pr | CF$_3$ | 2 | |
| 12-151 | H | N(Ac)CH$_2$CF$_3$ | CF$_3$ | 2 | |
| 12-152 | H | N(Ac)CH$_2$c-Pr | CF$_3$ | 2 | |
| 12-153 | H | NHCOOMe | CF$_3$ | 2 | |
| 12-154 | H | N(COOMe)Me | CF$_3$ | 2 | |

-continued

| Compound No. | $R^{21}$ | $R^{22}$ | $R^3$ | m | Physical Property |
|---|---|---|---|---|---|
| 12-155 | H | N(COOMe)i-Pr | $CF_3$ | 2 | |
| 12-156 | H | N(COOMe)$CH_2CF_3$ | $CF_3$ | 2 | |
| 12-157 | H | N(COOMe)$CH_2$c-Pr | $CF_3$ | 2 | |
| 12-158 | H | $NHCONMe_2$ | $CF_3$ | 2 | |
| 12-159 | H | $N(CONMe_2)Me$ | $CF_3$ | 2 | |
| 12-160 | H | $CH_2Cl$ | $CF_3$ | 2 | |
| 12-161 | $CO_2H$ | H | $SCF_3$ | 2 | |
| 12-162 | $CO_2Me$ | H | $SCF_3$ | 2 | |
| 12-163 | $CO_2$i-Pr | H | $SCF_3$ | 2 | |
| 12-164 | $CO_2CH_2CF_3$ | H | $SCF_3$ | 2 | |
| 12-165 | $CO_2CH_2$c-Pr | H | $SCF_3$ | 2 | |
| 12-166 | $CONH_2$ | H | $SCF_3$ | 2 | |
| 12-167 | CONHMe | H | $SCF_3$ | 2 | |
| 12-168 | CONHi-Pr | H | $SCF_3$ | 2 | |
| 12-169 | CONHc-Pr | H | $SCF_3$ | 2 | |
| 12-170 | $CONHCH_2CF_3$ | H | $SCF_3$ | 2 | |
| 12-171 | $CONHCH_2$c-Pr | H | $SCF_3$ | 2 | |
| 12-172 | $CONMe_2$ | H | $SCF_3$ | 2 | |
| 12-173 | CN | H | $SCF_3$ | 2 | |
| 12-174 | CHO | H | $SCF_3$ | 2 | |
| 12-175 | C(=O)Me | H | $SCF_3$ | 2 | |
| 12-176 | $CH_2OH$ | H | $SCF_3$ | 2 | |
| 12-177 | $CH_2OMe$ | H | $SCF_3$ | 2 | |
| 12-178 | $CH_2O$i-Pr | H | $SCF_3$ | 2 | |
| 12-179 | $CH_2OCH_2CF_3$ | H | $SCF_3$ | 2 | |
| 12-180 | $CH_2OCH_2$c-Pr | H | $SCF_3$ | 2 | |
| 12-181 | $CH_2OC(=O)Me$ | H | $SCF_3$ | 2 | |
| 12-182 | $CH_2OC(=O)$i-Pr | H | $SCF_3$ | 2 | |
| 12-183 | $CH_2OC(=O)$c-Pr | H | $SCF_3$ | 2 | |
| 12-184 | $CH_2OC(=O)OMe$ | H | $SCF_3$ | 2 | |
| 12-185 | $CH_2OC(=O)NHMe$ | H | $SCF_3$ | 2 | |
| 12-186 | $CH_2OC(=O)NMe_2$ | H | $SCF_3$ | 2 | |
| 12-187 | $CH_2CN$ | H | $SCF_3$ | 2 | |
| 12-188 | $CH_2NH_2$ | H | $SCF_3$ | 2 | |
| 12-189 | $CH_2NHMe$ | H | $SCF_3$ | 2 | |
| 12-190 | $CH_2NH$i-Pr | H | $SCF_3$ | 2 | |
| 12-191 | $CH_2NH$c-Pr | H | $SCF_3$ | 2 | |
| 12-192 | $CH_2NHCH_2CF_3$ | H | $SCF_3$ | 2 | |
| 12-193 | $CH_2NHCH_2$c-Pr | H | $SCF_3$ | 2 | |
| 12-194 | $CH_2NMe_2$ | H | $SCF_3$ | 2 | |
| 12-195 | $CH_2NHAc$ | H | $SCF_3$ | 2 | |
| 12-196 | $CH_2N(Ac)Me$ | H | $SCF_3$ | 2 | |
| 12-197 | $CH_2N(Ac)$i-Pr | H | $SCF_3$ | 2 | |
| 12-198 | $CH_2N(Ac)$c-Pr | H | $SCF_3$ | 2 | |
| 12-199 | $CH_2N(Ac)CH_2CF_3$ | H | $SCF_3$ | 2 | |
| 12-200 | $CH_2N(Ac)CH_2$c-Pr | H | $SCF_3$ | 2 | |
| 12-201 | $CH_2NHCOOMe$ | H | $SCF_3$ | 2 | |
| 12-202 | $CH_2NHCOO$t-Bu | H | $SCF_3$ | 2 | |
| 12-203 | $CH_2N(Me)CO_2Me$ | H | $SCF_3$ | 2 | |
| 12-204 | $CH_2N(Me)COO$t-Bu | H | $SCF_3$ | 2 | |
| 12-205 | $CH_2NHCONHMe$ | H | $SCF_3$ | 2 | |
| 12-206 | $CH_2N(Me)CONHMe$ | H | $SCF_3$ | 2 | |
| 12-207 | $CH_2SMe$ | H | $SCF_3$ | 2 | |
| 12-208 | $CH_2SOMe$ | H | $SCF_3$ | 2 | |
| 12-209 | $CH_2SO_2MeMe$ | H | $SCF_3$ | 2 | |
| 12-210 | CH=NOH | H | $SCF_3$ | 2 | |
| 12-211 | CH=NOMe | H | $SCF_3$ | 2 | |
| 12-212 | CH=NOi-Pr | H | $SCF_3$ | 2 | |
| 12-213 | CH=NO$CH_2CF_3$ | H | $SCF_3$ | 2 | |
| 12-214 | CH=NO$CH_2$c-Pr | H | $SCF_3$ | 2 | |
| 12-215 | C(Me)=NOH | H | $SCF_3$ | 2 | |
| 12-216 | C(Me)=NOMe | H | $SCF_3$ | 2 | |
| 12-217 | C(Me)=NOi-Pr | H | $SCF_3$ | 2 | |
| 12-218 | C(Me)=NO$CH_2CF_3$ | H | $SCF_3$ | 2 | |
| 12-219 | C(Me)=NO$CH_2$c-Pr | H | $SCF_3$ | 2 | |
| 12-220 | $NH_2$ | H | $SCF_3$ | 2 | |
| 12-221 | NHMe | H | $SCF_3$ | 2 | |
| 12-222 | NHi-Pr | H | $SCF_3$ | 2 | |
| 12-223 | $NHCH_2CF_3$ | H | $SCF_3$ | 2 | |
| 12-224 | $NHCH_2$c-Pr | H | $SCF_3$ | 2 | |
| 12-225 | $NMe_2$ | H | $SCF_3$ | 2 | |
| 12-226 | $N(Me)CH_2CF_3$ | H | $SCF_3$ | 2 | |
| 12-227 | $N(Me)CH_2$c-Pr | H | $SCF_3$ | 2 | |
| 12-228 | NHAc | H | $SCF_3$ | 2 | |
| 12-229 | N(Ac)Me | H | $SCF_3$ | 2 | |
| 12-230 | N(Ac)i-Pr | H | $SCF_3$ | 2 | |

-continued

| Compound No. | R²¹ | R²² | R³ | m | Physical Property |
|---|---|---|---|---|---|
| 12-231 | N(Ac)CH₂CF₃ | H | SCF₃ | 2 | |
| 12-232 | N(Ac)CH₂c-Pr | H | SCF₃ | 2 | |
| 12-233 | NHCOOMe | H | SCF₃ | 2 | |
| 12-234 | N(COOMe)Me | H | SCF₃ | 2 | |
| 12-235 | N(COOMe)i-Pr | H | SCF₃ | 2 | |
| 12-236 | N(COOMe)CH₂CF₃ | H | SCF₃ | 2 | |
| 12-237 | N(COOMe)CH₂c-Pr | H | SCF₃ | 2 | |
| 12-238 | NHCONMe₂ | H | SCF₃ | 2 | |
| 12-239 | N(CONMe₂)Me | H | SCF₃ | 2 | |
| 12-240 | CH₂Cl | H | SCF₃ | 2 | |
| 12-241 | H | CO₂H | SCF₃ | 2 | |
| 12-242 | H | CO₂Me | SCF₃ | 2 | |
| 12-243 | H | CO₂i-Pr | SCF₃ | 2 | |
| 12-244 | H | CO₂CH₂CF₃ | SCF₃ | 2 | |
| 12-245 | H | CO₂CH₂c-Pr | SCF₃ | 2 | |
| 12-246 | H | CONH₂ | SCF₃ | 2 | |
| 12-247 | H | CONHMe | SCF₃ | 2 | |
| 12-248 | H | CONHi-Pr | SCF₃ | 2 | |
| 12-249 | H | CONHc-Pr | SCF₃ | 2 | |
| 12-250 | H | CONHCH₂CF₃ | SCF₃ | 2 | |
| 12-251 | H | CONHCH₂c-Pr | SCF₃ | 2 | |
| 12-252 | H | CONMe₂ | SCF₃ | 2 | |
| 12-253 | H | CN | SCF₃ | 2 | |
| 12-254 | H | CHO | SCF₃ | 2 | |
| 12-255 | H | C(=O)Me | SCF₃ | 2 | |
| 12-256 | H | CH₂OH | SCF₃ | 2 | |
| 12-257 | H | CH₂OMe | SCF₃ | 2 | |
| 12-258 | H | CH₂Oi-Pr | SCF₃ | 2 | |
| 12-259 | H | CH₂OCH₂CF₃ | SCF₃ | 2 | |
| 12-260 | H | CH₂OCH₂c-Pr | SCF₃ | 2 | |
| 12-261 | H | CH₂OC(=O)Me | SCF₃ | 2 | |
| 12-262 | H | CH₂OC(=O)i-Pr | SCF₃ | 2 | |
| 12-263 | H | CH₂OC(=O)c-Pr | SCF₃ | 2 | |
| 12-264 | H | CH₂OC(=O)OMe | SCF₃ | 2 | |
| 12-265 | H | CH₂OC(=O)NHMe | SCF₃ | 2 | |
| 12-266 | H | CH₂OC(=O)NMe₂ | SCF₃ | 2 | |
| 12-267 | H | CH₂CN | SCF₃ | 2 | |
| 12-268 | H | CH₂NH₂ | SCF₃ | 2 | |
| 12-269 | H | CH₂NHMe | SCF₃ | 2 | |
| 12-270 | H | CH₂NHi-Pr | SCF₃ | 2 | |
| 12-271 | H | CH₂NHc-Pr | SCF₃ | 2 | |
| 12-272 | H | CH₂NHCH₂CF₃ | SCF₃ | 2 | |
| 12-273 | H | CH₂NHCH₂c-Pr | SCF₃ | 2 | |
| 12-274 | H | CH₂NMe₂ | SCF₃ | 2 | |
| 12-275 | H | CH₂NHAc | SCF₃ | 2 | |
| 12-276 | H | CH₂N(Ac)Me | SCF₃ | 2 | |
| 12-277 | H | CH₂N(Ac)i-Pr | SCF₃ | 2 | |
| 12-278 | H | CH₂N(Ac)c-Pr | SCF₃ | 2 | |
| 12-279 | H | CH₂N(Ac)CH₂CF₃ | SCF₃ | 2 | |
| 12-280 | H | CH₂N(Ac)CH₂c-Pr | SCF₃ | 2 | |
| 12-281 | H | CH₂NHCOOMe | SCF₃ | 2 | |
| 12-282 | H | CH₂NHCOOt-Bu | SCF₃ | 2 | |
| 12-283 | H | CH₂N(Me)CO₂Me | SCF₃ | 2 | |
| 12-284 | H | CH₂N(Me)COOt-Bu | SCF₃ | 2 | |
| 12-285 | H | CH₂NHCONHMe | SCF₃ | 2 | |
| 12-286 | H | CH₂N(Me)CONHMe | SCF₃ | 2 | |
| 12-287 | H | CH₂SMe | SCF₃ | 2 | |
| 12-288 | H | CH₂SOMe | SCF₃ | 2 | |
| 12-289 | H | CH₂SO₂MeMe | SCF₃ | 2 | |
| 12-290 | H | CH=NOH | SCF₃ | 2 | |
| 12-291 | H | CH=NOMe | SCF₃ | 2 | |
| 12-292 | H | CH=NOi-Pr | SCF₃ | 2 | |
| 12-293 | H | CH=NOCH₂CF₃ | SCF₃ | 2 | |
| 12-294 | H | CH=NOCH₂c-Pr | SCF₃ | 2 | |
| 12-295 | H | C(Me)=NOH | SCF₃ | 2 | |
| 12-296 | H | C(Me)=NOMe | SCF₃ | 2 | |
| 12-297 | H | C(Me)=NOi-Pr | SCF₃ | 2 | |
| 12-298 | H | C(Me)=NOCH₂CF₃ | SCF₃ | 2 | |
| 12-299 | H | C(Me)=NOCH₂c-Pr | SCF₃ | 2 | |
| 12-300 | H | NH₂ | SCF₃ | 2 | |
| 12-301 | H | NHMe | SCF₃ | 2 | |
| 12-302 | H | NHi-Pr | SCF₃ | 2 | |
| 12-303 | H | NHCH₂CF₃ | SCF₃ | 2 | |
| 12-304 | H | NHCH₂c-Pr | SCF₃ | 2 | |
| 12-305 | H | NMe₂ | SCF₃ | 2 | |
| 12-306 | H | N(Me)CH₂CF₃ | SCF₃ | 2 | |

-continued

| Compound No. | R²¹ | R²² | R³ | m | Physical Property |
|---|---|---|---|---|---|
| 12-307 | H | N(Me)CH₂c-Pr | SCF₃ | 2 | |
| 12-308 | H | NHAc | SCF₃ | 2 | |
| 12-309 | H | N(Ac)Me | SCF₃ | 2 | |
| 12-310 | H | N(Ac)i-Pr | SCF₃ | 2 | |
| 12-311 | H | N(Ac)CH₂CF₃ | SCF₃ | 2 | |
| 12-312 | H | N(Ac)CH₂c-Pr | SCF₃ | 2 | |
| 12-313 | H | NHCOOMe | SCF₃ | 2 | |
| 12-314 | H | N(COOMe)Me | SCF₃ | 2 | |
| 12-315 | H | N(COOMe)i-Pr | SCF₃ | 2 | |
| 12-316 | H | N(COOMe)CH₂CF₃ | SCF₃ | 2 | |
| 12-317 | H | N(COOMe)CH₂c-Pr | SCF₃ | 2 | |
| 12-318 | H | NHCONMe₂ | SCF₃ | 2 | |
| 12-319 | H | N(CONMe₂)Me | SCF₃ | 2 | |
| 12-320 | H | CH₂Cl | SCF₃ | 2 | |
| 12-321 | H | N(COOMe)i-Pr | SCF₃ | 2 | |
| 12-322 | H | N(COOMe)CH₂CF₃ | SCF₃ | 2 | |
| 12-323 | H | N(COOMe)CH₂c-Pr | SCF₃ | 2 | |
| 12-324 | H | NHCONHMe | SCF₃ | 2 | |
| 12-325 | H | NHCONMe₂ | SCF₃ | 2 | |
| 12-326 | H | N(CONHMe)Me | SCF₃ | 2 | |
| 12-327 | H | N(CONMe₂)Me | SCF₃ | 2 | |

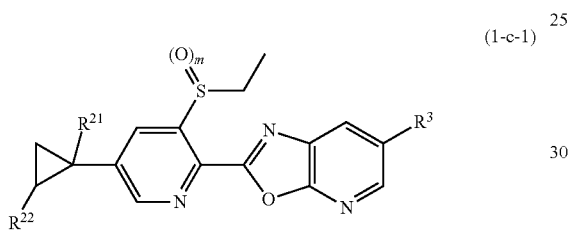

(1-c-1)

| Compound No. | R²¹ | R²² | R³ | m | Physical Property |
|---|---|---|---|---|---|
| 13-1 | CO₂H | H | CF₃ | 2 | |
| 13-2 | CO₂Me | H | CF₃ | 2 | |
| 13-3 | CO₂i-Pr | H | CF₃ | 2 | |
| 13-4 | CO₂CH₂CF₃ | H | CF₃ | 2 | |
| 13-5 | CO₂CH₂c-Pr | H | CF₃ | 2 | |
| 13-6 | CONH₂ | H | CF₃ | 2 | |
| 13-7 | CONHMe | H | CF₃ | 2 | |
| 13-8 | CONHi-Pr | H | CF₃ | 2 | |
| 13-9 | CONHc-Pr | H | CF₃ | 2 | |
| 13-10 | CONHCH₂CF₃ | H | CF₃ | 2 | |
| 13-11 | CONHCH₂c-Pr | H | CF₃ | 2 | |
| 13-12 | CONMe₂ | H | CF₃ | 2 | |
| 13-13 | CN | H | CF₃ | 2 | |
| 13-14 | CHO | H | CF₃ | 2 | |
| 13-15 | C(=O)Me | H | CF₃ | 2 | |
| 13-16 | CH₂OH | H | CF₃ | 2 | |
| 13-17 | CH₂OMe | H | CF₃ | 2 | |
| 13-18 | CH₂Oi-Pr | H | CF₃ | 2 | |
| 13-19 | CH₂OCH₂CF₃ | H | CF₃ | 2 | |
| 13-20 | CH₂OCH₂c-Pr | H | CF₃ | 2 | |
| 13-21 | CH₂OC(=O)Me | H | CF₃ | 2 | |
| 13-22 | CH₂OC(=O)i-Pr | H | CF₃ | 2 | |
| 13-23 | CH₂OC(=O)c-Pr | H | CF₃ | 2 | |
| 13-24 | CH₂OC(=O)OMe | H | CF₃ | 2 | |
| 13-25 | CH₂OC(=O)NHMe | H | CF₃ | 2 | |
| 13-26 | CH₂OC(=O)NMe₂ | H | CF₃ | 2 | |
| 13-27 | CH₂CN | H | CF₃ | 2 | |
| 13-28 | CH₂NH₂ | H | CF₃ | 2 | |
| 13-29 | CH₂NHMe | H | CF₃ | 2 | |
| 13-30 | CH₂NHi-Pr | H | CF₃ | 2 | |
| 13-31 | CH₂NHc-Pr | H | CF₃ | 2 | |
| 13-32 | CH₂NHCH₂CF₃ | H | CF₃ | 2 | |
| 13-33 | CH₂NHCH₂c-Pr | H | CF₃ | 2 | |
| 13-34 | CH₂NMe₂ | H | CF₃ | 2 | |

-continued

| Compound No. | $R^{21}$ | $R^{22}$ | $R^3$ | m | Physical Property |
|---|---|---|---|---|---|
| 13-35 | CH$_2$NHAc | H | CF$_3$ | 2 | |
| 13-36 | CH$_2$N(Ac)Me | H | CF$_3$ | 2 | |
| 13-37 | CH$_2$N(Ac)i-Pr | H | CF$_3$ | 2 | |
| 13-38 | CH$_2$N(Ac)c-Pr | H | CF$_3$ | 2 | |
| 13-39 | CH$_2$N(Ac)CH$_2$CF$_3$ | H | CF$_3$ | 2 | |
| 13-40 | CH$_2$N(Ac)CH$_2$c-Pr | H | CF$_3$ | 2 | |
| 13-41 | CH$_2$NHCOOMe | H | CF$_3$ | 2 | |
| 13-42 | CH$_2$NHCOOt-Bu | H | CF$_3$ | 2 | |
| 13-43 | CH$_2$N(Me)CO$_2$Me | H | CF$_3$ | 2 | |
| 13-44 | CH$_2$N(Me)COOt-Bu | H | CF$_3$ | 2 | |
| 13-45 | CH$_2$NHCONHMe | H | CF$_3$ | 2 | |
| 13-46 | CH$_2$N(Me)CONHMe | H | CF$_3$ | 2 | |
| 13-47 | CH$_2$SMe | H | CF$_3$ | 2 | |
| 13-48 | CH$_2$SOMe | H | CF$_3$ | 2 | |
| 13-49 | CH$_2$SO$_2$Me | H | CF$_3$ | 2 | |
| 13-50 | CH=NOH | H | CF$_3$ | 2 | |
| 13-51 | CH=NOMe | H | CF$_3$ | 2 | |
| 13-52 | CH=NOi-Pr | H | CF$_3$ | 2 | |
| 13-53 | CH=NOCH$_2$CF$_3$ | H | CF$_3$ | 2 | |
| 13-54 | CH=NOCH$_2$c-Pr | H | CF$_3$ | 2 | |
| 13-55 | C(Me)=NOH | H | CF$_3$ | 2 | |
| 13-56 | C(Me)=NOMe | H | CF$_3$ | 2 | |
| 13-57 | C(Me)=NOi-Pr | H | CF$_3$ | 2 | |
| 13-58 | C(Me)=NOCH$_2$CF$_3$ | H | CF$_3$ | 2 | |
| 13-59 | C(Me)=NOCH$_2$c-Pr | H | CF$_3$ | 2 | |
| 13-60 | NH$_2$ | H | CF$_3$ | 2 | |
| 13-61 | NHMe | H | CF$_3$ | 2 | |
| 13-62 | NHi-Pr | H | CF$_3$ | 2 | |
| 13-63 | NHCH$_2$CF$_3$ | H | CF$_3$ | 2 | |
| 13-64 | NHCH$_2$c-Pr | H | CF$_3$ | 2 | |
| 13-65 | NMe$_2$ | H | CF$_3$ | 2 | |
| 13-66 | N(Me)CH$_2$CF$_3$ | H | CF$_3$ | 2 | |
| 13-67 | N(Me)CH$_2$c-Pr | H | CF$_3$ | 2 | |
| 13-68 | NHAc | H | CF$_3$ | 2 | |
| 13-69 | N(Ac)Me | H | CF$_3$ | 2 | |
| 13-70 | N(Ac)i-Pr | H | CF$_3$ | 2 | |
| 13-71 | N(Ac)CH$_2$CF$_3$ | H | CF$_3$ | 2 | |
| 13-72 | N(Ac)CH$_2$c-Pr | H | CF$_3$ | 2 | |
| 13-73 | NHCOOMe | H | CF$_3$ | 2 | |
| 13-74 | N(COOMe)Me | H | CF$_3$ | 2 | |
| 13-75 | N(COOMe)i-Pr | H | CF$_3$ | 2 | |
| 13-76 | N(COOMe)CH$_2$CF$_3$ | H | CF$_3$ | 2 | |
| 13-77 | N(COOMe)CH$_2$c-Pr | H | CF$_3$ | 2 | |
| 13-78 | NHCONMe$_2$ | H | CF$_3$ | 2 | |
| 13-79 | N(CONMe$_2$)Me | H | CF$_3$ | 2 | |
| 13-80 | CH$_2$Cl | H | CF$_3$ | 2 | |
| 13-81 | H | CO$_2$H | CF$_3$ | 2 | |
| 13-82 | H | CO$_2$Me | CF$_3$ | 2 | |
| 13-83 | H | CO$_2$i-Pr | CF$_3$ | 2 | |
| 13-84 | H | CO$_2$CH$_2$CF$_3$ | CF$_3$ | 2 | |
| 13-85 | H | CO$_2$CH$_2$c-Pr | CF$_3$ | 2 | |
| 13-86 | H | CONH$_2$ | CF$_3$ | 2 | |
| 13-87 | H | CONHMe | CF$_3$ | 2 | |
| 13-88 | H | CONHi-Pr | CF$_3$ | 2 | |
| 13-89 | H | CONHc-Pr | CF$_3$ | 2 | |
| 13-90 | H | CONHCH$_2$CF$_3$ | CF$_3$ | 2 | |
| 13-91 | H | CONHCH$_2$c-Pr | CF$_3$ | 2 | |
| 13-92 | H | CONMe$_2$ | CF$_3$ | 2 | |
| 13-93 | H | CN | CF$_3$ | 2 | |
| 13-94 | H | CHO | CF$_3$ | 2 | |
| 13-95 | H | C(=O)Me | CF$_3$ | 2 | |
| 13-96 | H | CH$_2$OH | CF$_3$ | 2 | |
| 13-97 | H | CH$_2$OMe | CF$_3$ | 2 | |
| 13-98 | H | CH$_2$Oi-Pr | CF$_3$ | 2 | |
| 13-99 | H | CH$_2$OCH$_2$CF$_3$ | CF$_3$ | 2 | |
| 13-100 | H | CH$_2$OCH$_2$c-Pr | CF$_3$ | 2 | |
| 13-101 | H | CH$_2$OC(=O)Me | CF$_3$ | 2 | |
| 13-102 | H | CH$_2$OC(=O)i-Pr | CF$_3$ | 2 | |
| 13-103 | H | CH$_2$OC(=O)c-Pr | CF$_3$ | 2 | |
| 13-104 | H | CH$_2$OC(=O)OMe | CF$_3$ | 2 | |
| 13-105 | H | CH$_2$OC(=O)NHMe | CF$_3$ | 2 | |
| 13-106 | H | CH$_2$OC(=O)NMe$_2$ | CF$_3$ | 2 | |
| 13-107 | H | CH$_2$CN | CF$_3$ | 2 | |
| 13-108 | H | CH$_2$NH$_2$ | CF$_3$ | 2 | |
| 13-109 | H | CH$_2$NHMe | CF$_3$ | 2 | |
| 13-110 | H | CH$_2$NHi-Pr | CF$_3$ | 2 | |

| Compound No. | $R^{21}$ | $R^{22}$ | $R^3$ | m | Physical Property |
|---|---|---|---|---|---|
| 13-111 | H | $CH_2NHc$-Pr | $CF_3$ | 2 | |
| 13-112 | H | $CH_2NHCH_2CF_3$ | $CF_3$ | 2 | |
| 13-113 | H | $CH_2NHCH_2c$-Pr | $CF_3$ | 2 | |
| 13-114 | H | $CH_2NMe_2$ | $CF_3$ | 2 | |
| 13-115 | H | $CH_2NHAc$ | $CF_3$ | 2 | |
| 13-116 | H | $CH_2N(Ac)Me$ | $CF_3$ | 2 | |
| 13-117 | H | $CH_2N(Ac)i$-Pr | $CF_3$ | 2 | |
| 13-118 | H | $CH_2N(Ac)c$-Pr | $CF_3$ | 2 | |
| 13-119 | H | $CH_2N(Ac)CH_2CF_3$ | $CF_3$ | 2 | |
| 13-120 | H | $CH_2N(Ac)CH_2c$-Pr | $CF_3$ | 2 | |
| 13-121 | H | $CH_2NHCOOMe$ | $CF_3$ | 2 | |
| 13-122 | H | $CH_2NHCOOt$-Bu | $CF_3$ | 2 | |
| 13-123 | H | $CH_2N(Me)CO_2Me$ | $CF_3$ | 2 | |
| 13-124 | H | $CH_2N(Me)COOt$-Bu | $CF_3$ | 2 | |
| 13-125 | H | $CH_2NHCONHMe$ | $CF_3$ | 2 | |
| 13-126 | H | $CH_2N(Me)CONHMe$ | $CF_3$ | 2 | |
| 13-127 | H | $CH_2SMe$ | $CF_3$ | 2 | |
| 13-128 | H | $CH_2SOMe$ | $CF_3$ | 2 | |
| 13-129 | H | $CH_2SO_2Me$ | $CF_3$ | 2 | |
| 13-130 | H | CH=NOH | $CF_3$ | 2 | |
| 13-131 | H | CH=NOMe | $CF_3$ | 2 | |
| 13-132 | H | CH=NOi-Pr | $CF_3$ | 2 | |
| 13-133 | H | CH=NOCH$_2$CF$_3$ | $CF_3$ | 2 | |
| 13-134 | H | CH=NOCH$_2$c-Pr | $CF_3$ | 2 | |
| 13-135 | H | C(Me)=NOH | $CF_3$ | 2 | |
| 13-136 | H | C(Me)=NOMe | $CF_3$ | 2 | |
| 13-137 | H | C(Me)=NOi-Pr | $CF_3$ | 2 | |
| 13-138 | H | C(Me)=NOCH$_2$CF$_3$ | $CF_3$ | 2 | |
| 13-139 | H | C(Me)=NOCH$_2$c-Pr | $CF_3$ | 2 | |
| 13-140 | H | $NH_2$ | $CF_3$ | 2 | |
| 13-141 | H | NHMe | $CF_3$ | 2 | |
| 13-142 | H | NHi-Pr | $CF_3$ | 2 | |
| 13-143 | H | NHCH$_2$CF$_3$ | $CF_3$ | 2 | |
| 13-144 | H | NHCH$_2$c-Pr | $CF_3$ | 2 | |
| 13-145 | H | $NMe_2$ | $CF_3$ | 2 | |
| 13-146 | H | N(Me)CH$_2$CF$_3$ | $CF_3$ | 2 | |
| 13-147 | H | N(Me)CH$_2$c-Pr | $CF_3$ | 2 | |
| 13-148 | H | NHAc | $CF_3$ | 2 | |
| 13-149 | H | N(Ac)Me | $CF_3$ | 2 | |
| 13-150 | H | N(Ac)i-Pr | $CF_3$ | 2 | |
| 13-151 | H | N(Ac)CH$_2$CF$_3$ | $CF_3$ | 2 | |
| 13-152 | H | N(Ac)CH$_2$c-Pr | $CF_3$ | 2 | |
| 13-153 | H | NHCOOMe | $CF_3$ | 2 | |
| 13-154 | H | N(COOMe)Me | $CF_3$ | 2 | |
| 13-155 | H | N(COOMe)i-Pr | $CF_3$ | 2 | |
| 13-156 | H | N(COOMe)CH$_2$CF$_3$ | $CF_3$ | 2 | |
| 13-157 | H | N(COOMe)CH$_2$c-Pr | $CF_3$ | 2 | |
| 13-158 | H | $NHCONMe_2$ | $CF_3$ | 2 | |
| 13-159 | H | $N(CONMe_2)Me$ | $CF_3$ | 2 | |
| 13-160 | H | $CH_2Cl$ | $CF_3$ | 2 | |
| 13-161 | $CO_2H$ | H | $SCF_3$ | 2 | |
| 13-162 | $CO_2Me$ | H | $SCF_3$ | 2 | |
| 13-163 | $CO_2i$-Pr | H | $SCF_3$ | 2 | |
| 13-164 | $CO_2CH_2CF_3$ | H | $SCF_3$ | 2 | |
| 13-165 | $CO_2CH_2c$-Pr | H | $SCF_3$ | 2 | |
| 13-166 | $CONH_2$ | H | $SCF_3$ | 2 | |
| 13-167 | CONHMe | H | $SCF_3$ | 2 | |
| 13-168 | CONHi-Pr | H | $SCF_3$ | 2 | |
| 13-169 | CONHc-Pr | H | $SCF_3$ | 2 | |
| 13-170 | $CONHCH_2CF_3$ | H | $SCF_3$ | 2 | |
| 13-171 | $CONHCH_2c$-Pr | H | $SCF_3$ | 2 | |
| 13-172 | $CONMe_2$ | H | $SCF_3$ | 2 | |
| 13-173 | CN | H | $SCF_3$ | 2 | |
| 13-174 | CHO | H | $SCF_3$ | 2 | |
| 13-175 | C(=O)Me | H | $SCF_3$ | 2 | |
| 13-176 | $CH_2OH$ | H | $SCF_3$ | 2 | |
| 13-177 | $CH_2OMe$ | H | $SCF_3$ | 2 | |
| 13-178 | $CH_2Oi$-Pr | H | $SCF_3$ | 2 | |
| 13-179 | $CH_2OCH_2CF_3$ | H | $SCF_3$ | 2 | |
| 13-180 | $CH_2OCH_2c$-Pr | H | $SCF_3$ | 2 | |
| 13-181 | $CH_2OC(=O)Me$ | H | $SCF_3$ | 2 | |
| 13-182 | $CH_2OC(=O)i$-Pr | H | $SCF_3$ | 2 | |
| 13-183 | $CH_2OC(=O)c$-Pr | H | $SCF_3$ | 2 | |
| 13-184 | $CH_2OC(=O)OMe$ | H | $SCF_3$ | 2 | |
| 13-185 | $CH_2OC(=O)NHMe$ | H | $SCF_3$ | 2 | |
| 13-186 | $CH_2OC(=O)NMe_2$ | H | $SCF_3$ | 2 | |

-continued

| Compound No. | R²¹ | R²² | R³ | m | Physical Property |
|---|---|---|---|---|---|
| 13-187 | CH₂CN | H | SCF₃ | 2 | |
| 13-188 | CH₂NH₂ | H | SCF₃ | 2 | |
| 13-189 | CH₂NHMe | H | SCF₃ | 2 | |
| 13-190 | CH₂NHi-Pr | H | SCF₃ | 2 | |
| 13-191 | CH₂NHc-Pr | H | SCF₃ | 2 | |
| 13-192 | CH₂NHCH₂CF₃ | H | SCF₃ | 2 | |
| 13-193 | CH₂NHCH₂c-Pr | H | SCF₃ | 2 | |
| 13-194 | CH₂NMe₂ | H | SCF₃ | 2 | |
| 13-195 | CH₂NHAc | H | SCF₃ | 2 | |
| 13-196 | CH₂N(Ac)Me | H | SCF₃ | 2 | |
| 13-197 | CH₂N(Ac)i-Pr | H | SCF₃ | 2 | |
| 13-198 | CH₂N(Ac)c-Pr | H | SCF₃ | 2 | |
| 13-199 | CH₂N(Ac)CH₂CF₃ | H | SCF₃ | 2 | |
| 13-200 | CH₂N(Ac)CH₂c-Pr | H | SCF₃ | 2 | |
| 13-201 | CH₂NHCOOMe | H | SCF₃ | 2 | |
| 13-202 | CH₂NHCOOt-Bu | H | SCF₃ | 2 | |
| 13-203 | CH₂N(Me)CO₂Me | H | SCF₃ | 2 | |
| 13-204 | CH₂N(Me)COOt-Bu | H | SCF₃ | 2 | |
| 13-205 | CH₂NHCONHMe | H | SCF₃ | 2 | |
| 13-206 | CH₂N(Me)CONHMe | H | SCF₃ | 2 | |
| 13-207 | CH₂SMe | H | SCF₃ | 2 | |
| 13-208 | CH₂SOMe | H | SCF₃ | 2 | |
| 13-209 | CH₂SO₂Me | H | SCF₃ | 2 | |
| 13-210 | CH=NOH | H | SCF₃ | 2 | |
| 13-211 | CH=NOMe | H | SCF₃ | 2 | |
| 13-212 | CH=NOi-Pr | H | SCF₃ | 2 | |
| 13-213 | CH=NOCH₂CF₃ | H | SCF₃ | 2 | |
| 13-214 | CH=NOCH₂c-Pr | H | SCF₃ | 2 | |
| 13-215 | C(Me)=NOH | H | SCF₃ | 2 | |
| 13-216 | C(Me)=NOMe | H | SCF₃ | 2 | |
| 13-217 | C(Me)=NOi-Pr | H | SCF₃ | 2 | |
| 13-218 | C(Me)=NOCH₂CF₃ | H | SCF₃ | 2 | |
| 13-219 | C(Me)=NOCH₂c-Pr | H | SCF₃ | 2 | |
| 13-220 | NH₂ | H | SCF₃ | 2 | |
| 13-221 | NHMe | H | SCF₃ | 2 | |
| 13-222 | NHi-Pr | H | SCF₃ | 2 | |
| 13-223 | NHCH₂CF₃ | H | SCF₃ | 2 | |
| 13-224 | NHCH₂c-Pr | H | SCF₃ | 2 | |
| 13-225 | NMe₂ | H | SCF₃ | 2 | |
| 13-226 | N(Me)CH₂CF₃ | H | SCF₃ | 2 | |
| 13-227 | N(Me)CH₂c-Pr | H | SCF₃ | 2 | |
| 13-228 | NHAc | H | SCF₃ | 2 | |
| 13-229 | N(Ac)Me | H | SCF₃ | 2 | |
| 13-230 | N(Ac)i-Pr | H | SCF₃ | 2 | |
| 13-231 | N(Ac)CH₂CF₃ | H | SCF₃ | 2 | |
| 13-232 | N(Ac)CH₂c-Pr | H | SCF₃ | 2 | |
| 13-233 | NHCOOMe | H | SCF₃ | 2 | |
| 13-234 | N(COOMe)Me | H | SCF₃ | 2 | |
| 13-235 | N(COOMe)i-Pr | H | SCF₃ | 2 | |
| 13-236 | N(COOMe)CH₂CF₃ | H | SCF₃ | 2 | |
| 13-237 | N(COOMe)CH₂c-Pr | H | SCF₃ | 2 | |
| 13-238 | NHCONMe₂ | H | SCF₃ | 2 | |
| 13-239 | N(CONMe₂)Me | H | SCF₃ | 2 | |
| 13-240 | CH₂Cl | H | SCF₃ | 2 | |
| 13-241 | H | CO₂H | SCF₃ | 2 | |
| 13-242 | H | CO₂Me | SCF₃ | 2 | |
| 13-243 | H | CO₂i-Pr | SCF₃ | 2 | |
| 13-244 | H | CO₂CH₂CF₃ | SCF₃ | 2 | |
| 13-245 | H | CO₂CH₂c-Pr | SCF₃ | 2 | |
| 13-246 | H | CONH₂ | SCF₃ | 2 | |
| 13-247 | H | CONHMe | SCF₃ | 2 | |
| 13-248 | H | CONHi-Pr | SCF₃ | 2 | |
| 13-249 | H | CONHc-Pr | SCF₃ | 2 | |
| 13-250 | H | CONHCH₂CF₃ | SCF₃ | 2 | |
| 13-251 | H | CONHCH₂c-Pr | SCF₃ | 2 | |
| 13-252 | H | CONMe₂ | SCF₃ | 2 | |
| 13-253 | H | CN | SCF₃ | 2 | |
| 13-254 | H | CHO | SCF₃ | 2 | |
| 13-255 | H | C(=O)Me | SCF₃ | 2 | |
| 13-256 | H | CH₂OH | SCF₃ | 2 | |
| 13-257 | H | CH₂OMe | SCF₃ | 2 | |
| 13-258 | H | CH₂Oi-Pr | SCF₃ | 2 | |
| 13-259 | H | CH₂OCH₂CF₃ | SCF₃ | 2 | |

-continued

| Compound No. | $R^{21}$ | $R^{22}$ | $R^3$ | m | Physical Property |
|---|---|---|---|---|---|
| 13-260 | H | CH$_2$OCH$_2$c-Pr | SCF$_3$ | 2 | |
| 13-261 | H | CH$_2$OC(=O)Me | SCF$_3$ | 2 | |
| 13-262 | H | CH$_2$OC(=O)i-Pr | SCF$_3$ | 2 | |
| 13-263 | H | CH$_2$OC(=O)c-Pr | SCF$_3$ | 2 | |
| 13-264 | H | CH$_2$OC(=O)OMe | SCF$_3$ | 2 | |
| 13-265 | H | CH$_2$OC(=O)NHMe | SCF$_3$ | 2 | |
| 13-266 | H | CH$_2$OC(=O)NMe$_2$ | SCF$_3$ | 2 | |
| 13-267 | H | CH$_2$CN | SCF$_3$ | 2 | |
| 13-268 | H | CH$_2$NH$_2$ | SCF$_3$ | 2 | |
| 13-269 | H | CH$_2$NHMe | SCF$_3$ | 2 | |
| 13-270 | H | CH$_2$NHi-Pr | SCF$_3$ | 2 | |
| 13-271 | H | CH$_2$NHc-Pr | SCF$_3$ | 2 | |
| 13-272 | H | CH$_2$NHCH$_2$CF$_3$ | SCF$_3$ | 2 | |
| 13-273 | H | CH$_2$NHCH$_2$c-Pr | SCF$_3$ | 2 | |
| 13-274 | H | CH$_2$NMe$_2$ | SCF$_3$ | 2 | |
| 13-275 | H | CH$_2$NHAc | SCF$_3$ | 2 | |
| 13-276 | H | CH$_2$N(Ac)Me | SCF$_3$ | 2 | |
| 13-277 | H | CH$_2$N(Ac)i-Pr | SCF$_3$ | 2 | |
| 13-278 | H | CH$_2$N(Ac)c-Pr | SCF$_3$ | 2 | |
| 13-279 | H | CH$_2$N(Ac)CH$_2$CF$_3$ | SCF$_3$ | 2 | |
| 13-280 | H | CH$_2$N(Ac)CH$_2$c-Pr | SCF$_3$ | 2 | |
| 13-281 | H | CH$_2$NHCOOMe | SCF$_3$ | 2 | |
| 13-282 | H | CH$_2$NHCOOt-Bu | SCF$_3$ | 2 | |
| 13-283 | H | CH$_2$N(Me)CO$_2$Me | SCF$_3$ | 2 | |
| 13-284 | H | CH$_2$N(Me)COOt-Bu | SCF$_3$ | 2 | |
| 13-285 | H | CH$_2$NHCONHMe | SCF$_3$ | 2 | |
| 13-286 | H | CH$_2$N(Me)CONHMe | SCF$_3$ | 2 | |
| 13-287 | H | CH$_2$SMe | SCF$_3$ | 2 | |
| 13-288 | H | CH$_2$SOMe | SCF$_3$ | 2 | |
| 13-289 | H | CH$_2$SO$_2$Me | SCF$_3$ | 2 | |
| 13-290 | H | CH=NOH | SCF$_3$ | 2 | |
| 13-291 | H | CH=NOMe | SCF$_3$ | 2 | |
| 13-292 | H | CH=NOi-Pr | SCF$_3$ | 2 | |
| 13-293 | H | CH=NOCH$_2$CF$_3$ | SCF$_3$ | 2 | |
| 13-294 | H | CH=NOCH$_2$c-Pr | SCF$_3$ | 2 | |
| 13-295 | H | C(Me)=NOH | SCF$_3$ | 2 | |
| 13-296 | H | C(Me)=NOMe | SCF$_3$ | 2 | |
| 13-297 | H | C(Me)=NOi-Pr | SCF$_3$ | 2 | |
| 13-298 | H | C(Me)=NOCH$_2$CF$_3$ | SCF$_3$ | 2 | |
| 13-299 | H | C(Me)=NOCH$_2$c-Pr | SCF$_3$ | 2 | |
| 13-300 | H | NH$_2$ | SCF$_3$ | 2 | |
| 13-301 | H | NHMe | SCF$_3$ | 2 | |
| 13-302 | H | NHi-Pr | SCF$_3$ | 2 | |
| 13-303 | H | NHCH$_2$CF$_3$ | SCF$_3$ | 2 | |
| 13-304 | H | NHCH$_2$c-Pr | SCF$_3$ | 2 | |
| 13-305 | H | NMe$_2$ | SCF$_3$ | 2 | |
| 13-306 | H | N(Me)CH$_2$CF$_3$ | SCF$_3$ | 2 | |
| 13-307 | H | N(Me)CH$_2$c-Pr | SCF$_3$ | 2 | |
| 13-308 | H | NHAc | SCF$_3$ | 2 | |
| 13-309 | H | N(Ac)Me | SCF$_3$ | 2 | |
| 13-310 | H | N(Ac)i-Pr | SCF$_3$ | 2 | |
| 13-311 | H | N(Ac)CH$_2$CF$_3$ | SCF$_3$ | 2 | |
| 13-312 | H | N(Ac)CH$_2$c-Pr | SCF$_3$ | 2 | |
| 13-313 | H | NHCOOMe | SCF$_3$ | 2 | |
| 13-314 | H | N(COOMe)Me | SCF$_3$ | 2 | |
| 13-315 | H | N(COOMe)i-Pr | SCF$_3$ | 2 | |
| 13-316 | H | N(COOMe)CH$_2$CF$_3$ | SCF$_3$ | 2 | |
| 13-317 | H | N(COOMe)CH$_2$c-Pr | SCF$_3$ | 2 | |
| 13-318 | H | NHCONMe$_2$ | SCF$_3$ | 2 | |
| 13-319 | H | N(CONMe$_2$)Me | SCF$_3$ | 2 | |
| 13-320 | H | CH$_2$Cl | SCF$_3$ | 2 | |

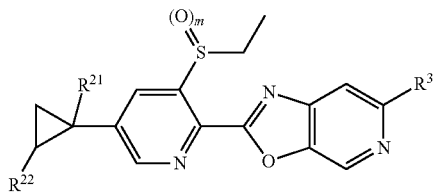

(1-d-1)

| Compound No. | $R^{21}$ | $R^{22}$ | $R^3$ | m | Physical Property |
|---|---|---|---|---|---|
| 14-1 | $CO_2H$ | H | $CF_3$ | 2 | |
| 14-2 | $CO_2Me$ | H | $CF_3$ | 2 | |
| 14-3 | $CO_2$i-Pr | H | $CF_3$ | 2 | |
| 14-4 | $CO_2CH_2CF_3$ | H | $CF_3$ | 2 | |
| 14-5 | $CO_2CH_2$c-Pr | H | $CF_3$ | 2 | |
| 14-6 | $CONH_2$ | H | $CF_3$ | 2 | |
| 14-7 | CONHMe | H | $CF_3$ | 2 | |
| 14-8 | CONHi-Pr | H | $CF_3$ | 2 | |
| 14-9 | CONHc-Pr | H | $CF_3$ | 2 | |
| 14-10 | $CONHCH_2CF_3$ | H | $CF_3$ | 2 | |
| 14-11 | $CONHCH_2$c-Pr | H | $CF_3$ | 2 | |
| 14-12 | $CONMe_2$ | H | $CF_3$ | 2 | |
| 14-13 | CN | H | $CF_3$ | 2 | |
| 14-14 | CHO | H | $CF_3$ | 2 | |
| 14-15 | C(=O)Me | H | $CF_3$ | 2 | |
| 14-16 | $CH_2OH$ | H | $CF_3$ | 2 | |
| 14-17 | $CH_2OMe$ | H | $CF_3$ | 2 | |
| 14-18 | $CH_2O$i-Pr | H | $CF_3$ | 2 | |
| 14-19 | $CH_2OCH_2CF_3$ | H | $CF_3$ | 2 | |
| 14-20 | $CH_2OCH_2$c-Pr | H | $CF_3$ | 2 | |
| 14-21 | $CH_2OC$(=O)Me | H | $CF_3$ | 2 | |
| 14-22 | $CH_2OC$(=O)i-Pr | H | $CF_3$ | 2 | |
| 14-23 | $CH_2OC$(=O)c-Pr | H | $CF_3$ | 2 | |
| 14-24 | $CH_2OC$(=O)OMe | H | $CF_3$ | 2 | |
| 14-25 | $CH_2OC$(=O)NHMe | H | $CF_3$ | 2 | |
| 14-26 | $CH_2OC$(=O)$NMe_2$ | H | $CF_3$ | 2 | |
| 14-27 | $CH_2CN$ | H | $CF_3$ | 2 | |
| 14-28 | $CH_2NH_2$ | H | $CF_3$ | 2 | |
| 14-29 | $CH_2NHMe$ | H | $CF_3$ | 2 | |
| 14-30 | $CH_2NH$i-Pr | H | $CF_3$ | 2 | |
| 14-31 | $CH_2NH$c-Pr | H | $CF_3$ | 2 | |
| 14-32 | $CH_2NHCH_2CF_3$ | H | $CF_3$ | 2 | |
| 14-33 | $CH_2NHCH_2$c-Pr | H | $CF_3$ | 2 | |
| 14-34 | $CH_2NMe_2$ | H | $CF_3$ | 2 | |
| 14-35 | $CH_2NHAc$ | H | $CF_3$ | 2 | |
| 14-36 | $CH_2N(Ac)Me$ | H | $CF_3$ | 2 | |
| 14-37 | $CH_2N(Ac)$i-Pr | H | $CF_3$ | 2 | |
| 14-38 | $CH_2N(Ac)$c-Pr | H | $CF_3$ | 2 | |
| 14-39 | $CH_2N(Ac)CH_2CF_3$ | H | $CF_3$ | 2 | |
| 14-40 | $CH_2N(Ac)CH_2$c-Pr | H | $CF_3$ | 2 | |
| 14-41 | $CH_2NHCOOMe$ | H | $CF_3$ | 2 | |
| 14-42 | $CH_2NHCOO$t-Bu | H | $CF_3$ | 2 | |
| 14-43 | $CH_2N(Me)CO_2Me$ | H | $CF_3$ | 2 | |
| 14-44 | $CH_2N(Me)COO$t-Bu | H | $CF_3$ | 2 | |
| 14-45 | $CH_2NHCONHMe$ | H | $CF_3$ | 2 | |
| 14-46 | $CH_2N(Me)CONHMe$ | H | $CF_3$ | 2 | |
| 14-47 | $CH_2SMe$ | H | $CF_3$ | 2 | |
| 14-48 | $CH_2SOMe$ | H | $CF_3$ | 2 | |
| 14-49 | $CH_2SO_2Me$ | H | $CF_3$ | 2 | |
| 14-50 | CH=NOH | H | $CF_3$ | 2 | |
| 14-51 | CH=NOMe | H | $CF_3$ | 2 | |
| 14-52 | CH=NOi-Pr | H | $CF_3$ | 2 | |
| 14-53 | CH=$NOCH_2CF_3$ | H | $CF_3$ | 2 | |
| 14-54 | CH=$NOCH_2$c-Pr | H | $CF_3$ | 2 | |
| 14-55 | C(Me)=NOH | H | $CF_3$ | 2 | |
| 14-56 | C(Me)=NOMe | H | $CF_3$ | 2 | |
| 14-57 | C(Me)=NOi-Pr | H | $CF_3$ | 2 | |
| 14-58 | C(Me)=$NOCH_2CF_3$ | H | $CF_3$ | 2 | |
| 14-59 | C(Me)=$NOCH_2$c-Pr | H | $CF_3$ | 2 | |
| 14-60 | $NH_2$ | H | $CF_3$ | 2 | |
| 14-61 | NHMe | H | $CF_3$ | 2 | |
| 14-62 | NHi-Pr | H | $CF_3$ | 2 | |
| 14-63 | $NHCH_2CF_3$ | H | $CF_3$ | 2 | |
| 14-64 | $NHCH_2$c-Pr | H | $CF_3$ | 2 | |
| 14-65 | $NMe_2$ | H | $CF_3$ | 2 | |
| 14-66 | $N(Me)CH_2CF_3$ | H | $CF_3$ | 2 | |
| 14-67 | $N(Me)CH_2$c-Pr | H | $CF_3$ | 2 | |
| 14-68 | NHAc | H | $CF_3$ | 2 | |
| 14-69 | N(Ac)Me | H | $CF_3$ | 2 | |
| 14-70 | N(Ac)i-Pr | H | $CF_3$ | 2 | |
| 14-71 | $N(Ac)CH_2CF_3$ | H | $CF_3$ | 2 | |
| 14-72 | $N(Ac)CH_2$c-Pr | H | $CF_3$ | 2 | |
| 14-73 | NHCOOMe | H | $CF_3$ | 2 | |
| 14-74 | N(COOMe)Me | H | $CF_3$ | 2 | |
| 14-75 | N(COOMe)i-Pr | H | $CF_3$ | 2 | |
| 14-76 | $N(COOMe)CH_2CF_3$ | H | $CF_3$ | 2 | |
| 14-77 | $N(COOMe)CH_2$c-Pr | H | $CF_3$ | 2 | |
| 14-78 | $NHCONMe_2$ | H | $CF_3$ | 2 | |

-continued

| Compound No. | $R^{21}$ | $R^{22}$ | $R^3$ | m | Physical Property |
|---|---|---|---|---|---|
| 14-79 | N(CONMe$_2$)Me | H | CF$_3$ | 2 | |
| 14-80 | CH$_2$Cl | H | CF$_3$ | 2 | |
| 14-81 | H | CO$_2$H | CF$_3$ | 2 | |
| 14-82 | H | CO$_2$Me | CF$_3$ | 2 | |
| 14-83 | H | CO$_2$i-Pr | CF$_3$ | 2 | |
| 14-84 | H | CO$_2$CH$_2$CF$_3$ | CF$_3$ | 2 | |
| 14-85 | H | CO$_2$CH$_2$c-Pr | CF$_3$ | 2 | |
| 14-86 | H | CONH$_2$ | CF$_3$ | 2 | |
| 14-87 | H | CONHMe | CF$_3$ | 2 | |
| 14-88 | H | CONHi-Pr | CF$_3$ | 2 | |
| 14-89 | H | CONHc-Pr | CF$_3$ | 2 | |
| 14-90 | H | CONHCH$_2$CF$_3$ | CF$_3$ | 2 | |
| 14-91 | H | CONHCH$_2$c-Pr | CF$_3$ | 2 | |
| 14-92 | H | CONMe$_2$ | CF$_3$ | 2 | |
| 14-93 | H | CN | CF$_3$ | 2 | |
| 14-94 | H | CHO | CF$_3$ | 2 | |
| 14-95 | H | C(=O)Me | CF$_3$ | 2 | |
| 14-96 | H | CH$_2$OH | CF$_3$ | 2 | |
| 14-97 | H | CH$_2$OMe | CF$_3$ | 2 | |
| 14-98 | H | CH$_2$Oi-Pr | CF$_3$ | 2 | |
| 14-99 | H | CH$_2$OCH$_2$CF$_3$ | CF$_3$ | 2 | |
| 14-100 | H | CH$_2$OCH$_2$c-Pr | CF$_3$ | 2 | |
| 14-101 | H | CH$_2$OC(=O)Me | CF$_3$ | 2 | |
| 14-102 | H | CH$_2$OC(=O)i-Pr | CF$_3$ | 2 | |
| 14-103 | H | CH$_2$OC(=O)c-Pr | CF$_3$ | 2 | |
| 14-104 | H | CH$_2$OC(=O)OMe | CF$_3$ | 2 | |
| 14-105 | H | CH$_2$OC(=O)NHMe | CF$_3$ | 2 | |
| 14-106 | H | CH$_2$OC(=O)NMe$_2$ | CF$_3$ | 2 | |
| 14-107 | H | CH$_2$CN | CF$_3$ | 2 | |
| 14-108 | H | CH$_2$NH$_2$ | CF$_3$ | 2 | |
| 14-109 | H | CH$_2$NHMe | CF$_3$ | 2 | |
| 14-110 | H | CH$_2$NHi-Pr | CF$_3$ | 2 | |
| 14-111 | H | CH$_2$NHc-Pr | CF$_3$ | 2 | |
| 14-112 | H | CH$_2$NHCH$_2$CF$_3$ | CF$_3$ | 2 | |
| 14-113 | H | CH$_2$NHCH$_2$c-Pr | CF$_3$ | 2 | |
| 14-114 | H | CH$_2$NMe$_2$ | CF$_3$ | 2 | |
| 14-115 | H | CH$_2$NHAc | CF$_3$ | 2 | |
| 14-116 | H | CH$_2$N(Ac)Me | CF$_3$ | 2 | |
| 14-117 | H | CH$_2$N(Ac)i-Pr | CF$_3$ | 2 | |
| 14-118 | H | CH$_2$N(Ac)c-Pr | CF$_3$ | 2 | |
| 14-119 | H | CH$_2$N(Ac)CH$_2$CF$_3$ | CF$_3$ | 2 | |
| 14-120 | H | CH$_2$N(Ac)CH$_2$c-Pr | CF$_3$ | 2 | |
| 14-121 | H | CH$_2$NHCOOMe | CF$_3$ | 2 | |
| 14-122 | H | CH$_2$NHCOOt-Bu | CF$_3$ | 2 | |
| 14-123 | H | CH$_2$N(Me)CO$_2$Me | CF$_3$ | 2 | |
| 14-124 | H | CH$_2$N(Me)COOt-Bu | CF$_3$ | 2 | |
| 14-125 | H | CH$_2$NHCONHMe | CF$_3$ | 2 | |
| 14-126 | H | CH$_2$N(Me)CONHMe | CF$_3$ | 2 | |
| 14-127 | H | CH$_2$SMe | CF$_3$ | 2 | |
| 14-128 | H | CH$_2$SOMe | CF$_3$ | 2 | |
| 14-129 | H | CH$_2$SO$_2$Me | CF$_3$ | 2 | |
| 14-130 | H | CH=NOH | CF$_3$ | 2 | |
| 14-131 | H | CH=NOMe | CF$_3$ | 2 | |
| 14-132 | H | CH=NOi-Pr | CF$_3$ | 2 | |
| 14-133 | H | CH=NOCH$_2$CF$_3$ | CF$_3$ | 2 | |
| 14-134 | H | CH=NOCH$_2$c-Pr | CF$_3$ | 2 | |
| 14-135 | H | C(Me)=NOH | CF$_3$ | 2 | |
| 14-136 | H | C(Me)=NOMe | CF$_3$ | 2 | |
| 14-137 | H | C(Me)=NOi-Pr | CF$_3$ | 2 | |
| 14-138 | H | C(Me)=NOCH$_2$CF$_3$ | CF$_3$ | 2 | |
| 14-139 | H | C(Me)=NOCH$_2$c-Pr | CF$_3$ | 2 | |
| 14-140 | H | NH$_2$ | CF$_3$ | 2 | |
| 14-141 | H | NHMe | CF$_3$ | 2 | |
| 14-142 | H | NHi-Pr | CF$_3$ | 2 | |
| 14-143 | H | NHCH$_2$CF$_3$ | CF$_3$ | 2 | |
| 14-144 | H | NHCH$_2$c-Pr | CF$_3$ | 2 | |
| 14-145 | H | NMe$_2$ | CF$_3$ | 2 | |
| 14-146 | H | N(Me)CH$_2$CF$_3$ | CF$_3$ | 2 | |
| 14-147 | H | N(Me)CH$_2$c-Pr | CF$_3$ | 2 | |
| 14-148 | H | NHAc | CF$_3$ | 2 | |
| 14-149 | H | N(Ac)Me | CF$_3$ | 2 | |
| 14-150 | H | N(Ac)i-Pr | CF$_3$ | 2 | |
| 14-151 | H | N(Ac)CH$_2$CF$_3$ | CF$_3$ | 2 | |
| 14-152 | H | N(Ac)CH$_2$c-Pr | CF$_3$ | 2 | |
| 14-153 | H | NHCOOMe | CF$_3$ | 2 | |
| 14-154 | H | N(COOMe)Me | CF$_3$ | 2 | |

-continued

| Compound No. | $R^{21}$ | $R^{22}$ | $R^3$ | m | Physical Property |
|---|---|---|---|---|---|
| 14-155 | H | N(COOMe)i-Pr | $CF_3$ | 2 | |
| 14-156 | H | N(COOMe)$CH_2CF_3$ | $CF_3$ | 2 | |
| 14-157 | H | N(COOMe)$CH_2$c-Pr | $CF_3$ | 2 | |
| 14-158 | H | $NHCONMe_2$ | $CF_3$ | 2 | |
| 14-159 | H | N($CONMe_2$)Me | $CF_3$ | 2 | |
| 14-160 | H | $CH_2Cl$ | $CF_3$ | 2 | |
| 14-161 | $CO_2H$ | H | $SCF_3$ | 2 | |
| 14-162 | $CO_2Me$ | H | $SCF_3$ | 2 | |
| 14-163 | $CO_2$i-Pr | H | $SCF_3$ | 2 | |
| 14-164 | $CO_2CH_2CF_3$ | H | $SCF_3$ | 2 | |
| 14-165 | $CO_2CH_2$c-Pr | H | $SCF_3$ | 2 | |
| 14-166 | $CONH_2$ | H | $SCF_3$ | 2 | |
| 14-167 | CONHMe | H | $SCF_3$ | 2 | |
| 14-168 | CONHi-Pr | H | $SCF_3$ | 2 | |
| 14-169 | CONHc-Pr | H | $SCF_3$ | 2 | |
| 14-170 | $CONHCH_2CF_3$ | H | $SCF_3$ | 2 | |
| 14-171 | $CONHCH_2$c-Pr | H | $SCF_3$ | 2 | |
| 14-172 | $CONMe_2$ | H | $SCF_3$ | 2 | |
| 14-173 | CN | H | $SCF_3$ | 2 | |
| 14-174 | CHO | H | $SCF_3$ | 2 | |
| 14-175 | C(=O)Me | H | $SCF_3$ | 2 | |
| 14-176 | $CH_2OH$ | H | $SCF_3$ | 2 | |
| 14-177 | $CH_2OMe$ | H | $SCF_3$ | 2 | |
| 14-178 | $CH_2O$i-Pr | H | $SCF_3$ | 2 | |
| 14-179 | $CH_2OCH_2CF_3$ | H | $SCF_3$ | 2 | |
| 14-180 | $CH_2OCH_2$c-Pr | H | $SCF_3$ | 2 | |
| 14-181 | $CH_2OC(=O)Me$ | H | $SCF_3$ | 2 | |
| 14-182 | $CH_2OC(=O)$i-Pr | H | $SCF_3$ | 2 | |
| 14-183 | $CH_2OC(=O)$c-Pr | H | $SCF_3$ | 2 | |
| 14-184 | $CH_2OC(=O)OMe$ | H | $SCF_3$ | 2 | |
| 14-185 | $CH_2OC(=O)NHMe$ | H | $SCF_3$ | 2 | |
| 14-186 | $CH_2OC(=O)NMe_2$ | H | $SCF_3$ | 2 | |
| 14-187 | $CH_2CN$ | H | $SCF_3$ | 2 | |
| 14-188 | $CH_2NH_2$ | H | $SCF_3$ | 2 | |
| 14-189 | $CH_2NHMe$ | H | $SCF_3$ | 2 | |
| 14-190 | $CH_2NH$i-Pr | H | $SCF_3$ | 2 | |
| 14-191 | $CH_2NH$c-Pr | H | $SCF_3$ | 2 | |
| 14-192 | $CH_2NHCH_2CF_3$ | H | $SCF_3$ | 2 | |
| 14-193 | $CH_2NHCH_2$c-Pr | H | $SCF_3$ | 2 | |
| 14-194 | $CH_2NMe_2$ | H | $SCF_3$ | 2 | |
| 14-195 | $CH_2NHAc$ | H | $SCF_3$ | 2 | |
| 14-196 | $CH_2N(Ac)Me$ | H | $SCF_3$ | 2 | |
| 14-197 | $CH_2N(Ac)$i-Pr | H | $SCF_3$ | 2 | |
| 14-198 | $CH_2N(Ac)$c-Pr | H | $SCF_3$ | 2 | |
| 14-199 | $CH_2N(Ac)CH_2CF_3$ | H | $SCF_3$ | 2 | |
| 14-200 | $CH_2N(Ac)CH_2$c-Pr | H | $SCF_3$ | 2 | |
| 14-201 | $CH_2NHCOOMe$ | H | $SCF_3$ | 2 | |
| 14-202 | $CH_2NHCOO$t-Bu | H | $SCF_3$ | 2 | |
| 14-203 | $CH_2N(Me)CO_2Me$ | H | $SCF_3$ | 2 | |
| 14-204 | $CH_2N(Me)COO$t-Bu | H | $SCF_3$ | 2 | |
| 14-205 | $CH_2NHCONHMe$ | H | $SCF_3$ | 2 | |
| 14-206 | $CH_2N(Me)CONHMe$ | H | $SCF_3$ | 2 | |
| 14-207 | $CH_2SMe$ | H | $SCF_3$ | 2 | |
| 14-208 | $CH_2SOMe$ | H | $SCF_3$ | 2 | |
| 14-209 | $CH_2SO_2Me$ | H | $SCF_3$ | 2 | |
| 14-210 | CH=NOH | H | $SCF_3$ | 2 | |
| 14-211 | CH=NOMe | H | $SCF_3$ | 2 | |
| 14-212 | CH=NOi-Pr | H | $SCF_3$ | 2 | |
| 14-213 | CH=NO$CH_2CF_3$ | H | $SCF_3$ | 2 | |
| 14-214 | CH=NO$CH_2$c-Pr | H | $SCF_3$ | 2 | |
| 14-215 | C(Me)=NOH | H | $SCF_3$ | 2 | |
| 14-216 | C(Me)=NOMe | H | $SCF_3$ | 2 | |
| 14-217 | C(Me)=NOi-Pr | H | $SCF_3$ | 2 | |
| 14-218 | C(Me)=NO$CH_2CF_3$ | H | $SCF_3$ | 2 | |
| 14-219 | C(Me)=NO$CH_2$c-Pr | H | $SCF_3$ | 2 | |
| 14-220 | $NH_2$ | H | $SCF_3$ | 2 | |
| 14-221 | NHMe | H | $SCF_3$ | 2 | |
| 14-222 | NHi-Pr | H | $SCF_3$ | 2 | |
| 14-223 | $NHCH_2CF_3$ | H | $SCF_3$ | 2 | |
| 14-224 | $NHCH_2$c-Pr | H | $SCF_3$ | 2 | |
| 14-225 | $NMe_2$ | H | $SCF_3$ | 2 | |
| 14-226 | N(Me)$CH_2CF_3$ | H | $SCF_3$ | 2 | |
| 14-227 | N(Me)$CH_2$c-Pr | H | $SCF_3$ | 2 | |
| 14-228 | NHAc | H | $SCF_3$ | 2 | |
| 14-229 | N(Ac)Me | H | $SCF_3$ | 2 | |
| 14-230 | N(Ac)i-Pr | H | $SCF_3$ | 2 | |

-continued

| Compound No. | $R^{21}$ | $R^{22}$ | $R^3$ | m | Physical Property |
|---|---|---|---|---|---|
| 14-231 | N(Ac)CH$_2$CF$_3$ | H | SCF$_3$ | 2 | |
| 14-232 | N(Ac)CH$_2$c-Pr | H | SCF$_3$ | 2 | |
| 14-233 | NHCOOMe | H | SCF$_3$ | 2 | |
| 14-234 | N(COOMe)Me | H | SCF$_3$ | 2 | |
| 14-235 | N(COOMe)i-Pr | H | SCF$_3$ | 2 | |
| 14-236 | N(COOMe)CH$_2$CF$_3$ | H | SCF$_3$ | 2 | |
| 14-237 | N(COOMe)CH$_2$c-Pr | H | SCF$_3$ | 2 | |
| 14-238 | NHCONMe$_2$ | H | SCF$_3$ | 2 | |
| 14-239 | N(CONMe$_2$)Me | H | SCF$_3$ | 2 | |
| 14-240 | CH$_2$Cl | H | SCF$_3$ | 2 | |
| 14-241 | H | CO$_2$H | SCF$_3$ | 2 | |
| 14-242 | H | CO$_2$Me | SCF$_3$ | 2 | |
| 14-243 | H | CO$_2$i-Pr | SCF$_3$ | 2 | |
| 14-244 | H | CO$_2$CH$_2$CF$_3$ | SCF$_3$ | 2 | |
| 14-245 | H | CO$_2$CH$_2$c-Pr | SCF$_3$ | 2 | |
| 14-246 | H | CONH$_2$ | SCF$_3$ | 2 | |
| 14-247 | H | CONHMe | SCF$_3$ | 2 | |
| 14-248 | H | CONHi-Pr | SCF$_3$ | 2 | |
| 14-249 | H | CONHc-Pr | SCF$_3$ | 2 | |
| 14-250 | H | CONHCH$_2$CF$_3$ | SCF$_3$ | 2 | |
| 14-251 | H | CONHCH$_2$c-Pr | SCF$_3$ | 2 | |
| 14-252 | H | CONMe$_2$ | SCF$_3$ | 2 | |
| 14-253 | H | CN | SCF$_3$ | 2 | |
| 14-254 | H | CHO | SCF$_3$ | 2 | |
| 14-255 | H | C(=O)Me | SCF$_3$ | 2 | |
| 14-256 | H | CH$_2$OH | SCF$_3$ | 2 | |
| 14-257 | H | CH$_2$OMe | SCF$_3$ | 2 | |
| 14-258 | H | CH$_2$Oi-Pr | SCF$_3$ | 2 | |
| 14-259 | H | CH$_2$OCH$_2$CF$_3$ | SCF$_3$ | 2 | |
| 14-260 | H | CH$_2$OCH$_2$c-Pr | SCF$_3$ | 2 | |
| 14-261 | H | CH$_2$OC(=O)Me | SCF$_3$ | 2 | |
| 14-262 | H | CH$_2$OC(=O)i-Pr | SCF$_3$ | 2 | |
| 14-263 | H | CH$_2$OC(=O)c-Pr | SCF$_3$ | 2 | |
| 14-264 | H | CH$_2$OC(=O)OMe | SCF$_3$ | 2 | |
| 14-265 | H | CH$_2$OC(=O)NHMe | SCF$_3$ | 2 | |
| 14-266 | H | CH$_2$OC(=O)NMe$_2$ | SCF$_3$ | 2 | |
| 14-267 | H | CH$_2$CN | SCF$_3$ | 2 | |
| 14-268 | H | CH$_2$NH$_2$ | SCF$_3$ | 2 | |
| 14-269 | H | CH$_2$NHMe | SCF$_3$ | 2 | |
| 14-270 | H | CH$_2$NHi-Pr | SCF$_3$ | 2 | |
| 14-271 | H | CH$_2$NHc-Pr | SCF$_3$ | 2 | |
| 14-272 | H | CH$_2$NHCH$_2$CF$_3$ | SCF$_3$ | 2 | |
| 14-273 | H | CH$_2$NHCH$_2$c-Pr | SCF$_3$ | 2 | |
| 14-274 | H | CH$_2$NMe$_2$ | SCF$_3$ | 2 | |
| 14-275 | H | CH$_2$NHAc | SCF$_3$ | 2 | |
| 14-276 | H | CH$_2$N(Ac)Me | SCF$_3$ | 2 | |
| 14-277 | H | CH$_2$N(Ac)i-Pr | SCF$_3$ | 2 | |
| 14-278 | H | CH$_2$N(Ac)c-Pr | SCF$_3$ | 2 | |
| 14-279 | H | CH$_2$N(Ac)CH$_2$CF$_3$ | SCF$_3$ | 2 | |
| 14-280 | H | CH$_2$N(Ac)CH$_2$c-Pr | SCF$_3$ | 2 | |
| 14-281 | H | CH$_2$NHCOOMe | SCF$_3$ | 2 | |
| 14-282 | H | CH$_2$NHCOOt-Bu | SCF$_3$ | 2 | |
| 14-283 | H | CH$_2$N(Me)CO$_2$Me | SCF$_3$ | 2 | |
| 14-284 | H | CH$_2$N(Me)COOt-Bu | SCF$_3$ | 2 | |
| 14-285 | H | CH$_2$NHCONHMe | SCF$_3$ | 2 | |
| 14-286 | H | CH$_2$N(Me)CONHMe | SCF$_3$ | 2 | |
| 14-287 | H | CH$_2$SMe | SCF$_3$ | 2 | |
| 14-288 | H | CH$_2$SOMe | SCF$_3$ | 2 | |
| 14-289 | H | CH$_2$SO$_2$Me | SCF$_3$ | 2 | |
| 14-290 | H | CH=NOH | SCF$_3$ | 2 | |
| 14-291 | H | CH=NOMe | SCF$_3$ | 2 | |
| 14-292 | H | CH=NOi-Pr | SCF$_3$ | 2 | |
| 14-293 | H | CH=NOCH$_2$CF$_3$ | SCF$_3$ | 2 | |
| 14-294 | H | CH=NOCH$_2$c-Pr | SCF$_3$ | 2 | |
| 14-295 | H | C(Me)=NOH | SCF$_3$ | 2 | |
| 14-296 | H | C(Me)=NOMe | SCF$_3$ | 2 | |
| 14-297 | H | C(Me)=NOi-Pr | SCF$_3$ | 2 | |
| 14-298 | H | C(Me)=NOCH$_2$CF$_3$ | SCF$_3$ | 2 | |
| 14-299 | H | C(Me)=NOCH$_2$c-Pr | SCF$_3$ | 2 | |
| 14-300 | H | NH$_2$ | SCF$_3$ | 2 | |
| 14-301 | H | NHMe | SCF$_3$ | 2 | |
| 14-302 | H | NHi-Pr | SCF$_3$ | 2 | |
| 14-303 | H | NHCH$_2$CF$_3$ | SCF$_3$ | 2 | |
| 14-304 | H | NHCH$_2$c-Pr | SCF$_3$ | 2 | |
| 14-305 | H | NMe$_2$ | SCF$_3$ | 2 | |
| 14-306 | H | N(Me)CH$_2$CF$_3$ | SCF$_3$ | 2 | |

| Compound No. | R²¹ | R²² | R³ | m | Physical Property |
|---|---|---|---|---|---|
| 14-307 | H | N(Me)CH₂c-Pr | SCF₃ | 2 | |
| 14-308 | H | NHAc | SCF₃ | 2 | |
| 14-309 | H | N(Ac)Me | SCF₃ | 2 | |
| 14-310 | H | N(Ac)i-Pr | SCF₃ | 2 | |
| 14-311 | H | N(Ac)CH₂CF₃ | SCF₃ | 2 | |
| 14-312 | H | N(Ac)CH₂c-Pr | SCF₃ | 2 | |
| 14-313 | H | NHCOOMe | SCF₃ | 2 | |
| 14-314 | H | N(COOMe)Me | SCF₃ | 2 | |
| 14-315 | H | N(COOMe)i-Pr | SCF₃ | 2 | |
| 14-316 | H | N(COOMe)CH₂CF₃ | SCF₃ | 2 | |
| 14-317 | H | N(COOMe)CH₂c-Pr | SCF₃ | 2 | |
| 14-318 | H | NHCONMe₂ | SCF₃ | 2 | |
| 14-319 | H | N(CONMe₂)Me | SCF₃ | 2 | |
| 14-320 | H | CH₂Cl | SCF₃ | 2 | |

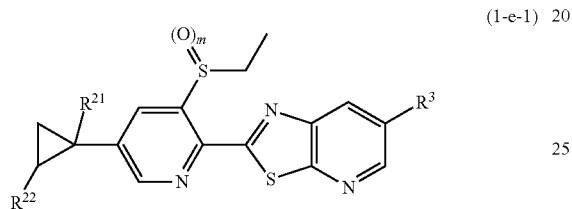

(1-e-1)

| Compound No. | R²¹ | R²² | R³ | m | Physical Property |
|---|---|---|---|---|---|
| 15-1 | CO₂H | H | CF₃ | 2 | |
| 15-2 | CO₂Me | H | CF₃ | 2 | |
| 15-3 | CO₂i-Pr | H | CF₃ | 2 | |
| 15-4 | CO₂CH₂CF₃ | H | CF₃ | 2 | |
| 15-5 | CO₂CH₂c-Pr | H | CF₃ | 2 | |
| 15-6 | CONH₂ | H | CF₃ | 2 | |
| 15-7 | CONHMe | H | CF₃ | 2 | |
| 15-8 | CONHi-Pr | H | CF₃ | 2 | |
| 15-9 | CONHc-Pr | H | CF₃ | 2 | |
| 15-10 | CONHCH₂CF₃ | H | CF₃ | 2 | |
| 15-11 | CONHCH₂c-Pr | H | CF₃ | 2 | |
| 15-12 | CONMe₂ | H | CF₃ | 2 | |
| 15-13 | CN | H | CF₃ | 2 | |
| 15-14 | CHO | H | CF₃ | 2 | |
| 15-15 | C(=O)Me | H | CF₃ | 2 | |
| 15-16 | CH₂OH | H | CF₃ | 2 | |
| 15-17 | CH₂OMe | H | CF₃ | 2 | |
| 15-18 | CH₂Oi-Pr | H | CF₃ | 2 | |
| 15-19 | CH₂OCH₂CF₃ | H | CF₃ | 2 | |
| 15-20 | CH₂OCH₂c-Pr | H | CF₃ | 2 | |
| 15-21 | CH₂OC(=O)Me | H | CF₃ | 2 | |
| 15-22 | CH₂OC(=O)i-Pr | H | CF₃ | 2 | |
| 15-23 | CH₂OC(=O)c-Pr | H | CF₃ | 2 | |
| 15-24 | CH₂OC(=O)OMe | H | CF₃ | 2 | |
| 15-25 | CH₂OC(=O)NHMe | H | CF₃ | 2 | |
| 15-26 | CH₂OC(=O)NMe₂ | H | CF₃ | 2 | |
| 15-27 | CH₂CN | H | CF₃ | 2 | |
| 15-28 | CH₂NH₂ | H | CF₃ | 2 | |
| 15-29 | CH₂NHMe | H | CF₃ | 2 | |
| 15-30 | CH₂NHi-Pr | H | CF₃ | 2 | |
| 15-31 | CH₂NHc-Pr | H | CF₃ | 2 | |
| 15-32 | CH₂NHCH₂CF₃ | H | CF₃ | 2 | |
| 15-33 | CH₂NHCH₂c-Pr | H | CF₃ | 2 | |
| 15-34 | CH₂NMe₂ | H | CF₃ | 2 | |
| 15-35 | CH₂NHAc | H | CF₃ | 2 | |
| 15-36 | CH₂N(Ac)Me | H | CF₃ | 2 | |
| 15-37 | CH₂N(Ac)i-Pr | H | CF₃ | 2 | |
| 15-38 | CH₂N(Ac)c-Pr | H | CF₃ | 2 | |
| 15-39 | CH₂N(Ac)CH₂CF₃ | H | CF₃ | 2 | |
| 15-40 | CH₂N(Ac)CH₂c-Pr | H | CF₃ | 2 | |
| 15-41 | CH₂NHCOOMe | H | CF₃ | 2 | |

-continued

| Compound No. | $R^{21}$ | $R^{22}$ | $R^3$ | m | Physical Property |
|---|---|---|---|---|---|
| 15-42 | CH$_2$NHCOOt-Bu | H | CF$_3$ | 2 | |
| 15-43 | CH$_2$N(Me)CO$_2$Me | H | CF$_3$ | 2 | |
| 15-44 | CH$_2$N(Me)COOt-Bu | H | CF$_3$ | 2 | |
| 15-45 | CH$_2$NHCONHMe | H | CF$_3$ | 2 | |
| 15-46 | CH$_2$N(Me)CONHMe | H | CF$_3$ | 2 | |
| 15-47 | CH$_2$SMe | H | CF$_3$ | 2 | |
| 15-48 | CH$_2$SOMe | H | CF$_3$ | 2 | |
| 15-49 | CH$_2$SO$_2$Me | H | CF$_3$ | 2 | |
| 15-50 | CH=NOH | H | CF$_3$ | 2 | |
| 15-51 | CH=NOMe | H | CF$_3$ | 2 | |
| 15-52 | CH=NOi-Pr | H | CF$_3$ | 2 | |
| 15-53 | CH=NOCH$_2$CF$_3$ | H | CF$_3$ | 2 | |
| 15-54 | CH=NOCH$_2$c-Pr | H | CF$_3$ | 2 | |
| 15-55 | C(Me)=NOH | H | CF$_3$ | 2 | |
| 15-56 | C(Me)=NOMe | H | CF$_3$ | 2 | |
| 15-57 | C(Me)=NOi-Pr | H | CF$_3$ | 2 | |
| 15-58 | C(Me)=NOCH$_2$CF$_3$ | H | CF$_3$ | 2 | |
| 15-59 | C(Me)=NOCH$_2$c-Pr | H | CF$_3$ | 2 | |
| 15-60 | NH$_2$ | H | CF$_3$ | 2 | |
| 15-61 | NHMe | H | CF$_3$ | 2 | |
| 15-62 | NHi-Pr | H | CF$_3$ | 2 | |
| 15-63 | NHCH$_2$CF$_3$ | H | CF$_3$ | 2 | |
| 15-64 | NHCH$_2$c-Pr | H | CF$_3$ | 2 | |
| 15-65 | NMe$_2$ | H | CF$_3$ | 2 | |
| 15-66 | N(Me)CH$_2$CF$_3$ | H | CF$_3$ | 2 | |
| 15-67 | N(Me)CH$_2$c-Pr | H | CF$_3$ | 2 | |
| 15-68 | NHAc | H | CF$_3$ | 2 | |
| 15-69 | N(Ac)Me | H | CF$_3$ | 2 | |
| 15-70 | N(Ac)i-Pr | H | CF$_3$ | 2 | |
| 15-71 | N(Ac)CH$_2$CF$_3$ | H | CF$_3$ | 2 | |
| 15-72 | N(Ac)CH$_2$c-Pr | H | CF$_3$ | 2 | |
| 15-73 | NHCOOMe | H | CF$_3$ | 2 | |
| 15-74 | N(COOMe)Me | H | CF$_3$ | 2 | |
| 15-75 | N(COOMe)i-Pr | H | CF$_3$ | 2 | |
| 15-76 | N(COOMe)CH$_2$CF$_3$ | H | CF$_3$ | 2 | |
| 15-77 | N(COOMe)CH$_2$c-Pr | H | CF$_3$ | 2 | |
| 15-78 | NHCONMe$_2$ | H | CF$_3$ | 2 | |
| 15-79 | N(CONMe$_2$)Me | H | CF$_3$ | 2 | |
| 15-80 | CH$_2$Cl | H | CF$_3$ | 2 | |
| 15-81 | H | CO$_2$H | CF$_3$ | 2 | |
| 15-82 | H | CO$_2$Me | CF$_3$ | 2 | |
| 15-83 | H | CO$_2$i-Pr | CF$_3$ | 2 | |
| 15-84 | H | CO$_2$CH$_2$CF$_3$ | CF$_3$ | 2 | |
| 15-85 | H | CO$_2$CH$_2$c-Pr | CF$_3$ | 2 | |
| 15-86 | H | CONH$_2$ | CF$_3$ | 2 | |
| 15-87 | H | CONHMe | CF$_3$ | 2 | |
| 15-88 | H | CONHi-Pr | CF$_3$ | 2 | |
| 15-89 | H | CONHc-Pr | CF$_3$ | 2 | |
| 15-90 | H | CONHCH$_2$CF$_3$ | CF$_3$ | 2 | |
| 15-91 | H | CONHCH$_2$c-Pr | CF$_3$ | 2 | |
| 15-92 | H | CONMe$_2$ | CF$_3$ | 2 | |
| 15-93 | H | CN | CF$_3$ | 2 | |
| 15-94 | H | CHO | CF$_3$ | 2 | |
| 15-95 | H | C(=O)Me | CF$_3$ | 2 | |
| 15-96 | H | CH$_2$OH | CF$_3$ | 2 | |
| 15-97 | H | CH$_2$OMe | CF$_3$ | 2 | |
| 15-98 | H | CH$_2$Oi-Pr | CF$_3$ | 2 | |
| 15-99 | H | CH$_2$OCH$_2$CF$_3$ | CF$_3$ | 2 | |
| 15-100 | H | CH$_2$OCH$_2$c-Pr | CF$_3$ | 2 | |
| 15-101 | H | CH$_2$OC(=O)Me | CF$_3$ | 2 | |
| 15-102 | H | CH$_2$OC(=O)i-Pr | CF$_3$ | 2 | |
| 15-103 | H | CH$_2$OC(=O)c-Pr | CF$_3$ | 2 | |
| 15-104 | H | CH$_2$OC(=O)OMe | CF$_3$ | 2 | |
| 15-105 | H | CH$_2$OC(=O)NHMe | CF$_3$ | 2 | |
| 15-106 | H | CH$_2$OC(=O)NMe$_2$ | CF$_3$ | 2 | |
| 15-107 | H | CH$_2$CN | CF$_3$ | 2 | |
| 15-108 | H | CH$_2$NH$_2$ | CF$_3$ | 2 | |
| 15-109 | H | CH$_2$NHMe | CF$_3$ | 2 | |
| 15-110 | H | CH$_2$NHi-Pr | CF$_3$ | 2 | |
| 15-111 | H | CH$_2$NHc-Pr | CF$_3$ | 2 | |
| 15-112 | H | CH$_2$NHCH$_2$CF$_3$ | CF$_3$ | 2 | |
| 15-113 | H | CH$_2$NHCH$_2$c-Pr | CF$_3$ | 2 | |
| 15-114 | H | CH$_2$NMe$_2$ | CF$_3$ | 2 | |
| 15-115 | H | CH$_2$NHAc | CF$_3$ | 2 | |
| 15-116 | H | CH$_2$N(Ac)Me | CF$_3$ | 2 | |
| 15-117 | H | CH$_2$N(Ac)i-Pr | CF$_3$ | 2 | |

-continued

| Compound No. | $R^{21}$ | $R^{22}$ | $R^3$ | m | Physical Property |
|---|---|---|---|---|---|
| 15-118 | H | CH$_2$N(Ac)c-Pr | CF$_3$ | 2 | |
| 15-119 | H | CH$_2$N(Ac)CH$_2$CF$_3$ | CF$_3$ | 2 | |
| 15-120 | H | CH$_2$N(Ac)CH$_2$c-Pr | CF$_3$ | 2 | |
| 15-121 | H | CH$_2$NHCOOMe | CF$_3$ | 2 | |
| 15-122 | H | CH$_2$NHCOOt-Bu | CF$_3$ | 2 | |
| 15-123 | H | CH$_2$N(Me)CO$_2$Me | CF$_3$ | 2 | |
| 15-124 | H | CH$_2$N(Me)COOt-Bu | CF$_3$ | 2 | |
| 15-125 | H | CH$_2$NHCONHMe | CF$_3$ | 2 | |
| 15-126 | H | CH$_2$N(Me)CONHMe | CF$_3$ | 2 | |
| 15-127 | H | CH$_2$SMe | CF$_3$ | 2 | |
| 15-128 | H | CH$_2$SOMe | CF$_3$ | 2 | |
| 15-129 | H | CH$_2$SO$_2$Me | CF$_3$ | 2 | |
| 15-130 | H | CH=NOH | CF$_3$ | 2 | |
| 15-131 | H | CH=NOMe | CF$_3$ | 2 | |
| 15-132 | H | CH=NOi-Pr | CF$_3$ | 2 | |
| 15-133 | H | CH=NOCH$_2$CF$_3$ | CF$_3$ | 2 | |
| 15-134 | H | CH=NOCH$_2$c-Pr | CF$_3$ | 2 | |
| 15-135 | H | C(Me)=NOH | CF$_3$ | 2 | |
| 15-136 | H | C(Me)=NOMe | CF$_3$ | 2 | |
| 15-137 | H | C(Me)=NOi-Pr | CF$_3$ | 2 | |
| 15-138 | H | C(Me)=NOCH$_2$CF$_3$ | CF$_3$ | 2 | |
| 15-139 | H | C(Me)=NOCH$_2$c-Pr | CF$_3$ | 2 | |
| 15-140 | H | NH$_2$ | CF$_3$ | 2 | |
| 15-141 | H | NHMe | CF$_3$ | 2 | |
| 15-142 | H | NHi-Pr | CF$_3$ | 2 | |
| 15-143 | H | NHCH$_2$CF$_3$ | CF$_3$ | 2 | |
| 15-144 | H | NHCH$_2$c-Pr | CF$_3$ | 2 | |
| 15-145 | H | NMe$_2$ | CF$_3$ | 2 | |
| 15-146 | H | N(Me)CH$_2$CF$_3$ | CF$_3$ | 2 | |
| 15-147 | H | N(Me)CH$_2$c-Pr | CF$_3$ | 2 | |
| 15-148 | H | NHAc | CF$_3$ | 2 | |
| 15-149 | H | N(Ac)Me | CF$_3$ | 2 | |
| 15-150 | H | N(Ac)i-Pr | CF$_3$ | 2 | |
| 15-151 | H | N(Ac)CH$_2$CF$_3$ | CF$_3$ | 2 | |
| 15-152 | H | N(Ac)CH$_2$c-Pr | CF$_3$ | 2 | |
| 15-153 | H | NHCOOMe | CF$_3$ | 2 | |
| 15-154 | H | N(COOMe)Me | CF$_3$ | 2 | |
| 15-155 | H | N(COOMe)i-Pr | CF$_3$ | 2 | |
| 15-156 | H | N(COOMe)CH$_2$CF$_3$ | CF$_3$ | 2 | |
| 15-157 | H | N(COOMe)CH$_2$c-Pr | CF$_3$ | 2 | |
| 15-158 | H | NHCONMe$_2$ | CF$_3$ | 2 | |
| 15-159 | H | N(CONMe$_2$)Me | CF$_3$ | 2 | |
| 15-160 | H | CH$_2$Cl | CF$_3$ | 2 | |
| 15-161 | CO$_2$H | H | SCF$_3$ | 2 | |
| 15-162 | CO$_2$Me | H | SCF$_3$ | 2 | |
| 15-163 | CO$_2$i-Pr | H | SCF$_3$ | 2 | |
| 15-164 | CO$_2$CH$_2$CF$_3$ | H | SCF$_3$ | 2 | |
| 15-165 | CO$_2$CH$_2$c-Pr | H | SCF$_3$ | 2 | |
| 15-166 | CONH$_2$ | H | SCF$_3$ | 2 | |
| 15-167 | CONHMe | H | SCF$_3$ | 2 | |
| 15-168 | CONHi-Pr | H | SCF$_3$ | 2 | |
| 15-169 | CONHc-Pr | H | SCF$_3$ | 2 | |
| 15-170 | CONHCH$_2$CF$_3$ | H | SCF$_3$ | 2 | |
| 15-171 | CONHCH$_2$c-Pr | H | SCF$_3$ | 2 | |
| 15-172 | CONMe$_2$ | H | SCF$_3$ | 2 | |
| 15-173 | CN | H | SCF$_3$ | 2 | |
| 15-174 | CHO | H | SCF$_3$ | 2 | |
| 15-175 | C(=O)Me | H | SCF$_3$ | 2 | |
| 15-176 | CH$_2$OH | H | SCF$_3$ | 2 | |
| 15-177 | CH$_2$OMe | H | SCF$_3$ | 2 | |
| 15-178 | CH$_2$Oi-Pr | H | SCF$_3$ | 2 | |
| 15-179 | CH$_2$OCH$_2$CF$_3$ | H | SCF$_3$ | 2 | |
| 15-180 | CH$_2$OCH$_2$c-Pr | H | SCF$_3$ | 2 | |
| 15-181 | CH$_2$OC(=O)Me | H | SCF$_3$ | 2 | |
| 15-182 | CH$_2$OC(=O)i-Pr | H | SCF$_3$ | 2 | |
| 15-183 | CH$_2$OC(=O)c-Pr | H | SCF$_3$ | 2 | |
| 15-184 | CH$_2$OC(=O)OMe | H | SCF$_3$ | 2 | |
| 15-185 | CH$_2$OC(=O)NHMe | H | SCF$_3$ | 2 | |
| 15-186 | CH$_2$OC(=O)NMe$_2$ | H | SCF$_3$ | 2 | |
| 15-187 | CH$_2$CN | H | SCF$_3$ | 2 | |
| 15-188 | CH$_2$NH$_2$ | H | SCF$_3$ | 2 | |
| 15-189 | CH$_2$NHMe | H | SCF$_3$ | 2 | |
| 15-190 | CH$_2$NHi-Pr | H | SCF$_3$ | 2 | |
| 15-191 | CH$_2$NHc-Pr | H | SCF$_3$ | 2 | |
| 15-192 | CH$_2$NHCH$_2$CF$_3$ | H | SCF$_3$ | 2 | |
| 15-193 | CH$_2$NHCH$_2$c-Pr | H | SCF$_3$ | 2 | |

-continued

| Compound No. | $R^{21}$ | $R^{22}$ | $R^3$ | m | Physical Property |
|---|---|---|---|---|---|
| 15-194 | $CH_2NMe_2$ | H | $SCF_3$ | 2 | |
| 15-195 | $CH_2NHAc$ | H | $SCF_3$ | 2 | |
| 15-196 | $CH_2N(Ac)Me$ | H | $SCF_3$ | 2 | |
| 15-197 | $CH_2N(Ac)i$-Pr | H | $SCF_3$ | 2 | |
| 15-198 | $CH_2N(Ac)c$-Pr | H | $SCF_3$ | 2 | |
| 15-199 | $CH_2N(Ac)CH_2CF_3$ | H | $SCF_3$ | 2 | |
| 15-200 | $CH_2N(Ac)CH_2c$-Pr | H | $SCF_3$ | 2 | |
| 15-201 | $CH_2NHCOOMe$ | H | $SCF_3$ | 2 | |
| 15-202 | $CH_2NHCOOt$-Bu | H | $SCF_3$ | 2 | |
| 15-203 | $CH_2N(Me)CO_2Me$ | H | $SCF_3$ | 2 | |
| 15-204 | $CH_2N(Me)COOt$-Bu | H | $SCF_3$ | 2 | |
| 15-205 | $CH_2NHCONHMe$ | H | $SCF_3$ | 2 | |
| 15-206 | $CH_2N(Me)CONHMe$ | H | $SCF_3$ | 2 | |
| 15-207 | $CH_2SMe$ | H | $SCF_3$ | 2 | |
| 15-208 | $CH_2SOMe$ | H | $SCF_3$ | 2 | |
| 15-209 | $CH_2SO_2Me$ | H | $SCF_3$ | 2 | |
| 15-210 | CH=NOH | H | $SCF_3$ | 2 | |
| 15-211 | CH=NOMe | H | $SCF_3$ | 2 | |
| 15-212 | CH=NOi-Pr | H | $SCF_3$ | 2 | |
| 15-213 | CH=NOCH$_2$CF$_3$ | H | $SCF_3$ | 2 | |
| 15-214 | CH=NOCH$_2$c-Pr | H | $SCF_3$ | 2 | |
| 15-215 | C(Me)=NOH | H | $SCF_3$ | 2 | |
| 15-216 | C(Me)=NOMe | H | $SCF_3$ | 2 | |
| 15-217 | C(Me)=NOi-Pr | H | $SCF_3$ | 2 | |
| 15-218 | C(Me)=NOCH$_2$CF$_3$ | H | $SCF_3$ | 2 | |
| 15-219 | C(Me)=NOCH$_2$c-Pr | H | $SCF_3$ | 2 | |
| 15-220 | $NH_2$ | H | $SCF_3$ | 2 | |
| 15-221 | NHMe | H | $SCF_3$ | 2 | |
| 15-222 | NHi-Pr | H | $SCF_3$ | 2 | |
| 15-223 | $NHCH_2CF_3$ | H | $SCF_3$ | 2 | |
| 15-224 | $NHCH_2c$-Pr | H | $SCF_3$ | 2 | |
| 15-225 | $NMe_2$ | H | $SCF_3$ | 2 | |
| 15-226 | $N(Me)CH_2CF_3$ | H | $SCF_3$ | 2 | |
| 15-227 | $N(Me)CH_2c$-Pr | H | $SCF_3$ | 2 | |
| 15-228 | NHAc | H | $SCF_3$ | 2 | |
| 15-229 | N(Ac)Me | H | $SCF_3$ | 2 | |
| 15-230 | N(Ac)i-Pr | H | $SCF_3$ | 2 | |
| 15-231 | $N(Ac)CH_2CF_3$ | H | $SCF_3$ | 2 | |
| 15-232 | $N(Ac)CH_2c$-Pr | H | $SCF_3$ | 2 | |
| 15-233 | NHCOOMe | H | $SCF_3$ | 2 | |
| 15-234 | N(COOMe)Me | H | $SCF_3$ | 2 | |
| 15-235 | N(COOMe)i-Pr | H | $SCF_3$ | 2 | |
| 15-236 | $N(COOMe)CH_2CF_3$ | H | $SCF_3$ | 2 | |
| 15-237 | $N(COOMe)CH_2c$-Pr | H | $SCF_3$ | 2 | |
| 15-238 | $NHCONMe_2$ | H | $SCF_3$ | 2 | |
| 15-239 | $N(CONMe_2)Me$ | H | $SCF_3$ | 2 | |
| 15-240 | $CH_2Cl$ | H | $SCF_3$ | 2 | |
| 15-241 | H | $CO_2H$ | $SCF_3$ | 2 | |
| 15-242 | H | $CO_2Me$ | $SCF_3$ | 2 | |
| 15-243 | H | $CO_2i$-Pr | $SCF_3$ | 2 | |
| 15-244 | H | $CO_2CH_2CF_3$ | $SCF_3$ | 2 | |
| 15-245 | H | $CO_2CH_2c$-Pr | $SCF_3$ | 2 | |
| 15-246 | H | $CONH_2$ | $SCF_3$ | 2 | |
| 15-247 | H | CONHMe | $SCF_3$ | 2 | |
| 15-248 | H | CONHi-Pr | $SCF_3$ | 2 | |
| 15-249 | H | CONHc-Pr | $SCF_3$ | 2 | |
| 15-250 | H | $CONHCH_2CF_3$ | $SCF_3$ | 2 | |
| 15-251 | H | $CONHCH_2c$-Pr | $SCF_3$ | 2 | |
| 15-252 | H | $CONMe_2$ | $SCF_3$ | 2 | |
| 15-253 | H | CN | $SCF_3$ | 2 | |
| 15-254 | H | CHO | $SCF_3$ | 2 | |
| 15-255 | H | C(=O)Me | $SCF_3$ | 2 | |
| 15-256 | H | $CH_2OH$ | $SCF_3$ | 2 | |
| 15-257 | H | $CH_2OMe$ | $SCF_3$ | 2 | |
| 15-258 | H | $CH_2Oi$-Pr | $SCF_3$ | 2 | |
| 15-259 | H | $CH_2OCH_2CF_3$ | $SCF_3$ | 2 | |
| 15-260 | H | $CH_2OCH_2c$-Pr | $SCF_3$ | 2 | |
| 15-261 | H | $CH_2OC(=O)Me$ | $SCF_3$ | 2 | |
| 15-262 | H | $CH_2OC(=O)i$-Pr | $SCF_3$ | 2 | |
| 15-263 | H | $CH_2OC(=O)c$-Pr | $SCF_3$ | 2 | |
| 15-264 | H | $CH_2OC(=O)OMe$ | $SCF_3$ | 2 | |
| 15-265 | H | $CH_2OC(=O)NHMe$ | $SCF_3$ | 2 | |
| 15-266 | H | $CH_2OC(=O)NMe_2$ | $SCF_3$ | 2 | |
| 15-267 | H | $CH_2CN$ | $SCF_3$ | 2 | |
| 15-268 | H | $CH_2NH_2$ | $SCF_3$ | 2 | |
| 15-269 | H | $CH_2NHMe$ | $SCF_3$ | 2 | |

-continued

| Compound No. | R²¹ | R²² | R³ | m | Physical Property |
|---|---|---|---|---|---|
| 15-270 | H | CH₂NHi-Pr | SCF₃ | 2 | |
| 15-271 | H | CH₂NHc-Pr | SCF₃ | 2 | |
| 15-272 | H | CH₂NHCH₂CF₃ | SCF₃ | 2 | |
| 15-273 | H | CH₂NHCH₂c-Pr | SCF₃ | 2 | |
| 15-274 | H | CH₂NMe₂ | SCF₃ | 2 | |
| 15-275 | H | CH₂NHAc | SCF₃ | 2 | |
| 15-276 | H | CH₂N(Ac)Me | SCF₃ | 2 | |
| 15-277 | H | CH₂N(Ac)i-Pr | SCF₃ | 2 | |
| 15-278 | H | CH₂N(Ac)c-Pr | SCF₃ | 2 | |
| 15-279 | H | CH₂N(Ac)CH₂CF₃ | SCF₃ | 2 | |
| 15-280 | H | CH₂N(Ac)CH₂c-Pr | SCF₃ | 2 | |
| 15-281 | H | CH₂NHCOOMe | SCF₃ | 2 | |
| 15-282 | H | CH₂NHCOOt-Bu | SCF₃ | 2 | |
| 15-283 | H | CH₂N(Me)CO₂Me | SCF₃ | 2 | |
| 15-284 | H | CH₂N(Me)COOt-Bu | SCF₃ | 2 | |
| 15-285 | H | CH₂NHCONHMe | SCF₃ | 2 | |
| 15-286 | H | CH₂N(Me)CONHMe | SCF₃ | 2 | |
| 15-287 | H | CH₂SMe | SCF₃ | 2 | |
| 15-288 | H | CH₂SOMe | SCF₃ | 2 | |
| 15-289 | H | CH₂SO₂Me | SCF₃ | 2 | |
| 15-290 | H | CH=NOH | SCF₃ | 2 | |
| 15-291 | H | CH=NOMe | SCF₃ | 2 | |
| 15-292 | H | CH=NOi-Pr | SCF₃ | 2 | |
| 15-293 | H | CH=NOCH₂CF₃ | SCF₃ | 2 | |
| 15-294 | H | CH=NOCH₂c-Pr | SCF₃ | 2 | |
| 15-295 | H | C(Me)=NOH | SCF₃ | 2 | |
| 15-296 | H | C(Me)=NOMe | SCF₃ | 2 | |
| 15-297 | H | C(Me)=NOi-Pr | SCF₃ | 2 | |
| 15-298 | H | C(Me)=NOCH₂CF₃ | SCF₃ | 2 | |
| 15-299 | H | C(Me)=NOCH₂c-Pr | SCF₃ | 2 | |
| 15-300 | H | NH₂ | SCF₃ | 2 | |
| 15-301 | H | NHMe | SCF₃ | 2 | |
| 15-302 | H | NHi-Pr | SCF₃ | 2 | |
| 15-303 | H | NHCH₂CF₃ | SCF₃ | 2 | |
| 15-304 | H | NHCH₂c-Pr | SCF₃ | 2 | |
| 15-305 | H | NMe₂ | SCF₃ | 2 | |
| 15-306 | H | N(Me)CH₂CF₃ | SCF₃ | 2 | |
| 15-307 | H | N(Me)CH₂c-Pr | SCF₃ | 2 | |
| 15-308 | H | NHAc | SCF₃ | 2 | |
| 15-309 | H | N(Ac)Me | SCF₃ | 2 | |
| 15-310 | H | N(Ac)i-Pr | SCF₃ | 2 | |
| 15-311 | H | N(Ac)CH₂CF₃ | SCF₃ | 2 | |
| 15-312 | H | N(Ac)CH₂c-Pr | SCF₃ | 2 | |
| 15-313 | H | NHCOOMe | SCF₃ | 2 | |
| 15-314 | H | N(COOMe)Me | SCF₃ | 2 | |
| 15-315 | H | N(COOMe)i-Pr | SCF₃ | 2 | |
| 15-316 | H | N(COOMe)CH₂CF₃ | SCF₃ | 2 | |
| 15-317 | H | N(COOMe)CH₂c-Pr | SCF₃ | 2 | |
| 15-318 | H | NHCONMe₂ | SCF₃ | 2 | |
| 15-319 | H | N(CONMe₂)Me | SCF₃ | 2 | |
| 15-320 | H | CH₂Cl | SCF₃ | 2 | |

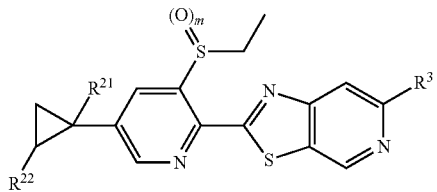

(1-f-1)

| Compound No. | R²¹ | R²² | R³ | m | Physical Property |
|---|---|---|---|---|---|
| 16-1 | CO₂H | H | CF₃ | 2 | |
| 16-2 | CO₂Me | H | CF₃ | 2 | |
| 16-3 | CO₂i-Pr | H | CF₃ | 2 | |
| 16-4 | CO₂CH₂CF₃ | H | CF₃ | 2 | |

-continued

| Compound No. | $R^{21}$ | $R^{22}$ | $R^3$ | m | Physical Property |
|---|---|---|---|---|---|
| 16-5 | $CO_2CH_2$c-Pr | H | $CF_3$ | 2 | |
| 16-6 | $CONH_2$ | H | $CF_3$ | 2 | |
| 16-7 | CONHMe | H | $CF_3$ | 2 | |
| 16-8 | CONHi-Pr | H | $CF_3$ | 2 | |
| 16-9 | CONHc-Pr | H | $CF_3$ | 2 | |
| 16-10 | $CONHCH_2CF_3$ | H | $CF_3$ | 2 | |
| 16-11 | $CONHCH_2$c-Pr | H | $CF_3$ | 2 | |
| 16-12 | $CONMe_2$ | H | $CF_3$ | 2 | |
| 16-13 | CN | H | $CF_3$ | 2 | |
| 16-14 | CHO | H | $CF_3$ | 2 | |
| 16-15 | C(=O)Me | H | $CF_3$ | 2 | |
| 16-16 | $CH_2OH$ | H | $CF_3$ | 2 | |
| 16-17 | $CH_2OMe$ | H | $CF_3$ | 2 | |
| 16-18 | $CH_2Oi$-Pr | H | $CF_3$ | 2 | |
| 16-19 | $CH_2OCH_2CF_3$ | H | $CF_3$ | 2 | |
| 16-20 | $CH_2OCH_2$c-Pr | H | $CF_3$ | 2 | |
| 16-21 | $CH_2OC(=O)Me$ | H | $CF_3$ | 2 | |
| 16-22 | $CH_2OC(=O)i$-Pr | H | $CF_3$ | 2 | |
| 16-23 | $CH_2OC(=O)c$-Pr | H | $CF_3$ | 2 | |
| 16-24 | $CH_2OC(=O)OMe$ | H | $CF_3$ | 2 | |
| 16-25 | $CH_2OC(=O)NHMe$ | H | $CF_3$ | 2 | |
| 16-26 | $CH_2OC(=O)NMe_2$ | H | $CF_3$ | 2 | |
| 16-27 | $CH_2CN$ | H | $CF_3$ | 2 | |
| 16-28 | $CH_2NH_2$ | H | $CF_3$ | 2 | |
| 16-29 | $CH_2NHMe$ | H | $CF_3$ | 2 | |
| 16-30 | $CH_2NHi$-Pr | H | $CF_3$ | 2 | |
| 16-31 | $CH_2NHc$-Pr | H | $CF_3$ | 2 | |
| 16-32 | $CH_2NHCH_2CF_3$ | H | $CF_3$ | 2 | |
| 16-33 | $CH_2NHCH_2$c-Pr | H | $CF_3$ | 2 | |
| 16-34 | $CH_2NMe_2$ | H | $CF_3$ | 2 | |
| 16-35 | $CH_2NHAc$ | H | $CF_3$ | 2 | |
| 16-36 | $CH_2N(Ac)Me$ | H | $CF_3$ | 2 | |
| 16-37 | $CH_2N(Ac)i$-Pr | H | $CF_3$ | 2 | |
| 16-38 | $CH_2N(Ac)c$-Pr | H | $CF_3$ | 2 | |
| 16-39 | $CH_2N(Ac)CH_2CF_3$ | H | $CF_3$ | 2 | |
| 16-40 | $CH_2N(Ac)CH_2$c-Pr | H | $CF_3$ | 2 | |
| 16-41 | $CH_2NHCOOMe$ | H | $CF_3$ | 2 | |
| 16-42 | $CH_2NHCOOt$-Bu | H | $CF_3$ | 2 | |
| 16-43 | $CH_2N(Me)CO_2Me$ | H | $CF_3$ | 2 | |
| 16-44 | $CH_2N(Me)COOt$-Bu | H | $CF_3$ | 2 | |
| 16-45 | $CH_2NHCONHMe$ | H | $CF_3$ | 2 | |
| 16-46 | $CH_2N(Me)CONHMe$ | H | $CF_3$ | 2 | |
| 16-47 | $CH_2SMe$ | H | $CF_3$ | 2 | |
| 16-48 | $CH_2SOMe$ | H | $CF_3$ | 2 | |
| 16-49 | $CH_2SO_2Me$ | H | $CF_3$ | 2 | |
| 16-50 | CH=NOH | H | $CF_3$ | 2 | |
| 16-51 | CH=NOMe | H | $CF_3$ | 2 | |
| 16-52 | CH=NOi-Pr | H | $CF_3$ | 2 | |
| 16-53 | $CH=NOCH_2CF_3$ | H | $CF_3$ | 2 | |
| 16-54 | $CH=NOCH_2$c-Pr | H | $CF_3$ | 2 | |
| 16-55 | C(Me)=NOH | H | $CF_3$ | 2 | |
| 16-56 | C(Me)=NOMe | H | $CF_3$ | 2 | |
| 16-57 | C(Me)=NOi-Pr | H | $CF_3$ | 2 | |
| 16-58 | $C(Me)=NOCH_2CF_3$ | H | $CF_3$ | 2 | |
| 16-59 | $C(Me)=NOCH_2$c-Pr | H | $CF_3$ | 2 | |
| 16-60 | $NH_2$ | H | $CF_3$ | 2 | |
| 16-61 | NHMe | H | $CF_3$ | 2 | |
| 16-62 | NHi-Pr | H | $CF_3$ | 2 | |
| 16-63 | $NHCH_2CF_3$ | H | $CF_3$ | 2 | |
| 16-64 | $NHCH_2$c-Pr | H | $CF_3$ | 2 | |
| 16-65 | $NMe_2$ | H | $CF_3$ | 2 | |
| 16-66 | $N(Me)CH_2CF_3$ | H | $CF_3$ | 2 | |
| 16-67 | $N(Me)CH_2$c-Pr | H | $CF_3$ | 2 | |
| 16-68 | NHAc | H | $CF_3$ | 2 | |
| 16-69 | N(Ac)Me | H | $CF_3$ | 2 | |
| 16-70 | N(Ac)i-Pr | H | $CF_3$ | 2 | |
| 16-71 | $N(Ac)CH_2CF_3$ | H | $CF_3$ | 2 | |
| 16-72 | $N(Ac)CH_2$c-Pr | H | $CF_3$ | 2 | |
| 16-73 | NHCOOMe | H | $CF_3$ | 2 | |
| 16-74 | N(COOMe)Me | H | $CF_3$ | 2 | |
| 16-75 | N(COOMe)i-Pr | H | $CF_3$ | 2 | |
| 16-76 | $N(COOMe)CH_2CF_3$ | H | $CF_3$ | 2 | |
| 16-77 | $N(COOMe)CH_2$c-Pr | H | $CF_3$ | 2 | |
| 16-78 | $NHCONMe_2$ | H | $CF_3$ | 2 | |
| 16-79 | $N(CONMe_2)Me$ | H | $CF_3$ | 2 | |
| 16-80 | $CH_2Cl$ | H | $CF_3$ | 2 | |

-continued

| Compound No. | $R^{21}$ | $R^{22}$ | $R^3$ | m | Physical Property |
|---|---|---|---|---|---|
| 16-81 | H | $CO_2H$ | $CF_3$ | 2 | |
| 16-82 | H | $CO_2Me$ | $CF_3$ | 2 | |
| 16-83 | H | $CO_2i$-Pr | $CF_3$ | 2 | |
| 16-84 | H | $CO_2CH_2CF_3$ | $CF_3$ | 2 | |
| 16-85 | H | $CO_2CH_2c$-Pr | $CF_3$ | 2 | |
| 16-86 | H | $CONH_2$ | $CF_3$ | 2 | |
| 16-87 | H | CONHMe | $CF_3$ | 2 | |
| 16-88 | H | CONHi-Pr | $CF_3$ | 2 | |
| 16-89 | H | CONHc-Pr | $CF_3$ | 2 | |
| 16-90 | H | $CONHCH_2CF_3$ | $CF_3$ | 2 | |
| 16-91 | H | $CONHCH_2c$-Pr | $CF_3$ | 2 | |
| 16-92 | H | $CONMe_2$ | $CF_3$ | 2 | |
| 16-93 | H | CN | $CF_3$ | 2 | |
| 16-94 | H | CHO | $CF_3$ | 2 | |
| 16-95 | H | C(=O)Me | $CF_3$ | 2 | |
| 16-96 | H | $CH_2OH$ | $CF_3$ | 2 | |
| 16-97 | H | $CH_2OMe$ | $CF_3$ | 2 | |
| 16-98 | H | $CH_2Oi$-Pr | $CF_3$ | 2 | |
| 16-99 | H | $CH_2OCH_2CF_3$ | $CF_3$ | 2 | |
| 16-100 | H | $CH_2OCH_2c$-Pr | $CF_3$ | 2 | |
| 16-101 | H | $CH_2OC(=O)Me$ | $CF_3$ | 2 | |
| 16-102 | H | $CH_2OC(=O)i$-Pr | $CF_3$ | 2 | |
| 16-103 | H | $CH_2OC(=O)c$-Pr | $CF_3$ | 2 | |
| 16-104 | H | $CH_2OC(=O)OMe$ | $CF_3$ | 2 | |
| 16-105 | H | $CH_2OC(=O)NHMe$ | $CF_3$ | 2 | |
| 16-106 | H | $CH_2OC(=O)NMe_2$ | $CF_3$ | 2 | |
| 16-107 | H | $CH_2CN$ | $CF_3$ | 2 | |
| 16-108 | H | $CH_2NH_2$ | $CF_3$ | 2 | |
| 16-109 | H | $CH_2NHMe$ | $CF_3$ | 2 | |
| 16-110 | H | $CH_2NHi$-Pr | $CF_3$ | 2 | |
| 16-111 | H | $CH_2NHc$-Pr | $CF_3$ | 2 | |
| 16-112 | H | $CH_2NHCH_2CF_3$ | $CF_3$ | 2 | |
| 16-113 | H | $CH_2NHCH_2c$-Pr | $CF_3$ | 2 | |
| 16-114 | H | $CH_2NMe_2$ | $CF_3$ | 2 | |
| 16-115 | H | $CH_2NHAc$ | $CF_3$ | 2 | |
| 16-116 | H | $CH_2N(Ac)Me$ | $CF_3$ | 2 | |
| 16-117 | H | $CH_2N(Ac)i$-Pr | $CF_3$ | 2 | |
| 16-118 | H | $CH_2N(Ac)c$-Pr | $CF_3$ | 2 | |
| 16-119 | H | $CH_2N(Ac)CH_2CF_3$ | $CF_3$ | 2 | |
| 16-120 | H | $CH_2N(Ac)CH_2c$-Pr | $CF_3$ | 2 | |
| 16-121 | H | $CH_2NHCOOMe$ | $CF_3$ | 2 | |
| 16-122 | H | $CH_2NHCOOt$-Bu | $CF_3$ | 2 | |
| 16-123 | H | $CH_2N(Me)CO_2Me$ | $CF_3$ | 2 | |
| 16-124 | H | $CH_2N(Me)COOt$-Bu | $CF_3$ | 2 | |
| 16-125 | H | $CH_2NHCONHMe$ | $CF_3$ | 2 | |
| 16-126 | H | $CH_2N(Me)CONHMe$ | $CF_3$ | 2 | |
| 16-127 | H | $CH_2SMe$ | $CF_3$ | 2 | |
| 16-128 | H | $CH_2SOMe$ | $CF_3$ | 2 | |
| 16-129 | H | $CH_2SO_2Me$ | $CF_3$ | 2 | |
| 16-130 | H | CH=NOH | $CF_3$ | 2 | |
| 16-131 | H | CH=NOMe | $CF_3$ | 2 | |
| 16-132 | H | CH=NOi-Pr | $CF_3$ | 2 | |
| 16-133 | H | $CH=NOCH_2CF_3$ | $CF_3$ | 2 | |
| 16-134 | H | $CH=NOCH_2c$-Pr | $CF_3$ | 2 | |
| 16-135 | H | C(Me)=NOH | $CF_3$ | 2 | |
| 16-136 | H | C(Me)=NOMe | $CF_3$ | 2 | |
| 16-137 | H | C(Me)=NOi-Pr | $CF_3$ | 2 | |
| 16-138 | H | $C(Me)=NOCH_2CF_3$ | $CF_3$ | 2 | |
| 16-139 | H | $C(Me)=NOCH_2c$-Pr | $CF_3$ | 2 | |
| 16-140 | H | $NH_2$ | $CF_3$ | 2 | |
| 16-141 | H | NHMe | $CF_3$ | 2 | |
| 16-142 | H | NHi-Pr | $CF_3$ | 2 | |
| 16-143 | H | $NHCH_2CF_3$ | $CF_3$ | 2 | |
| 16-144 | H | $NHCH_2c$-Pr | $CF_3$ | 2 | |
| 16-145 | H | $NMe_2$ | $CF_3$ | 2 | |
| 16-146 | H | $N(Me)CH_2CF_3$ | $CF_3$ | 2 | |
| 16-147 | H | $N(Me)CH_2c$-Pr | $CF_3$ | 2 | |
| 16-148 | H | NHAc | $CF_3$ | 2 | |
| 16-149 | H | N(Ac)Me | $CF_3$ | 2 | |
| 16-150 | H | N(Ac)i-Pr | $CF_3$ | 2 | |
| 16-151 | H | $N(Ac)CH_2CF_3$ | $CF_3$ | 2 | |
| 16-152 | H | $N(Ac)CH_2c$-Pr | $CF_3$ | 2 | |
| 16-153 | H | NHCOOMe | $CF_3$ | 2 | |
| 16-154 | H | N(COOMe)Me | $CF_3$ | 2 | |
| 16-155 | H | N(COOMe)i-Pr | $CF_3$ | 2 | |
| 16-156 | H | $N(COOMe)CH_2CF_3$ | $CF_3$ | 2 | |

-continued

| Compound No. | $R^{21}$ | $R^{22}$ | $R^3$ | m | Physical Property |
|---|---|---|---|---|---|
| 16-157 | H | N(COOMe)CH$_2$c-Pr | CF$_3$ | 2 | |
| 16-158 | H | NHCONMe$_2$ | CF$_3$ | 2 | |
| 16-159 | H | N(CONMe$_2$)Me | CF$_3$ | 2 | |
| 16-160 | H | CH$_2$Cl | CF$_3$ | 2 | |
| 16-161 | CO$_2$H | H | SCF$_3$ | 2 | |
| 16-162 | CO$_2$Me | H | SCF$_3$ | 2 | |
| 16-163 | CO$_2$i-Pr | H | SCF$_3$ | 2 | |
| 16-164 | CO$_2$CH$_2$CF$_3$ | H | SCF$_3$ | 2 | |
| 16-165 | CO$_2$CH$_2$c-Pr | H | SCF$_3$ | 2 | |
| 16-166 | CONH$_2$ | H | SCF$_3$ | 2 | |
| 16-167 | CONHMe | H | SCF$_3$ | 2 | |
| 16-168 | CONHi-Pr | H | SCF$_3$ | 2 | |
| 16-169 | CONHc-Pr | H | SCF$_3$ | 2 | |
| 16-170 | CONHCH$_2$CF$_3$ | H | SCF$_3$ | 2 | |
| 16-171 | CONHCH$_2$c-Pr | H | SCF$_3$ | 2 | |
| 16-172 | CONMe$_2$ | H | SCF$_3$ | 2 | |
| 16-173 | CN | H | SCF$_3$ | 2 | |
| 16-174 | CHO | H | SCF$_3$ | 2 | |
| 16-175 | C(=O)Me | H | SCF$_3$ | 2 | |
| 16-176 | CH$_2$OH | H | SCF$_3$ | 2 | |
| 16-177 | CH$_2$OMe | H | SCF$_3$ | 2 | |
| 16-178 | CH$_2$Oi-Pr | H | SCF$_3$ | 2 | |
| 16-179 | CH$_2$OCH$_2$CF$_3$ | H | SCF$_3$ | 2 | |
| 16-180 | CH$_2$OCH$_2$c-Pr | H | SCF$_3$ | 2 | |
| 16-181 | CH$_2$OC(=O)Me | H | SCF$_3$ | 2 | |
| 16-182 | CH$_2$OC(=O)i-Pr | H | SCF$_3$ | 2 | |
| 16-183 | CH$_2$OC(=O)c-Pr | H | SCF$_3$ | 2 | |
| 16-184 | CH$_2$OC(=O)OMe | H | SCF$_3$ | 2 | |
| 16-185 | CH$_2$OC(=O)NHMe | H | SCF$_3$ | 2 | |
| 16-186 | CH$_2$OC(=O)NMe$_2$ | H | SCF$_3$ | 2 | |
| 16-187 | CH$_2$CN | H | SCF$_3$ | 2 | |
| 16-188 | CH$_2$NH$_2$ | H | SCF$_3$ | 2 | |
| 16-189 | CH$_2$NHMe | H | SCF$_3$ | 2 | |
| 16-190 | CH$_2$NHi-Pr | H | SCF$_3$ | 2 | |
| 16-191 | CH$_2$NHc-Pr | H | SCF$_3$ | 2 | |
| 16-192 | CH$_2$NHCH$_2$CF$_3$ | H | SCF$_3$ | 2 | |
| 16-193 | CH$_2$NHCH$_2$c-Pr | H | SCF$_3$ | 2 | |
| 16-194 | CH$_2$NMe$_2$ | H | SCF$_3$ | 2 | |
| 16-195 | CH$_2$NHAc | H | SCF$_3$ | 2 | |
| 16-196 | CH$_2$N(Ac)Me | H | SCF$_3$ | 2 | |
| 16-197 | CH$_2$N(Ac)i-Pr | H | SCF$_3$ | 2 | |
| 16-198 | CH$_2$N(Ac)c-Pr | H | SCF$_3$ | 2 | |
| 16-199 | CH$_2$N(Ac)CH$_2$CF$_3$ | H | SCF$_3$ | 2 | |
| 16-200 | CH$_2$N(Ac)CH$_2$c-Pr | H | SCF$_3$ | 2 | |
| 16-201 | CH$_2$NHCOOMe | H | SCF$_3$ | 2 | |
| 16-202 | CH$_2$NHCOOt-Bu | H | SCF$_3$ | 2 | |
| 16-203 | CH$_2$N(Me)CO$_2$Me | H | SCF$_3$ | 2 | |
| 16-204 | CH$_2$N(Me)COOt-Bu | H | SCF$_3$ | 2 | |
| 16-205 | CH$_2$NHCONHMe | H | SCF$_3$ | 2 | |
| 16-206 | CH$_2$N(Me)CONHMe | H | SCF$_3$ | 2 | |
| 16-207 | CH$_2$SMe | H | SCF$_3$ | 2 | |
| 16-208 | CH$_2$SOMe | H | SCF$_3$ | 2 | |
| 16-209 | CH$_2$SO$_2$Me | H | SCF$_3$ | 2 | |
| 16-210 | CH=NOH | H | SCF$_3$ | 2 | |
| 16-211 | CH=NOMe | H | SCF$_3$ | 2 | |
| 16-212 | CH=NOi-Pr | H | SCF$_3$ | 2 | |
| 16-213 | CH=NOCH$_2$CF$_3$ | H | SCF$_3$ | 2 | |
| 16-214 | CH=NOCH$_2$c-Pr | H | SCF$_3$ | 2 | |
| 16-215 | C(Me)=NOH | H | SCF$_3$ | 2 | |
| 16-216 | C(Me)=NOMe | H | SCF$_3$ | 2 | |
| 16-217 | C(Me)=NOi-Pr | H | SCF$_3$ | 2 | |
| 16-218 | C(Me)=NOCH$_2$CF$_3$ | H | SCF$_3$ | 2 | |
| 16-219 | C(Me)=NOCH$_2$c-Pr | H | SCF$_3$ | 2 | |
| 16-220 | NH$_2$ | H | SCF$_3$ | 2 | |
| 16-221 | NHMe | H | SCF$_3$ | 2 | |
| 16-222 | NHi-Pr | H | SCF$_3$ | 2 | |
| 16-223 | NHCH$_2$CF$_3$ | H | SCF$_3$ | 2 | |
| 16-224 | NHCH$_2$c-Pr | H | SCF$_3$ | 2 | |
| 16-225 | NMe$_2$ | H | SCF$_3$ | 2 | |
| 16-226 | N(Me)CH$_2$CF$_3$ | H | SCF$_3$ | 2 | |
| 16-227 | N(Me)CH$_2$c-Pr | H | SCF$_3$ | 2 | |
| 16-228 | NHAc | H | SCF$_3$ | 2 | |
| 16-229 | N(Ac)Me | H | SCF$_3$ | 2 | |
| 16-230 | N(Ac)i-Pr | H | SCF$_3$ | 2 | |
| 16-231 | N(Ac)CH$_2$CF$_3$ | H | SCF$_3$ | 2 | |
| 16-232 | N(Ac)CH$_2$c-Pr | H | SCF$_3$ | 2 | |

| Compound No. | R²¹ | R²² | R³ | m | Physical Property |
|---|---|---|---|---|---|
| 16-233 | NHCOOMe | H | $SCF_3$ | 2 | |
| 16-234 | N(COOMe)Me | H | $SCF_3$ | 2 | |
| 16-235 | N(COOMe)i-Pr | H | $SCF_3$ | 2 | |
| 16-236 | N(COOMe)CH$_2$CF$_3$ | H | $SCF_3$ | 2 | |
| 16-237 | N(COOMe)CH$_2$c-Pr | H | $SCF_3$ | 2 | |
| 16-238 | NHCONMe$_2$ | H | $SCF_3$ | 2 | |
| 16-239 | N(CONMe$_2$)Me | H | $SCF_3$ | 2 | |
| 16-240 | CH$_2$Cl | H | $SCF_3$ | 2 | |
| 16-241 | H | CO$_2$H | $SCF_3$ | 2 | |
| 16-242 | H | CO$_2$Me | $SCF_3$ | 2 | |
| 16-243 | H | CO$_2$i-Pr | $SCF_3$ | 2 | |
| 16-244 | H | CO$_2$CH$_2$CF$_3$ | $SCF_3$ | 2 | |
| 16-245 | H | CO$_2$CH$_2$c-Pr | $SCF_3$ | 2 | |
| 16-246 | H | CONH$_2$ | $SCF_3$ | 2 | |
| 16-247 | H | CONHMe | $SCF_3$ | 2 | |
| 16-248 | H | CONHi-Pr | $SCF_3$ | 2 | |
| 16-249 | H | CONHc-Pr | $SCF_3$ | 2 | |
| 16-250 | H | CONHCH$_2$CF$_3$ | $SCF_3$ | 2 | |
| 16-251 | H | CONHCH$_2$c-Pr | $SCF_3$ | 2 | |
| 16-252 | H | CONMe$_2$ | $SCF_3$ | 2 | |
| 16-253 | H | CN | $SCF_3$ | 2 | |
| 16-254 | H | CHO | $SCF_3$ | 2 | |
| 16-255 | H | C(=O)Me | $SCF_3$ | 2 | |
| 16-256 | H | CH$_2$OH | $SCF_3$ | 2 | |
| 16-257 | H | CH$_2$OMe | $SCF_3$ | 2 | |
| 16-258 | H | CH$_2$Oi-Pr | $SCF_3$ | 2 | |
| 16-259 | H | CH$_2$OCH$_2$CF$_3$ | $SCF_3$ | 2 | |
| 16-260 | H | CH$_2$OCH$_2$c-Pr | $SCF_3$ | 2 | |
| 16-261 | H | CH$_2$OC(=O)Me | $SCF_3$ | 2 | |
| 16-262 | H | CH$_2$OC(=O)i-Pr | $SCF_3$ | 2 | |
| 16-263 | H | CH$_2$OC(=O)c-Pr | $SCF_3$ | 2 | |
| 16-264 | H | CH$_2$OC(=O)OMe | $SCF_3$ | 2 | |
| 16-265 | H | CH$_2$OC(=O)NHMe | $SCF_3$ | 2 | |
| 16-266 | H | CH$_2$OC(=O)NMe$_2$ | $SCF_3$ | 2 | |
| 16-267 | H | CH$_2$CN | $SCF_3$ | 2 | |
| 16-268 | H | CH$_2$NH$_2$ | $SCF_3$ | 2 | |
| 16-269 | H | CH$_2$NHMe | $SCF_3$ | 2 | |
| 16-270 | H | CH$_2$NHi-Pr | $SCF_3$ | 2 | |
| 16-271 | H | CH$_2$NHc-Pr | $SCF_3$ | 2 | |
| 16-272 | H | CH$_2$NHCH$_2$CF$_3$ | $SCF_3$ | 2 | |
| 16-273 | H | CH$_2$NHCH$_2$c-Pr | $SCF_3$ | 2 | |
| 16-274 | H | CH$_2$NMe$_2$ | $SCF_3$ | 2 | |
| 16-275 | H | CH$_2$NHAc | $SCF_3$ | 2 | |
| 16-276 | H | CH$_2$N(Ac)Me | $SCF_3$ | 2 | |
| 16-277 | H | CH$_2$N(Ac)i-Pr | $SCF_3$ | 2 | |
| 16-278 | H | CH$_2$N(Ac)c-Pr | $SCF_3$ | 2 | |
| 16-279 | H | CH$_2$N(Ac)CH$_2$CF$_3$ | $SCF_3$ | 2 | |
| 16-280 | H | CH$_2$N(Ac)CH$_2$c-Pr | $SCF_3$ | 2 | |
| 16-281 | H | CH$_2$NHCOOMe | $SCF_3$ | 2 | |
| 16-282 | H | CH$_2$NHCOOt-Bu | $SCF_3$ | 2 | |
| 16-283 | H | CH$_2$N(Me)CO$_2$Me | $SCF_3$ | 2 | |
| 16-284 | H | CH$_2$N(Me)COOt-Bu | $SCF_3$ | 2 | |
| 16-285 | H | CH$_2$NHCONHMe | $SCF_3$ | 2 | |
| 16-286 | H | CH$_2$N(Me)CONHMe | $SCF_3$ | 2 | |
| 16-287 | H | CH$_2$SMe | $SCF_3$ | 2 | |
| 16-288 | H | CH$_2$SOMe | $SCF_3$ | 2 | |
| 16-289 | H | CH$_2$SO$_2$Me | $SCF_3$ | 2 | |
| 16-290 | H | CH=NOH | $SCF_3$ | 2 | |
| 16-291 | H | CH=NOMe | $SCF_3$ | 2 | |
| 16-292 | H | CH=NOi-Pr | $SCF_3$ | 2 | |
| 16-293 | H | CH=NOCH$_2$CF$_3$ | $SCF_3$ | 2 | |
| 16-294 | H | CH=NOCH$_2$c-Pr | $SCF_3$ | 2 | |
| 16-295 | H | C(Me)=NOH | $SCF_3$ | 2 | |
| 16-296 | H | C(Me)=NOMe | $SCF_3$ | 2 | |
| 16-297 | H | C(Me)=NOi-Pr | $SCF_3$ | 2 | |
| 16-298 | H | C(Me)=NOCH$_2$CF$_3$ | $SCF_3$ | 2 | |
| 16-299 | H | C(Me)=NOCH$_2$c-Pr | $SCF_3$ | 2 | |
| 16-300 | H | NH$_2$ | $SCF_3$ | 2 | |
| 16-301 | H | NHMe | $SCF_3$ | 2 | |
| 16-302 | H | NHi-Pr | $SCF_3$ | 2 | |
| 16-303 | H | NHCH$_2$CF$_3$ | $SCF_3$ | 2 | |
| 16-304 | H | NHCH$_2$c-Pr | $SCF_3$ | 2 | |
| 16-305 | H | NMe$_2$ | $SCF_3$ | 2 | |
| 16-306 | H | N(Me)CH$_2$CF$_3$ | $SCF_3$ | 2 | |
| 16-307 | H | N(Me)CH$_2$c-Pr | $SCF_3$ | 2 | |
| 16-308 | H | NHAc | $SCF_3$ | 2 | |

| Compound No. | R²¹ | R²² | R³ | m | Physical Property |
|---|---|---|---|---|---|
| 16-309 | H | N(Ac)Me | SCF₃ | 2 | |
| 16-310 | H | N(Ac)i-Pr | SCF₃ | 2 | |
| 16-311 | H | N(Ac)CH₂CF₃ | SCF₃ | 2 | |
| 16-312 | H | N(Ac)CH₂c-Pr | SCF₃ | 2 | |
| 16-313 | H | NHCOOMe | SCF₃ | 2 | |
| 16-314 | H | N(COOMe)Me | SCF₃ | 2 | |
| 16-315 | H | N(COOMe)i-Pr | SCF₃ | 2 | |
| 16-316 | H | N(COOMe)CH₂CF₃ | SCF₃ | 2 | |
| 16-317 | H | N(COOMe)CH₂c-Pr | SCF₃ | 2 | |
| 16-318 | H | NHCONMe₂ | SCF₃ | 2 | |
| 16-319 | H | N(CONMe₂)Me | SCF₃ | 2 | |
| 16-320 | H | CH₂Cl | SCF₃ | 2 | |

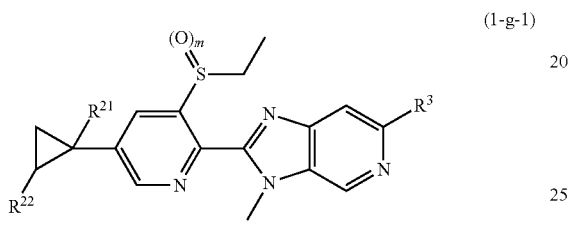

(1-g-1)

| Compound No. | R²¹ | R²² | R³ | m | Physical Property |
|---|---|---|---|---|---|
| 17-1 | CO₂H | H | CF₃ | 2 | |
| 17-2 | CO₂Me | H | CF₃ | 2 | |
| 17-3 | CO₂i-Pr | H | CF₃ | 2 | |
| 17-4 | CO₂CH₂CF₃ | H | CF₃ | 2 | |
| 17-5 | CO₂CH₂c-Pr | H | CF₃ | 2 | |
| 17-6 | CONH₂ | H | CF₃ | 2 | |
| 17-7 | CONHMe | H | CF₃ | 2 | |
| 17-8 | CONHi-Pr | H | CF₃ | 2 | |
| 17-9 | CONHc-Pr | H | CF₃ | 2 | |
| 17-10 | CONHCH₂CF₃ | H | CF₃ | 2 | |
| 17-11 | CONHCH₂c-Pr | H | CF₃ | 2 | |
| 17-12 | CONMe₂ | H | CF₃ | 2 | |
| 17-13 | CN | H | CF₃ | 2 | |
| 17-14 | CHO | H | CF₃ | 2 | |
| 17-15 | C(=O)Me | H | CF₃ | 2 | |
| 17-16 | CH₂OH | H | CF₃ | 2 | |
| 17-17 | CH₂OMe | H | CF₃ | 2 | |
| 17-18 | CH₂Oi-Pr | H | CF₃ | 2 | |
| 17-19 | CH₂OCH₂CF₃ | H | CF₃ | 2 | |
| 17-20 | CH₂OCH₂c-Pr | H | CF₃ | 2 | |
| 17-21 | CH₂OC(=O)Me | H | CF₃ | 2 | |
| 17-22 | CH₂OC(=O)i-Pr | H | CF₃ | 2 | |
| 17-23 | CH₂OC(=O)c-Pr | H | CF₃ | 2 | |
| 17-24 | CH₂OC(=O)OMe | H | CF₃ | 2 | |
| 17-25 | CH₂OC(=O)NHMe | H | CF₃ | 2 | |
| 17-26 | CH₂OC(=O)NMe₂ | H | CF₃ | 2 | |
| 17-27 | CH₂CN | H | CF₃ | 2 | |
| 17-28 | CH₂NH₂ | H | CF₃ | 2 | |
| 17-29 | CH₂NHMe | H | CF₃ | 2 | |
| 17-30 | CH₂NHi-Pr | H | CF₃ | 2 | |
| 17-31 | CH₂NHc-Pr | H | CF₃ | 2 | |
| 17-32 | CH₂NHCH₂CF₃ | H | CF₃ | 2 | |
| 17-33 | CH₂NHCH₂c-Pr | H | CF₃ | 2 | |
| 17-34 | CH₂NMe₂ | H | CF₃ | 2 | |
| 17-35 | CH₂NHAc | H | CF₃ | 2 | |
| 17-36 | CH₂N(Ac)Me | H | CF₃ | 2 | |
| 17-37 | CH₂N(Ac)i-Pr | H | CF₃ | 2 | |
| 17-38 | CH₂N(Ac)c-Pr | H | CF₃ | 2 | |
| 17-39 | CH₂N(Ac)CH₂CF₃ | H | CF₃ | 2 | |
| 17-40 | CH₂N(Ac)CH₂c-Pr | H | CF₃ | 2 | |
| 17-41 | CH₂NHCOOMe | H | CF₃ | 2 | |
| 17-42 | CH₂NHCOOt-Bu | H | CF₃ | 2 | |
| 17-43 | CH₂N(Me)CO₂Me | H | CF₃ | 2 | |

-continued

| Compound No. | $R^{21}$ | $R^{22}$ | $R^3$ | m | Physical Property |
|---|---|---|---|---|---|
| 17-44 | $CH_2N(Me)COOt$-Bu | H | $CF_3$ | 2 | |
| 17-45 | $CH_2NHCONHMe$ | H | $CF_3$ | 2 | |
| 17-46 | $CH_2N(Me)CONHMe$ | H | $CF_3$ | 2 | |
| 17-47 | $CH_2SMe$ | H | $CF_3$ | 2 | |
| 17-48 | $CH_2SOMe$ | H | $CF_3$ | 2 | |
| 17-49 | $CH_2SO_2Me$ | H | $CF_3$ | 2 | |
| 17-50 | CH=NOH | H | $CF_3$ | 2 | |
| 17-51 | CH=NOMe | H | $CF_3$ | 2 | |
| 17-52 | CH=NOi-Pr | H | $CF_3$ | 2 | |
| 17-53 | CH=$NOCH_2CF_3$ | H | $CF_3$ | 2 | |
| 17-54 | CH=$NOCH_2$c-Pr | H | $CF_3$ | 2 | |
| 17-55 | C(Me)=NOH | H | $CF_3$ | 2 | |
| 17-56 | C(Me)=NOMe | H | $CF_3$ | 2 | |
| 17-57 | C(Me)=NOi-Pr | H | $CF_3$ | 2 | |
| 17-58 | C(Me)=$NOCH_2CF_3$ | H | $CF_3$ | 2 | |
| 17-59 | C(Me)=$NOCH_2$c-Pr | H | $CF_3$ | 2 | |
| 17-60 | $NH_2$ | H | $CF_3$ | 2 | |
| 17-61 | NHMe | H | $CF_3$ | 2 | |
| 17-62 | NHi-Pr | H | $CF_3$ | 2 | |
| 17-63 | $NHCH_2CF_3$ | H | $CF_3$ | 2 | |
| 17-64 | $NHCH_2$c-Pr | H | $CF_3$ | 2 | |
| 17-65 | $NMe_2$ | H | $CF_3$ | 2 | |
| 17-66 | $N(Me)CH_2CF_3$ | H | $CF_3$ | 2 | |
| 17-67 | $N(Me)CH_2$c-Pr | H | $CF_3$ | 2 | |
| 17-68 | NHAc | H | $CF_3$ | 2 | |
| 17-69 | N(Ac)Me | H | $CF_3$ | 2 | |
| 17-70 | N(Ac)i-Pr | H | $CF_3$ | 2 | |
| 17-71 | $N(Ac)CH_2CF_3$ | H | $CF_3$ | 2 | |
| 17-72 | $N(Ac)CH_2$c-Pr | H | $CF_3$ | 2 | |
| 17-73 | NHCOOMe | H | $CF_3$ | 2 | |
| 17-74 | N(COOMe)Me | H | $CF_3$ | 2 | |
| 17-75 | N(COOMe)i-Pr | H | $CF_3$ | 2 | |
| 17-76 | $N(COOMe)CH_2CF_3$ | H | $CF_3$ | 2 | |
| 17-77 | $N(COOMe)CH_2$c-Pr | H | $CF_3$ | 2 | |
| 17-78 | $NHCONMe_2$ | H | $CF_3$ | 2 | |
| 17-79 | $N(CONMe_2)Me$ | H | $CF_3$ | 2 | |
| 17-80 | $CH_2Cl$ | H | $CF_3$ | 2 | |
| 17-81 | H | $CO_2H$ | $CF_3$ | 2 | |
| 17-82 | H | $CO_2Me$ | $CF_3$ | 2 | |
| 17-83 | H | $CO_2$i-Pr | $CF_3$ | 2 | |
| 17-84 | H | $CO_2CH_2CF_3$ | $CF_3$ | 2 | |
| 17-85 | H | $CO_2CH_2$c-Pr | $CF_3$ | 2 | |
| 17-86 | H | $CONH_2$ | $CF_3$ | 2 | |
| 17-87 | H | CONHMe | $CF_3$ | 2 | |
| 17-88 | H | CONHi-Pr | $CF_3$ | 2 | |
| 17-89 | H | CONHc-Pr | $CF_3$ | 2 | |
| 17-90 | H | $CONHCH_2CF_3$ | $CF_3$ | 2 | |
| 17-91 | H | $CONHCH_2$c-Pr | $CF_3$ | 2 | |
| 17-92 | H | $CONMe_2$ | $CF_3$ | 2 | |
| 17-93 | H | CN | $CF_3$ | 2 | |
| 17-94 | H | CHO | $CF_3$ | 2 | |
| 17-95 | H | C(=O)Me | $CF_3$ | 2 | |
| 17-96 | H | $CH_2OH$ | $CF_3$ | 2 | |
| 17-97 | H | $CH_2OMe$ | $CF_3$ | 2 | |
| 17-98 | H | $CH_2O$i-Pr | $CF_3$ | 2 | |
| 17-99 | H | $CH_2OCH_2CF_3$ | $CF_3$ | 2 | |
| 17-100 | H | $CH_2OCH_2$c-Pr | $CF_3$ | 2 | |
| 17-101 | H | $CH_2OC(=O)Me$ | $CF_3$ | 2 | |
| 17-102 | H | $CH_2OC(=O)$i-Pr | $CF_3$ | 2 | |
| 17-103 | H | $CH_2OC(=O)$c-Pr | $CF_3$ | 2 | |
| 17-104 | H | $CH_2OC(=O)OMe$ | $CF_3$ | 2 | |
| 17-105 | H | $CH_2OC(=O)NHMe$ | $CF_3$ | 2 | |
| 17-106 | H | $CH_2OC(=O)NMe_2$ | $CF_3$ | 2 | |
| 17-107 | H | $CH_2CN$ | $CF_3$ | 2 | |
| 17-108 | H | $CH_2NH_2$ | $CF_3$ | 2 | |
| 17-109 | H | $CH_2NHMe$ | $CF_3$ | 2 | |
| 17-110 | H | $CH_2NH$i-Pr | $CF_3$ | 2 | |
| 17-111 | H | $CH_2NH$c-Pr | $CF_3$ | 2 | |
| 17-112 | H | $CH_2NHCH_2CF_3$ | $CF_3$ | 2 | |
| 17-113 | H | $CH_2NHCH_2$c-Pr | $CF_3$ | 2 | |
| 17-114 | H | $CH_2NMe_2$ | $CF_3$ | 2 | |
| 17-115 | H | $CH_2NHAc$ | $CF_3$ | 2 | |
| 17-116 | H | $CH_2N(Ac)Me$ | $CF_3$ | 2 | |
| 17-117 | H | $CH_2N(Ac)$i-Pr | $CF_3$ | 2 | |
| 17-118 | H | $CH_2N(Ac)$c-Pr | $CF_3$ | 2 | |
| 17-119 | H | $CH_2N(Ac)CH_2CF_3$ | $CF_3$ | 2 | |

-continued

| Compound No. | $R^{21}$ | $R^{22}$ | $R^3$ | m | Physical Property |
|---|---|---|---|---|---|
| 17-120 | H | $CH_2N(Ac)CH_2c\text{-Pr}$ | $CF_3$ | 2 | |
| 17-121 | H | $CH_2NHCOOMe$ | $CF_3$ | 2 | |
| 17-122 | H | $CH_2NHCOOt\text{-Bu}$ | $CF_3$ | 2 | |
| 17-123 | H | $CH_2N(Me)CO_2Me$ | $CF_3$ | 2 | |
| 17-124 | H | $CH_2N(Me)COOt\text{-Bu}$ | $CF_3$ | 2 | |
| 17-125 | H | $CH_2NHCONHMe$ | $CF_3$ | 2 | |
| 17-126 | H | $CH_2N(Me)CONHMe$ | $CF_3$ | 2 | |
| 17-127 | H | $CH_2SMe$ | $CF_3$ | 2 | |
| 17-128 | H | $CH_2SOMe$ | $CF_3$ | 2 | |
| 17-129 | H | $CH_2SO_2Me$ | $CF_3$ | 2 | |
| 17-130 | H | $CH=NOH$ | $CF_3$ | 2 | |
| 17-131 | H | $CH=NOMe$ | $CF_3$ | 2 | |
| 17-132 | H | $CH=NOi\text{-Pr}$ | $CF_3$ | 2 | |
| 17-133 | H | $CH=NOCH_2CF_3$ | $CF_3$ | 2 | |
| 17-134 | H | $CH=NOCH_2c\text{-Pr}$ | $CF_3$ | 2 | |
| 17-135 | H | $C(Me)=NOH$ | $CF_3$ | 2 | |
| 17-136 | H | $C(Me)=NOMe$ | $CF_3$ | 2 | |
| 17-137 | H | $C(Me)=NOi\text{-Pr}$ | $CF_3$ | 2 | |
| 17-138 | H | $C(Me)=NOCH_2CF_3$ | $CF_3$ | 2 | |
| 17-139 | H | $C(Me)=NOCH_2c\text{-Pr}$ | $CF_3$ | 2 | |
| 17-140 | H | $NH_2$ | $CF_3$ | 2 | |
| 17-141 | H | NHMe | $CF_3$ | 2 | |
| 17-142 | H | NHi-Pr | $CF_3$ | 2 | |
| 17-143 | H | $NHCH_2CF_3$ | $CF_3$ | 2 | |
| 17-144 | H | $NHCH_2c\text{-Pr}$ | $CF_3$ | 2 | |
| 17-145 | H | $NMe_2$ | $CF_3$ | 2 | |
| 17-146 | H | $N(Me)CH_2CF_3$ | $CF_3$ | 2 | |
| 17-147 | H | $N(Me)CH_2c\text{-Pr}$ | $CF_3$ | 2 | |
| 17-148 | H | NHAc | $CF_3$ | 2 | |
| 17-149 | H | N(Ac)Me | $CF_3$ | 2 | |
| 17-150 | H | N(Ac)i-Pr | $CF_3$ | 2 | |
| 17-151 | H | $N(Ac)CH_2CF_3$ | $CF_3$ | 2 | |
| 17-152 | H | $N(Ac)CH_2c\text{-Pr}$ | $CF_3$ | 2 | |
| 17-153 | H | NHCOOMe | $CF_3$ | 2 | |
| 17-154 | H | N(COOMe)Me | $CF_3$ | 2 | |
| 17-155 | H | N(COOMe)i-Pr | $CF_3$ | 2 | |
| 17-156 | H | $N(COOMe)CH_2CF_3$ | $CF_3$ | 2 | |
| 17-157 | H | $N(COOMe)CH_2c\text{-Pr}$ | $CF_3$ | 2 | |
| 17-158 | H | $NHCONMe_2$ | $CF_3$ | 2 | |
| 17-159 | H | $N(CONMe_2)Me$ | $CF_3$ | 2 | |
| 17-160 | H | $CH_2Cl$ | $CF_3$ | 2 | |
| 17-161 | $CO_2H$ | H | $SCF_3$ | 2 | |
| 17-162 | $CO_2Me$ | H | $SCF_3$ | 2 | |
| 17-163 | $CO_2i\text{-Pr}$ | H | $SCF_3$ | 2 | |
| 17-164 | $CO_2CH_2CF_3$ | H | $SCF_3$ | 2 | |
| 17-165 | $CO_2CH_2c\text{-Pr}$ | H | $SCF_3$ | 2 | |
| 17-166 | $CONH_2$ | H | $SCF_3$ | 2 | |
| 17-167 | CONHMe | H | $SCF_3$ | 2 | |
| 17-168 | CONHi-Pr | H | $SCF_3$ | 2 | |
| 17-169 | CONHc-Pr | H | $SCF_3$ | 2 | |
| 17-170 | $CONHCH_2CF_3$ | H | $SCF_3$ | 2 | |
| 17-171 | $CONHCH_2c\text{-Pr}$ | H | $SCF_3$ | 2 | |
| 17-172 | $CONMe_2$ | H | $SCF_3$ | 2 | |
| 17-173 | CN | H | $SCF_3$ | 2 | |
| 17-174 | CHO | H | $SCF_3$ | 2 | |
| 17-175 | C(=O)Me | H | $SCF_3$ | 2 | |
| 17-176 | $CH_2OH$ | H | $SCF_3$ | 2 | |
| 17-177 | $CH_2OMe$ | H | $SCF_3$ | 2 | |
| 17-178 | $CH_2Oi\text{-Pr}$ | H | $SCF_3$ | 2 | |
| 17-179 | $CH_2OCH_2CF_3$ | H | $SCF_3$ | 2 | |
| 17-180 | $CH_2OCH_2c\text{-Pr}$ | H | $SCF_3$ | 2 | |
| 17-181 | $CH_2OC(=O)Me$ | H | $SCF_3$ | 2 | |
| 17-182 | $CH_2OC(=O)i\text{-Pr}$ | H | $SCF_3$ | 2 | |
| 17-183 | $CH_2OC(=O)c\text{-Pr}$ | H | $SCF_3$ | 2 | |
| 17-184 | $CH_2OC(=O)OMe$ | H | $SCF_3$ | 2 | |
| 17-185 | $CH_2OC(=O)NHMe$ | H | $SCF_3$ | 2 | |
| 17-186 | $CH_2OC(=O)NMe_2$ | H | $SCF_3$ | 2 | |
| 17-187 | $CH_2CN$ | H | $SCF_3$ | 2 | |
| 17-188 | $CH_2NH_2$ | H | $SCF_3$ | 2 | |
| 17-189 | $CH_2NHMe$ | H | $SCF_3$ | 2 | |
| 17-190 | $CH_2NHi\text{-Pr}$ | H | $SCF_3$ | 2 | |
| 17-191 | $CH_2NHc\text{-Pr}$ | H | $SCF_3$ | 2 | |
| 17-192 | $CH_2NHCH_2CF_3$ | H | $SCF_3$ | 2 | |
| 17-193 | $CH_2NHCH_2c\text{-Pr}$ | H | $SCF_3$ | 2 | |
| 17-194 | $CH_2NMe_2$ | H | $SCF_3$ | 2 | |
| 17-195 | $CH_2NHAc$ | H | $SCF_3$ | 2 | |

-continued

| Compound No. | R²¹ | R²² | R³ | m | Physical Property |
|---|---|---|---|---|---|
| 17-196 | CH₂N(Ac)Me | H | SCF₃ | 2 | |
| 17-197 | CH₂N(Ac)i-Pr | H | SCF₃ | 2 | |
| 17-198 | CH₂N(Ac)c-Pr | H | SCF₃ | 2 | |
| 17-199 | CH₂N(Ac)CH₂CF₃ | H | SCF₃ | 2 | |
| 17-200 | CH₂N(Ac)CH₂c-Pr | H | SCF₃ | 2 | |
| 17-201 | CH₂NHCOOMe | H | SCF₃ | 2 | |
| 17-202 | CH₂NHCOOt-Bu | H | SCF₃ | 2 | |
| 17-203 | CH₂N(Me)CO₂Me | H | SCF₃ | 2 | |
| 17-204 | CH₂N(Me)COOt-Bu | H | SCF₃ | 2 | |
| 17-205 | CH₂NHCONHMe | H | SCF₃ | 2 | |
| 17-206 | CH₂N(Me)CONHMe | H | SCF₃ | 2 | |
| 17-207 | CH₂SMe | H | SCF₃ | 2 | |
| 17-208 | CH₂SOMe | H | SCF₃ | 2 | |
| 17-209 | CH₂SO₂Me | H | SCF₃ | 2 | |
| 17-210 | CH=NOH | H | SCF₃ | 2 | |
| 17-211 | CH=NOMe | H | SCF₃ | 2 | |
| 17-212 | CH=NOi-Pr | H | SCF₃ | 2 | |
| 17-213 | CH=NOCH₂CF₃ | H | SCF₃ | 2 | |
| 17-214 | CH=NOCH₂c-Pr | H | SCF₃ | 2 | |
| 17-215 | C(Me)=NOH | H | SCF₃ | 2 | |
| 17-216 | C(Me)=NOMe | H | SCF₃ | 2 | |
| 17-217 | C(Me)=NOi-Pr | H | SCF₃ | 2 | |
| 17-218 | C(Me)=NOCH₂CF₃ | H | SCF₃ | 2 | |
| 17-219 | C(Me)=NOCH₂c-Pr | H | SCF₃ | 2 | |
| 17-220 | NH₂ | H | SCF₃ | 2 | |
| 17-221 | NHMe | H | SCF₃ | 2 | |
| 17-222 | NHi-Pr | H | SCF₃ | 2 | |
| 17-223 | NHCH₂CF₃ | H | SCF₃ | 2 | |
| 17-224 | NHCH₂c-Pr | H | SCF₃ | 2 | |
| 17-225 | NMe₂ | H | SCF₃ | 2 | |
| 17-226 | N(Me)CH₂CF₃ | H | SCF₃ | 2 | |
| 17-227 | N(Me)CH₂c-Pr | H | SCF₃ | 2 | |
| 17-228 | NHAc | H | SCF₃ | 2 | |
| 17-229 | N(Ac)Me | H | SCF₃ | 2 | |
| 17-230 | N(Ac)i-Pr | H | SCF₃ | 2 | |
| 17-231 | N(Ac)CH₂CF₃ | H | SCF₃ | 2 | |
| 17-232 | N(Ac)CH₂c-Pr | H | SCF₃ | 2 | |
| 17-233 | NHCOOMe | H | SCF₃ | 2 | |
| 17-234 | N(COOMe)Me | H | SCF₃ | 2 | |
| 17-235 | N(COOMe)i-Pr | H | SCF₃ | 2 | |
| 17-236 | N(COOMe)CH₂CF₃ | H | SCF₃ | 2 | |
| 17-237 | N(COOMe)CH₂c-Pr | H | SCF₃ | 2 | |
| 17-238 | NHCONMe₂ | H | SCF₃ | 2 | |
| 17-239 | N(CONMe₂)Me | H | SCF₃ | 2 | |
| 17-240 | CH₂Cl | H | SCF₃ | 2 | |
| 17-241 | H | CO₂H | SCF₃ | 2 | |
| 17-242 | H | CO₂Me | SCF₃ | 2 | |
| 17-243 | H | CO₂i-Pr | SCF₃ | 2 | |
| 17-244 | H | CO₂CH₂CF₃ | SCF₃ | 2 | |
| 17-245 | H | CO₂CH₂c-Pr | SCF₃ | 2 | |
| 17-246 | H | CONH₂ | SCF₃ | 2 | |
| 17-247 | H | CONHMe | SCF₃ | 2 | |
| 17-248 | H | CONHi-Pr | SCF₃ | 2 | |
| 17-249 | H | CONHc-Pr | SCF₃ | 2 | |
| 17-250 | H | CONHCH₂CF₃ | SCF₃ | 2 | |
| 17-251 | H | CONHCH₂c-Pr | SCF₃ | 2 | |
| 17-252 | H | CONMe₂ | SCF₃ | 2 | |
| 17-253 | H | CN | SCF₃ | 2 | |
| 17-254 | H | CHO | SCF₃ | 2 | |
| 17-255 | H | C(=O)Me | SCF₃ | 2 | |
| 17-256 | H | CH₂OH | SCF₃ | 2 | |
| 17-257 | H | CH₂OMe | SCF₃ | 2 | |
| 17-258 | H | CH₂Oi-Pr | SCF₃ | 2 | |
| 17-259 | H | CH₂OCH₂CF₃ | SCF₃ | 2 | |
| 17-260 | H | CH₂OCH₂c-Pr | SCF₃ | 2 | |
| 17-261 | H | CH₂OC(=O)Me | SCF₃ | 2 | |
| 17-262 | H | CH₂OC(=O)i-Pr | SCF₃ | 2 | |
| 17-263 | H | CH₂OC(=O)c-Pr | SCF₃ | 2 | |
| 17-264 | H | CH₂OC(=O)OMe | SCF₃ | 2 | |
| 17-265 | H | CH₂OC(=O)NHMe | SCF₃ | 2 | |
| 17-266 | H | CH₂OC(=O)NMe₂ | SCF₃ | 2 | |
| 17-267 | H | CH₂CN | SCF₃ | 2 | |
| 17-268 | H | CH₂NH₂ | SCF₃ | 2 | |
| 17-269 | H | CH₂NHMe | SCF₃ | 2 | |
| 17-270 | H | CH₂NHi-Pr | SCF₃ | 2 | |
| 17-271 | H | CH₂NHc-Pr | SCF₃ | 2 | |

-continued

| Compound No. | $R^{21}$ | $R^{22}$ | $R^3$ | m | Physical Property |
|---|---|---|---|---|---|
| 17-272 | H | $CH_2NHCH_2CF_3$ | $SCF_3$ | 2 | |
| 17-273 | H | $CH_2NHCH_2$c-Pr | $SCF_3$ | 2 | |
| 17-274 | H | $CH_2NMe_2$ | $SCF_3$ | 2 | |
| 17-275 | H | $CH_2NHAc$ | $SCF_3$ | 2 | |
| 17-276 | H | $CH_2N(Ac)Me$ | $SCF_3$ | 2 | |
| 17-277 | H | $CH_2N(Ac)$i-Pr | $SCF_3$ | 2 | |
| 17-278 | H | $CH_2N(Ac)$c-Pr | $SCF_3$ | 2 | |
| 17-279 | H | $CH_2N(Ac)CH_2CF_3$ | $SCF_3$ | 2 | |
| 17-280 | H | $CH_2N(Ac)CH_2$c-Pr | $SCF_3$ | 2 | |
| 17-281 | H | $CH_2NHCOOMe$ | $SCF_3$ | 2 | |
| 17-282 | H | $CH_2NHCOO$t-Bu | $SCF_3$ | 2 | |
| 17-283 | H | $CH_2N(Me)CO_2Me$ | $SCF_3$ | 2 | |
| 17-284 | H | $CH_2N(Me)COO$t-Bu | $SCF_3$ | 2 | |
| 17-285 | H | $CH_2NHCONHMe$ | $SCF_3$ | 2 | |
| 17-286 | H | $CH_2N(Me)CONHMe$ | $SCF_3$ | 2 | |
| 17-287 | H | $CH_2SMe$ | $SCF_3$ | 2 | |
| 17-288 | H | $CH_2SOMe$ | $SCF_3$ | 2 | |
| 17-289 | H | $CH_2SO_2Me$ | $SCF_3$ | 2 | |
| 17-290 | H | $CH=NOH$ | $SCF_3$ | 2 | |
| 17-291 | H | $CH=NOMe$ | $SCF_3$ | 2 | |
| 17-292 | H | $CH=NO$i-Pr | $SCF_3$ | 2 | |
| 17-293 | H | $CH=NOCH_2CF_3$ | $SCF_3$ | 2 | |
| 17-294 | H | $CH=NOCH_2$c-Pr | $SCF_3$ | 2 | |
| 17-295 | H | $C(Me)=NOH$ | $SCF_3$ | 2 | |
| 17-296 | H | $C(Me)=NOMe$ | $SCF_3$ | 2 | |
| 17-297 | H | $C(Me)=NO$i-Pr | $SCF_3$ | 2 | |
| 17-298 | H | $C(Me)=NOCH_2CF_3$ | $SCF_3$ | 2 | |
| 17-299 | H | $C(Me)=NOCH_2$c-Pr | $SCF_3$ | 2 | |
| 17-300 | H | $NH_2$ | $SCF_3$ | 2 | |
| 17-301 | H | NHMe | $SCF_3$ | 2 | |
| 17-302 | H | NHi-Pr | $SCF_3$ | 2 | |
| 17-303 | H | $NHCH_2CF_3$ | $SCF_3$ | 2 | |
| 17-304 | H | $NHCH_2$c-Pr | $SCF_3$ | 2 | |
| 17-305 | H | $NMe_2$ | $SCF_3$ | 2 | |
| 17-306 | H | $N(Me)CH_2CF_3$ | $SCF_3$ | 2 | |
| 17-307 | H | $N(Me)CH_2$c-Pr | $SCF_3$ | 2 | |
| 17-308 | H | NHAc | $SCF_3$ | 2 | |
| 17-309 | H | N(Ac)Me | $SCF_3$ | 2 | |
| 17-310 | H | N(Ac)i-Pr | $SCF_3$ | 2 | |
| 17-311 | H | $N(Ac)CH_2CF_3$ | $SCF_3$ | 2 | |
| 17-312 | H | $N(Ac)CH_2$c-Pr | $SCF_3$ | 2 | |
| 17-313 | H | NHCOOMe | $SCF_3$ | 2 | |
| 17-314 | H | N(COOMe)Me | $SCF_3$ | 2 | |
| 17-315 | H | N(COOMe)i-Pr | $SCF_3$ | 2 | |
| 17-316 | H | $N(COOMe)CH_2CF_3$ | $SCF_3$ | 2 | |
| 17-317 | H | $N(COOMe)CH_2$c-Pr | $SCF_3$ | 2 | |
| 17-318 | H | $NHCONMe_2$ | $SCF_3$ | 2 | |
| 17-319 | H | $N(CONMe_2)Me$ | $SCF_3$ | 2 | |
| 17-320 | H | $CH_2Cl$ | $SCF_3$ | 2 | |

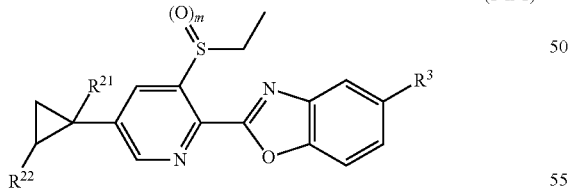

(1-h-1)

| Compound No. | $R^{21}$ | $R^{22}$ | $R^3$ | m | Physical Property |
|---|---|---|---|---|---|
| 18-1 | $CO_2H$ | H | $CF_3$ | 2 | 208-211 |
| 18-2 | $CO_2Me$ | H | $CF_3$ | 2 | 175-176 |
| 18-3 | $CO_2$i-Pr | H | $CF_3$ | 2 | |
| 18-4 | $CO_2CH_2CF_3$ | H | $CF_3$ | 2 | |
| 18-5 | $CO_2CH_2$c-Pr | H | $CF_3$ | 2 | |
| 18-6 | $CONH_2$ | H | $CF_3$ | 2 | 150 |

-continued

| Compound No. | $R^{21}$ | $R^{22}$ | $R^3$ | m | Physical Property |
|---|---|---|---|---|---|
| 18-7 | CONHMe | H | $CF_3$ | 2 | |
| 18-8 | CONHi-Pr | H | $CF_3$ | 2 | |
| 18-9 | CONHc-Pr | H | $CF_3$ | 2 | |
| 18-10 | $CONHCH_2CF_3$ | H | $CF_3$ | 2 | |
| 18-11 | $CONHCH_2$c-Pr | H | $CF_3$ | 2 | |
| 18-12 | $CONMe_2$ | H | $CF_3$ | 2 | |
| 18-13 | CN | H | $CF_3$ | 2 | 212-217 |
| 18-14 | CHO | H | $CF_3$ | 2 | |
| 18-15 | C(=O)Me | H | $CF_3$ | 2 | |
| 18-16 | $CH_2OH$ | H | $CF_3$ | 2 | |
| 18-17 | $CH_2OMe$ | H | $CF_3$ | 2 | |
| 18-18 | $CH_2$Oi-Pr | H | $CF_3$ | 2 | |
| 18-19 | $CH_2OCH_2CF_3$ | H | $CF_3$ | 2 | |
| 18-20 | $CH_2OCH_2$c-Pr | H | $CF_3$ | 2 | |
| 18-21 | $CH_2OC(=O)Me$ | H | $CF_3$ | 2 | |
| 18-22 | $CH_2OC(=O)$i-Pr | H | $CF_3$ | 2 | |
| 18-23 | $CH_2OC(=O)$c-Pr | H | $CF_3$ | 2 | |
| 18-24 | $CH_2OC(=O)OMe$ | H | $CF_3$ | 2 | |
| 18-25 | $CH_2OC(=O)NHMe$ | H | $CF_3$ | 2 | |
| 18-26 | $CH_2OC(=O)NMe_2$ | H | $CF_3$ | 2 | |
| 18-27 | $CH_2CN$ | H | $CF_3$ | 2 | |
| 18-28 | $CH_2NH_2$ | H | $CF_3$ | 2 | |
| 18-29 | $CH_2NHMe$ | H | $CF_3$ | 2 | |
| 18-30 | $CH_2$NHi-Pr | H | $CF_3$ | 2 | |
| 18-31 | $CH_2$NHc-Pr | H | $CF_3$ | 2 | |
| 18-32 | $CH_2NHCH_2CF_3$ | H | $CF_3$ | 2 | |
| 18-33 | $CH_2NHCH_2$c-Pr | H | $CF_3$ | 2 | |
| 18-34 | $CH_2NMe_2$ | H | $CF_3$ | 2 | |
| 18-35 | $CH_2NHAc$ | H | $CF_3$ | 2 | |
| 18-36 | $CH_2N(Ac)Me$ | H | $CF_3$ | 2 | |
| 18-37 | $CH_2N(Ac)$i-Pr | H | $CF_3$ | 2 | |
| 18-38 | $CH_2N(Ac)$c-Pr | H | $CF_3$ | 2 | |
| 18-39 | $CH_2N(Ac)CH_2CF_3$ | H | $CF_3$ | 2 | |
| 18-40 | $CH_2N(Ac)CH_2$c-Pr | H | $CF_3$ | 2 | |
| 18-41 | $CH_2NHCOOMe$ | H | $CF_3$ | 2 | |
| 18-42 | $CH_2NHCOO$t-Bu | H | $CF_3$ | 2 | |
| 18-43 | $CH_2N(Me)CO_2Me$ | H | $CF_3$ | 2 | |
| 18-44 | $CH_2N(Me)COO$t-Bu | H | $CF_3$ | 2 | |
| 18-45 | $CH_2NHCONHMe$ | H | $CF_3$ | 2 | |
| 18-46 | $CH_2N(Me)CONHMe$ | H | $CF_3$ | 2 | |
| 18-47 | $CH_2SMe$ | H | $CF_3$ | 2 | |
| 18-48 | $CH_2SOMe$ | H | $CF_3$ | 2 | |
| 18-49 | $CH_2SO_2Me$ | H | $CF_3$ | 2 | |
| 18-50 | CH=NOH | H | $CF_3$ | 2 | |
| 18-51 | CH=NOMe | H | $CF_3$ | 2 | |
| 18-52 | CH=NOi-Pr | H | $CF_3$ | 2 | |
| 18-53 | $CH=NOCH_2CF_3$ | H | $CF_3$ | 2 | |
| 18-54 | $CH=NOCH_2$c-Pr | H | $CF_3$ | 2 | |
| 18-55 | C(Me)=NOH | H | $CF_3$ | 2 | |
| 18-56 | C(Me)=NOMe | H | $CF_3$ | 2 | |
| 18-57 | C(Me)=NOi-Pr | H | $CF_3$ | 2 | |
| 18-58 | $C(Me)=NOCH_2CF_3$ | H | $CF_3$ | 2 | |
| 18-59 | $C(Me)=NOCH_2$c-Pr | H | $CF_3$ | 2 | |
| 18-60 | $NH_2$ | H | $CF_3$ | 2 | |
| 18-61 | NHMe | H | $CF_3$ | 2 | |
| 18-62 | NHi-Pr | H | $CF_3$ | 2 | |
| 18-63 | $NHCH_2CF_3$ | H | $CF_3$ | 2 | |
| 18-64 | $NHCH_2$c-Pr | H | $CF_3$ | 2 | |
| 18-65 | $NMe_2$ | H | $CF_3$ | 2 | |
| 18-66 | $N(Me)CH_2CF_3$ | H | $CF_3$ | 2 | |
| 18-67 | $N(Me)CH_2$c-Pr | H | $CF_3$ | 2 | |
| 18-68 | NHAc | H | $CF_3$ | 2 | |
| 18-69 | N(Ac)Me | H | $CF_3$ | 2 | |
| 18-70 | N(Ac)i-Pr | H | $CF_3$ | 2 | |
| 18-71 | $N(Ac)CH_2CF_3$ | H | $CF_3$ | 2 | |
| 18-72 | $N(Ac)CH_2$c-Pr | H | $CF_3$ | 2 | |
| 18-73 | NHCOOMe | H | $CF_3$ | 2 | |
| 18-74 | N(COOMe)Me | H | $CF_3$ | 2 | |
| 18-75 | N(COOMe)i-Pr | H | $CF_3$ | 2 | |
| 18-76 | $N(COOMe)CH_2CF_3$ | H | $CF_3$ | 2 | |
| 18-77 | $N(COOMe)CH_2$c-Pr | H | $CF_3$ | 2 | |
| 18-78 | $NHCONMe_2$ | H | $CF_3$ | 2 | |
| 18-79 | $N(CONMe_2)Me$ | H | $CF_3$ | 2 | |
| 18-80 | $CH_2Cl$ | H | $CF_3$ | 2 | |
| 18-81 | H | $CO_2H$ | $CF_3$ | 2 | |
| 18-82 | H | $CO_2Me$ | $CF_3$ | 2 | |

-continued

| Compound No. | R²¹ | R²² | R³ | m | Physical Property |
|---|---|---|---|---|---|
| 18-83 | H | CO₂i-Pr | CF₃ | 2 | |
| 18-84 | H | CO₂CH₂CF₃ | CF₃ | 2 | |
| 18-85 | H | CO₂CH₂c-Pr | CF₃ | 2 | |
| 18-86 | H | CONH₂ | CF₃ | 2 | |
| 18-87 | H | CONHMe | CF₃ | 2 | |
| 18-88 | H | CONHi-Pr | CF₃ | 2 | |
| 18-89 | H | CONHc-Pr | CF₃ | 2 | |
| 18-90 | H | CONHCH₂CF₃ | CF₃ | 2 | |
| 18-91 | H | CONHCH₂c-Pr | CF₃ | 2 | |
| 18-92 | H | CONMe₂ | CF₃ | 2 | |
| 18-93 | H | CN | CF₃ | 2 | |
| 18-94 | H | CHO | CF₃ | 2 | |
| 18-95 | H | C(=O)Me | CF₃ | 2 | |
| 18-96 | H | CH₂OH | CF₃ | 2 | |
| 18-97 | H | CH₂OMe | CF₃ | 2 | |
| 18-98 | H | CH₂Oi-Pr | CF₃ | 2 | |
| 18-99 | H | CH₂OCH₂CF₃ | CF₃ | 2 | |
| 18-100 | H | CH₂OCH₂c-Pr | CF₃ | 2 | |
| 18-101 | H | CH₂OC(=O)Me | CF₃ | 2 | |
| 18-102 | H | CH₂OC(=O)i-Pr | CF₃ | 2 | |
| 18-103 | H | CH₂OC(=O)c-Pr | CF₃ | 2 | |
| 18-104 | H | CH₂OC(=O)OMe | CF₃ | 2 | |
| 18-105 | H | CH₂OC(=O)NHMe | CF₃ | 2 | |
| 18-106 | H | CH₂OC(=O)NMe₂ | CF₃ | 2 | |
| 18-107 | H | CH₂CN | CF₃ | 2 | |
| 18-108 | H | CH₂NH₂ | CF₃ | 2 | |
| 18-109 | H | CH₂NHMe | CF₃ | 2 | |
| 18-110 | H | CH₂NHi-Pr | CF₃ | 2 | |
| 18-111 | H | CH₂NHc-Pr | CF₃ | 2 | |
| 18-112 | H | CH₂NHCH₂CF₃ | CF₃ | 2 | |
| 18-113 | H | CH₂NHCH₂c-Pr | CF₃ | 2 | |
| 18-114 | H | CH₂NMe₂ | CF₃ | 2 | |
| 18-115 | H | CH₂NHAc | CF₃ | 2 | |
| 18-116 | H | CH₂N(Ac)Me | CF₃ | 2 | |
| 18-117 | H | CH₂N(Ac)i-Pr | CF₃ | 2 | |
| 18-118 | H | CH₂N(Ac)c-Pr | CF₃ | 2 | |
| 18-119 | H | CH₂N(Ac)CH₂CF₃ | CF₃ | 2 | |
| 18-120 | H | CH₂N(Ac)CH₂c-Pr | CF₃ | 2 | |
| 18-121 | H | CH₂NHCOOMe | CF₃ | 2 | |
| 18-122 | H | CH₂NHCOOt-Bu | CF₃ | 2 | |
| 18-123 | H | CH₂N(Me)CO₂Me | CF₃ | 2 | |
| 18-124 | H | CH₂N(Me)COOt-Bu | CF₃ | 2 | |
| 18-125 | H | CH₂NHCONHMe | CF₃ | 2 | |
| 18-126 | H | CH₂N(Me)CONHMe | CF₃ | 2 | |
| 18-127 | H | CH₂SMe | CF₃ | 2 | |
| 18-128 | H | CH₂SOMe | CF₃ | 2 | |
| 18-129 | H | CH₂SO₂Me | CF₃ | 2 | |
| 18-130 | H | CH=NOH | CF₃ | 2 | |
| 18-131 | H | CH=NOMe | CF₃ | 2 | |
| 18-132 | H | CH=NOi-Pr | CF₃ | 2 | |
| 18-133 | H | CH=NOCH₂CF₃ | CF₃ | 2 | |
| 18-134 | H | CH=NOCH₂c-Pr | CF₃ | 2 | |
| 18-135 | H | C(Me)=NOH | CF₃ | 2 | |
| 18-136 | H | C(Me)=NOMe | CF₃ | 2 | |
| 18-137 | H | C(Me)=NOi-Pr | CF₃ | 2 | |
| 18-138 | H | C(Me)=NOCH₂CF₃ | CF₃ | 2 | |
| 18-139 | H | C(Me)=NOCH₂c-Pr | CF₃ | 2 | |
| 18-140 | H | NH₂ | CF₃ | 2 | |
| 18-141 | H | NHMe | CF₃ | 2 | |
| 18-142 | H | NHi-Pr | CF₃ | 2 | |
| 18-143 | H | NHCH₂CF₃ | CF₃ | 2 | |
| 18-144 | H | NHCH₂c-Pr | CF₃ | 2 | |
| 18-145 | H | NMe₂ | CF₃ | 2 | |
| 18-146 | H | N(Me)CH₂CF₃ | CF₃ | 2 | |
| 18-147 | H | N(Me)CH₂c-Pr | CF₃ | 2 | |
| 18-148 | H | NHAc | CF₃ | 2 | |
| 18-149 | H | N(Ac)Me | CF₃ | 2 | |
| 18-150 | H | N(Ac)i-Pr | CF₃ | 2 | |
| 18-151 | H | N(Ac)CH₂CF₃ | CF₃ | 2 | |
| 18-152 | H | N(Ac)CH₂c-Pr | CF₃ | 2 | |
| 18-153 | H | NHCOOMe | CF₃ | 2 | |
| 18-154 | H | N(COOMe)Me | CF₃ | 2 | |
| 18-155 | H | N(COOMe)i-Pr | CF₃ | 2 | |
| 18-156 | H | N(COOMe)CH₂CF₃ | CF₃ | 2 | |
| 18-157 | H | N(COOMe)CH₂c-Pr | CF₃ | 2 | |
| 18-158 | H | NHCONMe₂ | CF₃ | 2 | |

-continued

| Compound No. | $R^{21}$ | $R^{22}$ | $R^3$ | m | Physical Property |
|---|---|---|---|---|---|
| 18-159 | H | N(CONMe$_2$)Me | CF$_3$ | 2 | |
| 18-160 | H | CH$_2$Cl | CF$_3$ | 2 | |
| 18-161 | CO$_2$H | H | SCF$_3$ | 2 | 173-176 |
| 18-162 | CO$_2$Me | H | SCF$_3$ | 2 | 113-115 |
| 18-163 | CO$_2$i-Pr | H | SCF$_3$ | 2 | |
| 18-164 | CO$_2$CH$_2$CF$_3$ | H | SCF$_3$ | 2 | |
| 18-165 | CO$_2$CH$_2$c-Pr | H | SCF$_3$ | 2 | |
| 18-166 | CONH$_2$ | H | SCF$_3$ | 2 | 214-216 |
| 18-167 | CONHMe | H | SCF$_3$ | 2 | |
| 18-168 | CONHi-Pr | H | SCF$_3$ | 2 | |
| 18-169 | CONHc-Pr | H | SCF$_3$ | 2 | |
| 18-170 | CONHCH$_2$CF$_3$ | H | SCF$_3$ | 2 | |
| 18-171 | CONHCH$_2$c-Pr | H | SCF$_3$ | 2 | |
| 18-172 | CONMe$_2$ | H | SCF$_3$ | 2 | |
| 18-173 | CN | H | SCF$_3$ | 2 | 188-189 |
| 18-174 | CHO | H | SCF$_3$ | 2 | 135-136 |
| 18-175 | C(=O)Me | H | SCF$_3$ | 2 | |
| 18-176 | CH$_2$OH | H | SCF$_3$ | 2 | 126-127 |
| 18-177 | CH$_2$OMe | H | SCF$_3$ | 2 | |
| 18-178 | CH$_2$Oi-Pr | H | SCF$_3$ | 2 | |
| 18-179 | CH$_2$OCH$_2$CF$_3$ | H | SCF$_3$ | 2 | |
| 18-180 | CH$_2$OCH$_2$c-Pr | H | SCF$_3$ | 2 | |
| 18-181 | CH$_2$OC(=O)Me | H | SCF$_3$ | 2 | |
| 18-182 | CH$_2$OC(=O)i-Pr | H | SCF$_3$ | 2 | |
| 18-183 | CH$_2$OC(=O)c-Pr | H | SCF$_3$ | 2 | |
| 18-184 | CH$_2$OC(=O)OMe | H | SCF$_3$ | 2 | |
| 18-185 | CH$_2$OC(=O)NHMe | H | SCF$_3$ | 2 | |
| 18-186 | CH$_2$OC(=O)NMe$_2$ | H | SCF$_3$ | 2 | |
| 18-187 | CH$_2$CN | H | SCF$_3$ | 2 | 151-152 |
| 18-188 | CH$_2$NH$_2$ | H | SCF$_3$ | 2 | |
| 18-189 | CH$_2$NHMe | H | SCF$_3$ | 2 | |
| 18-190 | CH$_2$NHi-Pr | H | SCF$_3$ | 2 | |
| 18-191 | CH$_2$NHc-Pr | H | SCF$_3$ | 2 | |
| 18-192 | CH$_2$NHCH$_2$CF$_3$ | H | SCF$_3$ | 2 | |
| 18-193 | CH$_2$NHCH$_2$c-Pr | H | SCF$_3$ | 2 | |
| 18-194 | CH$_2$NMe$_2$ | H | SCF$_3$ | 2 | |
| 18-195 | CH$_2$NHAc | H | SCF$_3$ | 2 | |
| 18-196 | CH$_2$N(Ac)Me | H | SCF$_3$ | 2 | |
| 18-197 | CH$_2$N(Ac)i-Pr | H | SCF$_3$ | 2 | |
| 18-198 | CH$_2$N(Ac)c-Pr | H | SCF$_3$ | 2 | |
| 18-199 | CH$_2$N(Ac)CH$_2$CF$_3$ | H | SCF$_3$ | 2 | |
| 18-200 | CH$_2$N(Ac)CH$_2$c-Pr | H | SCF$_3$ | 2 | |
| 18-201 | CH$_2$NHCOOMe | H | SCF$_3$ | 2 | |
| 18-202 | CH$_2$NHCOOt-Bu | H | SCF$_3$ | 2 | |
| 18-203 | CH$_2$N(Me)CO$_2$Me | H | SCF$_3$ | 2 | |
| 18-204 | CH$_2$N(Me)COOt-Bu | H | SCF$_3$ | 2 | |
| 18-205 | CH$_2$NHCONHMe | H | SCF$_3$ | 2 | |
| 18-206 | CH$_2$N(Me)CONHMe | H | SCF$_3$ | 2 | |
| 18-207 | CH$_2$SMe | H | SCF$_3$ | 2 | |
| 18-208 | CH$_2$SOMe | H | SCF$_3$ | 2 | |
| 18-209 | CH$_2$SO$_2$Me | H | SCF$_3$ | 2 | |
| 18-210 | CH=NOH | H | SCF$_3$ | 2 | 157-159 |
| 18-211 | CH=NOMe | H | SCF$_3$ | 2 | 155-157 |
| 18-212 | CH=NOi-Pr | H | SCF$_3$ | 2 | |
| 18-213 | CH=NOCH$_2$CF$_3$ | H | SCF$_3$ | 2 | 125-127 |
| 18-214 | CH=NOCH$_2$c-Pr | H | SCF$_3$ | 2 | |
| 18-215 | C(Me)=NOH | H | SCF$_3$ | 2 | |
| 18-216 | C(Me)=NOMe | H | SCF$_3$ | 2 | |
| 18-217 | C(Me)=NOi-Pr | H | SCF$_3$ | 2 | |
| 18-218 | C(Me)=NOCH$_2$CF$_3$ | H | SCF$_3$ | 2 | |
| 18-219 | C(Me)=NOCH$_2$c-Pr | H | SCF$_3$ | 2 | |
| 18-220 | NH$_2$ | H | SCF$_3$ | 2 | 153-155 |
| 18-221 | NHMe | H | SCF$_3$ | 2 | 90-91 |
| 18-222 | NHi-Pr | H | SCF$_3$ | 2 | |
| 18-223 | NHCH$_2$CF$_3$ | H | SCF$_3$ | 2 | |
| 18-224 | NHCH$_2$c-Pr | H | SCF$_3$ | 2 | |
| 18-225 | NMe$_2$ | H | SCF$_3$ | 2 | |
| 18-226 | N(Me)CH$_2$CF$_3$ | H | SCF$_3$ | 2 | |
| 18-227 | N(Me)CH$_2$c-Pr | H | SCF$_3$ | 2 | |
| 18-228 | NHAc | H | SCF$_3$ | 2 | 206-207 |
| 18-229 | N(Ac)Me | H | SCF$_3$ | 2 | |
| 18-230 | N(Ac)i-Pr | H | SCF$_3$ | 2 | |
| 18-231 | N(Ac)CH$_2$CF$_3$ | H | SCF$_3$ | 2 | |
| 18-232 | N(Ac)CH$_2$c-Pr | H | SCF$_3$ | 2 | |
| 18-233 | NHCOOMe | H | SCF$_3$ | 2 | 76-79 |
| 18-234 | N(COOMe)Me | H | SCF$_3$ | 2 | 129-131 |

-continued

| Compound No. | $R^{21}$ | $R^{22}$ | $R^3$ | m | Physical Property |
|---|---|---|---|---|---|
| 18-235 | N(COOMe)i-Pr | H | $SCF_3$ | 2 | |
| 18-236 | N(COOMe)CH$_2$CF$_3$ | H | $SCF_3$ | 2 | |
| 18-237 | N(COOMe)CH$_2$c-Pr | H | $SCF_3$ | 2 | |
| 18-238 | NHCONMe$_2$ | H | $SCF_3$ | 2 | |
| 18-239 | N(CONMe$_2$)Me | H | $SCF_3$ | 2 | |
| 18-240 | CH$_2$Cl | H | $SCF_3$ | 2 | |
| 18-241 | H | CO$_2$H | $SCF_3$ | 2 | |
| 18-242 | H | CO$_2$Me | $SCF_3$ | 2 | |
| 18-243 | H | CO$_2$i-Pr | $SCF_3$ | 2 | |
| 18-244 | H | CO$_2$CH$_2$CF$_3$ | $SCF_3$ | 2 | |
| 18-245 | H | CO$_2$CH$_2$c-Pr | $SCF_3$ | 2 | |
| 18-246 | H | CONH$_2$ | $SCF_3$ | 2 | |
| 18-247 | H | CONHMe | $SCF_3$ | 2 | |
| 18-248 | H | CONHi-Pr | $SCF_3$ | 2 | |
| 18-249 | H | CONHc-Pr | $SCF_3$ | 2 | |
| 18-250 | H | CONHCH$_2$CF$_3$ | $SCF_3$ | 2 | |
| 18-251 | H | CONHCH$_2$c-Pr | $SCF_3$ | 2 | |
| 18-252 | H | CONMe$_2$ | $SCF_3$ | 2 | |
| 18-253 | H | CN | $SCF_3$ | 2 | |
| 18-254 | H | CHO | $SCF_3$ | 2 | |
| 18-255 | H | C(=O)Me | $SCF_3$ | 2 | |
| 18-256 | H | CH$_2$OH | $SCF_3$ | 2 | |
| 18-257 | H | CH$_2$OMe | $SCF_3$ | 2 | |
| 18-258 | H | CH$_2$Oi-Pr | $SCF_3$ | 2 | |
| 18-259 | H | CH$_2$OCH$_2$CF$_3$ | $SCF_3$ | 2 | |
| 18-260 | H | CH$_2$OCH$_2$c-Pr | $SCF_3$ | 2 | |
| 18-261 | H | CH$_2$OC(=O)Me | $SCF_3$ | 2 | |
| 18-262 | H | CH$_2$OC(=O)i-Pr | $SCF_3$ | 2 | |
| 18-263 | H | CH$_2$OC(=O)c-Pr | $SCF_3$ | 2 | |
| 18-264 | H | CH$_2$OC(=O)OMe | $SCF_3$ | 2 | |
| 18-265 | H | CH$_2$OC(=O)NHMe | $SCF_3$ | 2 | |
| 18-266 | H | CH$_2$OC(=O)NMe$_2$ | $SCF_3$ | 2 | |
| 18-267 | H | CH$_2$CN | $SCF_3$ | 2 | |
| 18-268 | H | CH$_2$NH$_2$ | $SCF_3$ | 2 | |
| 18-269 | H | CH$_2$NHMe | $SCF_3$ | 2 | |
| 18-270 | H | CH$_2$NHi-Pr | $SCF_3$ | 2 | |
| 18-271 | H | CH$_2$NHc-Pr | $SCF_3$ | 2 | |
| 18-272 | H | CH$_2$NHCH$_2$CF$_3$ | $SCF_3$ | 2 | |
| 18-273 | H | CH$_2$NHCH$_2$c-Pr | $SCF_3$ | 2 | |
| 18-274 | H | CH$_2$NMe$_2$ | $SCF_3$ | 2 | |
| 18-275 | H | CH$_2$NHAc | $SCF_3$ | 2 | |
| 18-276 | H | CH$_2$N(Ac)Me | $SCF_3$ | 2 | |
| 18-277 | H | CH$_2$N(Ac)i-Pr | $SCF_3$ | 2 | |
| 18-278 | H | CH$_2$N(Ac)c-Pr | $SCF_3$ | 2 | |
| 18-279 | H | CH$_2$N(Ac)CH$_2$CF$_3$ | $SCF_3$ | 2 | |
| 18-280 | H | CH$_2$N(Ac)CH$_2$c-Pr | $SCF_3$ | 2 | |
| 18-281 | H | CH$_2$NHCOOMe | $SCF_3$ | 2 | |
| 18-282 | H | CH$_2$NHCOOt-Bu | $SCF_3$ | 2 | |
| 18-283 | H | CH$_2$N(Me)CO$_2$Me | $SCF_3$ | 2 | |
| 18-284 | H | CH$_2$N(Me)COOt-Bu | $SCF_3$ | 2 | |
| 18-285 | H | CH$_2$NHCONHMe | $SCF_3$ | 2 | |
| 18-286 | H | CH$_2$N(Me)CONHMe | $SCF_3$ | 2 | |
| 18-287 | H | CH$_2$SMe | $SCF_3$ | 2 | |
| 18-288 | H | CH$_2$SOMe | $SCF_3$ | 2 | |
| 18-289 | H | CH$_2$SO$_2$Me | $SCF_3$ | 2 | |
| 18-290 | H | CH=NOH | $SCF_3$ | 2 | |
| 18-291 | H | CH=NOMe | $SCF_3$ | 2 | |
| 18-292 | H | CH=NOi-Pr | $SCF_3$ | 2 | |
| 18-293 | H | CH=NOCH$_2$CF$_3$ | $SCF_3$ | 2 | |
| 18-294 | H | CH=NOCH$_2$c-Pr | $SCF_3$ | 2 | |
| 18-295 | H | C(Me)=NOH | $SCF_3$ | 2 | |
| 18-296 | H | C(Me)=NOMe | $SCF_3$ | 2 | |
| 18-297 | H | C(Me)=NOi-Pr | $SCF_3$ | 2 | |
| 18-298 | H | C(Me)=NOCH$_2$CF$_3$ | $SCF_3$ | 2 | |
| 18-299 | H | C(Me)=NOCH$_2$c-Pr | $SCF_3$ | 2 | |
| 18-300 | H | NH$_2$ | $SCF_3$ | 2 | |
| 18-301 | H | NHMe | $SCF_3$ | 2 | |
| 18-302 | H | NHi-Pr | $SCF_3$ | 2 | |
| 18-303 | H | NHCH$_2$CF$_3$ | $SCF_3$ | 2 | |
| 18-304 | H | NHCH$_2$c-Pr | $SCF_3$ | 2 | |
| 18-305 | H | NMe$_2$ | $SCF_3$ | 2 | |
| 18-306 | H | N(Me)CH$_2$CF$_3$ | $SCF_3$ | 2 | |
| 18-307 | H | N(Me)CH$_2$c-Pr | $SCF_3$ | 2 | |
| 18-308 | H | NHAc | $SCF_3$ | 2 | |
| 18-309 | H | N(Ac)Me | $SCF_3$ | 2 | |
| 18-310 | H | N(Ac)i-Pr | $SCF_3$ | 2 | |

-continued

| Compound No. | $R^{21}$ | $R^{22}$ | $R^3$ | m | Physical Property |
|---|---|---|---|---|---|
| 18-311 | H | N(Ac)CH$_2$CF$_3$ | SCF$_3$ | 2 | |
| 18-312 | H | N(Ac)CH$_2$c-Pr | SCF$_3$ | 2 | |
| 18-313 | H | NHCOOMe | SCF$_3$ | 2 | |
| 18-314 | H | N(COOMe)Me | SCF$_3$ | 2 | |
| 18-315 | H | N(COOMe)i-Pr | SCF$_3$ | 2 | |
| 18-316 | H | N(COOMe)CH$_2$CF$_3$ | SCF$_3$ | 2 | |
| 18-317 | H | N(COOMe)CH$_2$c-Pr | SCF$_3$ | 2 | |
| 18-318 | H | NHCONMe$_2$ | SCF$_3$ | 2 | |
| 18-319 | H | N(CONMe$_2$)Me | SCF$_3$ | 2 | |
| 18-320 | H | CH$_2$Cl | SCF$_3$ | 2 | |

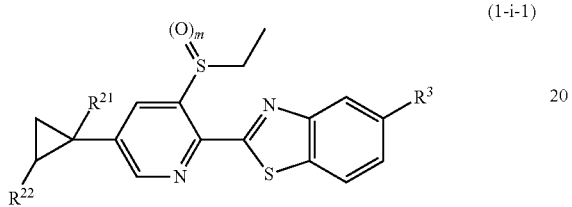

(1-i-1)

| Compound No. | $R^{21}$ | $R^{22}$ | $R^3$ | m | Physical Property |
|---|---|---|---|---|---|
| 19-1 | CO$_2$H | H | CF$_3$ | 2 | |
| 19-2 | CO$_2$Me | H | CF$_3$ | 2 | |
| 19-3 | CO$_2$i-Pr | H | CF$_3$ | 2 | |
| 19-4 | CO$_2$CH$_2$CF$_3$ | H | CF$_3$ | 2 | |
| 19-5 | CO$_2$CH$_2$c-Pr | H | CF$_3$ | 2 | |
| 19-6 | CONH$_2$ | H | CF$_3$ | 2 | |
| 19-7 | CONHMe | H | CF$_3$ | 2 | |
| 19-8 | CONHi-Pr | H | CF$_3$ | 2 | |
| 19-9 | CONHc-Pr | H | CF$_3$ | 2 | |
| 19-10 | CONHCH$_2$CF$_3$ | H | CF$_3$ | 2 | |
| 19-11 | CONHCH$_2$c-Pr | H | CF$_3$ | 2 | |
| 19-12 | CONMe$_2$ | H | CF$_3$ | 2 | |
| 19-13 | CN | H | CF$_3$ | 2 | |
| 19-14 | CHO | H | CF$_3$ | 2 | |
| 19-15 | C(=O)Me | H | CF$_3$ | 2 | |
| 19-16 | CH$_2$OH | H | CF$_3$ | 2 | |
| 19-17 | CH$_2$OMe | H | CF$_3$ | 2 | |
| 19-18 | CH$_2$Oi-Pr | H | CF$_3$ | 2 | |
| 19-19 | CH$_2$OCH$_2$CF$_3$ | H | CF$_3$ | 2 | |
| 19-20 | CH$_2$OCH$_2$c-Pr | H | CF$_3$ | 2 | |
| 19-21 | CH$_2$OC(=O)Me | H | CF$_3$ | 2 | |
| 19-22 | CH$_2$OC(=O)i-Pr | H | CF$_3$ | 2 | |
| 19-23 | CH$_2$OC(=O)c-Pr | H | CF$_3$ | 2 | |
| 19-24 | CH$_2$OC(=O)OMe | H | CF$_3$ | 2 | |
| 19-25 | CH$_2$OC(=O)NHMe | H | CF$_3$ | 2 | |
| 19-26 | CH$_2$OC(=O)NMe$_2$ | H | CF$_3$ | 2 | |
| 19-27 | CH$_2$CN | H | CF$_3$ | 2 | |
| 19-28 | CH$_2$NH$_2$ | H | CF$_3$ | 2 | |
| 19-29 | CH$_2$NHMe | H | CF$_3$ | 2 | |
| 19-30 | CH$_2$NHi-Pr | H | CF$_3$ | 2 | |
| 19-31 | CH$_2$NHc-Pr | H | CF$_3$ | 2 | |
| 19-32 | CH$_2$NHCH$_2$CF$_3$ | H | CF$_3$ | 2 | |
| 19-33 | CH$_2$NHCH$_2$c-Pr | H | CF$_3$ | 2 | |
| 19-34 | CH$_2$NMe$_2$ | H | CF$_3$ | 2 | |
| 19-35 | CH$_2$NHAc | H | CF$_3$ | 2 | |
| 19-36 | CH$_2$N(Ac)Me | H | CF$_3$ | 2 | |
| 19-37 | CH$_2$N(Ac)i-Pr | H | CF$_3$ | 2 | |
| 19-38 | CH$_2$N(Ac)c-Pr | H | CF$_3$ | 2 | |
| 19-39 | CH$_2$N(Ac)CH$_2$CF$_3$ | H | CF$_3$ | 2 | |
| 19-40 | CH$_2$N(Ac)CH$_2$c-Pr | H | CF$_3$ | 2 | |
| 19-41 | CH$_2$NHCOOMe | H | CF$_3$ | 2 | |
| 19-42 | CH$_2$NHCOOt-Bu | H | CF$_3$ | 2 | |
| 19-43 | CH$_2$N(Me)CO$_2$Me | H | CF$_3$ | 2 | |
| 19-44 | CH$_2$N(Me)COOt-Bu | H | CF$_3$ | 2 | |
| 19-45 | CH$_2$NHCONHMe | H | CF$_3$ | 2 | |

| Compound No. | R²¹ | R²² | R³ | m | Physical Property |
|---|---|---|---|---|---|
| 19-46 | CH₂N(Me)CONHMe | H | CF₃ | 2 | |
| 19-47 | CH₂SMe | H | CF₃ | 2 | |
| 19-48 | CH₂SOMe | H | CF₃ | 2 | |
| 19-49 | CH₂SO₂Me | H | CF₃ | 2 | |
| 19-50 | CH=NOH | H | CF₃ | 2 | |
| 19-51 | CH=NOMe | H | CF₃ | 2 | |
| 19-52 | CH=NOi-Pr | H | CF₃ | 2 | |
| 19-53 | CH=NOCH₂CF₃ | H | CF₃ | 2 | |
| 19-54 | CH=NOCH₂c-Pr | H | CF₃ | 2 | |
| 19-55 | C(Me)=NOH | H | CF₃ | 2 | |
| 19-56 | C(Me)=NOMe | H | CF₃ | 2 | |
| 19-57 | C(Me)=NOi-Pr | H | CF₃ | 2 | |
| 19-58 | C(Me)=NOCH₂CF₃ | H | CF₃ | 2 | |
| 19-59 | C(Me)=NOCH₂c-Pr | H | CF₃ | 2 | |
| 19-60 | NH₂ | H | CF₃ | 2 | |
| 19-61 | NHMe | H | CF₃ | 2 | |
| 19-62 | NHi-Pr | H | CF₃ | 2 | |
| 19-63 | NHCH₂CF₃ | H | CF₃ | 2 | |
| 19-64 | NHCH₂c-Pr | H | CF₃ | 2 | |
| 19-65 | NMe₂ | H | CF₃ | 2 | |
| 19-66 | N(Me)CH₂CF₃ | H | CF₃ | 2 | |
| 19-67 | N(Me)CH₂c-Pr | H | CF₃ | 2 | |
| 19-68 | NHAc | H | CF₃ | 2 | |
| 19-69 | N(Ac)Me | H | CF₃ | 2 | |
| 19-70 | N(Ac)i-Pr | H | CF₃ | 2 | |
| 19-71 | N(Ac)CH₂CF₃ | H | CF₃ | 2 | |
| 19-72 | N(Ac)CH₂c-Pr | H | CF₃ | 2 | |
| 19-73 | NHCOOMe | H | CF₃ | 2 | |
| 19-74 | N(COOMe)Me | H | CF₃ | 2 | |
| 19-75 | N(COOMe)i-Pr | H | CF₃ | 2 | |
| 19-76 | N(COOMe)CH₂CF₃ | H | CF₃ | 2 | |
| 19-77 | N(COOMe)CH₂c-Pr | H | CF₃ | 2 | |
| 19-78 | NHCONMe₂ | H | CF₃ | 2 | |
| 19-79 | N(CONMe₂)Me | H | CF₃ | 2 | |
| 19-80 | CH₂Cl | H | CF₃ | 2 | |
| 19-81 | H | CO₂H | CF₃ | 2 | |
| 19-82 | H | CO₂Me | CF₃ | 2 | |
| 19-83 | H | CO₂i-Pr | CF₃ | 2 | |
| 19-84 | H | CO₂CH₂CF₃ | CF₃ | 2 | |
| 19-85 | H | CO₂CH₂c-Pr | CF₃ | 2 | |
| 19-86 | H | CONH₂ | CF₃ | 2 | |
| 19-87 | H | CONHMe | CF₃ | 2 | |
| 19-88 | H | CONHi-Pr | CF₃ | 2 | |
| 19-89 | H | CONHc-Pr | CF₃ | 2 | |
| 19-90 | H | CONHCH₂CF₃ | CF₃ | 2 | |
| 19-91 | H | CONHCH₂c-Pr | CF₃ | 2 | |
| 19-92 | H | CONMe₂ | CF₃ | 2 | |
| 19-93 | H | CN | CF₃ | 2 | |
| 19-94 | H | CHO | CF₃ | 2 | |
| 19-95 | H | C(=O)Me | CF₃ | 2 | |
| 19-96 | H | CH₂OH | CF₃ | 2 | |
| 19-97 | H | CH₂OMe | CF₃ | 2 | |
| 19-98 | H | CH₂Oi-Pr | CF₃ | 2 | |
| 19-99 | H | CH₂OCH₂CF₃ | CF₃ | 2 | |
| 19-100 | H | CH₂OCH₂c-Pr | CF₃ | 2 | |
| 19-101 | H | CH₂OC(=O)Me | CF₃ | 2 | |
| 19-102 | H | CH₂OC(=O)i-Pr | CF₃ | 2 | |
| 19-103 | H | CH₂OC(=O)c-Pr | CF₃ | 2 | |
| 19-104 | H | CH₂OC(=O)OMe | CF₃ | 2 | |
| 19-105 | H | CH₂OC(=O)NHMe | CF₃ | 2 | |
| 19-106 | H | CH₂OC(=O)NMe₂ | CF₃ | 2 | |
| 19-107 | H | CH₂CN | CF₃ | 2 | |
| 19-108 | H | CH₂NH₂ | CF₃ | 2 | |
| 19-109 | H | CH₂NHMe | CF₃ | 2 | |
| 19-110 | H | CH₂NHi-Pr | CF₃ | 2 | |
| 19-111 | H | CH₂NHc-Pr | CF₃ | 2 | |
| 19-112 | H | CH₂NHCH₂CF₃ | CF₃ | 2 | |
| 19-113 | H | CH₂NHCH₂c-Pr | CF₃ | 2 | |
| 19-114 | H | CH₂NMe₂ | CF₃ | 2 | |
| 19-115 | H | CH₂NHAc | CF₃ | 2 | |
| 19-116 | H | CH₂N(Ac)Me | CF₃ | 2 | |
| 19-117 | H | CH₂N(Ac)i-Pr | CF₃ | 2 | |
| 19-118 | H | CH₂N(Ac)c-Pr | CF₃ | 2 | |
| 19-119 | H | CH₂N(Ac)CH₂CF₃ | CF₃ | 2 | |
| 19-120 | H | CH₂N(Ac)CH₂c-Pr | CF₃ | 2 | |
| 19-121 | H | CH₂NHCOOMe | CF₃ | 2 | |

-continued

| Compound No. | R²¹ | R²² | R³ | m | Physical Property |
|---|---|---|---|---|---|
| 19-122 | H | CH₂NHCOOt-Bu | CF₃ | 2 | |
| 19-123 | H | CH₂N(Me)CO₂Me | CF₃ | 2 | |
| 19-124 | H | CH₂N(Me)COOt-Bu | CF₃ | 2 | |
| 19-125 | H | CH₂NHCONHMe | CF₃ | 2 | |
| 19-126 | H | CH₂N(Me)CONHMe | CF₃ | 2 | |
| 19-127 | H | CH₂SMe | CF₃ | 2 | |
| 19-128 | H | CH₂SOMe | CF₃ | 2 | |
| 19-129 | H | CH₂SO₂Me | CF₃ | 2 | |
| 19-130 | H | CH=NOH | CF₃ | 2 | |
| 19-131 | H | CH=NOMe | CF₃ | 2 | |
| 19-132 | H | CH=NOi-Pr | CF₃ | 2 | |
| 19-133 | H | CH=NOCH₂CF₃ | CF₃ | 2 | |
| 19-134 | H | CH=NOCH₂c-Pr | CF₃ | 2 | |
| 19-135 | H | C(Me)=NOH | CF₃ | 2 | |
| 19-136 | H | C(Me)=NOMe | CF₃ | 2 | |
| 19-137 | H | C(Me)=NOi-Pr | CF₃ | 2 | |
| 19-138 | H | C(Me)=NOCH₂CF₃ | CF₃ | 2 | |
| 19-139 | H | C(Me)=NOCH₂c-Pr | CF₃ | 2 | |
| 19-140 | H | NH₂ | CF₃ | 2 | |
| 19-141 | H | NHMe | CF₃ | 2 | |
| 19-142 | H | NHi-Pr | CF₃ | 2 | |
| 19-143 | H | NHCH₂CF₃ | CF₃ | 2 | |
| 19-144 | H | NHCH₂c-Pr | CF₃ | 2 | |
| 19-145 | H | NMe₂ | CF₃ | 2 | |
| 19-146 | H | N(Me)CH₂CF₃ | CF₃ | 2 | |
| 19-147 | H | N(Me)CH₂c-Pr | CF₃ | 2 | |
| 19-148 | H | NHAc | CF₃ | 2 | |
| 19-149 | H | N(Ac)Me | CF₃ | 2 | |
| 19-150 | H | N(Ac)i-Pr | CF₃ | 2 | |
| 19-151 | H | N(Ac)CH₂CF₃ | CF₃ | 2 | |
| 19-152 | H | N(Ac)CH₂c-Pr | CF₃ | 2 | |
| 19-153 | H | NHCOOMe | CF₃ | 2 | |
| 19-154 | H | N(COOMe)Me | CF₃ | 2 | |
| 19-155 | H | N(COOMe)i-Pr | CF₃ | 2 | |
| 19-156 | H | N(COOMe)CH₂CF₃ | CF₃ | 2 | |
| 19-157 | H | N(COOMe)CH₂c-Pr | CF₃ | 2 | |
| 19-158 | H | NHCONMe₂ | CF₃ | 2 | |
| 19-159 | H | N(CONMe₂)Me | CF₃ | 2 | |
| 19-160 | H | CH₂Cl | CF₃ | 2 | |
| 19-161 | CO₂H | H | SCF₃ | 2 | |
| 19-162 | CO₂Me | H | SCF₃ | 2 | |
| 19-163 | CO₂i-Pr | H | SCF₃ | 2 | |
| 19-164 | CO₂CH₂CF₃ | H | SCF₃ | 2 | |
| 19-165 | CO₂CH₂c-Pr | H | SCF₃ | 2 | |
| 19-166 | CONH₂ | H | SCF₃ | 2 | |
| 19-167 | CONHMe | H | SCF₃ | 2 | |
| 19-168 | CONHi-Pr | H | SCF₃ | 2 | |
| 19-169 | CONHc-Pr | H | SCF₃ | 2 | |
| 19-170 | CONHCH₂CF₃ | H | SCF₃ | 2 | |
| 19-171 | CONHCH₂c-Pr | H | SCF₃ | 2 | |
| 19-172 | CONMe₂ | H | SCF₃ | 2 | |
| 19-173 | CN | H | SCF₃ | 2 | |
| 19-174 | CHO | H | SCF₃ | 2 | |
| 19-175 | C(=O)Me | H | SCF₃ | 2 | |
| 19-176 | CH₂OH | H | SCF₃ | 2 | |
| 19-177 | CH₂OMe | H | SCF₃ | 2 | |
| 19-178 | CH₂Oi-Pr | H | SCF₃ | 2 | |
| 19-179 | CH₂OCH₂CF₃ | H | SCF₃ | 2 | |
| 19-180 | CH₂OCH₂c-Pr | H | SCF₃ | 2 | |
| 19-181 | CH₂OC(=O)Me | H | SCF₃ | 2 | |
| 19-182 | CH₂OC(=O)i-Pr | H | SCF₃ | 2 | |
| 19-183 | CH₂OC(=O)c-Pr | H | SCF₃ | 2 | |
| 19-184 | CH₂OC(=O)OMe | H | SCF₃ | 2 | |
| 19-185 | CH₂OC(=O)NHMe | H | SCF₃ | 2 | |
| 19-186 | CH₂OC(=O)NMe₂ | H | SCF₃ | 2 | |
| 19-187 | CH₂CN | H | SCF₃ | 2 | |
| 19-188 | CH₂NH₂ | H | SCF₃ | 2 | |
| 19-189 | CH₂NHMe | H | SCF₃ | 2 | |
| 19-190 | CH₂NHi-Pr | H | SCF₃ | 2 | |
| 19-191 | CH₂NHc-Pr | H | SCF₃ | 2 | |
| 19-192 | CH₂NHCH₂CF₃ | H | SCF₃ | 2 | |
| 19-193 | CH₂NHCH₂c-Pr | H | SCF₃ | 2 | |
| 19-194 | CH₂NMe₂ | H | SCF₃ | 2 | |
| 19-195 | CH₂NHAc | H | SCF₃ | 2 | |
| 19-196 | CH₂N(Ac)Me | H | SCF₃ | 2 | |
| 19-197 | CH₂N(Ac)i-Pr | H | SCF₃ | 2 | |

-continued

| Compound No. | R²¹ | R²² | R³ | m | Physical Property |
|---|---|---|---|---|---|
| 19-198 | CH₂N(Ac)c-Pr | H | SCF₃ | 2 | |
| 19-199 | CH₂N(Ac)CH₂CF₃ | H | SCF₃ | 2 | |
| 19-200 | CH₂N(Ac)CH₂c-Pr | H | SCF₃ | 2 | |
| 19-201 | CH₂NHCOOMe | H | SCF₃ | 2 | |
| 19-202 | CH₂NHCOOt-Bu | H | SCF₃ | 2 | |
| 19-203 | CH₂N(Me)CO₂Me | H | SCF₃ | 2 | |
| 19-204 | CH₂N(Me)COOt-Bu | H | SCF₃ | 2 | |
| 19-205 | CH₂NHCONHMe | H | SCF₃ | 2 | |
| 19-206 | CH₂N(Me)CONHMe | H | SCF₃ | 2 | |
| 19-207 | CH₂SMe | H | SCF₃ | 2 | |
| 19-208 | CH₂SOMe | H | SCF₃ | 2 | |
| 19-209 | CH₂SO₂Me | H | SCF₃ | 2 | |
| 19-210 | CH=NOH | H | SCF₃ | 2 | |
| 19-211 | CH=NOMe | H | SCF₃ | 2 | |
| 19-212 | CH=NOi-Pr | H | SCF₃ | 2 | |
| 19-213 | CH=NOCH₂CF₃ | H | SCF₃ | 2 | |
| 19-214 | CH=NOCH₂c-Pr | H | SCF₃ | 2 | |
| 19-215 | C(Me)=NOH | H | SCF₃ | 2 | |
| 19-216 | C(Me)=NOMe | H | SCF₃ | 2 | |
| 19-217 | C(Me)=NOi-Pr | H | SCF₃ | 2 | |
| 19-218 | C(Me)=NOCH₂CF₃ | H | SCF₃ | 2 | |
| 19-219 | C(Me)=NOCH₂c-Pr | H | SCF₃ | 2 | |
| 19-220 | NH₂ | H | SCF₃ | 2 | |
| 19-221 | NHMe | H | SCF₃ | 2 | |
| 19-222 | NHi-Pr | H | SCF₃ | 2 | |
| 19-223 | NHCH₂CF₃ | H | SCF₃ | 2 | |
| 19-224 | NHCH₂c-Pr | H | SCF₃ | 2 | |
| 19-225 | NMe₂ | H | SCF₃ | 2 | |
| 19-226 | N(Me)CH₂CF₃ | H | SCF₃ | 2 | |
| 19-227 | N(Me)CH₂c-Pr | H | SCF₃ | 2 | |
| 19-228 | NHAc | H | SCF₃ | 2 | |
| 19-229 | N(Ac)Me | H | SCF₃ | 2 | |
| 19-230 | N(Ac)i-Pr | H | SCF₃ | 2 | |
| 19-231 | N(Ac)CH₂CF₃ | H | SCF₃ | 2 | |
| 19-232 | N(Ac)CH₂c-Pr | H | SCF₃ | 2 | |
| 19-233 | NHCOOMe | H | SCF₃ | 2 | |
| 19-234 | N(COOMe)Me | H | SCF₃ | 2 | |
| 19-235 | N(COOMe)i-Pr | H | SCF₃ | 2 | |
| 19-236 | N(COOMe)CH₂CF₃ | H | SCF₃ | 2 | |
| 19-237 | N(COOMe)CH₂c-Pr | H | SCF₃ | 2 | |
| 19-238 | NHCONMe₂ | H | SCF₃ | 2 | |
| 19-239 | N(CONMe₂)Me | H | SCF₃ | 2 | |
| 19-240 | CH₂Cl | H | SCF₃ | 2 | |
| 19-241 | H | CO₂H | SCF₃ | 2 | |
| 19-242 | H | CO₂Me | SCF₃ | 2 | |
| 19-243 | H | CO₂i-Pr | SCF₃ | 2 | |
| 19-244 | H | CO₂CH₂CF₃ | SCF₃ | 2 | |
| 19-245 | H | CO₂CH₂c-Pr | SCF₃ | 2 | |
| 19-246 | H | CONH₂ | SCF₃ | 2 | |
| 19-247 | H | CONHMe | SCF₃ | 2 | |
| 19-248 | H | CONHi-Pr | SCF₃ | 2 | |
| 19-249 | H | CONHc-Pr | SCF₃ | 2 | |
| 19-250 | H | CONHCH₂CF₃ | SCF₃ | 2 | |
| 19-251 | H | CONHCH₂c-Pr | SCF₃ | 2 | |
| 19-252 | H | CONMe₂ | SCF₃ | 2 | |
| 19-253 | H | CN | SCF₃ | 2 | |
| 19-254 | H | CHO | SCF₃ | 2 | |
| 19-255 | H | C(=O)Me | SCF₃ | 2 | |
| 19-256 | H | CH₂OH | SCF₃ | 2 | |
| 19-257 | H | CH₂OMe | SCF₃ | 2 | |
| 19-258 | H | CH₂Oi-Pr | SCF₃ | 2 | |
| 19-259 | H | CH₂OCH₂CF₃ | SCF₃ | 2 | |
| 19-260 | H | CH₂OCH₂c-Pr | SCF₃ | 2 | |
| 19-261 | H | CH₂OC(=O)Me | SCF₃ | 2 | |
| 19-262 | H | CH₂OC(=O)i-Pr | SCF₃ | 2 | |
| 19-263 | H | CH₂OC(=O)c-Pr | SCF₃ | 2 | |
| 19-264 | H | CH₂OC(=O)OMe | SCF₃ | 2 | |
| 19-265 | H | CH₂OC(=O)NHMe | SCF₃ | 2 | |
| 19-266 | H | CH₂OC(=O)NMe₂ | SCF₃ | 2 | |
| 19-267 | H | CH₂CN | SCF₃ | 2 | |
| 19-268 | H | CH₂NH₂ | SCF₃ | 2 | |
| 19-269 | H | CH₂NHMe | SCF₃ | 2 | |
| 19-270 | H | CH₂NHi-Pr | SCF₃ | 2 | |
| 19-271 | H | CH₂NHc-Pr | SCF₃ | 2 | |
| 19-272 | H | CH₂NHCH₂CF₃ | SCF₃ | 2 | |
| 19-273 | H | CH₂NHCH₂c-Pr | SCF₃ | 2 | |

-continued

| Compound No. | $R^{21}$ | $R^{22}$ | $R^3$ | m | Physical Property |
|---|---|---|---|---|---|
| 19-274 | H | CH$_2$NMe$_2$ | SCF$_3$ | 2 | |
| 19-275 | H | CH$_2$NHAc | SCF$_3$ | 2 | |
| 19-276 | H | CH$_2$N(Ac)Me | SCF$_3$ | 2 | |
| 19-277 | H | CH$_2$N(Ac)i-Pr | SCF$_3$ | 2 | |
| 19-278 | H | CH$_2$N(Ac)c-Pr | SCF$_3$ | 2 | |
| 19-279 | H | CH$_2$N(Ac)CH$_2$CF$_3$ | SCF$_3$ | 2 | |
| 19-280 | H | CH$_2$N(Ac)CH$_2$c-Pr | SCF$_3$ | 2 | |
| 19-281 | H | CH$_2$NHCOOMe | SCF$_3$ | 2 | |
| 19-282 | H | CH$_2$NHCOOt-Bu | SCF$_3$ | 2 | |
| 19-283 | H | CH$_2$N(Me)CO$_2$Me | SCF$_3$ | 2 | |
| 19-284 | H | CH$_2$N(Me)COOt-Bu | SCF$_3$ | 2 | |
| 19-285 | H | CH$_2$NHCONHMe | SCF$_3$ | 2 | |
| 19-286 | H | CH$_2$N(Me)CONHMe | SCF$_3$ | 2 | |
| 19-287 | H | CH$_2$SMe | SCF$_3$ | 2 | |
| 19-288 | H | CH$_2$SOMe | SCF$_3$ | 2 | |
| 19-289 | H | CH$_2$SO$_2$Me | SCF$_3$ | 2 | |
| 19-290 | H | CH=NOH | SCF$_3$ | 2 | |
| 19-291 | H | CH=NOMe | SCF$_3$ | 2 | |
| 19-292 | H | CH=NOi-Pr | SCF$_3$ | 2 | |
| 19-293 | H | CH=NOCH$_2$CF$_3$ | SCF$_3$ | 2 | |
| 19-294 | H | CH=NOCH$_2$c-Pr | SCF$_3$ | 2 | |
| 19-295 | H | C(Me)=NOH | SCF$_3$ | 2 | |
| 19-296 | H | C(Me)=NOMe | SCF$_3$ | 2 | |
| 19-297 | H | C(Me)=NOi-Pr | SCF$_3$ | 2 | |
| 19-298 | H | C(Me)=NOCH$_2$CF$_3$ | SCF$_3$ | 2 | |
| 19-299 | H | C(Me)=NOCH$_2$c-Pr | SCF$_3$ | 2 | |
| 19-300 | H | NH$_2$ | SCF$_3$ | 2 | |
| 19-301 | H | NHMe | SCF$_3$ | 2 | |
| 19-302 | H | NHi-Pr | SCF$_3$ | 2 | |
| 19-303 | H | NHCH$_2$CF$_3$ | SCF$_3$ | 2 | |
| 19-304 | H | NHCH$_2$c-Pr | SCF$_3$ | 2 | |
| 19-305 | H | NMe$_2$ | SCF$_3$ | 2 | |
| 19-306 | H | N(Me)CH$_2$CF$_3$ | SCF$_3$ | 2 | |
| 19-307 | H | N(Me)CH$_2$c-Pr | SCF$_3$ | 2 | |
| 19-308 | H | NHAc | SCF$_3$ | 2 | |
| 19-309 | H | N(Ac)Me | SCF$_3$ | 2 | |
| 19-310 | H | N(Ac)i-Pr | SCF$_3$ | 2 | |
| 19-311 | H | N(Ac)CH$_2$CF$_3$ | SCF$_3$ | 2 | |
| 19-312 | H | N(Ac)CH$_2$c-Pr | SCF$_3$ | 2 | |
| 19-313 | H | NHCOOMe | SCF$_3$ | 2 | |
| 19-314 | H | N(COOMe)Me | SCF$_3$ | 2 | |
| 19-315 | H | N(COOMe)i-Pr | SCF$_3$ | 2 | |
| 19-316 | H | N(COOMe)CH$_2$CF$_3$ | SCF$_3$ | 2 | |
| 19-317 | H | N(COOMe)CH$_2$c-Pr | SCF$_3$ | 2 | |
| 19-318 | H | NHCONMe$_2$ | SCF$_3$ | 2 | |
| 19-319 | H | N(CONMe$_2$)Me | SCF$_3$ | 2 | |
| 19-320 | H | CH$_2$Cl | SCF$_3$ | 2 | |

(1-j-1)

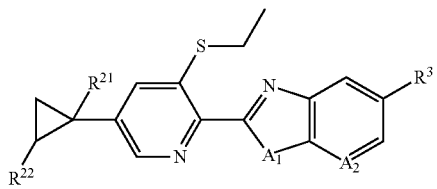

| Compound No. | $R^{21}$ | $R^{22}$ | $R^3$ | $A^1$ | $A^2$ | Physical Property |
|---|---|---|---|---|---|---|
| 20-1 | CO$_2$H | H | CF$_3$ | NMe | N | |
| 20-2 | CO$_2$Me | H | CF$_3$ | NMe | N | 122-124 |
| 20-3 | CONH$_2$ | H | CF$_3$ | NMe | N | |
| 20-4 | CN | H | CF$_3$ | NMe | N | |
| 20-5 | CHO | H | CF$_3$ | NMe | N | |
| 20-6 | CH$_2$OH | H | CF$_3$ | NMe | N | |
| 20-7 | CH$_2$OMe | H | CF$_3$ | NMe | N | |
| 20-8 | CH$_2$OC(=O)Me | H | CF$_3$ | NMe | N | |

-continued

| Compound No. | $R^{21}$ | $R^{22}$ | $R^3$ | $A^1$ | $A^2$ | Physical Property |
|---|---|---|---|---|---|---|
| 20-9 | CH$_2$CN | H | CF$_3$ | NMe | N | |
| 20-10 | CH$_2$NMe$_2$ | H | CF$_3$ | NMe | N | |
| 20-11 | CH$_2$N(Ac)Me | H | CF$_3$ | NMe | N | |
| 20-12 | CH$_2$SMe | H | CF$_3$ | NMe | N | |
| 20-13 | CH=NOH | H | CF$_3$ | NMe | N | |
| 20-14 | CH=NOMe | H | CF$_3$ | NMe | N | |
| 20-15 | CH=NOCH$_2$CF$_3$ | H | CF$_3$ | NMe | N | |
| 20-16 | NH$_2$ | H | CF$_3$ | NMe | N | |
| 20-17 | NHAc | H | CF$_3$ | NMe | N | |
| 20-18 | NHCOOMe | H | CF$_3$ | NMe | N | |
| 20-19 | NHCOOt-Bu | H | CF$_3$ | NMe | N | |
| 20-20 | CH$_2$Cl | H | CF$_3$ | NMe | N | |
| 20-21 | H | CO$_2$H | CF$_3$ | NMe | N | 139-141 |
| 20-22 | H | CO$_2$Me | CF$_3$ | NMe | N | 118-120 |
| 20-23 | H | CONH$_2$ | CF$_3$ | NMe | N | |
| 20-24 | H | CN | CF$_3$ | NMe | N | 156-158 |
| 20-25 | H | CHO | CF$_3$ | NMe | N | |
| 20-26 | H | CH$_2$OH | CF$_3$ | NMe | N | 55-58 |
| 20-27 | H | CH$_2$OMe | CF$_3$ | NMe | N | |
| 20-28 | H | CH$_2$OC(=O)Me | CF$_3$ | NMe | N | |
| 20-29 | H | CH$_2$CN | CF$_3$ | NMe | N | |
| 20-30 | H | CH$_2$NMe$_2$ | CF$_3$ | NMe | N | |
| 20-31 | H | CH$_2$N(Ac)Me | CF$_3$ | NMe | N | |
| 20-32 | H | CH$_2$SMe | CF$_3$ | NMe | N | |
| 20-33 | H | CH=NOH | CF$_3$ | NMe | N | |
| 20-34 | H | CH=NOMe | CF$_3$ | NMe | N | |
| 20-35 | H | CH=NOCH$_2$CF$_3$ | CF$_3$ | NMe | N | |
| 20-36 | H | NH$_2$ | CF$_3$ | NMe | N | |
| 20-37 | H | NHAc | CF$_3$ | NMe | N | |
| 20-38 | H | NHCOOMe | CF$_3$ | NMe | N | |
| 20-39 | H | NHCOOt-Bu | CF$_3$ | NMe | N | 101-103 |
| 20-40 | H | CH$_2$Cl | CF$_3$ | NMe | N | |
| 20-41 | CO$_2$H | H | SCF$_3$ | O | CH | 221-225 |
| 20-42 | CO$_2$Me | H | SCF$_3$ | O | CH | 172-174 |
| 20-43 | CONH$_2$ | H | SCF$_3$ | O | CH | |
| 20-44 | CN | H | SCF$_3$ | O | CH | 202-204 |
| 20-45 | CHO | H | SCF$_3$ | O | CH | 109-110 |
| 20-46 | CH$_2$OH | H | SCF$_3$ | O | CH | 123-125 |
| 20-47 | CH$_2$OMe | H | SCF$_3$ | O | CH | |
| 20-48 | CH$_2$OC(=O)Me | H | SCF$_3$ | O | CH | |
| 20-49 | CH$_2$CN | H | SCF$_3$ | O | CH | |
| 20-50 | CH$_2$NMe$_2$ | H | SCF$_3$ | O | CH | |
| 20-51 | CH$_2$N(Ac)Me | H | SCF$_3$ | O | CH | |
| 20-52 | CH$_2$SMe | H | SCF$_3$ | O | CH | |
| 20-53 | CH=NOH | H | SCF$_3$ | O | CH | 105-108 |
| 20-54 | CH=NOMe | H | SCF$_3$ | O | CH | |
| 20-55 | CH=NOCH$_2$CF$_3$ | H | SCF$_3$ | O | CH | |
| 20-56 | NH$_2$ | H | SCF$_3$ | O | CH | |
| 20-57 | NHAc | H | SCF$_3$ | O | CH | |
| 20-58 | NHCOOMe | H | SCF$_3$ | O | CH | |
| 20-59 | NHCOOt-Bu | H | SCF$_3$ | O | CH | |
| 20-60 | CH$_2$Cl | H | SCF$_3$ | O | CH | |
| 20-61 | H | CO$_2$H | SCF$_3$ | O | CH | |
| 20-62 | H | CO$_2$Me | SCF$_3$ | O | CH | |
| 20-63 | H | CONH$_2$ | SCF$_3$ | O | CH | |
| 20-64 | H | CN | SCF$_3$ | O | CH | |
| 20-65 | H | CHO | SCF$_3$ | O | CH | |
| 20-66 | H | CH$_2$OH | SCF$_3$ | O | CH | |
| 20-67 | H | CH$_2$OMe | SCF$_3$ | O | CH | |
| 20-68 | H | CH$_2$OC(=O)Me | SCF$_3$ | O | CH | |
| 20-69 | H | CH$_2$CN | SCF$_3$ | O | CH | |
| 20-70 | H | CH$_2$NMe$_2$ | SCF$_3$ | O | CH | |
| 20-71 | H | CH$_2$N(Ac)Me | SCF$_3$ | O | CH | |
| 20-72 | H | CH$_2$SMe | SCF$_3$ | O | CH | |
| 20-73 | H | CH=NOH | SCF$_3$ | O | CH | |
| 20-74 | H | CH=NOMe | SCF$_3$ | O | CH | |
| 20-75 | H | CH=NOCH$_2$CF$_3$ | SCF$_3$ | O | CH | |
| 20-76 | H | NH$_2$ | SCF$_3$ | O | CH | |
| 20-77 | H | NHAc | SCF$_3$ | O | CH | |
| 20-78 | H | NHCOOMe | SCF$_3$ | O | CH | |
| 20-79 | H | NHCOOt-Bu | SCF$_3$ | O | CH | |
| 20-80 | H | CH$_2$Cl | SCF$_3$ | O | CH | |

The agricultural and horticultural insecticide comprising the condensed heterocyclic compound represented by the general formula (1) of the present invention or a salt thereof as an active ingredient is suitable for controlling a variety of insect pests which may damage paddy rice, fruit trees, vegetables, other crops and ornamental flowering plants. The insect pests to be controlled are, for example, agricultural and forest pests, horticultural pests, stored grain pests, sanitary pests, nematodes, etc.

Specific examples of the pests, nematodes, etc. include the following:

the species of the order Lepidoptera such as *Parasa consocia, Anomis mesogona, Papilio xuthus, Matsumuraeses azukivora, Ostrinia scapulalis, Spodoptera exempta, Hyphantria cunea, Ostrinia furnacalis, Pseudaletia separata, Tinea translucens, Bactra furfurana, Parnara guttata, Marasmia exigua, Parnara guttata, Sesamia inferens, Brachmia triannulella, Monema flavescens, Trichoplusia ni, Pleuroptya ruralis, Cystidia couaggaria, Lampides boeticus, Cephonodes hylas, Helicoverpa armigera, Phalerodonta manleyi, Eumeta japonica, Pieris brassicae, Malacosoma neustria testacea, Stathmopoda masinissa, Cuphodes diospyrosella, Archips xylosteanus, Agrotis segetum, Tetramoera schistaceana, Papilio machaon hippocrates, Endoclyta sinensis, Lyonetia prunifoliella, Phyllonorycter ringoneella, Cydia kurokoi, Eucoenogenes aestuosa, Lobesia botrana, Latoia sinica, Euzophera batangensis, Phalonidia mesotypa, Spilosoma imparilis, Glyphodes pyloalis, Olethreutes mori, Tineola bisselliella, Endoclyta excrescens, Nemapogon granellus, Synanthedon hector, Cydia pomonella, Plutella xylostella, Cnaphalocrocis medinalis, Sesamia calamistis, Scirpophaga incertulas, Pediasia teterrellus, Phthorimaea operculella, Stauropus fagi persimilis, Etiella zinckenella, Spodoptera exigua, Palpifer sexnotata, Spodoptera mauritia, Scirpophaga innotata, Xestia c-nigrum, Spodoptera depravata, Ephestia kuehniella, Angerona prunaria, Clostera anastomosis, Pseudoplusia includens, Matsumuraeses falcana, Helicoverpa assulta, Autographa nigrisigna, Agrotis Ipsilon, Euproctis pseudoconspersa, Adoxophyes orana, Caloptilia theivora, Homona magnanima, Ephestia elutella, Eumeta minuscula, Clostera anachoreta, Heliothis maritima, Sparganothis pilleriana, Busseola fusca, Euproctis subflava, Biston robustum, Heliothis zea, Aedia leucomelas, Narosoideus flavidorsalis, Viminia rumicis, Bucculatrix pyrivorella, Grapholita molesta, Spulerina astaurota, Ectomyelois pyrivorella, Chilo suppressalis, Acrolepiopsis sapporensis, Plodia interpunctella, Hellula undalis, Sitotroga cerealella, Spodoptera litura*, a species of the family Tortricidae (*Eucosma aporema*), *Acleris comariana, Scopelodes contractus, Orgyia thyellina, Spodoptera frugiperda, Ostrinia zaguliaevi, Naranga aenescens, Andraca bipunctata, Paranthrene regalis, Acosmeryx castanea, Phyllocnistis toparcha, Endopiza viteana, Eupoecillia ambiguella, Anticarsia gemmatalis, Cnephasia cinereipalpana, Lymantria dispar, Dendrolimus spectabilis, Leguminivora glycinivorella, Maruca testulalis, Matsumuraeses phaseoli, Caloptilia soyella, Phyllocnistis citrella, Omiodes indicata, Archips fuscocupreanus, Acanthoplusia agnata, Bambalina* sp., *Carposina niponensis, Conogethes punctiferalis, Synanthedon* sp., *Lyonetia clerkella, Papilio helenus, Colias erate poliographus, Phalera flavescens*, the species of the family Pieridae such as *Pieris rapae crucivora* and *Pieris rapae, Euproctis similis, Acrolepiopsis suzukiella, Ostrinia nubilalis, Mamestra brassicae, Ascotis selenaria, Phtheochroides clandestine, Hoshinoa adumbratana, Odonestis pruni japonensis, Triaena intermedia, Adoxophyes orana fasciata, Grapholita inopinata, Spilonota ocellana, Spilonota lechriaspis, Illiberis pruni, Argyresthia conjugella, Caloptilia zachrysa, Archips breviplicanus, Anomis flava, Pectinophora gossypiella, Notarcha derogate, Diaphania indica, Heliothis virescens* and *Earias cupreoviridis;* the species of the order Hemiptera such as *Nezara antennata, Stenotus rubrovittatus, Graphosoma rubrolineatum, Trigonotylus coelestialium, Aeschynteles maculatus, Creontiades pallidifer, Dysdercus cingulatus, Chrysomphalus ficus, Aonidiella aurantii, Graptopsaltria nigrofuscata, Blissus leucopterus, Icerya purchasi, Piezodorus hybneri, Lagynotomus elongatus, Thaia subrufa, Scotinophara lurida, Sitobion ibarae, Stariodes iwasakii, Aspidiotus destructor, Taylorilygus pallidulus, Myzus mumecola, Pseudaulacaspis prunicola, Acyrthosiphon pisum, Anacanthocoris striicornis, Ectometopterus micantulus, Eysarcoris lewisi, Molipteryx fuliginosa, Cicadella viridis, Rhopalosiphum rufiabdominalis, Saissetia oleae, Trialeurodes vaporariorum, Aguriahana quercus, Lygus* spp., *Euceraphis punctipennis, Andaspis kashicola, Coccus pseudomagnoliarum, Cavelerius saccharivorus, Galeatus spinifrons, Macrosiphoniella sanborni, Aonidiella citrina, Halyomorpha mista, Stephanitis fasciicarina, Trioza camphorae, Leptocorisa chinensis, Trioza quercicola, Uhlerites latius, Erythroneura comes, Paromius exiguus, Duplaspidiotus claviger, Nephotettix nigropictus, Halticiellus insularis, Perkinsiella saccharicida, Psylla malivorella, Anomomeura mori, Pseudococcus longispinis, Pseudaulacaspis pentagona, Pulvinaria kuwacola, Apolygus lucorum, Togo hemipterus, Toxoptera aurantii, Saccharicoccus sacchari, Geoica lucifuga, Numata muiri, Comstockaspis perniciosa, Unaspis citri, Aulacorthum solani, Eysarcoris ventralis, Bemisia argentifolii, Cicadella spectra, Aspidiotus hederae, Liorhyssus hyalinus, Calophya nigridorsalis, Sogatella furcifera, Megoura crassicauda, Brevicoryne brassicae, Aphis glycines, Leptocorisa oratorius, Nephotettix virescens, Uroeucon formosanum, Cyrtopeltis tennuis, Bemisia tabaci, Lecanium persicae, Parlatoria theae, Pseudaonidia paeoniae, Empoasca onukii, Plautia stali, Dysaphis tulipae, Macrosiphum euphorbiae, Stephanitis pyrioides, Ceroplastes ceriferus, Parlatoria camelliae, Apolygus spinolai, Nephotettix cincticeps, Glaucias subpunctatus, Orthotylus flavosparsus, Rhopalosiphum maidis, Peregrinus maidis, Eysarcoris parvus, Cimex lectularius, Psylla abieti, Nilaparvata lugens, Psylla tobirae, Eurydema rugosum, Schizaphis piricola, Psylla pyricola, Parlatoreopsis pyri, Stephanitis nashi, Dysmicoccus wistariae, Lepholeucaspis japonica, Sappaphis piri, Lipaphis erysimi, Neotoxoptera formosana, Rhopalosophum nymphaeae, Edwardsiana rosae, Pinnaspis aspidistrae, Psylla alni, Speusotettix subfusculus, Alnetoidia alneti, Sogatella panicicola, Adelphocoris lineolatus, Dysdercus poecilus, Parlatoria ziziphi, Uhlerites debile, Laodelphax striatella, Eurydema pulchrum, Cletus trigonus, Clovia punctata, Empoasca* spp., *Coccus hesperidum, Pachybrachius luridus, Planococcus kraunhiae, Stenotus binotatus, Arboridia apicalis, Macros teles fascifrons, Dolycoris baccarum, Adelphocoris triannulatus, Viteus vitifolii, Acanthocoris sordidus, Leptocorisa acuta, Macropes obnubilus, Cletus punctiger, Riptortus clavatus, Paratrioza cockerelli, Aphrophora costalis, Lygus disponsi, Lygus saundersi, Crisicoccus pini, Empoasca abietis, Crisicoccus matsumotoi, Aphis craccivora, Megacopta punctatissimum, Eysarcoris guttiger, Lepidosaphes beckii, Diaphorina citri, Toxoptera citricidus, Planococcus citri, Dialeurodes citri, Aleurocanthus spiniferus, Pseudococcus citriculus, Zyginella citri, Pulvinaria citricola, Coccus discrepans, Pseudaonidia duplex, Pulvinaria aurantii, Lecanium corni,*

*Nezara viridula, Stenodema calcaratum, Rhopalosiphum padi, Sitobion akebiae, Schizaphis graminum, Sorhoanus tritici, Brachycaudus helichrysi, Carpocoris purpureipennis, Myzus persicae, Hyalopterus pruni, Aphis farinose yanagicola, Metasalis populi, Unaspis yanonensis, Mesohomotoma camphorae, Aphis spiraecola, Aphis pomi, Lepidosaphes ulmi, Psylla mali, Heterocordylus flavipes, Myzus malisuctus, Aphidonuguis mali, Orientus ishidai, Ovatus malicolens, Eriosoma lanigerum, Ceroplastes rubens* and *Aphis gossypii;* the species of the order Coleoptera such as *Xystrocera globosa, Paederus fuscipes, Eucetonia roelofsi, Callosobruchus chinensis, Cylas formicarius, Hypera postica, Echinocnemus squameus, Oulema oryzae, Donacia provosti, Lissorhoptrus oryzophilus, Colasposoma dauricum, Eucepes post fasciatus, Epilachna varivestis, Acanthoscelides obtectus, Diabrotica virgifera virgifera, Involvulus cupreus, Aulacophora femoralis, Bruchus pisorum, Epilachna vigintioctomaculata, Carpophilus dimidiatus, Cassida nebulosa, Luperomorpha tunebrosa, Phyllotreta striolata, Psacothea hilaris, Aeolesthes chrysothrix, Curculio sikkimensis, Carpophilus hemipterus, Oxycetonia jucunda, Diabrotica* spp., *Mimela splendens, Sitophilus zeamais, Tribolium castaneum, Sitophilus oryzae, Palorus subdepressus, Melolontha japonica, Anoplophora malasiaca, Neatus picipes, Leptinotarsa decemlineata, Diabrotica undecimpunctata howardi, Sphenophorus venatus, Crioceris quatuordecimpunctata, Conotrachelus nenuphar, Ceuthorhynchidius albosuturalis, Phaedon brassicae, Lasioderma serricorne, Sitona japonicus, Adoretus tenuimaculatus, Tenebrio molitor, Basilepta balyi, Hypera nigrirostris, Chaetocnema concinna, Anomala cuprea, Heptophylla picea, Epilachna vigintioctopunctata, Diabrotica longicornis, Eucetonia pilifera, Agriotes* spp., *Attagenus unicolor japonicus, Pagria signata, Anomala rufocuprea, Palorus ratzeburgii, Alphitobius laevigatus, Anthrenus verbasci, Lyctus brunneus, Tribolium confusum, Medythia nigrobilineata, Xylotrechus pyrrhoderus, Epitrix cucumeris, Tomicus piniperda, Monochamus alternatus, Popillia japonica, Epicauta gorhami, Sitophilus zeamais, Rhynchites heros, Listroderes costirostris, Callosobruchus maculatus, Phyllobius armatus, Anthonomus pomorum, Linaeidea aenea* and *Anthonomus grandis;* the species of the order Diptera such as *Culex pipiens pallens, Pegomya hyoscyami, Liriomyza huidobrensis, Musca domestica, Chlorops oryzae, Hydrellia sasakii, Agromyza oryzae, Hydrellia griseola, Hydrellia griseola, Ophiomyia phaseoli, Dacus cucurbitae, Drosophila suzukii, Rhacochlaena japonica, Muscina stabulans,* the species of the family Phoridae such as *Megaselia spiracularis, Clogmia albipunctata, Tipula aino, Phormia regina, Culex tritaeniorhynchus, Anopheles sinensis, Hylemya brassicae, Asphondylia* sp., *Delia platura, Delia antiqua, Rhagoletis cerasi, Culex pipiens molestus* Forskal, *Ceratitis capitata, Bradysia agrestis, Pegomya cunicularia, Liriomyza sativae, Liriomyza bryoniae, Chromatomyia horticola, Liriomyza chinensis, Culex quinquefasciatus, Aedes aegypti, Aedes albopictus, Liriomyza trifolii, Liriomyza sativae, Dacus dorsalis, Dacus tsuneonis, Sitodiplosis mosellana, Meromuza nigriventris, Anastrepha ludens* and *Rhagoletis pomonella;* the species of the order Hymenoptera such as *Pristomyrmex pungens,* the species of the family Bethylidae, *Monomorium pharaonis, Pheidole noda, Athalia rosae, Dryocosmus kuriphilus, Formica fusca japonica,* the species of the subfamily Vespinae, *Athalia infumata infumata, Arge pagana, Athalia japonica, Acromyrmex* spp., *Solenopsis* spp., *Arge mali* and *Ochetellus glaber;* the species of the order Orthoptera such as *Homorocoryphus lineosus, Gryllotalpa* sp., *Oxya hyla intricata, Oxya yezoensis, Locusta migratoria, Oxya japonica, Homorocoryphus jezoensis* and *Teleogryllus emma;* the species of the order Thysanoptera such as *Selenothrips rubrocinctus, Stenchaetothrips biformis, Haplothrips aculeatus, Ponticulothrips diospyrosi, Thrips flavus, Anaphothrips obscurus, Liothrips floridensis, Thrips simplex, Thrips nigropilosus, Heliothrips haemorrhoidalis, Pseudodendrothrips mori, Microcephalothrips abdominalis, Leeuwenia pasanii, Litotetothrips pasaniae, Scirtothrips citri, Haplothrips chinensis, Mycterothrips glycines, Thrips setosus, Scirtothrips dorsalis, Dendrothrips minowai, Haplothrips niger, Thrips tabaci, Thrips alliorum, Thrips hawaiiensis, Haplothrips kurdjumovi, Chirothrips manicatus, Frankliniella intonsa, Thrips coloratus, Franklinella occidentalis, Thrips palmi, Frankliniella lilivora* and *Liothrips vaneeckei;* the species of the order Acari such as *Leptotrombidium akamushi, Tetranychus ludeni, Dermacentor variabilis, Tetranychus truncatus, Ornithonyssus bacoti, Demodex canis, Tetranychus viennensis, Tetranychus kanzawai,* the species of the family Ixodidae such as *Rhipicephalus sanguineus, Cheyletus malaccensis, Tyrophagus putrescentiae, Dermatophagoides farinae, Latrodectus hasseltii, Dermacentor taiwanicus, Acaphylla theavagrans, Polyphagotarsonemus latus, Aculops lycopersici, Ornithonyssus sylvairum, Tetranychus urticae, Eriophyes chibaensis, Sarcoptes scabiei, Haemaphysalis longicornis, Ixodes scapularis, Tyrophagus similis, Cheyletus eruditus, Panonychus citri, Cheyletus moorei, Brevipalpus phoenicis, Octodectes cynotis, Dermatophagoides ptrenyssnus, Haemaphysalis flava, Ixodes ovatus, Phyllocoptruta citri, Aculus schlechtendali, Panonychus ulmi, Amblyomma americanum, Dermanyssus gallinae, Rhyzoglyphus robini* and *Sancassania* sp.;

the species of the order Isoptera such as *Reticulitermes miyatakei, Incisitermes minor, Coptotermes formosanus, Hodotermopsis japonica, Reticulitermes* sp., *Reticulitermes flaviceps amamianus, Glyptotermes kushimensis, Coptotermes guangzhoensis, Neotermes koshunensis, Glyptotermes kodamai, Glyptotermes satsumensis, Cryptotermes domesticus, Odontotermes formosanus, Glyptotermes nakajimai, Pericapritermes nitobei* and *Reticulitermes speratus;* the species of the order Blattodea such as *Periplaneta fuliginosa, Blattella germanica, Blatta orientalis, Periplaneta brunnea, Blattella lituricollis, Periplaneta japonica* and *Periplaneta americana;* the species of the order Siphonaptera such as *Pulex irritans, Ctenocephalides felis* and *Ceratophyllus gallinae;* the species of the phylum Nematoda such as *Nothotylenchus acris, Aphelenchoides besseyi, Pratylenchus penetrans, Meloidogyne hapla, Meloidogyne incognita, Globodera rostochiensis, Meloidogyne javanica, Heterodera glycines, Pratylenchus coffeae, Pratylenchus neglectus* and *Tylenchus semipenetrans;* and the species of the phylum Mollusca such as *Pomacea canaliculata, Achatina fulica, Meghimatium bilineatum, Lehmannina valentiana, Limax flavus* and *Acusta despecta sieboldiana.*

In addition, the agricultural and horticultural insecticide of the present invention has a strong insecticidal effect on *Tuta absoluta* as well.

Further, mites parasitic on animals are also included in the insect pests to be controlled, and the examples include the species of the family Ixodidae such as *Boophilus microplus, Rhipicephalus sanguineus, Haemaphysalis longicornis, Haemaphysalis flava, Haemaphysalis campanulata, Hae-*

*maphysalis concinna, Haemaphysalis japonica, Haemaphysalis kitaokai, Haemaphysalis ias, Ixodes ovatus, Ixodes nipponensis, Ixodes persulcatus, Amblyomma testudinarium, Haemaphysalis megaspinosa, Dermacentor reticulatus* and *Dermacentor taiwanesis; Dermanyssus gallinae*; the species of the genus *Ornithonyssus* such as *Ornithonyssus sylviarum* and *Ornithonyssus bursa*; the species of the family Trombiculidae such as *Eutrombicula wichmanni, Leptotrombidium akamushi, Leptotrombidium pallidum, Leptotrombidium fuji, Leptotrombidium tosa, Neotrombicula autumnalis, Eutrombicula alfreddugesi* and *Helenicula miyagawai*; the species of the family Cheyletidae such as *Cheyletiella yasguri, Cheyletiella parasitivorax* and *Cheyletiella blakei*; the species of the superfamily Sarcoptoidea such as *Psoroptes cuniculi, Chorioptes bovis, Otodectes cynotis, Sarcoptes scabiei* and *Notoedres cati*; and the species of the family Demodicidae such as *Demodex canis.*

Other insect pests to be controlled include fleas including ectoparasitic wingless insects belonging to the order Siphonaptera, more specifically, the species belonging to the families Pulicidae and Ceratophyllidae. Examples of the species belonging to the family Pulicidae include *Ctenocephalides canis, Ctenocephalides felis, Pulex irritans, Echidnophaga gallinacea, Xenopsylla cheopis, Leptopsylla segnis, Nosopsyllus fasciatus* and *Nosopsyllus anisus.*

Other insect pests to be controlled include ectoparasites, for example, the species of the suborder Anoplura such as *Haematopinus eurysternus, Haematopinus asini, Dalmalinia ovis, Linognathus vituli, Haematopinus suis, Phthirus pubis* and *Pediculus capitis*; the species of the suborder Mallophaga such as *Trichodectes canis*; and hematophagous Dipteran insect pests such as *Tabanus trigonus, Culicoides schultzei* and *Simulium ornatum*. In addition, examples of endoparasites include nematodes such as lungworms, whipworms, nodular worms, endogastric parasitic worms, ascarides and filarial worms; cestodes such as *Spirometra erinacei, Diphyllobothrium latum, Dipylidium caninum, Multiceps multiceps, Echinococcus granulosus* and *Echinococcus multilocularis*; trematodes such as *Schistosoma japonicum* and *Fasciola hepatica*; and protozoa such as coccidia, *Plasmodium*, intestinal *Sarcocystis, Toxoplasma* and *Cryptosporidium.*

The agricultural and horticultural insecticide comprising the condensed heterocyclic compound represented by the general formula (1) of the present invention or a salt thereof as an active ingredient has a remarkable control effect on the above-described insect pests which damage lowland crops, field crops, fruit trees, vegetables, other crops, ornamental flowering plants, etc., and exerts the desired effect when applied to nursery facilities for seedlings, paddy fields, fields, fruit trees, vegetables, other crops, ornamental flowering plants, etc. and their seeds, paddy water, foliage, cultivation media such as soil, or the like around the expected time of insect pest infestation, i.e., before the infestation or upon the confirmation of the infestation. Particularly preferred are embodiments utilizing so-called penetration and translocation of the agricultural and horticultural insecticide into crops, ornamental flowering plants, etc. In such embodiments, the compound of the present invention is applied to nursery soil, soil in transplanting holes, plant foot, irrigation water, cultivation water in hydroponics, or the like, and thereby absorbed through the plant roots via soil or otherwise.

The useful plants to which the agricultural and horticultural insecticide of the present invention can be applied include, but are not particularly limited to, for example, cereals (e.g., rice, barley, wheat, rye, oats, corn, etc.), legumes (e.g., soybeans, azuki beans, broad beans, green peas, kidney beans, peanuts, etc.), fruit trees and fruits (e.g., apples, citrus fruits, pears, grapes, peaches, plums, cherries, walnuts, chestnuts, almonds, bananas, etc.), leaf and fruit vegetables (e.g., cabbages, tomatoes, spinach, broccoli, lettuce, onions, green onions (chives and Welsh onions), green peppers, eggplants, strawberries, pepper crops, okra, Chinese chives, etc.), root vegetables (e.g., carrots, potatoes, sweet potatoes, taros, Japanese radishes, turnips, lotus roots, burdock roots, garlic, Chinese scallions, etc.), crops for processing (e.g., cotton, hemp, beet, hops, sugarcane, sugar beet, olives, rubber, coffee, tobacco, tea, etc.), gourds (e.g., Japanese pumpkins, cucumbers, watermelons, oriental sweet melons, melons, etc.), pasture grass (e.g., orchardgrass, sorghum, timothy, clover, alfalfa, etc.), lawn grass (e.g., Korean lawn grass, bent grass, etc.), spice and aromatic crops and ornamental crops (e.g., lavender, rosemary, thyme, parsley, pepper, ginger, etc.), ornamental flowering plants (e.g., *chrysanthemum*, rose, carnation, orchid, tulip, lily, etc.), garden trees (e.g., ginkgo trees, cherry trees, Japanese *aucuba*, etc.) and forest trees (e.g., *Abies sachalinensis, Picea jezoensis*, pine, yellow cedar, Japanese cedar, hinoki cypress, *eucalyptus*, etc.).

The above-mentioned "plants" also include plants provided with herbicide tolerance by a classical breeding technique or a gene recombination technique. Examples of such herbicide tolerance include tolerance to HPPD inhibitors, such as isoxaflutole; ALS inhibitors, such as imazethapyr and thifensulfuron-methyl; EPSP synthase inhibitors, such as glyphosate; glutamine synthetase inhibitors, such as glufosinate; acetyl-CoA carboxylase inhibitors, such as sethoxydim; or other herbicides, such as bromoxynil, dicamba and 2,4-D.

Examples of the plants provided with herbicide tolerance by a classical breeding technique include varieties of rapeseed, wheat, sunflower and rice tolerant to the imidazolinone family of ALS-inhibiting herbicides such as imazethapyr, and such plants are sold under the trade name of Clearfield (registered trademark). Also included is a variety of soybean provided with tolerance to the sulfonyl urea family of ALS-inhibiting herbicides such as thifensulfuron-methyl by a classical breeding technique, and this is sold under the trade name of STS soybean. Also included are plants provided with tolerance to acetyl-CoA carboxylase inhibitors such as trione oxime herbicides and aryloxy phenoxy propionic acid herbicides by a classical breeding technique, for example, SR corn and the like.

Plants provided with tolerance to acetyl-CoA carboxylase inhibitors are described in Proc. Natl. Acad. Sci. USA, 87, 7175-7179 (1990), and the like. Further, acetyl-CoA carboxylase mutants resistant to acetyl-CoA carboxylase inhibitors are reported in Weed Science, 53, 728-746 (2005), and the like, and by introducing the gene of such an acetyl-CoA carboxylase mutant into plants by a gene recombination technique, or introducing a resistance-conferring mutation into acetyl-CoA carboxylase of plants, plants tolerant to acetyl-CoA carboxylase inhibitors can be engineered. Alternatively, by introducing a nucleic acid causing base substitution mutation into plant cells (a typical example of this technique is chimeraplasty technique (Gura T. 1999. Repairing the Genome's Spelling Mistakes. Science 285: 316-318.)) to allow site-specific substitution mutation in the amino acids encoded by an acetyl-CoA carboxylase gene, an ALS gene or the like of plants, plants tolerant to acetyl-CoA carboxylase inhibitors, ALS inhibitors or the like can be engineered. The agricultural and horticultural insecticide of the present invention can be applied to these plants as well.

Further, exemplary toxins expressed in genetically modified plants include insecticidal proteins derived from *Bacillus cereus* or *Bacillus popilliae*; *Bacillus thuringiensis*-derived delta-endotoxins, such as Cry1Ab, Cry1Ac, Cry1F, Cry1Fa2, Cry2Ab, Cry3A, Cry3Bb1 and Cry9C, and other insecticidal proteins, such as VIP1, VIP2, VIP3 and VIP3A; nematode-derived insecticidal proteins; toxins produced by animals, such as scorpion toxins, spider toxins, bee toxins and insect-specific neurotoxins; toxins of filamentous fungi; plant lectins; agglutinin; protease inhibitors, such as trypsin inhibitors, serine protease inhibitors, patatin, cystatin and papain inhibitors; ribosome inactivating proteins (RIP), such as ricin, maize RIP, abrin, luffin, saporin and bryodin; steroid metabolizing enzymes, such as 3-hydroxy steroid oxidase, ecdysteroid-UDP-glucosyltransferase and cholesterol oxidase; ecdysone inhibitors; HMG-CoA reductase; ion channel inhibitors, such as sodium channel inhibitors and calcium channel inhibitors; juvenile hormone esterase; diuretic hormone receptors; stilbene synthase; bibenzyl synthase; chitinase; and glucanase.

Also included are hybrid toxins, partially deficient toxins and modified toxins derived from the following: delta-endotoxin proteins such as Cry1Ab, Cry1Ac, Cry1F, Cry1Fa2, Cry2Ab, Cry3A, Cry3Bb1, Cry9C, Cry34Ab and Cry35Ab, and other insecticidal proteins such as VIP1, VIP2, VIP3 and VIP3A. The hybrid toxin can be produced by combining domains derived from these proteins differently from the original combination in nature with the use of a recombination technique. As the partially deficient toxin, a Cry1Ab toxin in which a part of the amino acid sequence is deleted is known. In the modified toxin, one or more amino acids of a naturally occurring toxin are substituted.

Examples of the foregoing toxins and genetically modified plants capable of synthesizing these toxins are described in EP-A-0 374 753, WO 93/07278, WO 95/34656, EP-A-0 427 529, EP-A-451 878, WO 03/052073, etc.

Due to the toxins contained in such genetically modified plants, the plants exhibit resistance to pests, in particular, Coleopteran insect pests, Hemipteran insect pests, Dipteran insect pests, Lepidopteran insect pests and nematodes. The above-described technologies and the agricultural and horticultural insecticide of the present invention can be used in combination or used systematically.

In order to control various insect pests, the agricultural and horticultural insecticide of the present invention, with or without appropriate dilution or suspension in water etc., is applied to plants potentially infested with insect pests and nematodes in an amount effective for control of the insect pests or the nematodes. For example, in order to control insect pests and nematodes that may damage crop plants such as fruit trees, cereals and vegetables, foliar application and seed treatment such as dipping, dust coating and calcium peroxide coating can be performed. Further, treatment of soil or the like may also be performed to allow plants to absorb agrochemicals through their roots. Examples of such treatment include whole soil incorporation, planting row treatment, bed soil incorporation, plug seedling treatment, planting hole treatment, plant foot treatment, top-dressing, treatment of nursery boxes for paddy rice, and submerged application. In addition, application to culture media in hydroponics, smoking treatment, trunk injection and the like can also be performed.

Further, the agricultural and horticultural insecticide of the present invention, with or without appropriate dilution or suspension in water etc., can be applied to sites potentially infested with insect pests in an amount effective for control of the insect pests. For example, it can be directly applied to stored grain pests, house pests, sanitary pests, forest pests, etc., and also be used for coating of residential building materials, for smoking treatment, or as a bait formulation.

Exemplary methods of seed treatment include dipping of seeds in a diluted or undiluted fluid of a liquid or solid formulation for the permeation of agrochemicals into the seeds; mixing and dust coating of seeds with a liquid or solid formulation for the adherence of the formulation onto the surfaces of the seeds; coating of seeds with a mixture of a liquid or solid formulation and an adhesive carrier such as resins and polymers; and application of a liquid or solid formulation to the vicinity of seeds at the same time as seeding.

The term "seed" in the above-mentioned seed treatment refers to a plant body which is in the early stages of cultivation and used for plant propagation. The examples include, in addition to a so-called seed, a plant body for vegetative propagation, such as a bulb, a tuber, a seed potato, a bulbil, a propagule, a discoid stem and a stem used for cuttage.

In the method of the present invention for using an agricultural and horticultural insecticide, the term "soil" or "cultivation medium" refers to a support medium for crop cultivation, in particular a support medium which allows crop plants to spread roots therein, and the materials are not particularly limited as long as plants can grow. Examples of the support medium include so-called soils, seedling mats and water, and specific examples of the materials include sand, pumice, vermiculite, diatomite, agar, gelatinous substances, high-molecular-weight substances, rock wool, glass wool, wood chip and bark.

Exemplary methods of the application to crop foliage or to stored grain pests, house pests, sanitary pests, forest pests, etc. include application of a liquid formulation, such as an emulsifiable concentrate and a flowable, or a solid formulation, such as a wettable powder and a water-dispersible granule, after appropriate dilution in water; dust application; and smoking.

Exemplary methods of soil application include application of a water-diluted or undiluted liquid formulation to the foot of plants, nursery beds for seedlings, or the like; application of a granule to the foot of plants, nursery beds for seedlings, or the like; application of a dust, a wettable powder, a water-dispersible granule, a granule or the like onto soil and subsequent incorporation of the formulation into the whole soil before seeding or transplanting; and application of a dust, a wettable powder, a water-dispersible granule, a granule or the like to planting holes, planting rows or the like before seeding or planting.

To nursery boxes for paddy rice, for example, a dust, a water-dispersible granule, a granule or the like can be applied, although the suitable formulation may vary depending on the application time, in other words, depending on the cultivation stage such as seeding time, greening period and planting time. A formulation such as a dust, a water-dispersible granule, a granule or the like may be mixed with soil. For example, such a formulation is incorporated into bed soil, covering soil or the whole soil. Simply, soil and such a formulation may be alternately layered.

In the application to paddy fields, a solid formulation, such as a jumbo, a pack, a granule and a water-dispersible granule, or a liquid formulation, such as a flowable and an emulsifiable concentrate, is applied usually to flooded paddy fields. In a rice planting period, a suitable formulation, as it is or after mixed with a fertilizer or the like, may be applied onto soil or injected into soil. In addition, a solution of an emulsifiable concentrate, a flowable or the like may be applied to the source of water supply for paddy fields, such as a water inlet and an irrigation device. In this case, treatment can be accomplished with the supply of water and thus achieved in a labor-saving manner.

In the case of field crops, their seeds, cultivation media in the vicinity of plants, or the like may be treated in the period of seeding to seedling culture. In the case of plants of which the seeds are directly sown in the field, in addition to direct seed treatment, plant foot treatment during cultivation is preferable. Specifically, the treatment can be performed by, for example, applying a granule onto soil, or drenching soil with a formulation in a water-diluted or undiluted liquid form. Another preferable treatment is incorporation of a granule into cultivation media before seeding.

In the case of culture plants to be transplanted, preferable examples of the treatment in the period of seeding to seedling culture include, in addition to direct seed treatment, drench treatment of nursery beds for seedlings with a formulation in a liquid form; and granule application to nursery beds for seedlings. Also included are treatment of planting holes with a granule; and incorporation of a granule into cultivation media in the vicinity of planting points at the time of fix planting.

The agricultural and horticultural insecticide of the present invention is commonly used as a formulation convenient for application, which is prepared in the usual method for preparing agrochemical formulations.

That is, the condensed heterocyclic compound represented by the general formula (1) of the present invention or a salt thereof and an appropriate inactive carrier, and if needed an adjuvant, are blended in an appropriate ratio, and through the step of dissolution, separation, suspension, mixing, impregnation, adsorption and/or adhesion, are formulated into an appropriate form for application, such as a suspension concentrate, an emulsifiable concentrate, a soluble concentrate, a wettable powder, a water-dispersible granule, a granule, a dust, a tablet and a pack.

The composition (agricultural and horticultural insecticide or animal parasite control agent) of the present invention can optionally contain an additive usually used for agrochemical formulations or animal parasite control agents in addition to the active ingredient. Examples of the additive include carriers such as solid or liquid carriers, surfactants, dispersants, wetting agents, binders, tackifiers, thickeners, colorants, spreaders, sticking/spreading agents, antifreezing agents, anti-caking agents, disintegrants and stabilizing agents. If needed, preservatives, plant fragments, etc. may also be used as the additive. These additives may be used alone or in a combination of two or more kinds.

Examples of the solid carriers include natural minerals, such as quartz, clay, kaolinite, pyrophyllite, sericite, talc, bentonite, acid clay, attapulgite, zeolite and diatomite; inorganic salts, such as calcium carbonate, ammonium sulfate, sodium sulfate and potassium chloride; organic solid carriers, such as synthetic silicic acid, synthetic silicates, starch, cellulose and plant powders (for example, sawdust, coconut shell, corn cob, tobacco stalk, etc.); plastics carriers, such as polyethylene, polypropylene and polyvinylidene chloride; urea; hollow inorganic materials; hollow plastic materials; and fumed silica (white carbon). These solid carriers may be used alone or in a combination of two or more kinds.

Examples of the liquid carriers include alcohols including monohydric alcohols, such as methanol, ethanol, propanol, isopropanol and butanol, and polyhydric alcohols, such as ethylene glycol, diethylene glycol, propylene glycol, hexylene glycol, polyethylene glycol, polypropylene glycol and glycerin; polyol compounds, such as propylene glycol ether; ketones, such as acetone, methyl ethyl ketone, methyl isobutyl ketone, diisobutyl ketone and cyclohexanone; ethers, such as ethyl ether, dioxane, ethylene glycol monoethyl ether, dipropyl ether and tetrahydrofuran; aliphatic hydrocarbons, such as normal paraffin, naphthene, isoparaffin, kerosene and mineral oil; aromatic hydrocarbons, such as benzene, toluene, xylene, solvent naphtha and alkyl naphthalene; halogenated hydrocarbons, such as dichloromethane, chloroform and carbon tetrachloride; esters, such as ethyl acetate, diisopropyl phthalate, dibutyl phthalate, dioctyl phthalate and dimethyl adipate; lactones, such as gamma-butyrolactone; amides, such as dimethylformamide, diethylformamide, dimethylacetamide and N-alkyl pyrrolidinone; nitriles, such as acetonitrile; sulfur compounds, such as dimethyl sulfoxide; vegetable oils, such as soybean oil, rapeseed oil, cotton seed oil and castor oil; and water. These liquid carriers may be used alone or in a combination of two or more kinds.

Exemplary surfactants used as the dispersant or the wetting/spreading agent include nonionic surfactants, such as sorbitan fatty acid ester, polyoxyethylene sorbitan fatty acid ester, sucrose fatty acid ester, polyoxyethylene fatty acid ester, polyoxyethylene resin acid ester, polyoxyethylene fatty acid diester, polyoxyethylene alkyl ether, polyoxyethylene alkyl aryl ether, polyoxyethylene alkyl phenyl ether, polyoxyethylene dialkyl phenyl ether, polyoxyethylene alkyl phenyl ether-formaldehyde condensates, polyoxyethylene-polyoxypropylene block copolymers, polystyrene-polyoxyethylene block polymers, alkyl polyoxyethylene-polypropylene block copolymer ether, polyoxyethylene alkylamine, polyoxyethylene fatty acid amide, polyoxyethylene fatty acid bis(phenyl ether), polyalkylene benzyl phenyl ether, polyoxyalkylene styryl phenyl ether, acetylene diol, polyoxyalkylene-added acetylene diol, polyoxyethylene ether-type silicone, ester-type silicone, fluorosurfactants, polyoxyethylene castor oil and polyoxyethylene hydrogenated castor oil; anionic surfactants, such as alkyl sulfates, polyoxyethylene alkyl ether sulfates, polyoxyethylene alkyl phenyl ether sulfates, polyoxyethylene styryl phenyl ether sulfates, alkylbenzene sulfonates, alkylaryl sulfonates, lignosulfonates, alkyl sulfosuccinates, naphthalene sulfonates, alkylnaphthalene sulfonates, salts of naphthalenesulfonic acid-formaldehyde condensates, salts of alkylnaphthalenesulfonic acid-formaldehyde condensates, fatty acid salts, polycarboxylic acid salts, polyacrylates, N-methyl-fatty acid sarcosinates, resinates, polyoxyethylene alkyl ether phosphates and polyoxyethylene alkyl phenyl ether phosphates; cationic surfactants including alkyl amine salts, such as lauryl amine hydrochloride, stearyl amine hydrochloride, oleyl amine hydrochloride, stearyl amine acetate, stearyl aminopropyl amine acetate, alkyl trimethyl ammonium chloride and alkyl dimethyl benzalkonium chloride; and amphoteric surfactants, such as amino acid-type or betaine-type amphoteric surfactants. These surfactants may be used alone or in a combination of two or more kinds.

Examples of the binders or the tackifiers include carboxymethyl cellulose or salts thereof, dextrin, soluble starch, xanthan gum, guar gum, sucrose, polyvinyl pyrrolidone, gum arabic, polyvinyl alcohol, polyvinyl acetate, sodium polyacrylate, polyethylene glycols with an average molecular weight of 6,000 to 20,000, polyethylene oxides with an average molecular weight of 100,000 to 5,000,000, phospholipids (for example, cephalin, lecithin, etc.), cellulose powder, dextrin, modified starch, polyaminocarboxylic acid chelating compounds, cross-linked polyvinyl pyrrolidone, maleic acid-styrene copolymers, (meth)acrylic acid copolymers, half esters of polyhydric alcohol polymer and dicarboxylic anhydride, water soluble polystyrene sulfonates, paraffin, terpene, polyamide resins, polyacrylates, polyoxyethylene, waxes, polyvinyl alkyl ether, alkylphenol-formaldehyde condensates and synthetic resin emulsions.

Examples of the thickeners include water soluble polymers, such as xanthan gum, guar gum, diutan gum, carboxymethyl cellulose, polyvinyl pyrrolidone, carboxyvinyl polymers, acrylic polymers, starch compounds and polysaccharides; and inorganic fine powders, such as high grade bentonite and fumed silica (white carbon).

Examples of the colorants include inorganic pigments, such as iron oxide, titanium oxide and prussian blue; and organic dyes, such as alizarin dyes, azo dyes and metal phthalocyanine dyes.

Examples of the antifreezing agents include polyhydric alcohols, such as ethylene glycol, diethylene glycol, propylene glycol and glycerin.

Examples of the adjuvants serving to prevent caking or facilitate disintegration include polysaccharides (starch, alginic acid, mannose, galactose, etc.), polyvinyl pyrrolidone, fumed silica (white carbon), ester gum, petroleum resin, sodium tripolyphosphate, sodium hexametaphosphate, metal stearates, cellulose powder, dextrin, methacrylate copolymers, polyvinyl pyrrolidone, polyaminocarboxylic acid chelating compounds, sulfonated styrene-isobutylene-maleic anhydride copolymers and starch-polyacrylonitrile graft copolymers.

Examples of the stabilizing agents include desiccants, such as zeolite, quicklime and magnesium oxide; antioxidants, such as phenolic compounds, amine compounds, sulfur compounds and phosphoric acid compounds; and ultraviolet absorbers, such as salicylic acid compounds and benzophenone compounds.

Examples of the preservatives include potassium sorbate and 1,2-benzothiazolin-3-one.

Further, other adjuvants including functional spreading agents, activity enhancers such as metabolic inhibitors (piperonyl butoxide etc.), antifreezing agents (propylene glycol etc.), antioxidants (BHT etc.) and ultraviolet absorbers can also be used if needed.

The content of the active ingredient compound in the agricultural and horticultural insecticide of the present invention can be adjusted as needed, and for example, is appropriately selected from the range of 0.01 to 90 parts by weight in 100 parts by weight of the agricultural and horticultural insecticide. For example, in the case where the agricultural and horticultural insecticide is a dust, a granule, an emulsifiable concentrate or a wettable powder, it is suitable that the content of the active ingredient compound is 0.01 to 50 parts by weight (0.01 to 50% by weight relative to the total weight of the agricultural and horticultural insecticide).

The application amount of the agricultural and horticultural insecticide of the present invention may vary with various factors, for example, the purpose, the target insect pest, the growing conditions of crops, the tendency of insect pest infestation, the weather, the environmental conditions, the dosage form, the application method, the application site, the application time, etc., but for example, the application amount of the active ingredient compound per 10 ares is appropriately selected from the range of 0.001 g to 10 kg, and preferably 0.01 g to 1 kg depending on the purpose.

Furthermore, for the expansion of the range of target insect pests to be controlled and the appropriate application time for control of insect pests, or for dose reduction, the agricultural and horticultural insecticide of the present invention can be used after mixed with other agricultural or horticultural insecticides, miticides, nematicides, microbicides, biopesticides and/or the like. Further, the agricultural and horticultural insecticide can be used after mixed with herbicides, plant growth regulators, fertilizers and/or the like depending on its application.

Examples of such additional agricultural and horticultural insecticides, miticides and nematicides used for the above-mentioned purposes include 3,5-xylyl methylcarbamate (XMC), crystalline protein toxins produced by *Bacillus thuringiensis* strains such as *Bacillus thuringiensis aizawai, Bacillus thuringiensis israelensis, Bacillus thuringiensis japonensis, Bacillus thuringiensis kurstaki* and *Bacillus thuringiensis* tenebrionis, BPMC, Bt toxin-derived insecticidal compounds, chlorfenson (CPCBS), dichlorodiisopropyl ether (DCIP), 1,3-dichloropropene (D-D), DDT, NAC, O-4-dimethylsulfamoylphenyl O,O-diethyl phosphorothioate (DSP), O-ethyl O-4-nitrophenyl phenylphosphonothioate (EPN), tripropylisocyanurate (TPIC), acrinathrin, azadirachtin, azinphos-methyl, acequinocyl, acetamiprid, acetoprole, acephate, abamectin, avermectin-B, amidoflumet, amitraz, alanycarb, aldicarb, aldoxycarb, aldrin, alpha-endosulfan, alpha-cypermethrin, albendazole, allethrin, isazofos, isamidofos, isoamidofos, isoxathion, isofenphos, isoprocarb (MIPC), ivermectin, imicyafos, imidacloprid, imiprothrin, indoxacarb, esfenvalerate, ethiofencarb, ethion, ethiprole, etoxazole, ethofenprox, ethoprophos, etrimfos, emamectin, emamectin-benzoate, endosulfan, empenthrin, oxamyl, oxydemeton-methyl, oxydeprofos (ESP), oxibendazole, oxfendazole, potassium oleate, sodium oleate, cadusafos, cartap, carbaryl, carbosulfan, carbofuran, gamma-cyhalothrin, xylylcarb, quinalphos, kinoprene, chinomethionat, cloethocarb, clothianidin, clofentezine, chromafenozide, chlorantraniliprole, chlorethoxyfos, chlordimeform, chlordane, chlorpyrifos, chlorpyrifos-methyl, chlorphenapyr, chlorfenson, chlorfenvinphos, chlorfluazuron, chlorobenzilate, chlorobenzoate, kelthane (dicofol), salithion, cyanophos (CYAP), diafenthiuron, diamidafos, cyantraniliprole, theta-cypermethrin, dienochlor, cyenopyrafen, dioxabenzofos, diofenolan, sigma-cypermethrin, dichlofenthion (ECP), cycloprothrin, dichlorvos (DDVP), disulfoton, dinotefuran, cyhalothrin, cyphenothrin, cyfluthrin, diflubenzuron, cyflumetofen, diflovidazin, cyhexatin, cypermethrin, dimethylvinphos, dimethoate, dimefluthrin, silafluofen, cyromazine, spinetoram, spinosad, spirodiclofen, spirotetramat, spiromesifen, sulfluramid, sulprofos, sulfoxaflor, zeta-cypermethrin, diazinon, tau-fluvalinate, dazomet, thiacloprid, thiamethoxam, thiodicarb, thiocyclam, thiosultap, thiosultap-sodium, thionazin, thiometon, deet, dieldrin, tetrachlorvinphos, tetradifon, tetramethylfluthrin, tetramethrin, tebupirimfos, tebufenozide, tebufenpyrad, tefluthrin, teflubenzuron, demeton-S-methyl, temephos, deltamethrin, terbufos, tralopyril, tralomethrin, transfluthrin, triazamate, triazuron, trichlamide, trichlorphon (DEP), triflumuron, tolfenpyrad, naled (BRP), nithiazine, nitenpyram, novaluron, noviflumuron, hydroprene, vaniliprole, vamidothion, parathion, parathion-methyl, halfenprox, halofenozide, bistrifluron, bisultap, hydramethylnon, hydroxy propyl starch, binapacryl, bifenazate, bifenthrin, pymetrozine, pyraclofos, pyrafluprole, pyridafenthion, pyridaben, pyridalyl, pyrifluquinazon, pyriprole, pyriproxyfen, pirimicarb, pyrimidifen, pirimiphos-methyl, pyrethrins, fipronil, fenazaquin, fenamiphos, phenisobromolate, fenitrothion (MEP), fenoxycarb, fenothiocarb, phenothrin, fenobucarb, fensulfothion, fenthion (MPP), phenthoate (PAP), fenvalerate, fenpyroximate, fenpropathrin, fenbendazole, fosthiazate, formetanate, butathiofos, buprofezin, furathiocarb, prallethrin, fluacrypyrim, fluazinam, fluazuron, fluensulfone, flucycloxuron, flucythrinate, fluvalinate, flupyrazofos, flufenerim, flufenoxuron, flufenzine, flufenprox, fluproxyfen, flubrocythrinate, flubendiamide, flumethrin, flurimfen, prothiofos, protrifenbute, flonicamid, propaphos, propargite (BPPS), profenofos, profluthrin, propoxur (PHC), bromopropylate, beta-cyfluthrin, hexaflumuron, hexythiazox, heptenophos, permethrin, benclothiaz, bendiocarb, bensultap, benzoximate, benfuracarb, phoxim, phosalone, fosthiazate, fosthietan, phosphamidon, phosphocarb, phosmet (PMP), polynactins, formetanate, formothion, phorate, machine oil, malathion, milbemycin, milbemycin-A, milbemectin, mecarbam, mesulfenfos, methomyl, metaldehyde, metaflumizone, methamidophos, metam-ammonium, metam-sodium, methiocarb, methidathion (DMTP), methylisothiocyanate, methylneodecanamide, methylparathion, metoxadiazone, methoxychlor, methoxyfenozide, metofluthrin, methoprene, metolcarb, meperfluthrin, mevinphos, monocrotophos, monosultap, lambda-cyhalothrin, ryanodine, lufenuron, resmethrin, lepimectin, rotenone, levamisole hydrochloride, fenbutatin oxide, morantel tartarate, methyl bromide, tricyclohexyltin hydroxide (cyhexatin), calcium cyanamide, calcium polysulfide, sulfur and nicotine-sulfate.

Examples of the agricultural and horticultural microbicides used for the same purposes as above include aureofungin, azaconazole, azithiram, acypetacs, acibenzolar, acibenzolar-S-methyl, azoxystrobin, anilazine, amisulbrom, ampropylfos, ametoctradin, allyl alcohol, aldimorph, amobam, isotianil, isovaledione, isopyrazam, isoprothiolane, ipconazole, iprodione, iprovalicarb, iprobenfos, imazalil, iminoctadine, iminoctadine-albesilate, iminoctadine-triacetate, imibenconazole, uniconazole, uniconazole-P, echlomezole, edifenphos, etaconazole, ethaboxam, ethirimol, etem, ethoxyquin, etridiazole, enestroburin, epoxiconazole, oxadixyl, oxycarboxin, copper-8-quinolinolate, oxytetracycline, copper-oxinate, oxpoconazole, oxpoconazole-fumarate, oxolinic acid, octhilinone, ofurace, orysastrobin, metam-sodium, kasugamycin, carbamorph, carpropamid, carbendazim, carboxin, carvone, quinazamid, quinacetol, quinoxyfen, quinomethionate, captafol, captan, kiralaxyl, quinconazole, quintozene, guazatine, cufraneb, cuprobam, glyodin, griseofulvin, climbazole, cresol, kresoxim-methyl, chlozolinate, clotrimazole, chlobenthiazone, chloraniformethan, chloranil, chlorquinox, chloropicrin, chlorfenazole, chlorodinitronaphthalene, chlorothalonil, chloroneb, zarilamid, salicylanilide, cyazofamid, diethyl pyrocarbonate, diethofencarb, cyclafuramid, diclocymet, dichlozoline, diclobutrazol, dichlofluanid, cycloheximide, diclomezine, dicloran, dichlorophen, dichlone, disulfiram, ditalimfos, dithianon, diniconazole, diniconazole-M, zineb, dinocap, dinocton, dinosulfon, dinoterbon, dinobuton, dinopenton, dipyrithione, diphenylamine, difenoconazole, cyflufenamid, diflumetorim, cyproconazole, cyprodinil, cyprofuram, cypendazole, simeconazole, dimethirimol, dimethomorph, cymoxanil, dimoxystrobin, methyl bromide, ziram, silthiofam, streptomycin, spiroxamine, sultropen, sedaxane, zoxamide, dazomet, thiadiazin, tiadinil, thiadifluor, thiabendazole, tioxymid, thiochlorfenphim, thiophanate, thiophanate-methyl, thicyofen, thioquinox, chinomethionat, thifluzamide, thiram, decafentin, tecnazene, tecloftalam, tecoram, tetraconazole, debacarb, dehydroacetic acid, tebuconazole, tebufloquin, dodicin, dodine, dodecyl benzensulfonate bis-ethylene diamine copper(II) (DBEDC), dodemorph, drazoxolon, triadimenol, triadimefon, triazbutil, triazoxide, triamiphos, triarimol, trichlamide, tricyclazole, triticonazole, tridemorph, tributyltin oxide, triflumizole, trifloxystrobin, triforine, tolylfluanid, tolclofos-methyl, natamycin, nabam, nitrothal-isopropyl, nitrostyrene, nuarimol, copper nonylphenol sulfonate, halacrinate, validamycin, valifenalate, harpin protein, bixafen, picoxystrobin, picobenzamide, bithionol, bitertanol, hydroxyisoxazole, hydroxyisoxazole-potassium, binapacryl, biphenyl, piperalin, hymexazol, pyraoxystrobin, pyracarbolid, pyraclostrobin, pyrazophos, pyrametostrobin, pyriofenone, pyridinitril, pyrifenox, pyribencarb, pyrimethanil, pyroxychlor, pyroxyfur, pyroquilon, vinclozolin, famoxadone, fenapanil, fenamidone, fenaminosulf, fenarimol, fenitropan, fenoxanil, ferimzone, ferbam, fentin, fenpiclonil, fenpyrazamine, fenbuconazole, fenfuram, fenpropidin, fenpropimorph, fenhexamid, phthalide, buthiobate, butylamine, bupirimate, fuberidazole, blasticidin-S, furametpyr, furalaxyl, fluacrypyrim, fluazinam, fluoxastrobin, fluotrimazole, fluopicolide, fluopyram, fluoroimide, furcarbanil, fluxapyroxad, fluquinconazole, furconazole, furconazole-cis, fludioxonil, flusilazole, flusulfamide, flutianil, flutolanil, flutriafol, furfural, furmecyclox, flumetover, flumorph, proquinazid, prochloraz, procymidone, prothiocarb, prothioconazole, propamocarb, propiconazole, propineb, furophanate, probenazole, bromuconazole, hexachlorobutadiene, hexaconazole, hexylthiofos, bethoxazin, benalaxyl, benalaxyl-M, benodanil, benomyl, pefurazoate, benquinox, penconazole, benzamorf, pencycuron, benzohydroxamic acid, bentaluron, benthiazole, benthiavalicarb-isopropyl, penthiopyrad, penflufen, boscalid, phosdiphen, fosetyl, fosetyl-Al, polyoxins, polyoxorim, polycarbamate, folpet, formaldehyde, machine oil, maneb, mancozeb, mandipropamid, myclozolin, myclobutanil, mildiomycin, milneb, mecarbinzid, methasulfocarb, metazoxolon, metam, metam-sodium, metalaxyl, metalaxyl-M, metiram, methyl isothiocyanate, meptyldinocap, metconazole, metsulfovax, methfuroxam, metominostrobin, metrafenone, mepanipyrim, mefenoxam, meptyldinocap, mepronil, mebenil, iodomethane, rabenzazole, benzalkonium chloride, inorganic microbicides such as basic copper chloride, basic copper sulfate and silver, sodium hypochlorite, cupric hydroxide, wettable sulfur, calcium polysulfide, potassium hydrogen carbonate, sodium hydrogen carbonate, sulfur, copper sulfate anhydride, nickel dimethyldithiocarbamate, copper compounds such as copper-8-quinolinolate (oxine copper), zinc sulfate and copper sulfate pentahydrate.

Further, examples of the herbicides include 1-naphthylacetamide, 2,4-PA, 2,3,6-TBA, 2,4,5-T, 2,4,5-TB, 2,4-D, 2,4-DB, 2,4-DEB, 2,4-DEP, 3,4-DA, 3,4-DB, 3,4-DP, 4-CPA, 4-CPB, 4-CPP, MCP, MCPA, MCPA-thioethyl, MCPB, ioxynil, aclonifen, azafenidin, acifluorfen, aziprotryne, azimsulfuron, asulam, acetochlor, atrazine, atraton, anisuron, anilofos, aviglycine, abscisic acid, amicarbazone, amidosulfuron, amitrole, aminocyclopyrachlor, aminopyralid, amibuzin, amiprophos-methyl, ametridione, ametryn, alachlor, allidochlor, alloxydim, alorac, isouron, isocarbamid, isoxachlortole, isoxapyrifop, isoxaflutole, isoxaben, isocil, isonoruron, isoproturon, isopropalin, isopolinate, isomethiozin, inabenfide, ipazine, ipfencarbazone, iprymidam, imazaquin, imazapic, imazapyr, imazamethapyr, imazamethabenz, imazamethabenz-methyl, imazamox, imazethapyr, imazosulfuron, indaziflam, indanofan, indolebutyric acid, uniconazole-P, eglinazine, esprocarb, ethametsulfuron, ethametsulfuron-methyl, ethalfluralin, ethiolate, ethychlozate-ethyl, ethidimuron, etinofen, ephon, ethoxysulfuron, ethoxyfen, etnipromid, ethofumesate, etobenzanid, epronaz, erbon, endothal, oxadiazon, oxadiargyl, oxaziclomefone, oxasulfuron, oxapyrazon, oxyfluorfen, oryzalin, orthosulfamuron, orbencarb, cafenstrole, cambendichlor, carbasulam, carfentrazone, carfentrazone-ethyl, karbutilate, carbetamide, carboxazole, quizalofop, quizalofop-P, quizalofop-ethyl, xylachlor, quinoclamine, quinonamid, quinclorac, quinmerac, cumyluron, cliodinate, glyphosate, glufosinate, glufosinate-P, credazine, clethodim, cloxyfonac, clodinafop, clodinafop-propargyl, chlorotoluron, clopyralid, cloproxydim, cloprop, chlorbromuron, clofop, clomazone, chlomethoxynil, chlomethoxyfen, clomeprop, chlorazifop, chlorazine, cloransulam, chloranocryl, chloramben, cloransulam-methyl, chloridazon, chlorimuron, chlorimuron-ethyl, chlorsulfuron, chlorthal, chlorthiamid, chlortoluron, chlornitrofen, chlorfenac, chlorfenprop, chlorbufam, chlorflurazole, chlorflurenol, chlorprocarb, chlorpropham, chlormequat, chloreturon, chloroxynil, chloroxuron, chloropon, saflufenacil, cyanazine, cyanatryn, di-allate, diuron, diethamquat, dicamba, cycluron, cycloate, cycloxydim, diclosulam, cyclosulfamuron, dichlorprop, dichlorprop-P, dichlobenil, diclofop, diclofop-methyl, dichlormate, dichloralurea, diquat, cisanilide, disul, siduron, dithiopyr, dinitramine, cinidon-ethyl, dinosam, cinosulfuron, dinoseb, dinoterb, dinofenate, dinoprop, cyhalofop-butyl, diphenamid, difenoxuron, difenopenten, difenzoquat, cybutryne, cyprazine, cyprazole, diflufenican, diflufenzopyr, dipropetryn, cypromid, cyperquat, gibberellin, simazine, dimexano, dimethachlor, dimidazon, dimethametryn, dimethenamid, simetryn, simeton, dimepiperate, dimefuron, cinmethylin, swep, sulglycapin, sulcotrione, sulfallate, sulfentrazone, sulfosulfuron, sulfometuron, sulfometuron-methyl, secbumeton, sethoxydim, sebuthylazine, terbacil, daimuron, dazomet, dalapon, thiazafluron, thiazopyr, thiencarbazone, thiencarbazone-methyl, tiocarbazil, tioclorim, thiobencarb, thidiazimin, thidiazuron, thifensulfuron, thifensulfuron-methyl, desmedipham, desmetryn, tetrafluron, thenylchlor, tebutam, tebuthiuron, terbumeton, tepraloxydim, tefuryltrione, tembotrione, delachlor, terbacil, terbucarb, terbuchlor, terbuthylazine, terbutryn, topramezone, tralkoxydim, triaziflam, triasulfuron, tri-allate, trietazine, tricamba, triclopyr, tridiphane, tritac, tritosulfuron, triflusulfuron, triflusulfuron-methyl, trifluralin, trifloxysulfuron, tripropindan, tribenuron-methyl, tribenuron, trifop, trifopsime, trimeturon, naptalam, naproanilide, napropamide, nicosulfuron, nitralin, nitrofen, nitrofluorfen, nipyraclofen, neburon, norflurazon, noruron, barban, paclobutrazol, paraquat, parafluron, haloxydine, haloxyfop, haloxyfop-P, haloxyfop-methyl, halosafen, halosulfuron, halosulfuron-methyl, picloram, picolinafen, bicyclopyrone, bispyribac, bispyribac-sodium, pydanon, pinoxaden, bifenox, piperophos, hymexazol, pyraclonil, pyrasulfotole, pyrazoxyfen, pyrazosulfuron, pyrazosulfuron-ethyl, pyrazolate, bilanafos, pyraflufen-ethyl, pyriclor, pyridafol, pyrithiobac, pyrithiobac-sodium, pyridate, pyriftalid, pyributicarb, pyribenzoxim, pyrimisulfan, primisulfuron, pyriminobac-methyl, pyroxasulfone, pyroxsulam, fenasulam, phenisopham, fenuron, fenoxasulfone, fenoxaprop, fenoxaprop-P, fenoxaprop-ethyl, phenothiol, fenoprop, phenobenzuron, fenthiaprop, fenteracol, fentrazamide, phenmedipham, phenmedipham-ethyl, butachlor, butafenacil, butamifos, buthiuron, buthidazole, butylate, buturon, butenachlor, butroxydim, butralin, flazasulfuron, flamprop, furyloxyfen, prynachlor, primisulfuron-methyl, fluazifop, fluazifop-P, fluazifop-butyl, fluazolate, fluroxypyr, fluothiuron, fluometuron, fluoroglycofen, flurochloridone, fluorodifen, fluoronitrofen, fluoromidine, flucarbazone, flucarbazone-sodium, fluchloralin, flucetosulfuron, fluthiacet, fluthiacet-methyl, flupyrsulfuron, flufenacet, flufenican, flufenpyr, flupropacil, flupropanate, flupoxam, flumioxazin, flumiclorac, flumiclorac-pentyl, flumipropyn, flumezin, fluometuron, flumetsulam, fluridone, flurtamone, fluroxypyr, pretilachlor, proxan, proglinazine, procyazine, prodiamine, prosulfalin, prosulfuron, prosulfocarb, propaquizafop, propachlor, propazine, propanil, propyzamide, propisochlor, prohydrojasmon, propyrisulfuron, propham, profluazol, profluralin, prohexadione-calcium, propoxycarbazone, propoxycarbazone-sodium, profoxydim, bromacil, brompyrazon, prometryn, prometon, bromoxynil, bromofenoxim, bromobutide, bromobonil, florasulam, hexachloroacetone, hexazinone, pethoxamid, benazolin, penoxsulam, pebulate, beflubutamid, vernolate, perfluidone, bencarbazone, benzadox, benzipram, benzylaminopurine, benzthiazuron, benzfendizone, bensulide, bensulfuron-methyl, benzoylprop, benzobicyclon, benzofenap, benzofluor, bentazone, pentanochlor, benthiocarb, pendimethalin, pentoxazone, benfluralin, benfuresate, fosamine, fomesafen, foramsulfuron, forchlorfenuron, maleic hydrazide, mecoprop, mecoprop-P, medinoterb, mesosulfuron, mesosulfuron-methyl, mesotrione, mesoprazine, methoprotryne, metazachlor, methazole, metazosulfuron, methabenzthiazuron, metamitron, metamifop, metam, methalpropalin, methiuron, methiozolin, methiobencarb, methyldymron, metoxuron, metosulam, metsulfuron, metsulfuron-methyl, metflurazon, metobromuron, metobenzuron, methometon, metolachlor, metribuzin, mepiquat-chloride, mefenacet, mefluidide, monalide, monisouron, monuron, monochloroacetic acid, monolinuron, molinate, morfamquat, iodosulfuron, iodosulfuron-methyl-sodium, iodobonil, iodomethane, lactofen, linuron, rimsulfuron, lenacil, rhodethanil, calcium peroxide and methyl bromide.

Examples of the biopesticides include viral formulations such as nuclear polyhedrosis viruses (NPV), granulosis viruses (GV), cytoplasmic polyhedrosis viruses (CPV) and entomopox viruses (EPV); microbial pesticides used as an insecticide or a nematicide, such as *Monacrosporium phymatophagum, Steinernema carpocapsae, Steinernema kushidai* and *Pasteuria penetrans*; microbial pesticides used as a microbicide, such as *Trichoderma lignorum, Agrobacterium radiobactor,* avirulent *Erwinia carotovora* and *Bacillus subtilis*; and biopesticides used as a herbicide, such as *Xanthomonas campestris.* A combined use of the agricultural and horticultural insecticide of the present invention with the foregoing biopesticide as a mixture can be expected to provide the same effect as above.

Other examples of the biopesticides include natural predators such as *Encarsia formosa, Aphidius colemani, Aphidoletes aphidimyza, Diglyphus isaea, Dacnusa sibirica, Phytoseiulus persimilis, Amblyseius cucumeris* and *Orius sauteri*; microbial pesticides such as *Beauveria brongniartii*; and pheromones such as (Z)-10-tetradecenyl acetate, (E,Z)-4,10-tetradecadienyl acetate, (Z)-8-dodecenyl acetate, (Z)-11-tetradecenyl acetate, (Z)-13-icosen-10-one and 14-methyl-1-octadecene.

Hereinafter, the production examples of representative compounds of the present invention and their intermediates will be described in more detail, but the present invention is not limited only to these examples.

EXAMPLES

Reference Examples

Production Example of Intermediate (2)

Production Method of
5-chloro-6-ethoxycarbonylnicotinic acid

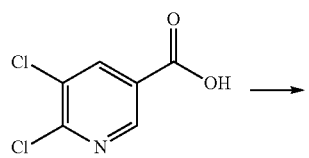

DPPB (1,4-bis(diphenylphosphino)butane) (2.2 g, 10 mol %), triethylamine (14 g, 2.5 eq.) and PdCl$_2$(PPh$_3$)$_2$ (911 mg, 2.5 mol %) were added to a solution of 5,6-dichloronicotinic acid (10 g, 52 mmol) in ethanol (60 mL) in an autoclave. The reaction system was replaced with carbon monoxide (CO pressure: 4.0 MPa) and the mixture was stirred at 135° C. for 4 hours. Water and 3 N hydrochloric acid were added to the reaction mixture to acidify the aqueous layer, and extraction with ethyl acetate was performed several times. The organic layer was dried over sodium sulfate and concentrated. The resulting solid was washed with a solution of hexane and ethyl acetate in a 2:1 (v/v) ratio to give the desired product, 5-chloro-6-ethoxycarbonylnicotinic acid (10.9 g, 76%).

Physical property: $^1$H-NMR (CDCl$_3$): 9.02 (d, 1H), 8.44 (d, 1H), 4.42 (dd, 2H), 1.33 (t, 3H)

Production Method of
5-chloro-6-ethoxycarbonylnicotinic acid t-butyl ester

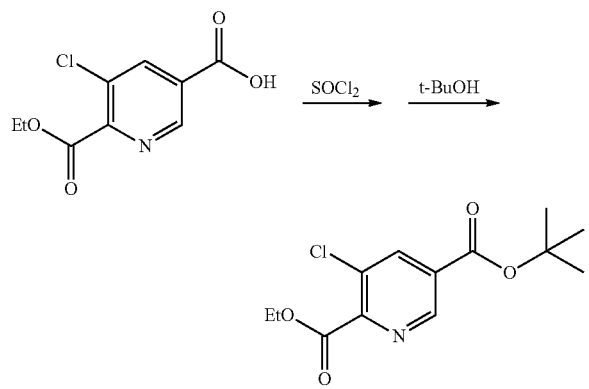

The 5-chloro-6-ethoxycarbonylnicotinic acid (10.9 g, 47.6 mmol) produced in the previous step was dissolved in toluene (30 mL). To the solution, DMF (N,N-dimethylformamide) (4 mL) was added. After adding thionyl chloride (11 g, 2 eq.), the mixture was heated under stirring at 90° C. for 3 hours. The reaction mixture was allowed to cool back to room temperature, and then concentrated. In a separate container, a mixed solution of t-butanol (35 mL, 10 eq.), THF (tetrahydrofuran) (100 mL), diisopropylethylamine (50 mL, 7 eq.) and DMAP (N,N-dimethyl-4-aminopyridine) (6 g, 1 eq.) was prepared. Then, the above concentrated residue was slowly added to the solution under ice cooling. The reaction mixture was heated under reflux for 3 hours. After the reaction mixture was allowed to cool down to room temperature, water and ethyl acetate were added and extraction was performed several times. The organic layer was dried over sodium sulfate and concentrated. The residue was subjected to column chromatography (hexane:ethyl acetate=5:1 (v/v)) to give the desired product, 5-chloro-6-ethoxycarbonylnicotinic acid t-butyl ester (8.43 g, 62%).

Physical property: $^1$H-NMR (CDCl$_3$): 9.05 (d, 1H), 8.30 (d, 1H), 4.50 (dd, 2H), 1.61 (s, 9H), 1.44 (t, 3H)

Production Method of
5-ethylthio-6-ethoxycarbonylnicotinic acid t-butyl ester

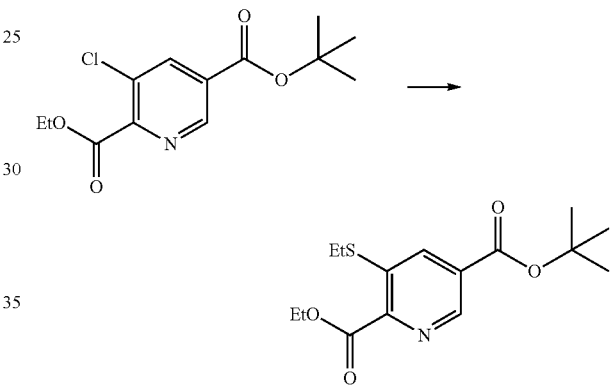

In DMF (100 mL) was dissolved 5-chloro-6-ethoxycarbonylnicotinic acid t-butyl ester (8.43 g, 21.65 mmol). Sodium ethanethiolate (2.27 g, 1 eq.) was slowly added to the solution under ice cooling. After stirring for 5 minutes, water was added to the mixture, and then 0.5 N hydrochloric acid was added. Extraction with ethyl acetate was performed several times. The organic layer was dried over sodium sulfate and concentrated. The residue was subjected to column chromatography (hexane:AcOEt=5:1 (v/v)) to give the desired product, 5-ethylthio-6-ethoxycarbonylnicotinic acid t-butyl ester (6.17 g, 92%).

Physical property: $^1$H-NMR (CDCl$_3$): 8.91 (d, 1H), 8.22 (d, 1H), 4.49 (dd, 2H), 2.99 (dd, 2H), 1.61 (s, 9H), 1.45 (t, 3H), 1.40 (t, 3H)

Production Method of
3-ethylthio-5-t-butoxycarbonylaminopicolinic acid ethyl ester

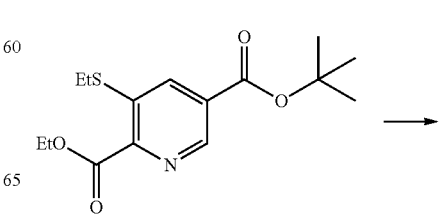

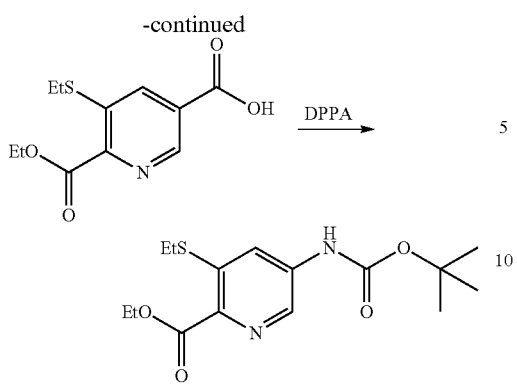

In trifluoroacetic acid (30 mL) was dissolved 5-ethylthio-6-ethoxycarbonylnicotinic acid t-butyl ester (6.17 g, 19.9 mmol). The solution was heated under reflux for 30 minutes. The reaction mixture was concentrated, and toluene and ethyl acetate were added. The mixture was concentrated again. To the residue were added t-butanol (100 mL), triethylamine (6.5 g, 3 eq.) and diphenylphosphoryl azide (DPPA) (11.74 g, 2 eq.). After stirring at room temperature for 1 hour, the mixture was refluxed for 4 hours. The reaction mixture was concentrated and the residue was subjected to column chromatography (hexane:ethyl acetate=2:1 (v/v)) to give the desired product, 3-ethylthio-5-t-butoxycarbonylaminopicolinic acid ethyl ester (3.63 g, 56%).

Physical property: $^1$H-NMR (CDCl$_3$): 8.25 (d, 1H), 8.09 (d, 1H), 6.74 (s, 1H), 4.46 (dd, 2H), 2.97 (dd, 2H), 1.53 (s, 9H), 1.44 (t, 3H), 1.41 (t, 3H)

Production Method of 5-amino-3-ethylthiopicolinic acid ethyl ester

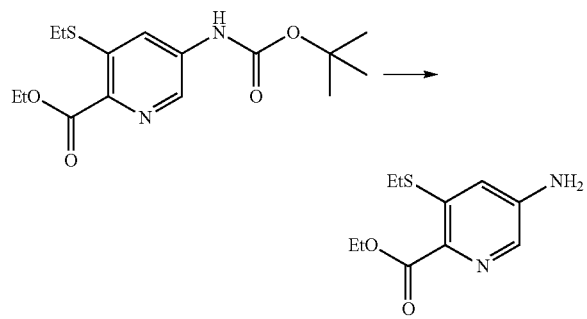

In trifluoroacetic acid (30 mL) was dissolved 3-ethylthio-5-t-butoxycarbonylaminopicolinic acid ethyl ester (670 mg, 2.06 mmol), and the solution was stirred at room temperature for 30 minutes. The reaction mixture was concentrated, and water, ethyl acetate and potassium carbonate were added. After extraction with ethyl acetate was performed several times, the organic layer was dried over sodium sulfate and concentrated. The residue was subjected to column chromatography (hexane:AcOEt=1:3 (v/v)) to give the desired product, 5-amino-3-ethylthiopicolinic acid ethyl ester (358 mg, 77%).

Physical property: $^1$H-NMR (CDCl$_3$): 7.89 (d, 1H), 6.80 (s, 1H), 4.43 (dd, 2H), 4.08 (s, 2H), 2.88 (dd, 2H), 1.56 (s, 9H), 1.42 (t, 3H), 1.40 (t, 3H)

Production Method of 3-ethylthio-5-iodopicolinic acid ethyl ester

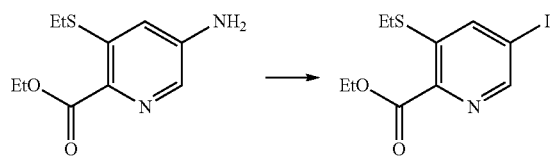

In acetonitrile (10 mL) was dissolved 5-amino-3-ethylthiopicolinic acid ethyl ester (1 g, 4.44 mmol). To the solution were added trifluoroacetic acid (500 mg, 1 eq.) and p-toluenesulfonic acid (2.6 g, 3 eq.). The mixture was cooled in a water bath at about 5° C. In a separate container, an aqueous solution (10 mL) of potassium iodide (2.25 g, 3 eq.) and sodium nitrite (612 mg, 2 eq.) was prepared. To the solution, the above reaction mixture was slowly added and the mixture was stirred for 30 minutes. The mixture was further stirred at room temperature for 30 minutes. A sodium thiosulfate aqueous solution was added to the reaction mixture, and extraction with ethyl acetate was performed several times. The organic layer was dried and concentrated. The residue was subjected to column chromatography to give the desired product, 3-ethylthio-5-iodopicolinic acid ethyl ester (761 mg, 51%).

Physical property: $^1$H-NMR (CDCl$_3$): 8.61 (s, 1H), 7.95 (s, 1H), 4.45 (dd, 2H), 2.91 (dd, 2H), 1.43 (t, 3H), 1.39 (t, 3H)

Production Method of 3-ethylthio-5-iodopicolinic acid

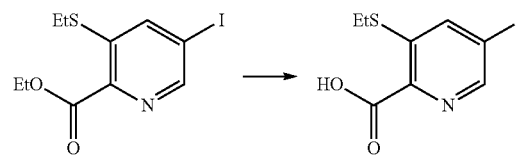

In ethanol (5 mL) was dissolved 3-ethylthio-5-iodo-2-pyridinecarboxylic acid ethyl ester (761 mg, 2.26 mmol). To the solution, a 3 M sodium hydroxide aqueous solution (1.2 mL, 1.5 eq.) was added. The mixture was stirred at room temperature for 5 minutes, and water and 3 N hydrochloric acid were added thereto. Extraction with ethyl acetate was performed several times. The organic layer was dried and concentrated to give the desired product, 3-ethylthio-5-iodopicolinic acid in a quantitative yield.

Physical property: $^1$H-NMR (CDCl$_3$): 13.30 (brs, 1H), 8.60 (d, 1H), 8.16 (d, 1H), 3.00 (dd, 2H), 1.24 (t, 3H)

Production Method of 3-ethylthio-5-cyclopropylpicolinic acid

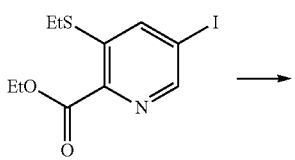

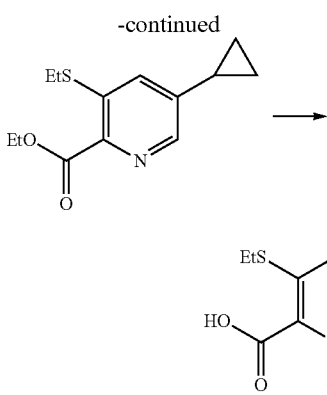

In a mixed solvent of toluene (40 mL) and water (10 mL) were dissolved 3-ethylthio-5-iodopicolinic acid ethyl ester (2 g, 5.9 mmol), cyclopropylboronic acid (1.0 g, 2 eq.), potassium phosphate (tribasic) (6.3 g, 5 eq.) and $PdCl_2$ (dppf)-acetone complex (1.0 g, 0.2 eq.). The mixture was heated under reflux for 2 hours. After cooling, the reaction was quenched with 1 N HCl. Extraction with ethyl acetate was performed, and the extract was dried over anhydrous sodium sulfate and then concentrated. The residue was purified by column chromatography to give 3-ethylthio-5-cyclopropylpicolinic acid ethyl ester (1.32 g, 89%).

$^1$H-NMR: 8.19 (d, 1H), 7.27 (d, 1H), 4.46 (q, 2H), 2.92 (q, 2H), 1.97-1.90 (m, 1H), 1.46-1.37 (m, 6H), 1.13-1.10 (m, 2H), 0.82-0.78 (m, 2H)

The corresponding methyl ester, isopropyl ester, n-butyl ester, amide and methyl amide were synthesized in the same manner as above.

Methyl ester $^1$H-NMR: 8.18 (d, 1H), 7.263 (s, 1H), 3.99 (s, 3H), 3.93 (2H, q), 1.97-1.92 (m, 1H), 1.39 (t, 3H), 1.17-1.12 (m, 2H), 0.84-0.80 (m, 2H)

Isopropyl ester $^1$H-NMR: 8.20 (d, 2H), 2.27 (d, 2H), 5.33 (m, 1H), 2.97-2.89 (m, 2H), 1.96-1.91 (m, 1H), 1.45-1.37 (m, 9H), 1.14-1.10 (m, 2H), 0.92-0.82 (m, 2H)

n-butyl ester $^1$H-NMR: 8.19 (d, 2H), 7.27 (d, 1H), 4.40 (t, 2H), 2.92 (q, 2H), 1.94-1.91 (m, 1H), 1.82-1.77 (m, 2H), 1.46-1.39 (m, 5H), 1.15-1.10 (m, 2H), 0.98 (t, 3H), 0.83-0.78 (m, 2H)

Amide $^1$H-NMR: 8.00 (d, 1H), 7.77 (brs, 1H), 5.41 (brs, 1H), 2.90 (q, 2H), 1.944 (m, 1H), 1.41 (t, 3H), 1.13-1.11 (m, 2H), 0.81-0.80 (m, 2H)

Methyl amide $^1$H-NMR: 7.97 (d, 2H), 7.92 (brs, 1H), 7.23 (s, 2H), 3.00 (d, 3H), 2.88 (q, 2H), 1.96-1.89 (m, 1H), 1.39 (t, 3H), 1.12-1.08 (m, 2H), 0.81-0.77 (m, 2H)

In ethanol (10 mL) was dissolved 3-ethylthio-5-cyclopropylpicolinic acid ethyl ester (1.12 g, 4.5 mmol). To the solution, a 15% NaOH aqueous solution (2.4 g, 2 eq.) was added. The mixture was stirred at room temperature for 3 hours, and ethanol was evaporated. Water was added to the residue to completely dissolve it. To the solution, 1 N HCl was added dropwise to adjust the pH to 3 to 4. The resulting solid was collected by filtration, and dissolved in ethyl acetate. The solution was dried over anhydrous sodium sulfate and concentrated to give 3-ethylthio-5-cyclopropylpicolinic acid (0.91 g, 91%).

$^1$H-NMR: 8.01 (d, 1H), 7.31 (d, 1H), 2.95 (q, 2H), 2.00-1.94 (m, 1H), 1.42 (t, 3H), 1.21-1.16 (m, 2H), 0.87-0.84 (m, 2H)

Production Example of Intermediate (3)

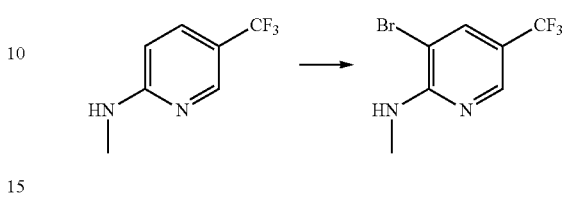

To a mixture of N-methyl-(5-trifluoromethyl-pyridin-2-yl)-amine (3.48 g) and DMF (20 mL) was added N-bromo-succinimide (4.27 g), and the mixture was stirred at room temperature for 1 hour. A saturated ammonium chloride aqueous solution was added to the reaction mixture, and extraction with ethyl acetate was performed. The organic layer was dried over sodium sulfate and concentrated in vacuo. The residue was subjected to silica gel column chromatography to give N-methyl-(3-bromo-5-trifluoromethyl-pyridin-2-yl)-amine (4.8 g).

$^1$H-NMR (CDCl$_3$) δ: 3.08 (3H, d), 5.40 (1H, brs), 7.78 (1H, d), 8.34 (1H, s).

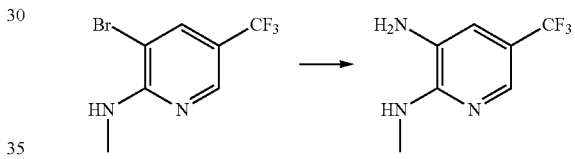

In a pressure-resistant reactor were placed N-methyl-(3-bromo-5-trifluoromethyl-pyridin-2-yl)-amine (0.51 g), copper (II) acetylacetonate (0.11 g), acetylacetone (0.20 g), cesium carbonate (1.30 g), NMP (N-methylpyrrolidone) (2 mL) and 28% aqueous ammonia (1 mL). The mixture was stirred at 120° C. for 7 hours and then 130° C. for 3 hours. After the reaction mixture was left to cool down to room temperature, a saturated ammonium chloride aqueous solution was added to the reaction mixture, and extraction with ethyl acetate was performed. The organic layer was dried over sodium sulfate and concentrated in vacuo. The residue was subjected to silica gel column chromatography to give $N^2$-methyl-5-trifluoromethylpyridine-2,3-diamine (0.28 g).

Reference Example 1

Production of 2-(3-ethylthio-5-iodopyridin-2-yl)-3-methyl-6-trifluoromethyl-3H-imidazo[4,5-b]pyridine

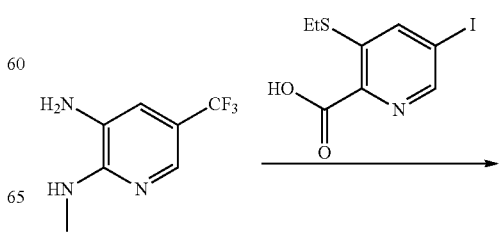

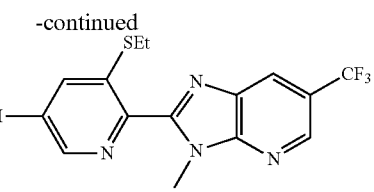

In THF (5 mL) was dissolved pyridinecarboxylic acid (856 mg, 2.8 mmol) and 3-amino-2-methylamino-5-trifluoromethylpyridine (690 mg). To the mixture were successively added triethylamine (1 mL), 4-dimethylaminopyridine (683 mg) and 1-methyl-2-chloropyridinium iodide (1.1 g). The reaction mixture was stirred at room temperature for 30 minutes and then heated under reflux for 3 hours. After the reaction mixture was allowed to cool down to room temperature, water was added to the mixture, and extraction with ethyl acetate was performed several times. The organic layer was dried and concentrated. The residue was dissolved in NMP (5 mL), and p-toluenesulfonic acid (1.5 g) was added to the solution, followed by stirring at 150° C. for 1 hour. The reaction container was allowed to cool down to room temperature and the mixture was subjected to column chromatography to give the desired imidazopyridine (411 mg, 32%, mp: 89 to 90° C.)

In the same manner as above, 2-(3-ethylthio-5-iodopyridin-2-yl)-3-methyl-6-tetrafluoroethyl-3H-imidazo[4,5-b]pyridine (mp: 110 to 112° C.) was synthesized.

Reference Example 2

Production of 2-(3-ethylsulfonyl-5-iodopyridin-2-yl)-3-methyl-6-trifluoromethyl-3H-imidazo[4,5-b]pyridine

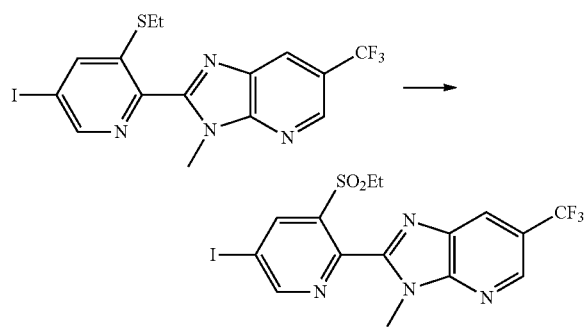

The imidazopyridine (361 mg, 0.776 mmol) produced in the previous reaction was dissolved in ethyl acetate (5 mL). To the solution, m-chloroperbenzoic acid (455 mg) was added, and the mixture was stirred at room temperature for 2 hours. To the reaction mixture were added a few drops of FAMSO (methyl (methylsulfinyl)methyl sulfide) and triethylamine (1 mL). After concentration, the residue was subjected to column chromatography to give the desired sulfone (378 mg, 98%, mp: 174 to 175° C.)

In the same manner as above, 2-(3-ethylsulfonyl-5-iodopyridin-2-yl)-3-methyl-6-tetrafluoroethyl-3H-imidazo[4,5-b]pyridine (mp: 138 to 140° C.) was synthesized.

Example 1

Production of 2-(3-ethylsulfonyl-5-cyclopropylpyridin-2-yl)-3-methyl-6-pentafluoroethyl-3H-imidazo[4,5-c]pyridine (Compound No. 1-15)

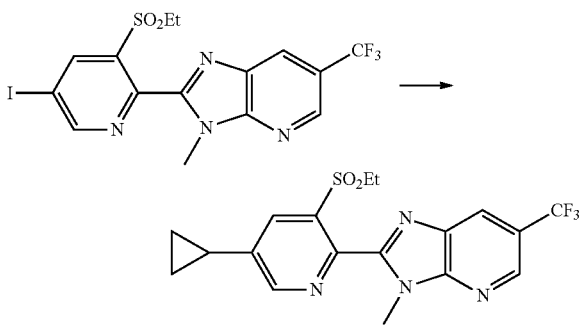

In DMF (2 mL) were dissolved the sulfone (110 mg, 0.22 mmol) produced in the previous reaction and cyclopropyl-cyclic-triolborate sodium salt (127 mg). To the solution, water (400 μL) was added. To the mixture, [(diphenylphosphino)ferrocene]dichloro palladium (18 mg) was added under argon, and the mixture was heated under stirring at 100° C. for 1 hour. The reaction mixture was allowed to cool down to room temperature and then concentrated. The residue was subjected to column chromatography to give the desired cyclopropane (75 mg, 82%).

Reference Example 3

Production of N-(5-trifluoromethyl-2-aminomethylphenyl)-3-ethylthio-5-cyclopropyl-picolinic acid amide

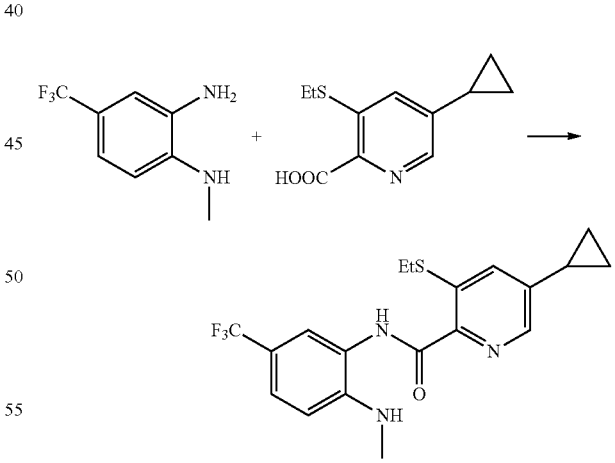

In pyridine (2 mL) was dissolved 3-ethylthio-5-cyclopropylpicolinic acid (230 mg). To the solution were added 1-hydroxybenzotriazole (13 mg, 0.1 eq.) and EDC (1-ethyl-3-(3-dimethylaminopropyl)carbodiimide hydrochloride) (400 mg, 2.0 eq.). After stirring at room temperature for 10 minutes, 2-methylamino-6-trifluoromethylaniline (200 mg, 1.0 eq.) was added, and the mixture was further stirred for 2.5 hours. An ammonium chloride aqueous solution was added to the mixture, and extraction with ethyl acetate was performed. The organic layer was dried over sodium sulfate and the solvent was evaporated in vacuo to give N-(5-trifluoromethyl-2-aminomethylphenyl)-3-ethylthio-5-cyclopropyl-picolinic acid amide (470 mg, quantitative yield).

Production Example 1

Production Method of 2-(3-ethylthio-5-cyclopropylpyridin-2-yl)-1-methyl-5-trifluoromethyl-1H-benzimidazole (Compound No. 7-13)

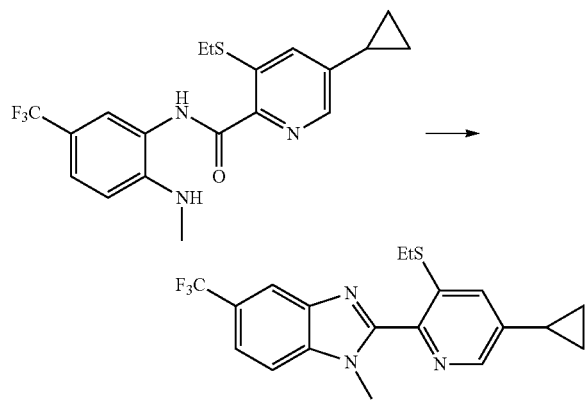

In toluene (1.5 mL) was dissolved N-(5-trifluoromethyl-2-aminomethylphenyl)-3-ethylthio-5-cyclopropyl-picolinic acid amide (470 mg). To the solution, acetic acid (1.5 mL) was added. The mixture was stirred at 100° C. for 1.5 hours. After the disappearance of the starting material was confirmed by TLC, water was added to the reaction mixture, and extraction with ethyl acetate was performed. The extract was dehydrated with the addition of sodium sulfate, and the solvent was evaporated with the addition of silica gel. The residue was purified by column chromatography to give 2-(3-ethylthio-5-cyclopropylpyridin-2-yl)-1-methyl-5-trifluoromethyl-1H-benzimidazole (395 mg, 81%).

Production Example 2

Production of 2-(3-ethylsulfinyl-5-cyclopropylpyridin-2-yl)-1-methyl-5-trifluoromethyl-1H-benzimidazole (Compound No. 7-14) and 2-(3-ethylsulfonyl-5-cyclopropylpyridin-2-yl)-1-methyl-5-trifluoromethyl-1H-benzimidazole (Compound No. 7-15)

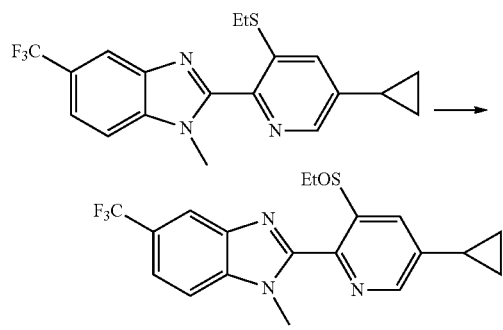

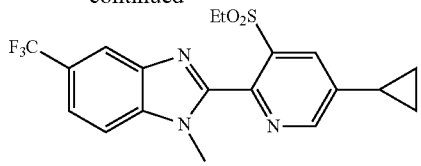

In ethyl acetate (2 mL) was dissolved 2-(3-ethylthio-5-cyclopropylpyridin-2-yl)-1-methyl-5-trifluoromethyl-1H-benzimidazole (190 mg). To the solution, m-CPBA (m-chloroperbenzoic acid) (185 mg, 1.5 eq.) was added. The mixture was stirred at room temperature for 1 hour. After the disappearance of the starting material was confirmed by TLC, a sodium thiosulfate aqueous solution was added to the reaction mixture, and extraction with ethyl acetate was performed. The extract was dehydrated with the addition of sodium sulfate, and the solvent was evaporated with the addition of silica gel. The residue was purified by column chromatography to give 2-(3-ethylsulfinyl-5-cyclopropylpyridin-2-yl)-1-methyl-5-trifluoromethyl-1H-benzimidazole (55 mg, 30%) and 2-(3-ethylsulfonyl-5-cyclopropylpyridin-2-yl)-1-methyl-5-trifluoromethyl-1H-benzimidazole (84 mg, 45%).

Reference Example 4

Production of 5-trifluoromethylpyridine-3-nitro-2-ol

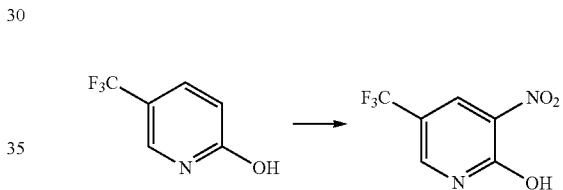

In sulfuric acid (6 mL) was dissolved 5-trifluoromethylpyridin-2-ol (500 mg). Nitric acid was added to the solution under ice cooling. After the temperature was raised to room temperature, the reaction mixture was stirred for 1.5 hours, and then heated under stirring at 70° C. for 4 hours. Water was added to the mixture, and extraction with ethyl acetate was performed. The extract was dehydrated with the addition of sodium sulfate and the solvent was evaporated to give 5-trifluoromethylpyridine-3-nitro-2-ol (426 mg, purity: about 50%).

Reference Example 5

Production of 3-amino-5-trifluoromethylpyridin-2-ol

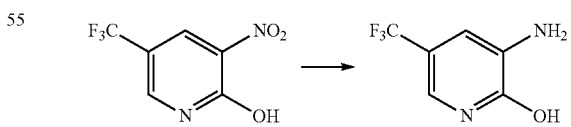

In ethanol (4 mL) was dissolved 5-trifluoromethylpyridine-3-nitro-2-ol (420 mg). To the solution, a solution of ammonium chloride (110 mg, 1.0 eq.) in water (1 mL) was added. Iron powder (560 mg, 5.0 eq.) was added to the solution under stirring at room temperature, and the mixture was stirred under heating and reflux for 1.5 hours. After the disappearance of the starting material was confirmed, metals and other impurities were removed by filtration through Celite. The solvent was evaporated and the residue was purified by column chromatography to give 3-amino-5-trifluoromethylpyridin-2-ol (102 mg, 19%).

Reference Example 6

Production Method of N-(5-trifluoromethyl-2-hydroxypyridin-3-yl)-3-ethylthio-5-cyclopropyl-picolinic acid amide

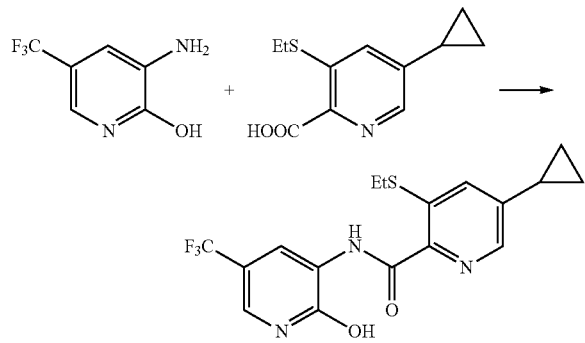

In pyridine (2 mL) was dissolved 3-ethylthio-5-cyclopropylpicolinic acid (140 mg). To the solution, 1-hydroxybenzotriazole (8 mg, 0.1 eq.) and EDC (215 mg, 2.0 eq.) were added. After stirring at room temperature for 10 minutes, 3-amino-5-trifluoromethylpyridin-2-ol (100 mg, 1.0 eq.) was added to the mixture, and the mixture was further stirred for 2.5 hours. After the disappearance of the starting materials was confirmed, an ammonium chloride aqueous solution was added to the reaction mixture, and extraction with ethyl acetate was performed. The organic layer was dried over sodium sulfate and the solvent was evaporated in vacuo to give N-(5-trifluoromethyl-2-hydroxypyridin-3-yl)-3-ethylthio-5-cyclopropyl-picolinic acid amide (132 mg, 62%).

Example 2

Production of 2-(3-ethylthio-5-cyclopropylpyridin-2-yl)-5-trifluoromethyl-oxazolo[5,4-b]pyridine (Compound No. 3-13)

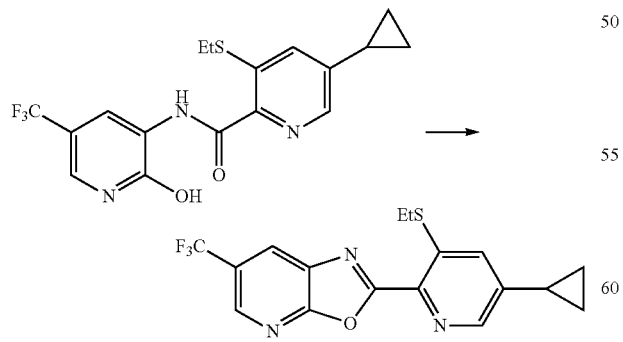

In toluene (1 mL) was dissolved N-(5-trifluoromethyl-2-hydroxypyridin-3-yl)-3-ethylthio-5-cyclopropyl-picolinic acid amide (130 mg). To the solution were added triphenylphosphine (270 mg, 3.0 eq.) and bis(2-methoxyethyl) azodicarboxylate (240 mg, 3.0 eq.) at room temperature. The mixture was stirred under heating at 50° C. for 3 hours. After the disappearance of the starting material was confirmed by TLC, water was added to the reaction mixture, and extraction with ethyl acetate was performed. The extract was dehydrated with the addition of sodium sulfate, and the solvent was evaporated with the addition of silica gel. The residue was purified by column chromatography to give the desired compound (64 mg, 52%).

Example 3

Production Method of 2-(3-ethylsulfonyl-5-cyclopropylpyridin-2-yl)-5-trifluoromethyl-oxazolo[5,4-b]pyridine (Compound No. 3-15)

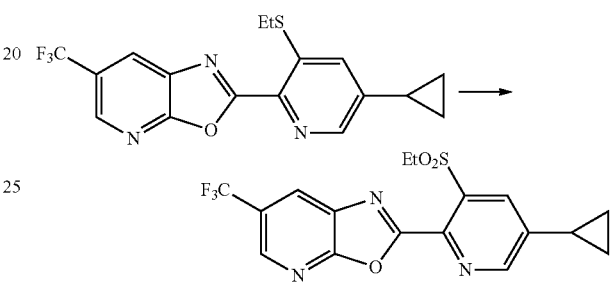

In ethyl acetate (1 mL) was dissolved 2-(3-ethylthio-5-cyclopropylpyridin-2-yl)-5-trifluoromethyl-oxazolo[5,4-b]pyridine (130 mg, 1.0 eq.). To the solution, m-CPBA (106 mg, 2.5 eq.) was added. The mixture was stirred at room temperature for 3.5 hours. After the disappearance of the starting material was confirmed by TLC, a sodium thiosulfate aqueous solution was added to the reaction mixture, and extraction with ethyl acetate was performed. The extract was dehydrated with the addition of sodium sulfate, and the solvent was evaporated with the addition of silica gel. The residue was purified by column chromatography to give 2-(3-ethylsulfonyl-5-cyclopropylpyridin-2-yl)-5-trifluoromethyl-oxazolo[5,4-b]pyridine (60 mg, 94%).

Compound Nos. 8-12, 8-15, 8-18 and 2-15 were produced from known compounds, 2-amino-4-(trifluoromethylthio) phenol, 2-amino-4-(trifluoromethyl) phenol, 2-amino-4-(pentafluoroethyl)phenol, and N3-methyl-6-(trifluoromethyl)pyridine-3,4-diamine, respectively, in the same manner as in the above Example.

Reference Example 7

Production of 5-trifluoromethyl-2-mercapto-3-nitropyridine

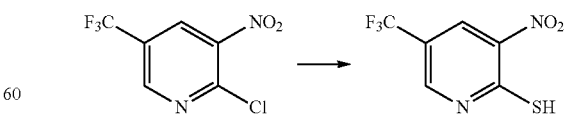

In DMF (4 mL) was dissolved 2-chloro-5-trifluoromethyl-3-nitropyridine (500 mg). To the solution, sodium hydrogen sulfide (150 mg, 1.2 eq.) was added. The mixture was stirred at room temperature for 3 hours. After the disappearance of the starting material was confirmed by TLC, water was added to the reaction mixture, and extraction with ethyl acetate was performed. The extract was dehydrated with the addition of sodium sulfate, and the solvent was evaporated with the addition of silica gel. The residue was purified by column chromatography to give 5-trifluoromethyl-2-mercapto-3-nitropyridine (193 mg, 39%).

Reference Example 8

Production of 3-amino-5-trifluoromethyl-2-mercaptopyridine

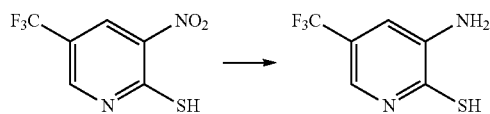 [SMILES: O=[N+]([O-])c1cc(C(F)(F)F)cnc1S ; Nc1cc(C(F)(F)F)cnc1S]

In ethanol (2 mL) was dissolved 5-trifluoromethyl-2-mercapto-3-nitropyridine (190 mg). To the solution, a solution of ammonium chloride (45 mg, 1 eq.) in water (0.5 mL) was added. Iron powder (240 mg, 5.0 eq.) was added to the solution under stirring at room temperature, and the mixture was stirred under reflux for 5.5 hours. After the disappearance of the starting material was confirmed by TLC, metals were removed by filtration through Celite. The solvent was evaporated with the addition of silica gel. The residue was purified by column chromatography to give 3-amino-5-trifluoromethyl-2-mercaptopyridine (70 mg, 46%).

Reference Example 9

Production Method of N-(5-trifluoromethyl-2-mercaptopyridin-3-yl)-3-ethylthio-5-cyclopropyl-picolinic acid amide

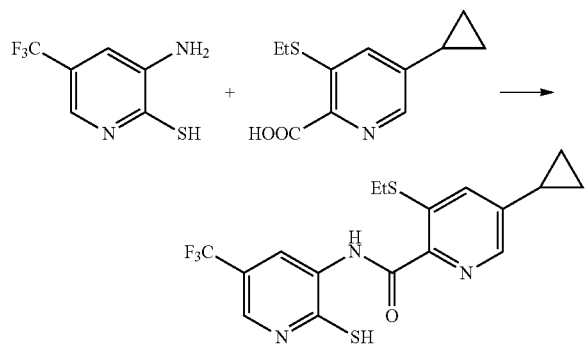

In pyridine (1.5 mL) was dissolved 3-ethylthio-5-cyclopropylpicolinic acid (96 mg). To the solution, 1-hydroxybenzotriazole (5 mg, 0.1 eq.) and EDC (165 mg, 2.4 eq.) were added. The mixture was stirred at room temperature for 20 minutes. To the mixture, a solution of 3-amino-5-trifluoromethyl-2-mercaptopyridine (70 mg, 1.0 eq.) in pyridine (2 mL) was added dropwise and the mixture was stirred at room temperature for 4 hours. After the disappearance of the starting material was confirmed by TLC, water was added to the reaction mixture, and extraction with ethyl acetate was performed. The extract was dehydrated with the addition of sodium sulfate and the solvent was evaporated to give the crude N-(5-trifluoromethyl-2-mercaptopyridin-3-yl)-3-ethylthio-5-cyclopropyl-picolinic acid amide (160 mg).

Example 4

Production Method of 2-(3-ethylthio-5-cyclopropylpyridin-2-yl)-5-trifluoromethyl-thiazolo[5,4-b]pyridine (Compound No. 5-13)

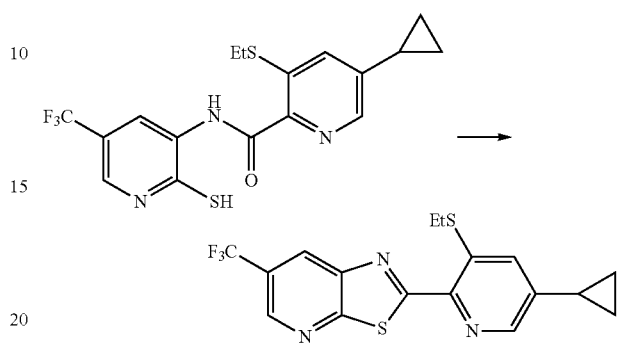

The crude N-(5-trifluoromethyl-2-mercaptopyridin-3-yl)-3-ethylthio-5-cyclopropyl-picolinic acid amide (160 mg) was dissolved in NMP (1 mL). To the solution, p-toluenesulfonic acid (115 mg) was added. The mixture was stirred at 150° C. for 2 hours. After the disappearance of the starting material was confirmed by TLC, water was added to the reaction mixture, and extraction with ethyl acetate was performed. The extract was dehydrated with the addition of sodium sulfate, and the solvent was evaporated with the addition of silica gel. The residue was purified by column chromatography to give 2-(3-ethylthio-5-cyclopropylpyridin-2-yl)-5-trifluoromethyl-thiazolo[5,4-b]pyridine (64 mg, 47%).

Example 5

Production of 2-(3-ethylsulfonyl-5-cyclopropylpyridin-2-yl)-5-trifluoromethyl-thiazolo[5,4-b]pyridine (Compound No. 5-15)

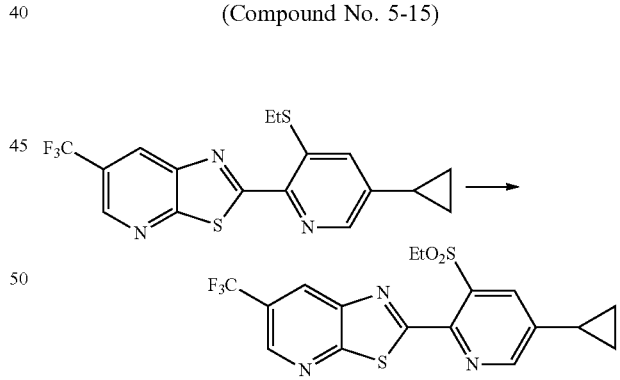

In ethyl acetate (1 mL) was dissolved 2-(3-ethylthio-5-cyclopropylpyridin-2-yl)-5-trifluoromethyl-thiazolo[5,4-b]pyridine (55 mg). To the solution, m-CPBA (82 mg, 2.2 eq.) was added. The mixture was stirred at room temperature for 1.5 hours. After the disappearance of the starting material was confirmed, a sodium thiosulfate aqueous solution was added to the reaction mixture, and extraction with ethyl acetate was performed. The extract was dehydrated with the addition of sodium sulfate, and the solvent was evaporated with the addition of silica gel. The residue was purified by column chromatography to give 2-(3-ethylsulfonyl-5-cyclopropylpyridin-2-yl)-5-trifluoromethyl-thiazolo[5,4-b]pyridine (15 mg, 28%).

Reference Example 10

Production Method of 6,6-disulfandiylbis(3-trifluoromethylaniline)

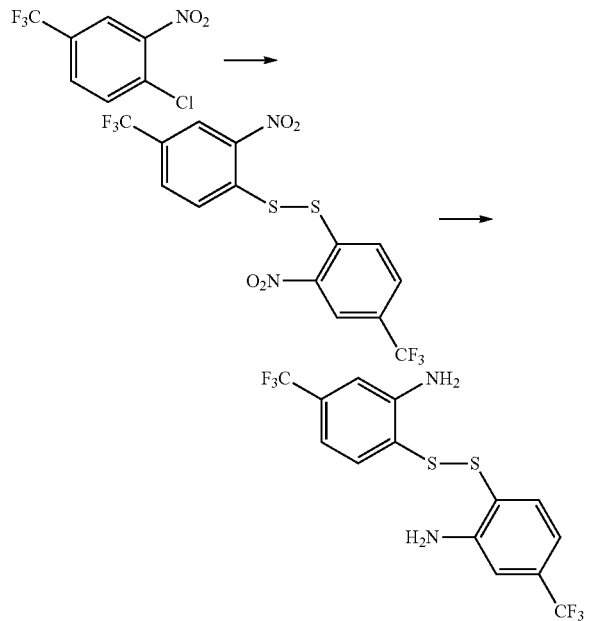

In DMF (15 mL) was dissolved 4-trifluoromethyl-2-nitrochlorobenzene (2.0 g). To the solution, sodium hydrogen sulfide (1.0 g, 2.0 eq.) was added at room temperature, and the mixture was stirred for 5 hours. After the disappearance of the starting material was confirmed by TLC, water was added to the reaction mixture, and extraction with ethyl acetate was performed to give a crude product (1.65 g, purity: <50%). The crude product was dissolved in ethanol (15 mL), and a solution of ammonium chloride (200 mg) in water (5 mL) was added to the mixture. Iron powder (2.1 g, excess amount) was added to the solution under stirring at room temperature, and the mixture was stirred under heating and reflux for 2 hours. Metals were removed by filtration through Celite. The solvent was evaporated with the addition of silica gel. The residue was purified by column chromatography to give 6,6-disulfanediylbis(3-trifluoromethylaniline) (274 mg, 16%).

Reference Example 11

Production Method of 3-ethylthio-5-cyclopropylpicolinic acid chloride

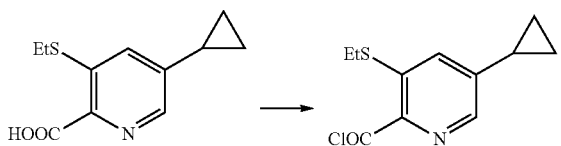

In THF (1 mL) was dissolved 3-ethylthio-5-cyclopropylpicolinic acid (220 mg). To the solution, a catalytic amount of DMF was added. Oxalyl chloride (150 mg, 1.2 eq.) was added dropwise to the solution, and the mixture was stirred at room temperature for 5 hours. The solvent was evaporated to give 3-ethylthio-5-cyclopropylpicolinic acid chloride.

Reference Example 12

Production Method of N-(2-((2-amino-4-trifluoromethylphenyl)disulfanyl)-5-trifluorophenyl)-5-cyclopropyl-3-ethylthiopicolinic acid amide

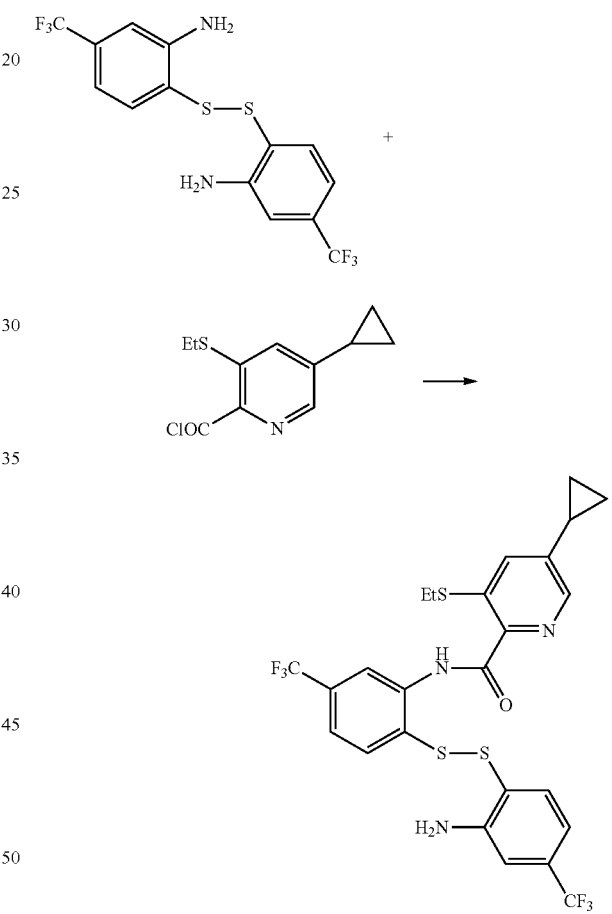

In THF (1 mL) was dissolved 6,6-disulfandiylbis(3-trifluoromethyl aniline) (150 mg). To the solution, triethylamine (158 mg, 4.0 eq.) was added. To the mixture, 3-ethylthio-5-cyclopropylpicolinic acid chloride was gradually added, and the mixture was stirred at room temperature for 3 hours. Water was added to the mixture, and extraction with ethyl acetate was performed. The extract was dehydrated with the addition of sodium sulfate, and the solvent was evaporated with the addition of silica gel. The residue was purified by column chromatography to give N-(2-((2-amino-4-trifluoromethylphenyl)disulfanyl)-5-trifluorophenyl)-5-cyclopropyl-3-ethylthiopicolinic acid amide (134 mg, 58%).

Example 6

Production of 2-(3-ethylthio-5-cyclopropylpyridin-2-yl)-5-trifluoromethyl-benzothiazole (Compound No. 9-10)

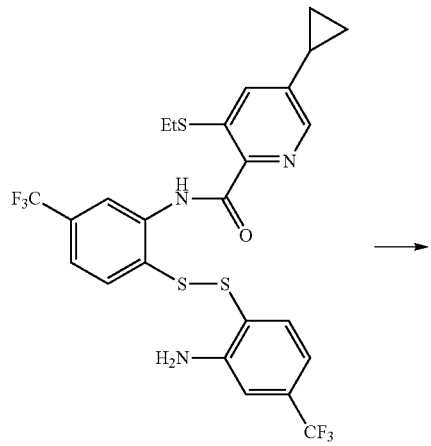

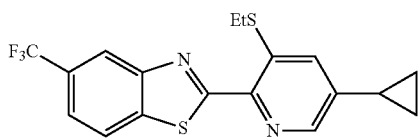

The picolinic acid amide produced in the previous step (130 mg) was dissolved in NMP (2 mL), and then Rongalit (51 mg, 1.5 eq.) was added to the solution under argon. To the mixture, p-toluenesulfonic acid monohydrate (63 mg, 1.5 eq.) was added, and the mixture was stirred at 150° C. for 1 hour. Water was added to the mixture, and extraction with ethyl acetate was performed. The extract was dehydrated with the addition of sodium sulfate, and the solvent was evaporated with the addition of silica gel. The residue was purified by column chromatography to give 2-(3-ethylthio-5-cyclopropylpyridin-2-yl)-5-trifluoromethyl-benzothiazole (66 mg, 79%).

Example 7

Production of 2-(3-ethylsulfonyl-5-cyclopropylpyridin-2-yl)-5-trifluoromethyl-benzothiazole (Compound No. 9-12)

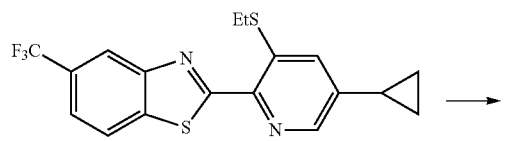

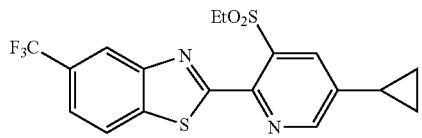

In ethyl acetate (1 mL) was dissolved 2-(3-ethylthio-5-cyclopropylpyridin-2-yl)-5-trifluoromethyl-benzothiazole (50 mg). To the mixture, m-CPBA (76 mg, 2.2 eq.) was added. The mixture was stirred at room temperature for 2.5 hours. After the disappearance of the starting material was confirmed by TLC, a sodium thiosulfate aqueous solution was added to the reaction mixture, and extraction with ethyl acetate was performed. The extract was dehydrated with the addition of sodium sulfate, and the solvent was evaporated with the addition of silica gel. The residue was purified by column chromatography to give 2-(3-ethylsulfonyl-5-cyclopropylpyridin-2-yl)-5-trifluoromethyl-benzothiazole (15 mg, 28%).

Reference Example 13

Production Method of 1-(4-methoxybenzyl)-3-methyl 2-(5-ethylthio-6-(3-methyl-6-trifluoromethyl-3H-imidazo[4,5-b]pyridin-2-yl)pyridin-3-yl) malonate

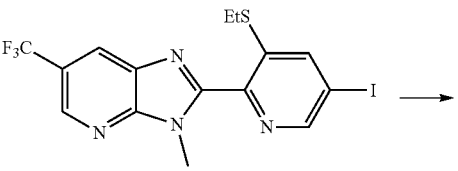

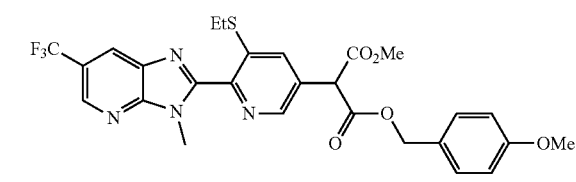

In THF (48 mL) were dissolved 2-(3-ethylthio-5-iodopyridin-2-yl)-3-methyl-6-trifluoromethyl-3H-imidazo[4,5-b]pyridine (1.1 g, 2.4 mmol), copper(I) iodide (0.09 g, 0.2 eq.), picolinic acid (0.12 g, 0.4 eq.), methyl p-methoxybenzyl malonate (0.68 g, 1.2 eq.) and cesium carbonate (3.1 g, 4 eq.). The solution was stirred at 60° C. for 1 hour. After the reaction was completed, a saturated ammonium chloride aqueous solution was added to the reaction mixture, and extraction with ethyl acetate was performed. The extract was dried over anhydrous sodium sulfate and concentrated in vacuo. The residue was subjected to column chromatography to give 1-(4-methoxybenzyl)-3-methyl 2-(5-ethylthio-6-(3-methyl-6-trifluoromethyl-3H-imidazo[4,5-b]pyridin-2-yl)pyridin-3-yl)malonate (1.4 g).

Reference Example 14

Production Method of methyl 2-(5-ethylthio-6-(3-methyl-6-trifluoromethyl-3H-imidazo[4,5-b]pyridin-2-yl)pyridin-3-yl)acetate

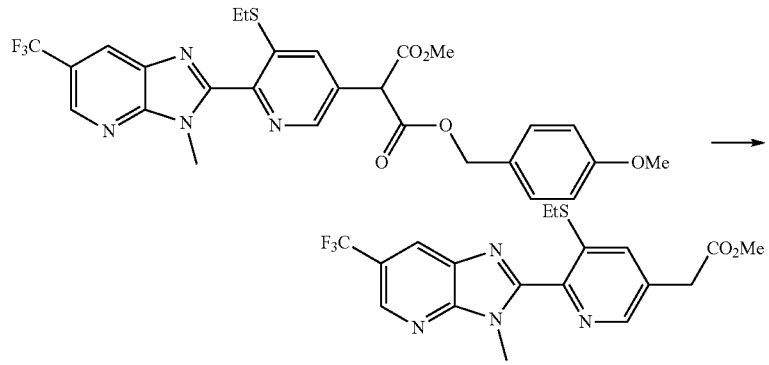

The malonic acid ester (1.4 g, 2.4 mmol) produced in the previous step was dissolved in trifluoroacetic acid (10 mL), and the solution was stirred at 50° C. for 2 hours. After concentration, the residue was subjected to column chromatography to give methyl 2-(5-ethylthio-6-(3-methyl-6-trifluoromethyl-3H-imidazo[4,5-b]pyridin-2-yl)pyridin-3-yl)acetate (818 mg, 82%).

Reference Example 15

Methyl 1-(5-ethylthio-6-(3-methyl-6-trifluoromethyl-3H-imidazo[4,5-b]pyridin-2-yl)pyridine)-3-yl)cyclopropanecarboxylate

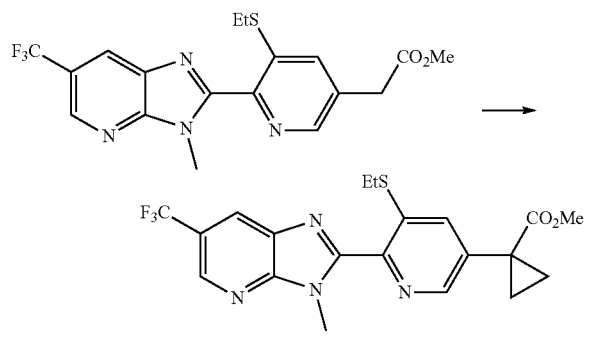

The acetic acid ester (818 mg, 2.0 mmol) produced in the previous step was dissolved in DMF (20 mL), and then 1,2-dibromoethane (1.5 g, 4 eq.) was added to the solution. After cooling to 0° C., 60% NaH (160 mg, 2 eq.) was added to the mixture. The mixture was stirred at 0° C. for 1 hour, and then stirred at room temperature for 3 hours. The reaction mixture was added dropwise to a 1 N HCl aqueous solution. After extraction with ethyl acetate, the extract was dried over anhydrous sodium sulfate and concentrated in vacuo. The residue was subjected to column chromatography to give methyl 1-(5-ethylthio-6-(3-methyl-6-trifluoromethyl-3H-imidazo[4,5-b]pyridin-2-yl)pyridine)-3-yl)cyclopropanecarboxylate (700 mg, 80%).

Example 8

Methyl 1-(5-ethylsulfonyl-6-(3-methyl-6-trifluoromethyl-3H-imidazo[4,5-b]pyridin-2-yl)pyridine)-3-yl)cyclopropanecarboxylate (Compound No. 11-2)

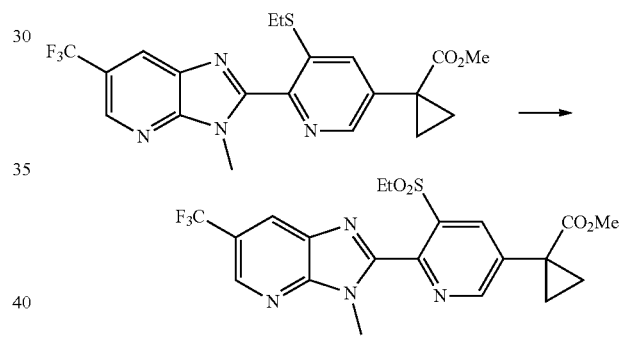

The cyclopropanecarboxylic acid ester (510 mg, 1.1 mmol) produced in the previous step was dissolved in ethyl acetate (10 mL), and then 65% m-CPBA (670 mg, 2 eq.) was added to the solution. After stirring at room temperature for 3 hours, FAMSO and triethylamine were added to the mixture. The solution was concentrated and the residue was subjected to column chromatography to give methyl 1-(5-ethylsulfonyl-6-(3-methyl-6-trifluoromethyl-3H-imidazo[4,5-b]pyridin-2-yl)pyridine)-3-yl)cyclopropanecarboxylate (530 mg, 97%).

Example 9

Production Method of 1-(5-ethylsulfonyl-6-(3-methyl-6-trifluoromethyl-3H-imidazo[4,5-b]pyridin-2-yl)pyridine)-3-yl)cyclopropanecarboxylic acid (Compound No. 11-1)

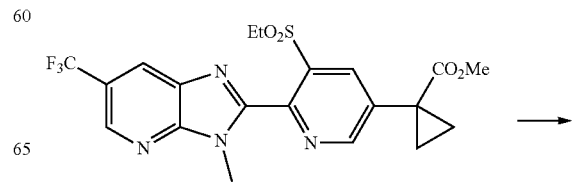

-continued

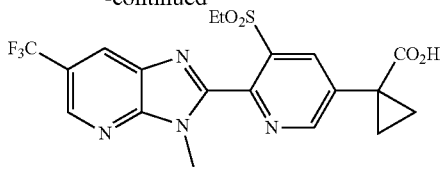

The cyclopropanecarboxylic acid ester (530 mg, 1.1 mmol) produced in the previous step was dissolved in methanol (10 mL), and then a 15% sodium hydroxide aqueous solution (0.3 g, 1.1 eq.) was added to the solution. The mixture was stirred at 40° C. for 2 hours, and water was added to the mixture. After the methanol was evaporated, the pH was adjusted to 4 with 1 N HCl. After extraction with ethyl acetate, the extract was dried over anhydrous sodium sulfate and the solvent was evaporated to give 1-(5-ethylsulfonyl-6-(3-methyl-6-trifluoromethyl-3H-imidazo[4,5-b]pyridin-2-yl)pyridine)-3-yl)cyclopropanecarboxylic acid (510 mg, 99%).

Example 10

Production Method of 1-(5-ethylsulfonyl-6-(3-methyl-6-trifluoromethyl-3H-imidazo[4,5-b]pyridin-2-yl)pyridine)-3-yl)cyclopropanecarboxylic acid amide (Compound No. 11-6)

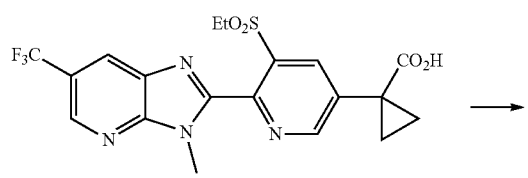

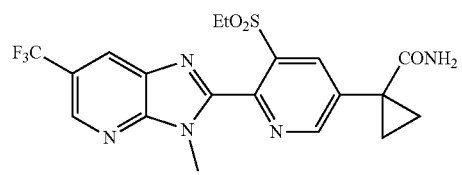

The cyclopropanecarboxylic acid (530 mg, 1.1 mmol) produced in the previous step was dissolved in THF (10 mL), and then oxalyl chloride (160 mg, 1.1 eq.) was added to the solution. The solution was stirred at room temperature for 1 hour, and the solution was concentrated to give an acid chloride (500 mg, 90%). The acid chloride (360 mg, 0.76 mmol) was gradually added to 28% aqueous ammonia (5 mL). After stirring at room temperature for 1 hour, extraction with ethyl acetate was performed. The extract was dried over anhydrous sodium sulfate and concentrated. The residue was subjected to column chromatography to give 1-(5-ethylsulfonyl-6-(3-methyl-6-trifluoromethyl-3H-imidazo[4,5-b]pyridin-2-yl)pyridine)-3-yl)cyclopropanecarboxylic acid amide (300 mg, 87%).

Example 11

Production Method of 1-(5-ethylsulfonyl-6-(3-methyl-6-trifluoromethyl-3H-imidazo[4,5-b]pyridin-2-yl)pyridine)-3-yl)cyclopropanecarbonitrile (Compound No. 11-13)

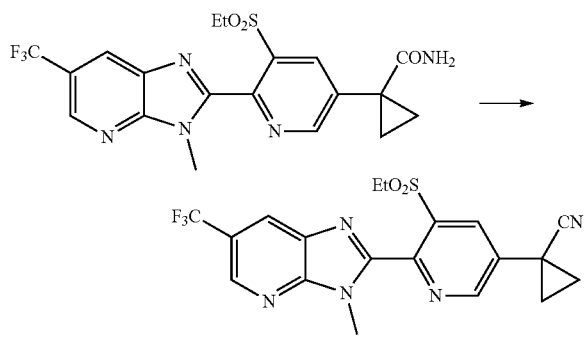

The cyclopropanecarboxylic acid amide (300 mg, 0.66 mmol) produced in the previous step was dissolved in DMF (2 mL), and then phosphorus oxychloride (41 mg, 0.4 eq.) was added to the solution. After stirring at room temperature for 1 hour, a saturated sodium bicarbonate aqueous solution was added to the mixture. After extraction with ethyl acetate, the extract was dried over anhydrous sodium sulfate and concentrated. The residue was subjected to column chromatography to give 1-(5-ethylsulfonyl-6-(3-methyl-6-trifluoromethyl-3H-imidazo[4,5-b]pyridin-2-yl)pyridine)-3-yl)cyclopropanecarbonitrile (150 mg, 52%).

Compound Nos. 18-173 and 2-13 were produced from known compounds, 2-amino-4-(trifluoromethylthio)phenol and N3-methyl-6-(trifluoromethyl)pyridine-3,4-diamine, respectively, in the same manner as in the above Example.

Reference Example 16

Production Method of methyl 3-(5-ethylthio-6-(3-methyl-6-trifluoromethyl-3H-imidazo[4,5-b]pyridin-2-yl)pyridin-3-yl)acrylate

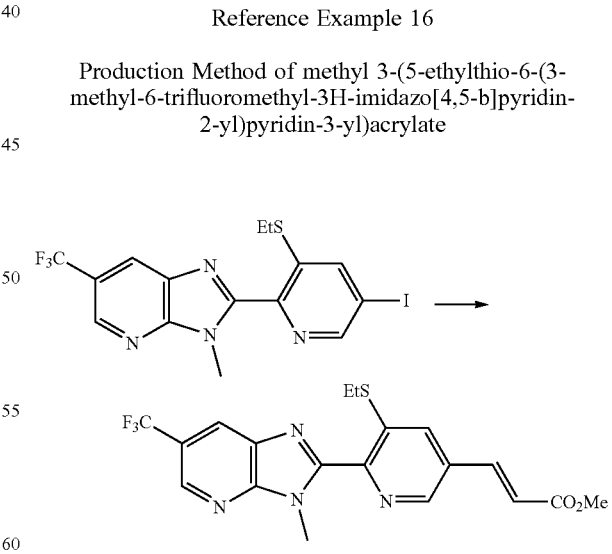

To 2-(3-ethylthio-5-iodopyridin-2-yl)-3-methyl-6-trifluoromethyl-3H-imidazo[4,5-b]pyridine (1700 mg) were added methyl acrylate (630 mg), palladium(II) acetate (82 mg), tri(o-tolyl)phosphine (220 mg), N,N-diisopropylethylamine (940 mg) and dimethylformamide (36 mL). After the air was replaced with argon, the mixture was stirred at 90° C. for 3 hours. After the reaction mixture was allowed to cool down to room temperature, water was added to the mixture, and extraction with ethyl acetate was performed. The organic layer was washed with saturated brine. The organic layer was dried over anhydrous sodium sulfate, and concentrated in vacuo. The residue was subjected to silica gel column chromatography to give methyl 3-(5-ethylthio-6-(3-methyl-6-trifluoromethyl-3H-imidazo[4,5-b]pyridin-2-yl)pyridin-3-yl)acrylate (1100 mg). Physical property: melting point 159 to 161° C.

Reference Example 17

Production of methyl 2-(5-ethylthio-6-(3-methyl-6-trifluoromethyl-3H-imidazo[4,5-b]pyridin-2-yl)pyridine)-3-yl)cyclopropanecarboxylate

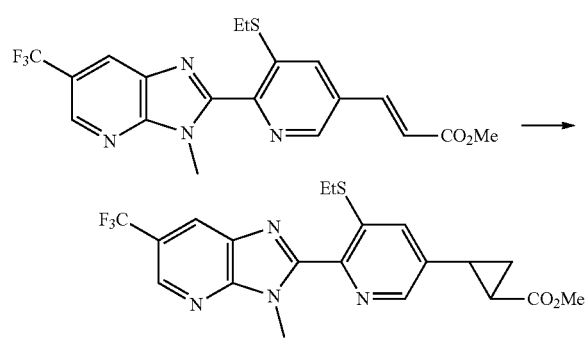

Sodium hydride (6 mg) was added to a mixed solution of trimethylsulfoxonium iodide (26 mg) and DMSO (dimethyl sulfoxide) (0.6 mL), and then the mixture was stirred at room temperature for 30 minutes. To the mixed solution, a mixed solution of the ester (50 mg) produced in the previous step and THF (0.6 mL) was added at 0° C. The mixture was stirred for 20 minutes, and further stirred at room temperature for 3 hours. Ice water was added to the mixture, and extraction with ethyl acetate was performed. The organic layer was washed with saturated brine. The organic layer was dried over anhydrous sodium sulfate, and concentrated in vacuo. The residue was subjected to silica gel column chromatography to give methyl 2-(5-ethylthio-6-(3-methyl-6-trifluoromethyl-3H-imidazo[4,5-b]pyridin-2-yl)pyridine)-3-yl)cyclopropanecarboxylate (16 mg).

Physical property: melting point 118 to 120° C.

Example 12

Production of methyl 2-(5-ethylsulfonyl-6-(3-methyl-6-trifluoromethyl-3H-imidazo[4,5-b]pyridin-2-yl)pyridine)-3-yl)cyclopropanecarboxylate (Compound No. 11-82)

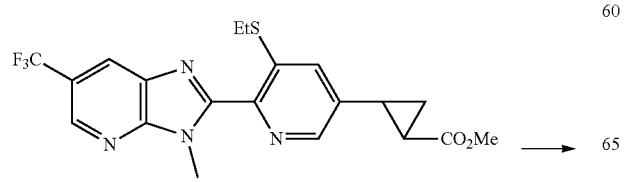

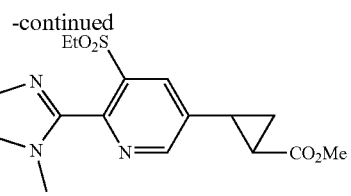

m-CPBA (23 mg) was added to a mixed solution of the cyclopropanecarboxylic acid methyl ester (16 mg) produced in the previous step and ethyl acetate (0.4 mL) at 0° C., and then the mixture was stirred at room temperature for 2 hours. To the reaction mixture was added a saturated sodium hydrogen thiosulfate solution, and extraction with ethyl acetate was performed. The organic layer was washed with a saturated sodium bicarbonate aqueous solution and then with saturated brine. The organic layer was dried over anhydrous sodium sulfate, and concentrated in vacuo. The residue was subjected to column chromatography to give methyl 2-(5-ethylsulfonyl-6-(3-methyl-6-trifluoromethyl-3H-imidazo[4,5-b]pyridin-2-yl)pyridine)-3-yl)cyclopropanecarboxylate (8.0 mg).

Hereinafter, formulation examples are shown, but the present invention is not limited thereto. In the formulation examples, the "parts" means parts by weight.

Formulation Example 1

| | |
|---|---|
| Compound of the present invention | 10 parts |
| Xylene | 70 parts |
| N-methyl pyrrolidone | 10 parts |
| Mixture of polyoxyethylene nonylphenyl ether and calcium alkylbenzene sulfonate | 10 parts |

The above ingredients are uniformly mixed for dissolution to give an emulsifiable concentrate.

Formulation Example 2

| | |
|---|---|
| Compound of the present invention | 3 parts |
| Clay powder | 82 parts |
| Diatomite powder | 15 parts |

The above ingredients are uniformly mixed and then pulverized to give a dust.

Formulation Example 3

| | |
|---|---|
| Compound of the present invention | 5 parts |
| Mixture of bentonite powder and clay powder | 90 parts |
| Calcium lignosulfonate | 5 parts |

The above ingredients are uniformly mixed. After addition of an appropriate volume of water, the mixture is kneaded, granulated and dried to give a granule.

Formulation Example 4

| | |
|---|---|
| Compound of the present invention | 20 parts |
| Kaolin and synthetic high-dispersion silicic acid | 75 parts |

-continued

| Mixture of polyoxyethylene nonylphenyl ether and calcium alkylbenzene sulfonate | 5 parts |
|---|---|

The above ingredients are uniformly mixed and then pulverized to give a wettable powder.

Hereinafter, test examples in connection with the present invention are shown, but the present invention is not limited thereto.

Test Example 1

Test of Control Effect on *Myzus persicae*

Chinese cabbage plants were planted in plastic pots (diameter: 8 cm, height: 8 cm), green peach aphids (*Myzus persicae*) were propagated on the plants, and the number of surviving green peach aphids in each pot was counted. The condensed heterocyclic compounds represented by the general formula (1) of the present invention or salts thereof were separately dispersed in water and diluted to 500 ppm, and the agrochemical dispersions were applied to the foliage of the potted Chinese cabbage plants. After the plants were air-dried, the pots were kept in a greenhouse. At 6 days after the foliar application, the number of surviving green peach aphids on the Chinese cabbage plant in each pot was counted, the control rate was calculated according to the formula shown below, and the control effect was evaluated according to the criterion shown below.

Control rate=100−{(T×Ca)/(Ta×C)}×100

Ta: the number of survivors before the foliar application in a treatment plot
T: the number of survivors after the foliar application in a treatment plot
Ca: the number of survivors before the foliar application in a non-treatment plot
C: the number of survivors after the foliar application in a non-treatment plot
Criterion
A: the control rate is 100%.
B: the control rate is 90 to 99%.
C: the control rate is 80 to 89%.
D: the control rate is 50 to 79%.

As a result, the compounds 1-15, 1-16, 1-18, 2-15, 3-13, 3-15, 5-13, 5-15, 7-13, 7-14, 7-15, 8-10, 8-12, 8-15, 8-16, 8-18, 9-10, 9-12, 11-1, 11-2, 11-3, 11-6, 11-10, 11-13, 11-14, 11-16, 11-27, 11-50, 11-53, 11-60, 11-68, 11-73, 11-80, 11-81, 11-82, 11-86, 11-93, 11-94, 11-96, 11-131, 11-140, 11-141, 11-148, 12-1, 12-2, 12-6, 12-13, 18-1, 18-2, 18-6, 18-13, 18-161, 18-162, 18-166, 18-173, 18-174, 18-176, 18-187, 18-210, 18-211, 18-213, 18-220, 18-221, 18-228, 18-233, 18-234, 20-2, 20-21, 20-22, 20-24, 20-26, 20-39, 20-41, 20-42, 20-44, 20-45, 20-46, and 20-53 of the present invention showed the activity level evaluated as A.

Test Example 2

Test of Insecticidal Effect on *Laodelphax striatella*

The condensed heterocyclic compounds represented by the general formula (1) of the present invention or salts thereof were separately dispersed in water and diluted to 500 ppm, and rice plant seedlings (variety: Nihonbare) were dipped in the agrochemical dispersions for 30 seconds. After air-dried, each seedling was put into a separate glass test tube and inoculated with ten 3rd-instar larvae of *Laodelphax striatella*, and then the glass test tubes were capped with cotton plugs. At 8 days after the inoculation, the numbers of surviving larvae and dead larvae were counted, the corrected mortality rate was calculated according to the formula shown below, and the insecticidal effect was evaluated according to the criterion of Test Example 1.

Corrected mortality rate (%)=100×(Survival rate in a non-treatment plot−Survival rate in a treatment plot)/Survival rate in a non-treatment plot As a result, the compounds 1-15, 1-16, 1-18, 2-15, 3-13, 3-15, 5-13, 5-15, 7-13, 7-14, 7-15, 8-10, 8-12, 8-15, 8-16, 8-18, 9-10, 9-12, 11-1, 11-2, 11-3, 11-6, 11-10, 11-13, 11-14, 11-16, 11-27, 11-50, 11-53, 11-60, 11-68, 11-73, 11-80, 11-81, 11-82, 11-86, 11-93, 11-94, 11-96, 11-131, 11-140, 11-141, 11-148, 12-1, 12-2, 12-6, 12-13, 18-1, 18-2, 18-6, 18-13, 18-161, 18-162, 18-166, 18-173, 18-174, 18-176, 18-187, 18-210, 18-211, 18-213, 18-220, 18-221, 18-228, 18-233, 18-234, 20-2, 20-21, 20-22, 20-24, 20-26, 20-39, 20-41, 20-42, 20-44, 20-45, 20-46, and 20-53 of the present invention showed the activity level evaluated as A.

Test Example 3

Test of Insecticidal Effect on *Plutella xylostella*

Adults of *Plutella xylostella* were released onto Chinese cabbage seedlings and allowed to lay eggs thereon. At 2 days after the release of the adults, the Chinese cabbage seedlings with laid eggs were dipped for about 30 seconds in agrochemical dispersions diluted to 500 ppm, each of which contained a different condensed heterocyclic compound represented by the general formula (1) of the present invention as an active ingredient. The seedlings were air-dried and then kept in a thermostatic chamber at 25° C. At 6 days after the dip treatment, the number of hatched larvae per plot was counted, the mortality rate was calculated according to the formula shown below, and the insecticidal effect was evaluated according to the criterion of Test Example 1. This test was conducted in triplicate using 10 adults of *Plutella xylostella* per plot.

Corrected mortality rate (%)=100×(Number of hatched larvae in a non-treatment plot−Number of hatched larvae in a treatment plot)/Number of hatched larvae in a non-treatment plot As a result, the compounds 1-15, 1-16, 1-18, 2-15, 3-13, 3-15, 5-13, 5-15, 7-13, 7-14, 7-15, 8-10, 8-12, 8-15, 8-16, 8-18, 9-10, 9-12, 11-1, 11-2, 11-3, 11-6, 11-10, 11-13, 11-14, 11-16, 11-27, 11-50, 11-53, 11-60, 11-68, 11-73, 11-80, 11-81, 11-86, 11-93, 11-94, 11-96, 11-131, 11-140, 11-141, 11-148, 12-1, 12-2, 12-6, 12-13, 18-1, 18-2, 18-6, 18-13, 18-161, 18-162, 18-166, 18-173, 18-174, 18-176, 18-187, 18-210, 18-211, 18-213, 18-220, 18-221, 18-228, 18-233, 18-234, 20-2, 20-21, 20-22, 20-24, 20-26, 20-39, 20-41, 20-42, 20-44, 20-45, 20-46, and 20-53 of the present invention showed the activity level evaluated as A.

INDUSTRIAL APPLICABILITY

The compound of the present invention has an excellent control effect on a wide range of agricultural and horticultural insect pests and thus is useful.

The invention claimed is:
1. A condensed heterocyclic compound represented by the general formula (1):

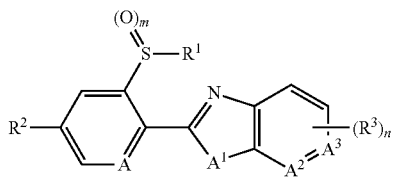

(1)

wherein R¹ represents:
(a1) a $(C_1-C_6)$ alkyl group,
R² represents:
(b1) a $(C_3-C_6)$ cycloalkyl group; or
(b5) a $(C_3-C_6)$ cycloalkyl group having, on the ring, 1 or 2 of the same or different substituting groups selected from:
(a) a halogen atom,
(b) a cyano group,
(c) a cyano $(C_1-C_6)$ alkyl group,
(d) a formyl group;
(e) a hydroxy $(C_1-C_6)$ alkyl group,
(f) a halo $(C_1-C_6)$ alkyl group,
(g) a $(C_1-C_6)$ alkoxy $(C_1-C_6)$ alkyl group,
(h) a halo $(C_1-C_6)$ alkoxy $(C_1-C_6)$ alkyl group,
(i) a $(C_3-C_6)$ cycloalkyl $(C_1-C_6)$ alkoxy $(C_1-C_6)$ alkyl group,
(j) a $(C_1-C_6)$ alkylthio $(C_1-C_6)$ alkyl group,
(k) a $(C_1-C_6)$ alkylsulfinyl $(C_1-C_6)$ alkyl group,
(l) a $(C_1-C_6)$ alkylsulfonyl $(C_1-C_6)$ alkyl group,
(m) a $(C_1-C_6)$ alkylcarbonyl group,
(n) a carboxyl group,
(o) a $(C_1-C_6)$ alkoxycarbonyl group,
(p) a halo $(C_1-C_6)$ alkoxycarbonyl group,
(q) a $(C_3-C_6)$ cycloalkyl $(C_1-C_6)$ alkoxycarbonyl group,
(r) a $(C_1-C_6)$ alkylcarbonyloxy $(C_1-C_6)$ alkyl group,
(s) a $(C_3-C_6)$ cycloalkylcarbonyloxy $(C_1-C_6)$ alkyl group,
(t) a $(C_1-C_6)$ alkoxycarbonyloxy $(C_1-C_6)$ alkyl group,
(u) a $R^5(R^6)N$ group (wherein $R^5$ and $R^6$ may be the same or different, and each represent a hydrogen atom, a $(C_1-C_6)$ alkyl group, a $(C_3-C_6)$ cycloalkyl group, a $(C_3-C_6)$ cycloalkyl $(C_1-C_6)$ alkyl group, a halo $(C_1-C_6)$ alkyl group, a $(C_1-C_6)$ alkylcarbonyl group, a $(C_1-C_6)$ alkoxycarbonyl group, or a di-$(C_1-C_6)$ alkylaminocarbonyl group (wherein the alkyl groups of the di-$(C_1-C_6)$ alkylamino moiety may be the same or different)),
(v) a $R^5(R^6)N(C_1-C_6)$ alkyl group (wherein $R^5$ and $R^6$ are as defined above),
(w) a $R^5(R^6)N$ carbonyl group (wherein $R^5$ and $R^6$ are as defined above),
(x) a $R^5(R^6)N$ carbonyloxy $(C_1-C_6)$ alkyl group (wherein $R^5$ and $R^6$ are as defined above), or
(y) a $C(R^5)=NOR^6$ group (wherein $R^5$ and $R^6$ are as defined above),
R³ represents:
(c8) a halo $(C_1-C_6)$ alkyl group;
(c9) a halo $(C_1-C_6)$ alkoxy group;
(c15) a halo $(C_1-C_6)$ alkylthio group;
(c16) a halo $(C_1-C_6)$ alkylsulfinyl group; or
(c17) a halo $(C_1-C_6)$ alkylsulfonyl group,
A represents a nitrogen atom,
A² and A³ each represent CH,
A¹ represents O, S or N—R⁴ (wherein R⁴ represents (d1) a $(C_1-C_6)$ alkyl group),
m represents 0, 1 or 2, and
n represents 1 or 2, or
a salt thereof.

2. The condensed heterocyclic compound according to claim 1,
wherein R² is:
(b1) a $(C_3-C_6)$ cycloalkyl group; or
(b5) a $(C_3-C_6)$ cycloalkyl group having, on the ring, 1 or 2 of the same or different substituting groups selected from;
(b) a cyano group,
(c) a cyano $(C_1-C_6)$ alkyl group,
(d) a formyl group,
(e) a hydroxy $(C_1-C_6)$ alkyl group,
(f) a halo $(C_1-C_6)$ alkyl group,
(g) a $(C_1-C_6)$ alkoxy $(C_1-C_6)$ alkyl group,
(h) a halo $(C_1-C_6)$ alkoxy $(C_1-C_6)$ alkyl group,
(i) a $(C_3-C_6)$ cycloalkyl $(C_1-C_6)$ alkoxy $(C_1-C_6)$ alkyl group,
(j) a $(C_1-C_6)$ alkylthio $(C_1-C_6)$ alkyl group,
(k) a $(C_1-C_6)$ alkylsulfinyl $(C_1-C_6)$ alkyl group,
(l) a $(C_1-C_6)$ alkylsulfonyl $(C_1-C_6)$ alkyl group,
(m) a $(C_1-C_6)$ alkylcarbonyl group,
(n) a carboxyl group,
(o) a $(C_1-C_6)$ alkoxycarbonyl group,
(p) a halo $(C_1-C_6)$ alkoxycarbonyl group,
(q) a $(C_3-C_6)$ cycloalkyl $(C_1-C_6)$ alkoxycarbonyl group,
(r) a $(C_1-C_6)$ alkylcarbonyloxy $(C_1-C_6)$ alkyl group,
(s) a $(C_3-C_6)$ cycloalkylcarbonyloxy $(C_1-C_6)$ alkyl group,
(t) a $(C_1-C_6)$ alkoxycarbonyloxy $(C_1-C_6)$ alkyl group,
(u) a $R^5(R^6)N$ group (wherein $R^5$ and $R^6$ may be the same or different, and each represent a hydrogen atom, a $(C_1-C_6)$ alkyl group, a $(C_3-C_6)$ cycloalkyl group, a $(C_3-C_6)$ cycloalkyl $(C_1-C_6)$ alkyl group, a halo $(C_1-C_6)$ alkyl group, a $(C_1-C_6)$ alkylcarbonyl group, a $(C_1-C_6)$ alkoxycarbonyl group, or a di-$(C_1-C_6)$ alkylaminocarbonyl group (wherein the alkyl groups of the di-$(C_1-C_6)$ alkylamino moiety may be the same or different)),
(v) a $R^5(R^6)N(C_1-C_6)$ alkyl group (wherein $R^5$ and $R^6$ are as defined above),
(w) a $R^5(R^6)N$ carbonyl group (wherein $R^5$ and $R^6$ are as defined above),
(x) a $R^5(R^6)N$ carbonyloxy $(C_1-C_6)$ alkyl group (wherein $R^5$ and $R^6$ are as defined above), or
(y) a $C(R^5)=NOR^6$ group (wherein $R^5$ and $R^6$ are as defined above), and
n is 1, or
a salt thereof.

3. The condensed heterocyclic compound according to claim 1,
wherein
R² is:
(b1) a $(C_3-C_6)$ cycloalkyl group; or
(b5) a $(C_3-C_6)$ cycloalkyl group having, on the ring, 1 or 2 of the same or different substituting groups selected from:
(b) a cyano group,
(n) a carboxyl group,
(o) a $(C_1-C_6)$ alkoxycarbonyl group,
(t) a $(C_1-C_6)$ alkoxycarbonyloxy $(C_1-C_6)$ alkyl group, or
(w) a $R^5(R^6)N$ carbonyl group (wherein $R^5$ and $R^6$ are as defined above),
R³ is (c8) a halo $(C_1-C_6)$ alkyl group;
(c15) a halo $(C_1-C_6)$ alkylthio group;
(c16) a halo $(C_1-C_6)$ alkylsulfinyl group; or
(c17) a halo $(C_1-C_6)$ alkylsulfonyl group,
A¹ is O, or N—R⁴ (wherein R⁴ represents (d1) a $(C_1-C_6)$ alkyl group),
m is 0 or 2, and
n is 1, or
a salt thereof.

4. A condensed heterocyclic compound represented by the formula:

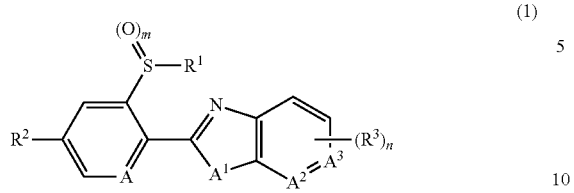

wherein $R^1$ represents (a1) a ($C_1$-$C_6$) alkyl group,
$R^2$ represents (b1) a ($C_3$-$C_6$) cycloalkyl group; or (b5) a ($C_3$-$C_6$) cycloalkyl group having, on the ring, 1 or 2 of the same or different substituting groups selected from:
(b) a cyano group,
(n) a carboxyl group, or
(o) a ($C_1$-$C_6$) alkoxycarbonyl group,
$R^3$ represents (c8) a halo ($C_1$-$C_6$) alkyl group; (c9) a halo ($C_1$-$C_6$) alkoxy group; (c15) a halo ($C_1$-$C_6$) alkylthio group; (c16) a halo ($C_1$-$C_6$) alkylsulfinyl group; or (c17) a halo ($C_1$-$C_6$) alkylsulfonyl group,
A represents a nitrogen atom,
$A^2$ and $A^3$ each represent CH,
$A^1$ represents O, S or N—$R^4$ (wherein $R^4$ represents (d1) a ($C_1$-$C_6$) alkyl group),
m represents 0, 1 or 2, and
n represents 1 or 2.

5. The condensed heterocyclic compound according to claim 4,
wherein $A^1$ represents O, or N—$R^4$ (wherein $R^4$ represents (d1) a ($C_1$-$C_6$) alkyl group),
m represents 0 or 2, and
n represents 1.

6. The condensed heterocyclic compound according to claim 4,
wherein
$R^3$ represents (c8) a halo ($C_1$-$C_6$) alkyl group;
(c15) a halo ($C_1$-$C_6$) alkylthio group;
(c16) a halo ($C_1$-$C_6$) alkylsulfinyl group; or
(c17) a halo ($C_1$-$C_6$) alkylsulfonyl group,
m represents 0 or 2, and
n represents 1.

7. An agricultural and horticultural insecticide comprising the condensed heterocyclic compound or a salt thereof according to claim 1 as an active ingredient.

8. A method for using an agricultural and horticultural insecticide, comprising contacting plants or soil with an effective amount of the condensed heterocyclic compound or a salt thereof according to claim 1.

9. An ectoparasite control agent comprising an effective amount of the condensed heterocyclic compound or a salt thereof according to claim 1 as an active ingredient.

* * * * *

UNITED STATES PATENT AND TRADEMARK OFFICE
CERTIFICATE OF CORRECTION

PATENT NO. : 10,266,552 B2
APPLICATION NO. : 15/545078
DATED : April 23, 2019
INVENTOR(S) : Ikki Yonemura et al.

It is certified that error appears in the above-identified patent and that said Letters Patent is hereby corrected as shown below:

In the Specification

In Columns 27-28, Line 15 (Approx.), change "(m.2H)," to --(m,2H),--.

In Columns 33-34, Line 26, change "$CH_2SO_2MeMe$" to --$CH_2SO_2Me$--.

In Columns 35-36, Line 32 (Approx.), change "$CH_2SO_2MeMe$" to --CH2SO2Me--.

In Columns 37-38, Line 51, change "$CH_2SO_2MeMe$" to --$CH_2SO_2Me$--.

In Columns 39-40, Line 53, change "$CH_2SO_2MeMe$" to --$CH_2SO_2Me$--.

In Columns 41-42, Line 57, change "$CH_2SO_2MeMe$" to --$CH_2SO_2Me$--.

In Columns 43-44, Line 61, change "$CH_2SO_2MeMe$" to --$CH_2SO_2Me$--.

In Column 111, Line 39, change "Ipsilon," to --ipsilon,--.

In Column 111, Line 54, change "Eupoecillia" to --Eupoecilia--.

In Column 112, Line 13, change "iwasakii," to --iwasaki,--.

In Column 112, Line 17, change "Rhopalosophum" to --Rhopalosiphum--.

In Column 112, Line 36, change "Uroeucon" to --Uroleucon--.

In Column 112, Line 48, change "Rhopalosophum" to --Rhopalosiphum--.

In Column 112, Line 56, change "Macros teles" to --Macrosteles--.

Signed and Sealed this
Fifth Day of November, 2019

Andrei Iancu
*Director of the United States Patent and Trademark Office*

CERTIFICATE OF CORRECTION (continued)
U.S. Pat. No. 10,266,552 B2

In Column 113, Line 4, change "farinose" to --farinosa--.

In Column 113, Line 16, change "post fasciatus," to --postfasciatus,--.

In Column 113, Line 47, change "Hydrellia griseola, Hydrellia griseola," to --Hydrellia griseola,--.

In Column 114, Line 16, change "Franklinella" to --Frankliniella--.

In Column 114, Line 27, change "sylvairum," to --sylviarum,--.

In Column 114, Line 31, change "Octodectes" to --Otodectes--.

In Column 114, Line 32, change "ptrenyssnus," to --pteronyssinus,--.

In Column 114, Line 54, change "Tylenchus" to --Tylenchulus--.

In Column 114, Line 58, change "Lehmannina" to --Lehmannia--.

In Column 115, Line 5, change "taiwanesis;" to --taiwanensis;--.

In Column 115, Line 25, change "Nosopsyllus" to --Monopsyllus--.

In Column 115, Lines 28-29, change "Dalmalinia" to --Damalinia--.

In Column 122, Line 26, change "ethofenprox," to --etofenprox,--.

In Column 123, Line 20, change "tartarate," to --tartrate,--.

In Column 123, Lines 66-67, change "benzensulfonate" to --benzenesulfonate--.

In Column 126, Line 48 (Approx.), change "radiobactor," to --radiobacter,--.

In Column 138, Lines 44-45 (Approx.), change "(trifluoromethylthio) phenol," to --(trifluoromethylthio)phenol,--.

In Column 138, Line 45 (Approx.), change "(trifluoromethyl) phenol," to --(trifluoromethyl)phenol,--.